United States Patent [19]

Wissner

[11] 4,254,036

[45] Mar. 3, 1981

[54] 1-HYDROXYMETHYL-1-OXO-PROSTANE-DERIVATIVES OF THE E, A AND F-SERIES

[75] Inventor: Allan Wissner, Ardsley, N.Y.

[73] Assignee: American Cyanamid Company, Stamford, Conn.

[21] Appl. No.: 46,722

[22] Filed: Jun. 7, 1979

Related U.S. Application Data

[63] Continuation-in-part of Ser. No. 3,953, Jan. 16, 1979, which is a continuation-in-part of Ser. No. 961,032, Nov. 18, 1978, which is a continuation-in-part of Ser. No. 858,589, Dec. 8, 1977, Pat. No. 4,202,822, which is a continuation-in-part of Ser. No. 858,588, Dec. 8, 1977, Pat. No. 4,170,597, which is a continuation-in-part of Ser. No. 858,580, Dec. 8, 1977, Pat. No. 4,197,245, which is a continuation-in-part of Ser. No. 858,487, Dec. 8, 1977, abandoned, which is a continuation-in-part of Ser. No. 858,504, Dec. 8, 1977, Pat. No. 4,172,839, which is a continuation-in-part of Ser. No. 858,579, Dec. 8, 1977, Pat. No. 4,212,909.

[51] Int. Cl.$^3$ .......................................... C07C 177/00
[52] U.S. Cl. .......................... 260/340.9 P; 260/463; 560/18; 560/73; 560/106; 560/162; 560/231; 568/379
[58] Field of Search .............. 260/340.9 P, 463, 586 R; 568/379; 560/231, 162, 106, 73, 18

[56] References Cited

U.S. PATENT DOCUMENTS 4,202,822  5/1980  Wissner ........................... 542/429

Primary Examiner—Robert Gerstl
Attorney, Agent, or Firm—Richard J. Hammond

[57] ABSTRACT

The invention disclosed herein relates to pharmacologically active prostaglandin derivatives of the E, F, or A series having on the terminal methylene carbon of the alpha chain a substituent selected from the group consisting of:

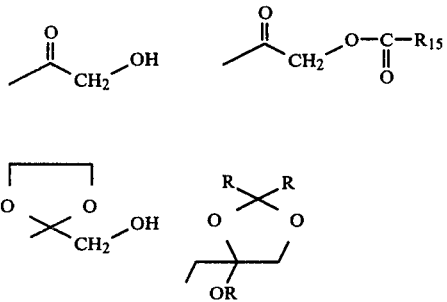

wherein R is an alkyl group and $R_{15}$ is $C_1$–$C_4$ alkyl, di-$C_1$–$C_4$-alkylamino, $C_1$–$C_4$ alkoxy, and phenyl or phenyl substituted with one or more substituents from the group consisting of $C_1$–$C_4$, OR, SR, F, or Cl wherein R is as previously defined.

37 Claims, No Drawings

1-HYDROXYMETHYL-1-OXO-PROSTANE-DERIVATIVES OF THE E, A AND F-SERIES

CROSS REFERENCE TO RELATED APPLICATIONS

This application is a continuation-in-part of application Ser. No. 3953 filed Jan. 16, 1979, which is in turn a continuation-in-part of application Ser. No. 961,032 filed Nov. 18, 1978 which is in turn a continuation-in-part of application Ser. Nos. 858,589 U.S. Pat. No. 4,202,822, 858,588 U.S. Pat. No. 4,170,597, 858,580 U.S. Pat. No. 4,197,245, 858,487 abandoned, 858,504 U.S. Pat. No. 4,172,839 and 858,579 U.S. Pat. No. 4,212,969 each of which was filed on Dec. 8, 1977.

BRIEF DESCRIPTION OF THE INVENTION

This invention relates to the optically active compound of the formula:

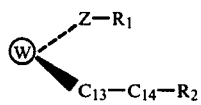

wherein Z is —$(CH_2)_g$— or

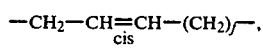

wherein g is an integer from 5 to 7 inclusive, and f is an integer from 2 to 5, inclusive; $C_{13}$–$C_{14}$ is ethylene or trans-vinylene; W is selected from the group consisting of:

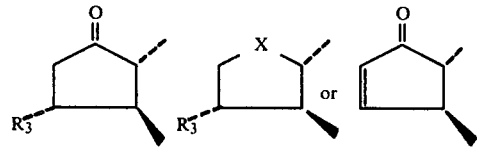

wherein X is:

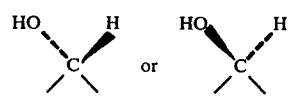

and $R_3$ is hydrogen or hydroxyl, $R_1$ is selected from the group consisting of:

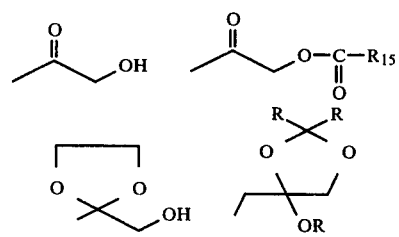

wherein R is $C_1$ to $C_6$ alkyl, and $R_{15}$ is selected from the group consisting of $C_1$–$C_4$ alkyl, di-($C_1$–$C_4$)-alkylamino, $C_1$–$C_4$ alkoxy and phenyl or phenyl substituted with one or more substituents selected from the group consisting of $C_1$–$C_4$ alkyl, —OR, —SR, F or Cl wherein R is as previously defined; and $R_2$ is selected from the group consisting of:

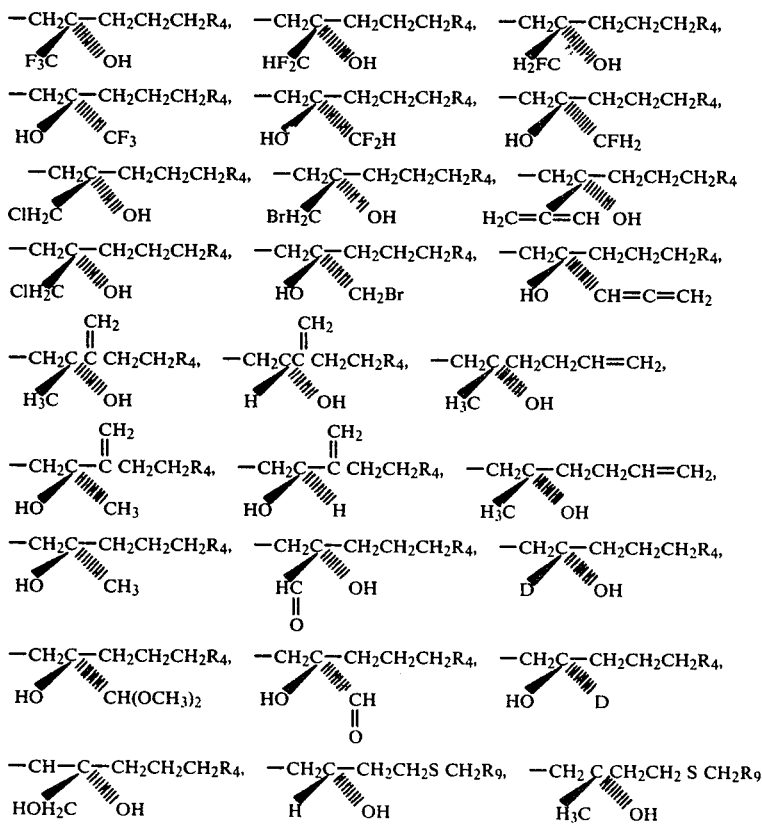

-continued

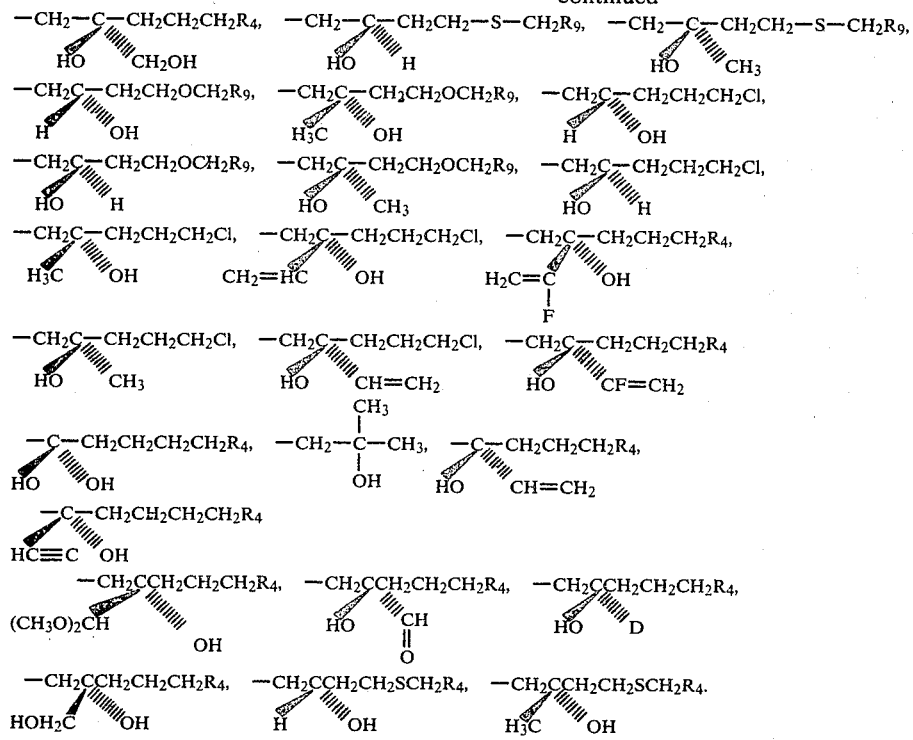

R₄ is hydrogen, methyl, ethyl, propyl or chloro; and R₉ is hydrogen or $C_1$-$C_3$ alkyl.

This invention also relates to the method of preparing the above-described compounds, as well as to novel intermediates useful for the preparation of the prostaglandin compounds described herein. The present invention will be fully described with reference to the flowsheets and examples of this application.

DETAILED DESCRIPTION OF THE INVENTION

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic suspensions are preferred. For subcutaneous or intramuscular injection, sterile suspensions of the compounds in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom, et al., J. Biol. Chem., 238, 3555 (1963) and Horton, Experientia, 21, 113 (1965) and references cited therein. All of the so called natural prostaglandins are derivatives of prostanoic acid:

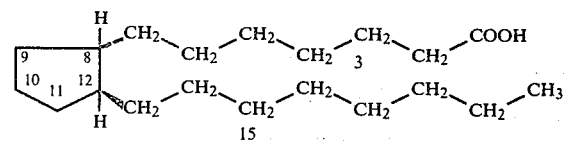

The hydrogen atoms attached to C-8 and C-12 are in transconfiguration. The natural prostaglandins represent only one of the possible optical isomers. The compounds of this invention include all possible optical isomers and racemates.

The configuration of substituents on the prostaglandin molecule are designated to be in the α-configuration if they lie beneath the plane of the molecule as drawn above and are designated with a ---bond. Those substituents which lie above the plane of the molecule as drawn above are designated β and are represented by a ▭bond.

The compounds of this invention which have the structure as shown in formula (A) wherein $R_1$, Z, $R_3$, Y, m, n, s and X are as herein below defined are said to be in the same configuration as the natural prostaglandins with respect to the configurations at $C_8$, $C_{11}$ and $C_{12}$ and are designated by the prefix nat. The enantiomer, represented by formula (B) is said to be in the mirror image or ent configuration. A substituent at $C_{11}$ drawn with a dotted line ($C_{11}$---$R_3$) is said to have an α configuration; a solid line ($C_{11}$—$R_3$) indicates a β configuration. The configuration at Y and X will be expressed in terms of R and S as is understood in the art. For example, the compound represented by formula (C) is named nat-15S,16S-11α,15-dihydroxy-1-(hydroxymethyl)-1,9-dioxo-15,-16-trimethylene-13-trans-prostene; its enantiomer (formula D) is named ent-15R,16R-11α,15-dihydroxy-1-(hydroxymethyl)-1,9-dioxo-15,16-trimethylene-13-trans-prostene. The racemate [1:1 mixture of (C) and (D)] is named nat-15S,16S-(and ent-15R,16R)11α,15-dihydroxy-1-(hydroxymethyl)-1,9-dioxo-15,16-trimethylene-13-trans-prostene. In a similar manner, the compounds represented by formulae (E) to (J) have the configurations shown below.

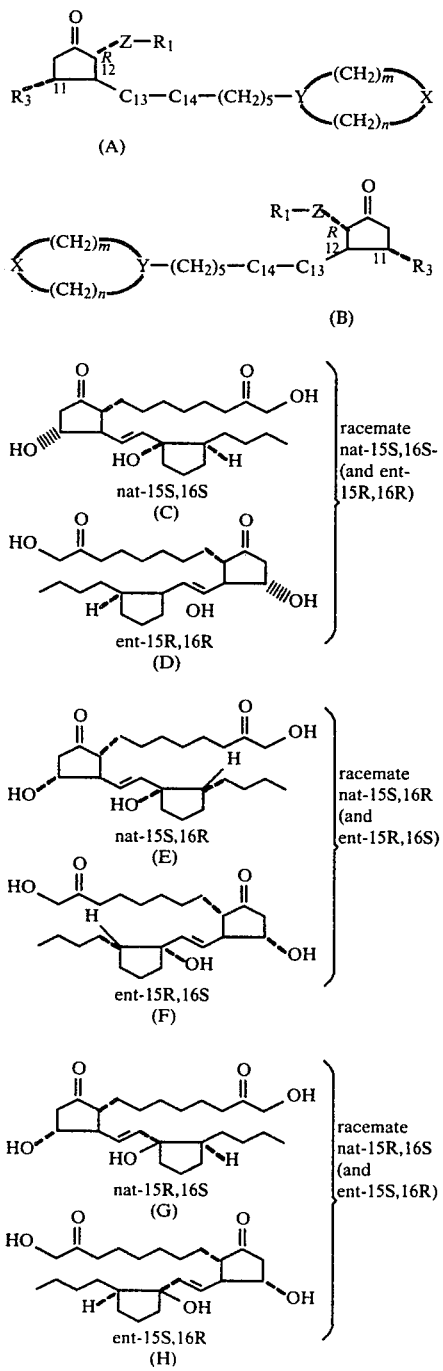

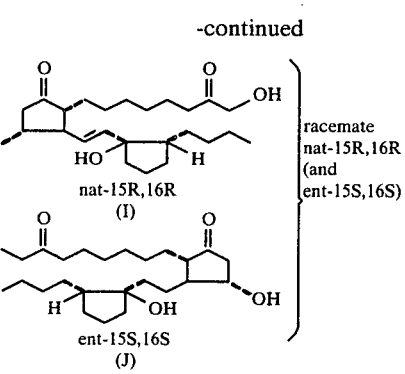

In each of the above formulae (C to J) the hydroxy at $C_{11}$ is named 11-alpha-hydroxy, and M is zero or the integer 1 to 4 inclusive; N is zero or the integer 1 to 4, inclusive; S is zero or 1 and X is:

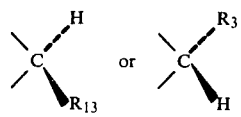

wherein $R_{13}$ is selected from the group consisting of $C_1$–$C_7$ alkyl, hydrogen, and a phenoxy group optionally substituted with a substituent selected from the group consisting of halogen, trifluoromethyl, and $C_1$–$C_4$ alkoxy.

The novel compounds of this invention can be prepared by a novel 1,4-conjugate-addition procedure involving treatment of the ether blocked cyclopentenone such as (151) with a lithio cuprate reagent such as (148), (149), or (150) prepared as illustrated in Flowsheets A through N.

The 1,4-conjugate-addition procedure is described hereinbelow in Flowsheet N. The preparation of the various requisite 1-iodo-trans-1-alkenyl or 1-tributylstannyl-trans-1-alkenyl derivative is illustrated in Flowsheets A-H and the novel and important methods of preparation of the 4-hydroxycyclopentenones embracing the 1-(hydroxymethyl)-oxo α chain is described in connection with Flowsheets I–M.

In accordance with the procedure outlined in Flowsheet A, treatment of the ketone (1) with propargylmagnesium bromide (2) provides the hydroxyalkyne (3) which is silylated to give the ether (4). The TMS ether (4) is heated with tri-n-butylstannane in the presence of azobisisobutyronitrile (AIBN) to afford the trans vinylstannane (5) which contains 10% to 20% of the corresponding cis vinylstannane (6).

Treatment of the vinylstannyl reagents (5,6) with n-butyl lithium at temperatures of −78° C. to −10° C. generates the vinyl lithium reagents (7).

FLOWSHEET A

1

-continued
FLOWSHEET A

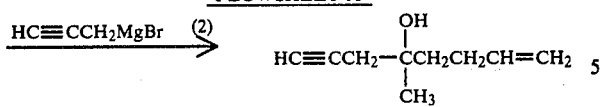

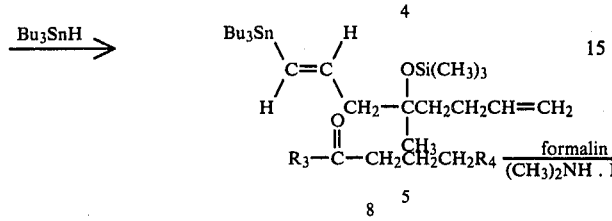

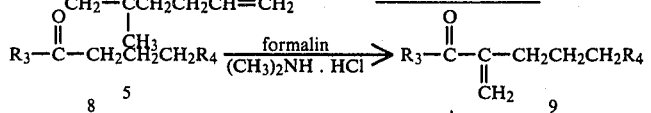

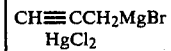

Treatment of an aldehyde or ketone such as (8), wherein $R_5$ is hydrogen, methyl or ethyl and $R_4$ is hydrogen, or $C_1$ to $C_3$ alkyl, with formalin and dimethylamine hydrochloride provides the α-methylene aldehyde or ketone (9). Treatment of the carbonyl compound (9) with propargylmagnesium bromide (10) provides the hydroxy alkyne (12) which is silylated to give (11) wherein $R_5$ is methyl or ethyl. The selection of the silylating reagent is determined by the nature of the group at $R_5$ when $R_3$ is hydrogen, then $R_5$ is ethyl, when $R_3$ is methyl or ethyl, then $R_5$ is methyl. The silyl ether 11 is treated with tributylstannane in the presence of azobisisobutyronitrile (AIBN) to generate the vinylstannane 13 and 14 in an approximate ratio of 10:1, respectively. Lithiation provides the trans vinyllithium 15.

FLOWSHEET B

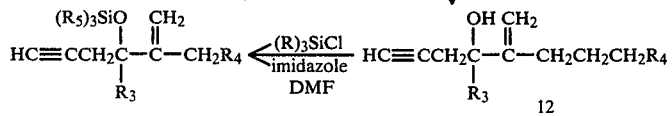

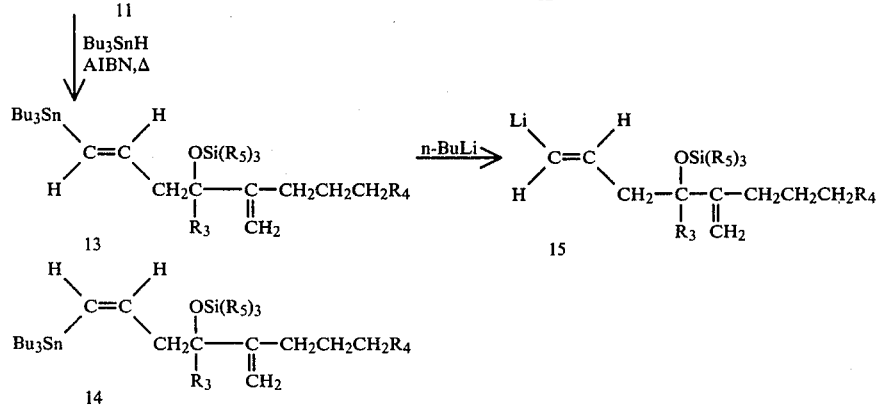

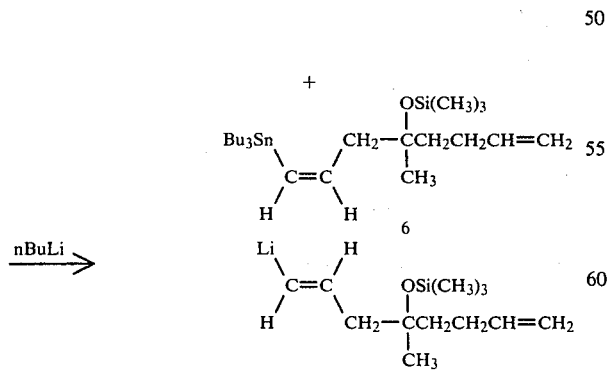

The 17-methylene precursors are prepared in accordance with the procedure outlined in Flowsheet B.

The precursor to the 16 allenyl analogs are prepared in accordance with the procedure outlined in Flowsheet C. Treatment of esters such as 16 with propargyl Grignard 17 (wherein $R_4$ is hydrogen, methyl, ethyl, propyl or chloro provides the dienylketone 18. Treatment of the ketone 18 with propargylmagnesium bromide provides the hydroxy alkyne 19 which is silylated to give the ether 20. The alkyne 20 is converted to the trans vinyliodide 21 by successive treatment with diisoamylborane, triethylamine oxide and $I_2$/NaOH as described by Kluge et al., [J. Amer. Chem. Soc., 94, 7827 (1972)]. Treatment of the vinyliodide 21 with 1 eq. n-BuLi at −70° to −50° C. affords the vinyl lithium 22.

FLOWSHEET C

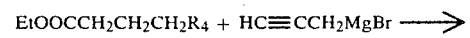

-continued
FLOWSHEET C

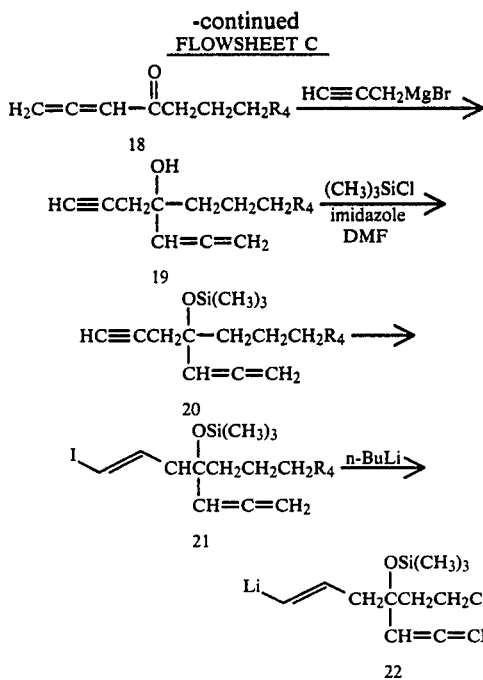

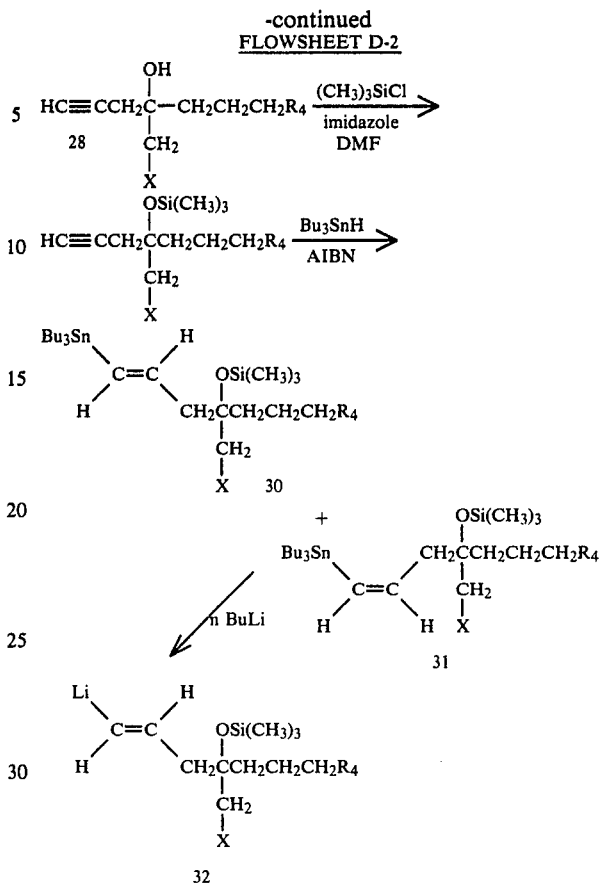

The 16-chloromethyl and 16-bromomethyl analogs are prepared from the precursors shown in Flowsheet D-1 and D-2. In accordance with the procedure outlined in Flowsheet D-1 treatment of a carboxylic acid halide such as 23, wherein $R_4$ is hydrogen, methyl, ethyl or propyl, with 1,1,2-tris trimethylsilyloxyethylene 24 [*Tet. Letters*, 2749, (1978)] provides the α-hydroxyketone (25). Treatment of (25) with methansulfonylchloride in dimethylformamide (DMF) provides the α-chloroketone 26.

In accordance with Flowsheet D-2, treatment of the α-haloketones (27) with propargylmagnesium bromide in the presence of mercuric chloride provides the hydroxyalkyne (28) that is treated with an trialkylchlorosilane such as chlorotrimethylsilane to provide the ether (29). The alkyne (29) is treated with tri-n-butylstannane in the presence of azobisisobutrylnitrile (AIBN) to provide the trans-vinylstannane (30) containing 10 to 20% of the corresponding cis isomer (31). Lithiation then provides the vinyllithium reagent (32).

FLOWSHEET D-1

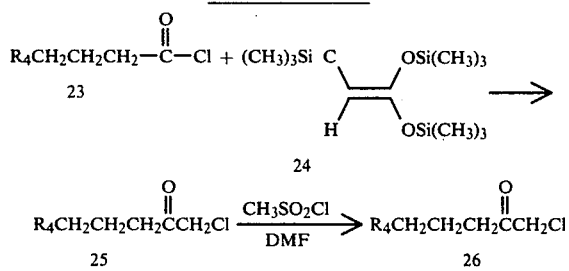

FLOWSHEET D-2

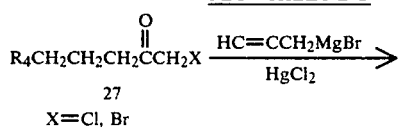
X=Cl, Br

The 19-chloro-20-nor analogs are prepared from the precursors shown in Flowsheet E.

In accordance with Flowsheet E-1 wherein $R_3'$ is hydrogen, methyl, vinyl, and trimethylsilylethynyl, treatment of the carbonyl compound 33 with propargylmagnesium bromide 34 in the presence of mercuric chloride provides the hydroxyalkyne 35. The hydroxy portion of 35 is protected with a trialkylsilyl group; triethylsilyl when $R_3'$ is hydrogen and trimethylsilyl when $R_3'$ is methyl, vinyl or trimethylsilylethynyl. The silyl ether 37 is heated with tri-n-butylstannane (38) in the presence of azobisisobutryonitrile (AIBN) to afford the trans-vinylstannane 39 which contains 10 to 20% of the corresponding cis-vinylstannane 40. Treatment of the vinylstannane 39 with n-butyl lithium at temperature of −78° C. to −10° C. generates the vinyl lithium reagents 40.

The preparation of the carbonyl compound 43 wherein $R_3'$ is vinyl (7-chloro-hept-1-en-2-one) is shown in Flowsheet E-2. In accordance with Flowsheet E-2, 4-chlorobutrylchloride 42 is treated with vinyltrimethylsilane in the presence of aluminum trichloride at −20° C. to provide, after quenching with NH4Cl the vinylketone 43. A similar sequence for the preparation of the trimethylsilylethynyl ketone 44 is also illustrated in Flowsheet E-2 by utilizing bis-trimethylsilylacetylene.

An alternate procedure to prepare precursors to the vinyl lithium reagent is shown in Flowsheet E-3. In accordance with Flowsheet E-3 the silylether alkyne 37 is treated with diisoamylborane followed by treatment with trimethylamine oxide and then with $I_2$/NaOH, to provide to 1-iodo-trans-alkenes 45. Treatment of the vinyl iodide 45 with two equivalents of t-BuLi generates the vinyl lithium reagent 41.

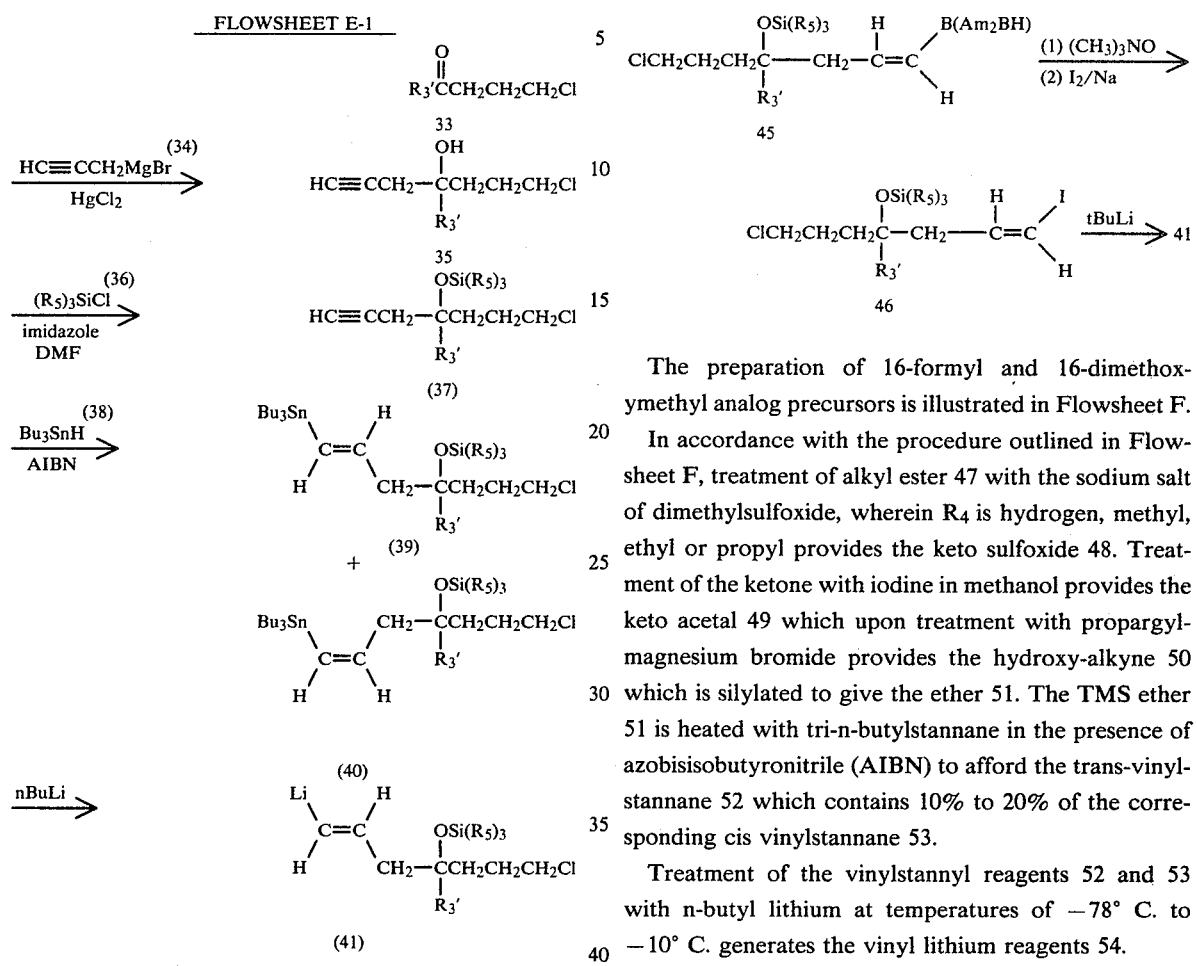

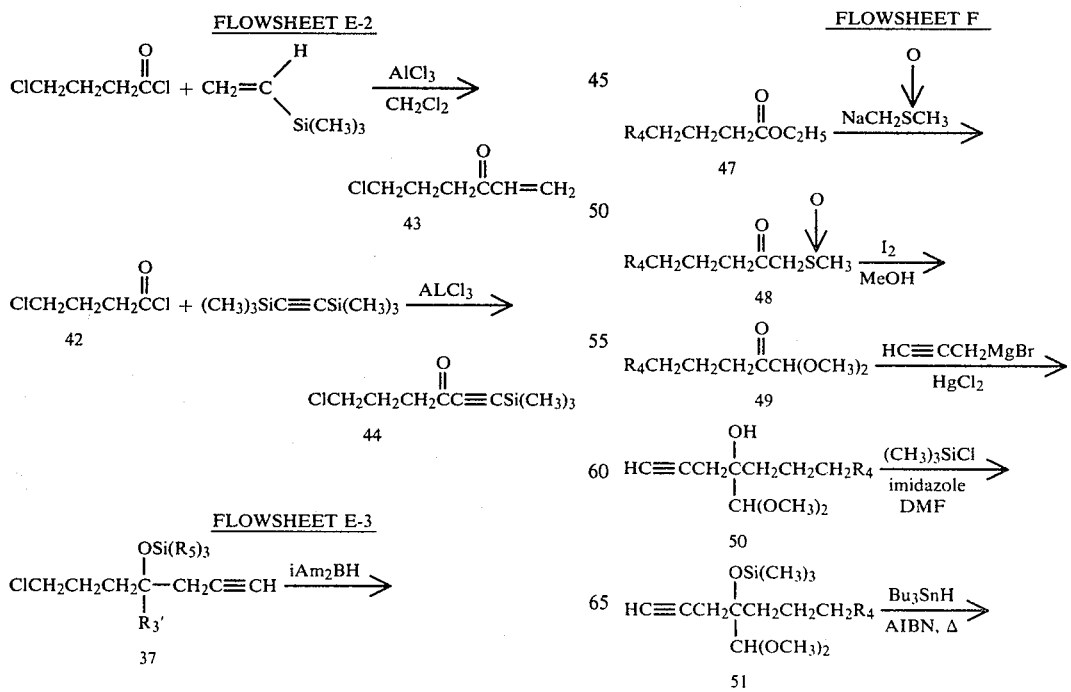

The preparation of 16-formyl and 16-dimethoxymethyl analog precursors is illustrated in Flowsheet F.

In accordance with the procedure outlined in Flowsheet F, treatment of alkyl ester 47 with the sodium salt of dimethylsulfoxide, wherein $R_4$ is hydrogen, methyl, ethyl or propyl provides the keto sulfoxide 48. Treatment of the ketone with iodine in methanol provides the keto acetal 49 which upon treatment with propargylmagnesium bromide provides the hydroxy-alkyne 50 which is silylated to give the ether 51. The TMS ether 51 is heated with tri-n-butylstannane in the presence of azobisisobutyronitrile (AIBN) to afford the trans-vinylstannane 52 which contains 10% to 20% of the corresponding cis vinylstannane 53.

Treatment of the vinylstannyl reagents 52 and 53 with n-butyl lithium at temperatures of $-78°$ C. to $-10°$ C. generates the vinyl lithium reagents 54.

-continued
FLOWSHEET F

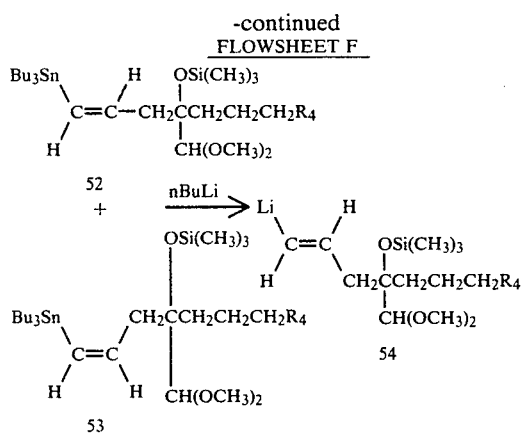

The precursor for the 16-fluoromethyl analogs are prepared as illustrated in Flowsheets G-1 and G-2.

In accordance with the procedure outlined in Flowsheet G-1, treatment of ethyl fluoroacetate with alkyl lithium 56 wherein $R_4$ is hydrogen, methyl, ethyl or propyl provides the fluoromethylketone 57. Treatment of the ketone 57 with propargylmagnesium bromide 58 provides the hydroxyalkyne 59 which is silylated to give the ether 60. The TMS ether 60 is heated with tri-n-butylstannane in the presence of azobisisobutyronitrile (AIBN) to afford the trans vinylstannane 61 which contains 10% to 20% of the corresponding cis vinylstannane 62.

Treatment of the vinylstannyl reagents (61,62) with n-butyl lithium at temperatures of $-78°$ C. to $-10°$ C. generates the vinyl lithium reagent 63.

In accordance with Flowsheet G-2 the treatment of acid 64 ($R_7=CF_2H, CF_3$) with alkyl lithium 56 wherein $R_4$ is hydrogen, methyl, ethyl or propyl, provides the ketone 65 which upon addition of propargylmagnesium bromide provides the hydroxyalkyne 66. The alcohol 66 is treated with chlorotrimethylsilane to provide the TMS-ether 67 which is heated with tri-n-butylstannane to provide the trans-vinylstannane 68 that contains 10% to 20% of the corresponding cis-vinylstannane 69.

Treatment of the vinylstannane reagents 68, 69 with n-butyl lithium at temperatures of $-78°$ C. to $-10°$ C. generates the vinyl lithium reagents 70.

FLOWSHEET G-1

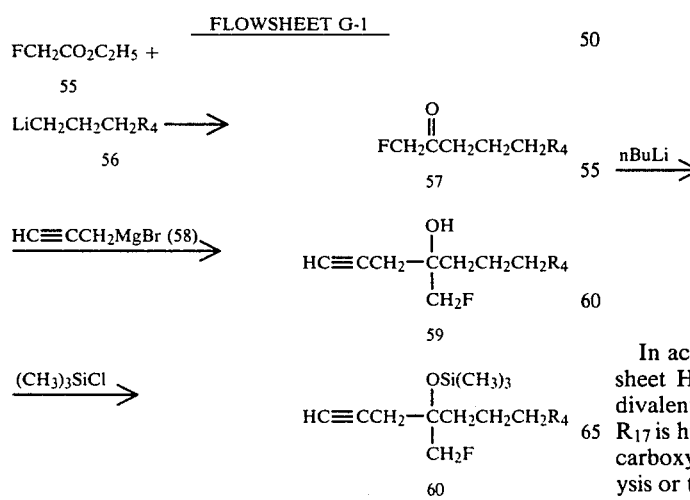

-continued
FLOWSHEET G-1

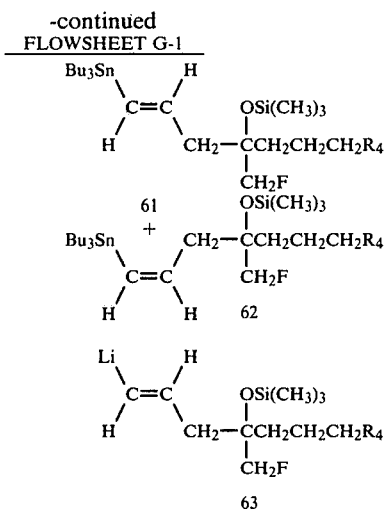

FLOWSHEET G-2

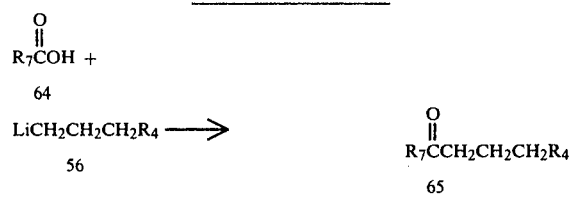

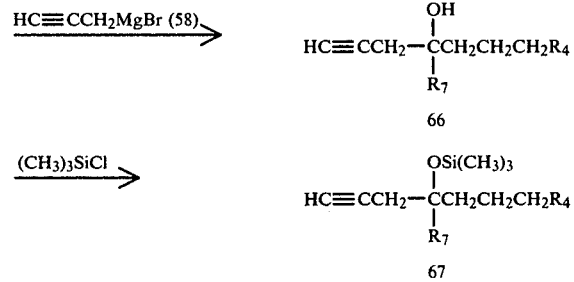

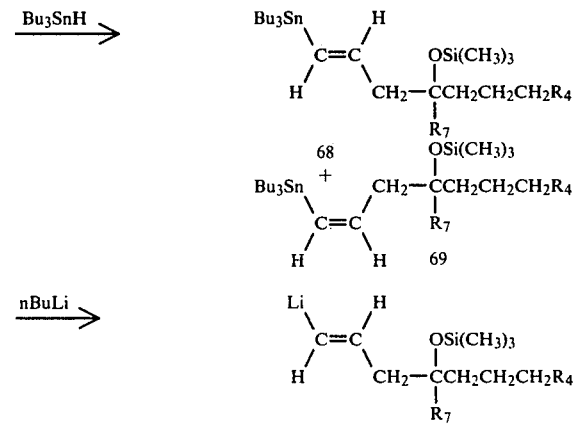

In accordance with the procedure outlined in Flowsheet H wherein $R_4$ is as defined previously and T is divalent oxygen (—O—) or divalent sulfur (—S—) and $R_{17}$ is hydrogen or methyl, treatment of the unsaturated carboxyl 71 with an alcohol 72 with acid (PTSA) catalysis or treatment of 71 with a mercaptan 73 with a basic catalysis such as piperidine provides the ketone 73.

Treatment of the ketone 73 with propargylmagnesium bromide 74 provides the hydroxyalkyne 75 which is silyated to give the ether 76. The TMS ether 76 is heated with tri-n-butylstannane in the presence of azobisisobutyronitrile (AIBN) to afford the trans-vinylstannane 77 which contains 10% to 20% of the corresponding cis vinylstannane 78.

Treatment of the vinylstannyl reagents 77 with n-butyl lithium at temperatures of $-78°$ C. to $-10°$ C. generates the vinyl lithium reagents 79.

The preparation of the precursors for the 16-vinyl and ethynyl-19oxa congeners is shown in Flowsheet H-2.

In accordance with Flowsheet H-2, wheren $R_4$ is as herein above defined an aldehyde 80 is treated with propargylicmagnesium bromide to form the homopropargylic alcohol 82 which is converted to its trimethylsilylether in the usual manner. The silylated ether is then treated with diisoamylborane in tetrahydrofuran and then with anhydrous trimethylamine oxide. The resulting solution and an iodine solution in tetrahydrofuran are then added simultaneously to an aqueous solution of sodium hydroxide to give the 1-iodo-4-trimethylsilyloxy-7-oxa -trans-1-alkene 83.

The trimethylsilyl protecting group on the alcohol function is removed with mild acid and the resulting vinyl iodide alcohol is oxidized with pyridinium chlorochromate to provide the 1-iodo-4-oxo-7-oxa-trans-1-alkene 84, which upon treatment with the appropriate Grignard reagent ($R_6MgX$) provides the 1-iodo-4-hydroxy-7-oxa-trans-1-alkene which is silylated in the usual manner to provide the silyl ether 85.

Lithiation of 85 (1 eq. n-butyl lithium or 2 eq. t-butyl lithium) at $-70°$ C. provides the lithio alkene 86.

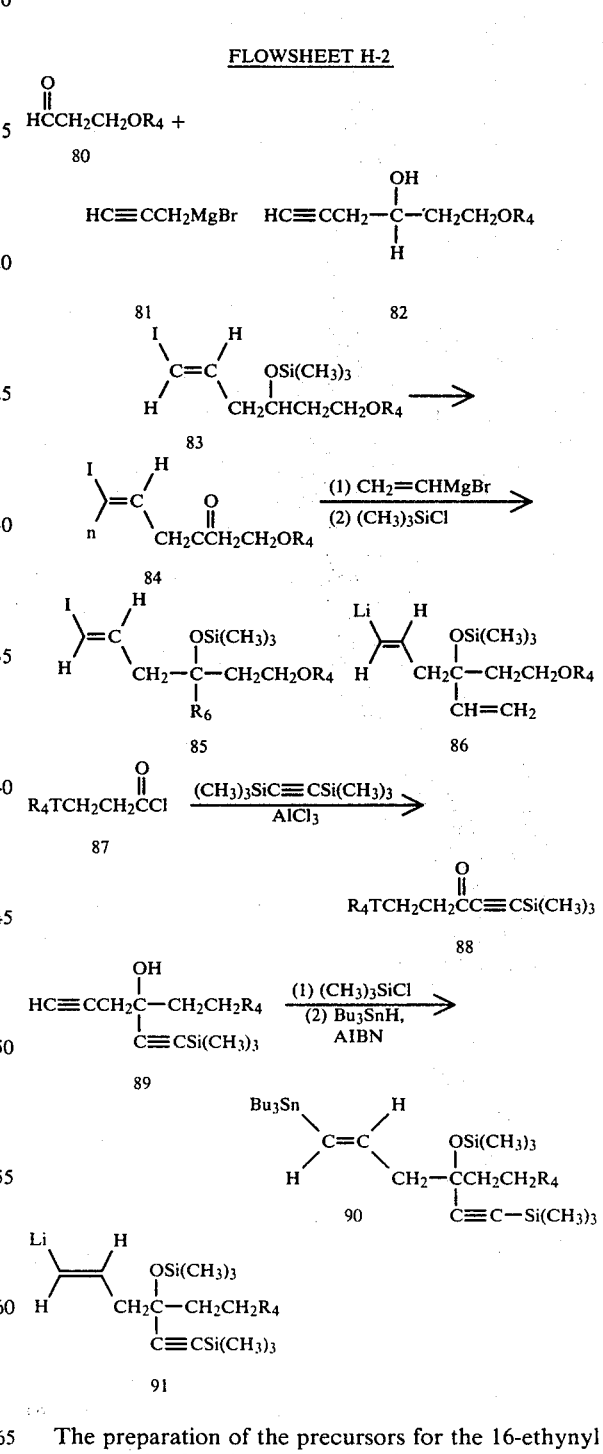

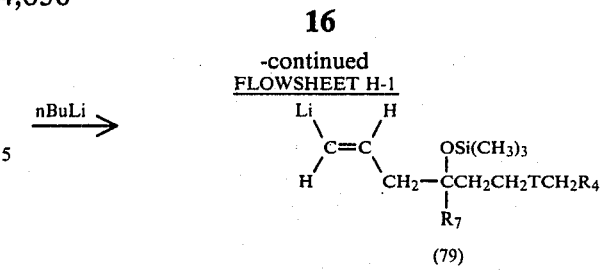

The preparation of the precursors for the 16-ethynyl congeners is also shown in Flowsheet H-2. In accordance with Flowsheet H-2, wherein $R_4$ and T are as previously defined, treatment of the carboxylic acid chloride 87 with bis-trimethylsilylacetylene in the presence of aluminum trichloride provides the acylacetylene 88. Treatment of the acylacetylene 88 with propargylmagnesium bromide forms the diacetylenic alcohol 87 which is silylated to provide the ether. The ether is converted to the vinylstannane 90 by treatment with tri-n-butylstannane in the presence of azobisisobutrylnitrile (AIBN).

The preparation of the cyclopentenones of this invention containing the hydroxyketone feature 93 wherein Z is hereinabove defined and $R_3$ is hydrogen or a hydroxy group can be accomplished in several ways one of which involves the conversion of the corresponding cyclopentenone containing a carboxylate function 92 to the respective hydroxyketone analog 93.

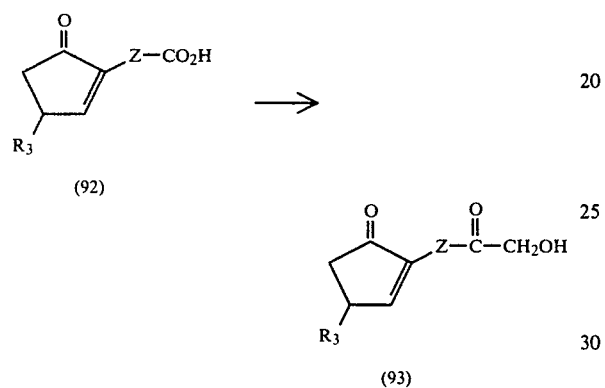

Most of the cyclopentenone carboxylic acids (92) required for the purposes of this invention have been described in the literature or can be prepared by procedures quite analogous to those already described. Appropriate references are provided in the examples which follow. The synthesis of certain non-reference requisite cyclopentenone carboxylic acids (92) is also described herein.

The preparation of the requisite 4-hydroxythiacyclopentenones (99) is described in Flowsheet I. In accordance with Flowsheet I which is hereinbelow described, treatment of 2-furyllithium (94) with a ω-chloroaldehyde (95) provides the chloroalcohol (96). Treatment of the chloroalcohol (96) with ethylmercaptoacetate furnishes the hydroxyester (97) which upon hydrolysis with sodium formate/formic acid provides the 3-hydroxy-cyclopentenone (98). Treatment of the cyclopentenone (98) with sulfuric acid provides the required 4-hydroxy-cyclopentenone (99).

FLOWSHEET I

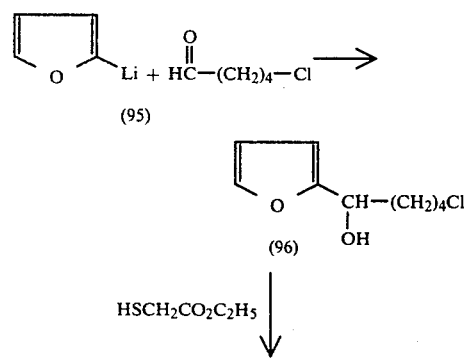

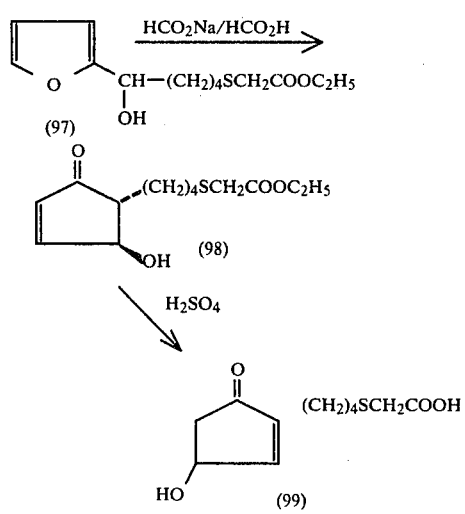

The conversion of the cyclopentenone carboxylic acid (92) to the respective hydroxyketone analogs (93) and the protection of these compounds for a conjugate addition reaction is described hereinbelow in Flowsheets J and K.

For the preparation of cyclopentenones of the type (103) wherein Z is hereinabove defined, the carboxylic acid (100) is converted to the acid chloride (101) by first forming the sodium salt with sodium hydride in tetrahydrofuran (THF) and then reacting the resulting suspension with oxalyl chloride in the presence of a catalytic amount of dimethylformamide (DMF). The resulting acid chloride (101), dissolved in ether, is then added dropwise to an ether solution containing two to three equivalents of diazomethane to produce the diazoketone (103). The diazoketone can be hydrolized to the hydroxy ketone (105) by refluxing an etheral solution in the presence of a dilute aqueous solution of sulfuric acid.

Alternatively, the acid chloride (101) can be heated with two equivalents of 1,1,2-tris-trimethylsilyloxyethylene at 90°–100° for 2 to 4 hours to produce compound (104). Compound (104) can be readily hydrolized and decarboxylated to give the hydroxyketone (105) by treatment with dilute hydrochloric acid in tetrahydrofuran (THF).

Protection of the hydroxy detone function of (105) suitable for a conjugate addition reaction, can be accomplished in two ways. Ketalization of (105) with ethylene glycol is accomplished by refluxing a benzene or toluene solution of (105) and ethylene glycol into a Dean-Stark trap. The resulting ketal (106) is then treated with trimethylsilylchloride (TMSCl) and imidazole in dimethylformamide (DMF) to give (107) which is suitably protected for a conjugate addition reaction.

Alternatively (103) can be protected by the reaction with a mixture of 2-methoxy-1-propene (108) and 2,2-dimethoxy-propane (109) in benzene in the presence of an acid catalyst such as p-toluenesulfonic acid to give the ketal (110) which is suitably protected for a conjugate addition reaction.

Flowsheet J

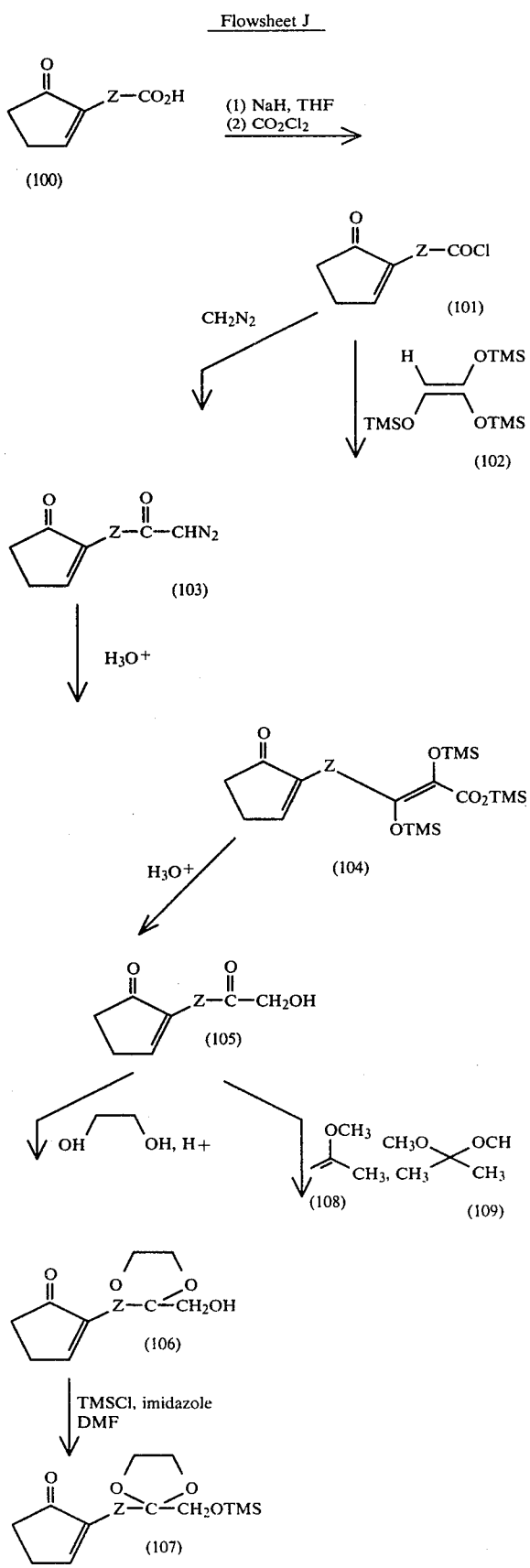

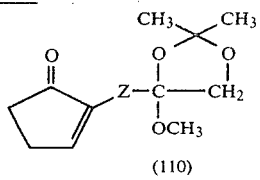

(110)

The preparation of the 4-hydroxycyclopentenones of this invention (116) wherein Z is hereinabove defined is outlined in Flowsheet K below. The reaction of the hydroxy acid (111) with at least two equivalents of dimethyl-t-butyl-silylchloride in the presence of imidazole in dimethylformamide at 30°-40° C. gives the bis-dimethyl-t-butylsilated compound (112). The carboxylate dimethyl-t-butylsilyl group can be selectively removed by treatment with acetic acid, tetrahydrofuran and water (4:2:1) to give the carboxylic acid (113). The acid chloride (114) is prepared by first treating the acid (113) with sodium hydride in tetrahydrofuran to give the sodium salt. The resulting suspension of the sodium salt is then treated with oxalyl chloride in the presence of a catalytic amount of dimethylformamide. Alternatively the acid chloride (114) can be prepared directly by the reaction of the acid (113) or the dimethyl-t-butylsilyl ester (112) with oxalyl chloride in tetrahydrofuran in the presence of a catalytic amount of dimethylformamide at 0° C. The slow addition of an etheral solution of the acid chloride (114) to an etheral solutiom of two to three equivalents of diazomethane gives the diazoketone (115) which on acid hydrolysis gives the 4-hydroxy cyclopentenone (116) containing the hydroxyketone function.

The acid chloride 114 can be heated with at least two equivalents of 1,1,2-tris-trimethylsilyloxyethylene in an inert solvent such as chlorobenzene to give compound (117) which is readily hydrolized and decarboxylated to give the 4-hydroxy cyclopentenone (116) containing the hydroxymethylketone feature.

Alternatively, to the acid chloride in a solvent such as tetrahydrofuran at 0° C. is added 1 equiv. of the 1,1,2-tris-trimethylsilyloxyethylene followed by the dropwise addition of a base such as triethylamine. The reaction is stirred for 24 hours at ambient temperature to provide, after the hydrolysis described above, the cyclopentone (116).

Alternatively the acid chloride (114) can be heated with at least two equivalents of 1,1,2-tris-trimethyl-silyloxyethylene at 90°-120° C. in the absence of a solvent to give compound (117) which is readily hydrolized and decarboxylated to give the 4-hydroxy-cyclopentenone (116) containing the hydroxyketone feature. Protecting of (116) can be accomplished by treatment with an excess of a mixture of 2-methoxy-1-propene (108) and 2,2-dimethoxypropane (109) in benzene with an acid catalyst such as p-toluenesulfonic acid to give the bis-ketal (119) which is suitably protected for a conjugate addition reaction.

Alternatively, the two hydroxyl moieties may be protected using 2 equivalents of 2-methoxypropene per equivalent of 16 in the presence of a catalyst such as chloroacetic acid to provide compounds such as 120. Other useful protecting dihydro-2H-pyran, ethylvinylether and the like.

Other acid sensitive protecting groups are the two hydroxyl groups are the triloweralkylsilyls (from silyl-chlorides) (such as 118) triphenylmethane (from tritylchloride or bromide), mono-p-methoxytriphenylmethane (from mono-p-methoxytriphenylmethylchloride or bromide), methoxymethyl (from chloromethylmethylether) and the like.

Preparation of the ethylene ketal (121) is accomplished using ethylene glycol and Amberyst 15 resins as catalyst. Protection of the two hydroxyls as trialkylsilyl ethers (trimethylsilylethers) provides (122).

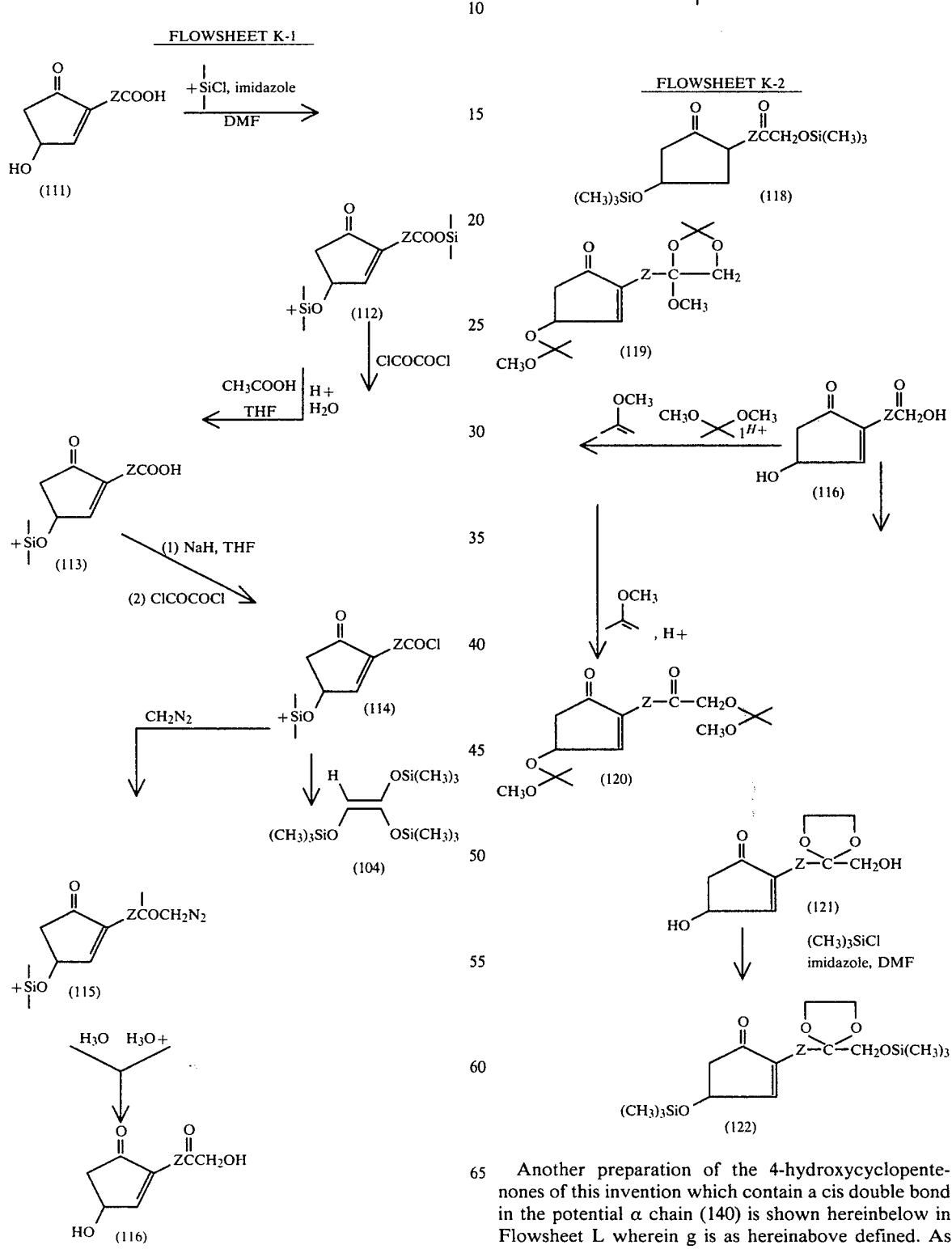

Another preparation of the 4-hydroxycyclopentenones of this invention which contain a cis double bond in the potential α chain (140) is shown hereinbelow in Flowsheet L wherein g is as hereinabove defined. As illustrated in Flowsheet L there are three methods available to prepare the important intermediate (127). The reaction of the w-bromo carboxylic acid (123) with oxalyl chloride in an inert solvent such as benzene gives the acid chloride (124). Addition of the acid chloride (124) in ether to an etheral solution of diazomethane (2 to 3 equivalents) yields the diazoketone (126) which can be hydrolized in a two phase system consisting of ether and dilute sulfuric acid to hydroxyketone (127). Alternatively, the acid chloride (125) can be treated with an excess of 1,1,2-tris-trimethylsilyloxyethylene in the presence of a catalytic amount of stannic chloride in the absence of solvent to give compound (125) which can readily be hydrolyzed and decarboxylated to the desired hydroxyketone (127) using dilute hydrochloric acid in tetrahydrofuran. An alternate method to prepare (127) involves the reaction of the bromoolefin (130) with aqueous N-bromosuccinimide (NBS) in the presence of a catalytic amount of acetic acid to give a mixture of bromohydrins (131) and (132). Oxidation of the mixture of bromohydrins with an oxidizing agent such as pyridinium chlorochromate in methylene chloride gives a mixture of bromoketone (128) and bromoaldehyde (129). Refluxing this mixture with soldium formate in methanol then gives the desired intermediate (127). Protection of the ketone function of (127) is accomplished using ethylene gycol in refluxing toluene using a catalytic amount of p-toluenesulfonic acid. The ketal (133) is then reacted with dimethyl-t-butylsilylchloride and imidazole in dimethylformamide to give the fully protected compound (135). The phosphonium salt (136) is obtained by refluxing a solution of (135) and triphenylphosphine in acetonitrile. Treatment of the phosphonium salt (135) with sodium methylsulfinylmethide in dimethylsulfoxide generates a phosphonium yield which on reaction with aldehyde (137) gives (138). Refluxing a water-dioxane solution of (138) in the presence of a phosphate buffer (PH 5 to 6) gives the cyclopentenone (139). Treatment of (139) with chloral and triethylamine in ether gives (140) which on hydrolysis in a mixture of tetrahydrofuran and dilute hydrochloric acid at 50°–70° C. then gives the desired 4-hydroxycyclopentenone (141) which can be protected as described hereinabove in Flowsheet K.

Treatment of (140) with trimethylsilylchloride and imidazole in DMF gives (142) which is also suitably protected for a conjugate addition reaction.

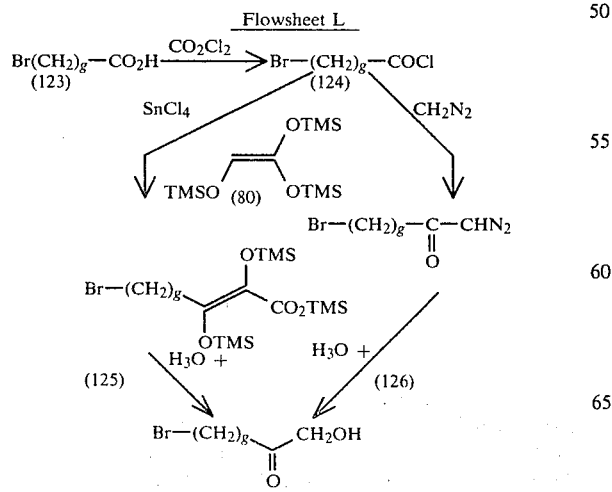

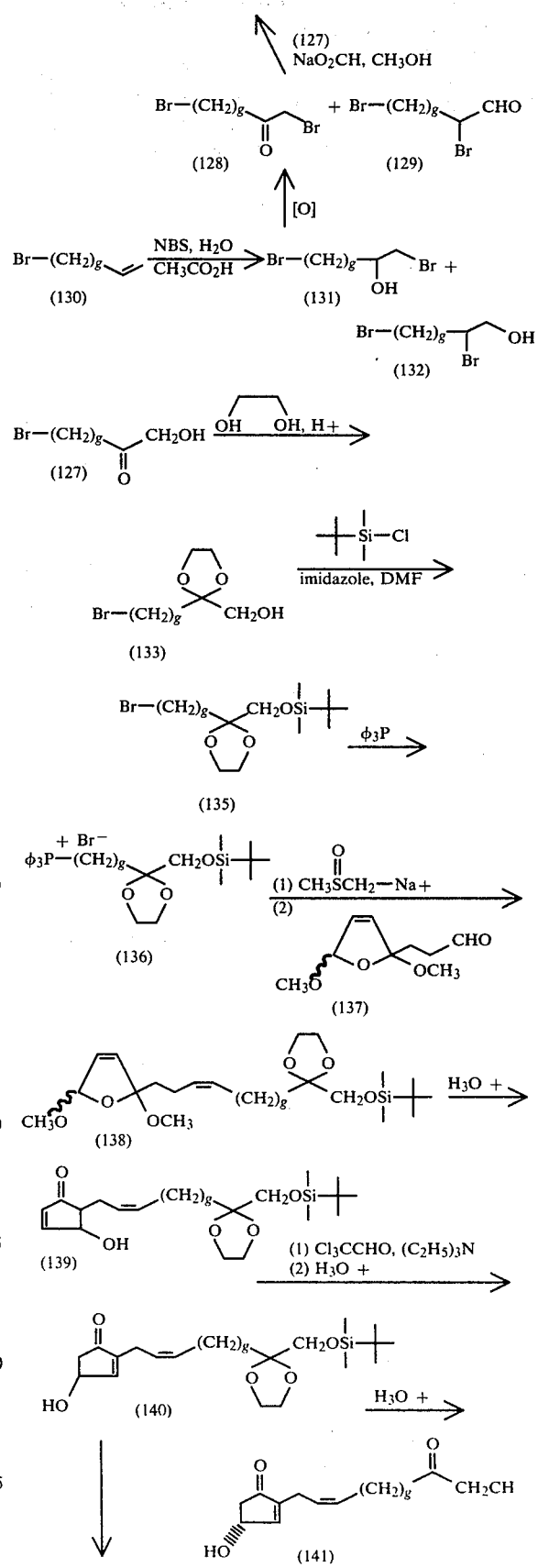

-continued
Flowsheet L

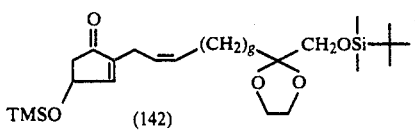
TMSO  (142)

The reagent 1,1,2-tris-trimethylsilyloxyethylene (102) and its use for the conversion of acid chlorides to hydroxyketone (for example 124 to 127 and 114 to 116) are claimed in this invention. The reagent preparation is described hereinbelow in Flowsheet M. The reaction of glycolic acid (143) with 1,1,1,-3,3,3-hexamethyldisilazane and trimethylsilylchloride in pyridine gives bis-trimethylsilated glycolic acid (144.) Addition of (144) to a tetrahydrofuran solution of one equivalent of lithium 1,1,1,3,3,3-hexamethyldisilazane amide at −78° C. generates a lithium enolate which is trapped with trimethylsilylchloride to produce the desired reagent (102).

Flowsheet M

HOCH$_2$CO$_2$H  $\xrightarrow{[(CH_3)_3Si]_2NH, (CH_3)_3SiCl}{\text{pyridine}}$
(143)

(CH$_3$)$_3$SIOCH$_2$CO$_2$Si(CH$_3$)$_3$  $\xrightarrow{(1) [(CH_3)_3Si]_2N^-Li^+, -78° C.}{(2) (CH_3)_3SiCl}$
(144)

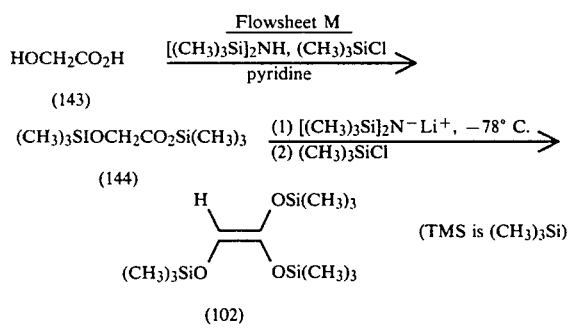
(102)            (TMS is (CH$_3$)$_3$Si)

The preparation of the prostaglandin congeners of this invention are described hereinbelow in Flowsheet N wherein Z is as hereinabove defined; R$_3''$ is hydrogen, 2-methoxy-propyl-2-oxy (—OC(CH$_3$)$_2$OCH$_3$) or trimethylsilyloxy; R$_3$ is hydrogen or hydroxy; T' is the radical

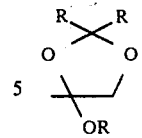

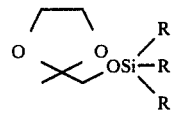

$$-\overset{O}{\overset{\|}{C}}-CH_2-O \diagdown_{CH_3}^{CH_3} \diagup^{CH_3} \quad \text{or} \quad -\overset{O}{\overset{\|}{C}}-CH_2-O-Si(R)_3$$

wherein R is as hereinabove defined. R' is selected from the group consisting of:

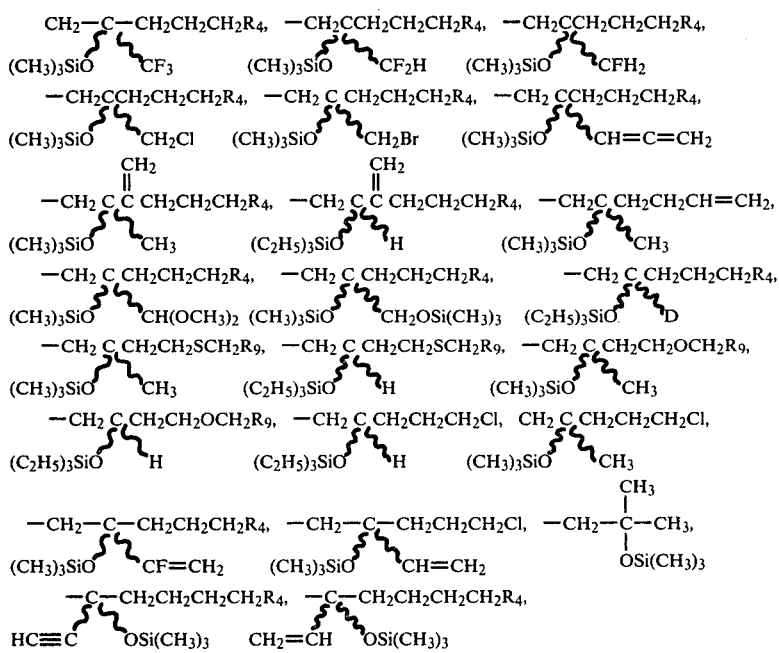

In accordance with Flowsheet N the vinyliodide (145) is treated with either one equivalent of n-butyllithium or 2 equivalents of t-butyllithium at low temperature, preferably −30° C. to −70 ° C. in an inert solvent, eg. hexane, ether or toluene to provide the trans-alkenyl-lithium reagent (147).

Alternatively, the vinyllithium reagent (147) can be prepared by treatment of a vinylstannyl derivative such as (146) with n-butyllithium at −10° to −78° C. in ether or THF.

For the preparation of the asymmetrical lithio cuprate (148) or the like, a solution of one molar equivalent of copper (I)-1-alkyne, preferably copper (I)-1-pentyne in anhydrous hexamethylphosphorous triamide preferably one to five molar equivalents, and anhydrous ether is added to one molar equivalent of the aforementioned vinyllithium solution cooled to about −78° C. After about one hour at this temperature, a molar equivalent of the requisite cyclopentenone (151) is added. After several hours at −78° C. to −20° C. the reaction mixture is quenched with aqueous ammonium chloride solution and the blocked product (152) is isolated in the usual manner.

It is also possible to effect conjugate 1,4-addition with the asymmetrical lithio cuprate (150) derived from vinyllithium (147) and cuprous thiophenoxide. A solution of vinyllithium (147) in ether at −78° C. is reacted with an equimolar amount of a reagent prepared by admixture, in ether at a temperature of 0° C. to −78° C., of equimolar amounts of cuprous thiophenoxide and copper (I) iodide tributylphosphonium complex. After about 30 minutes at this temperature, the lithio cuprate (150) is treated with the requisite cyclopentenone (120) as described hereinabove for the conjugate addition with 1-alkynyl lithio cuprate (148).

For the preparation of the symmetrical lithio cuprate (149) one molar equivalent of copper (I) iodide tributylphosphine complex, dissolved in anhydrous ether, is added at about −78° C. to two molar equivalents of the aforementioned vinyllithium (147) solution in hexanes, cooled to −78° C. After about one hour at this temperature, the lithio cuprate (149) is treated with the requisite cyclopentenone (151) as described hereinabove for the conjugate addition with the 1-alkynyl lithio cuprate (148).

The procedures for conjugate addition involving organocopper reagents are well known in the art, see for example, C. J. Sih, et al., J.A.C.S., 97, 865 (1975).

All available evidence leads us to believe that the $-CH=CH-R_2'$ function introduced by the cuprate process occupies a position trans to the 11-oxy function. Similarly, we are led to the conclusion that in the product (152) the two side-chains attached to $C_8$ and $C_{12}$ are trans to each other. However, we are not certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8ε. In order to ensure a trans-relationship in (152) these products can be submitted to conditions known in the literature to equilibrate the cis-8-iso-$PGE_1$ to a mixture containing about 90% of the trans product. These conditions involve treatment with potassium acetate in aqueous methanol for 96 hours at room temperature.

FLOWSHEET N

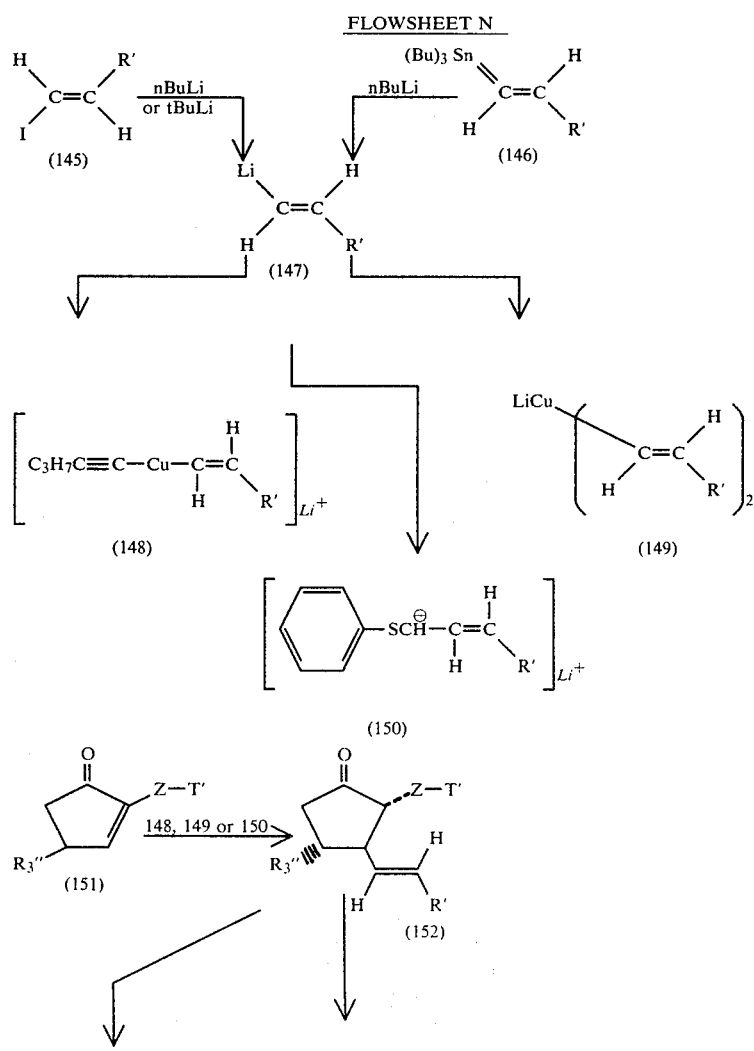

FLOWSHEET N

-continued

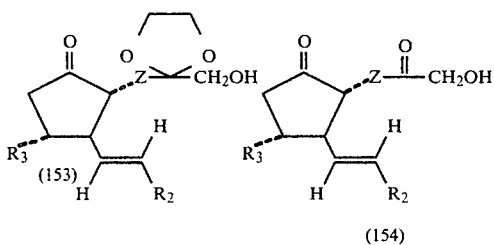

(154)

When T' is

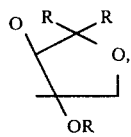

removal of the blocking groups from (152) to give the prostaglandin congener (154) is accomplished by treatment of (152) with a mixture of acetic acid, tetrahydrofuran and water (4:2:1) at 25° to 55° C. When T' is

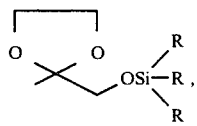

(152) can be partially deblocked to give ketal (153) by treatment of (151) with 0.6N hydrochloric acid in tetrahydrofuran at room temperature for 4 to 7 hours. ($R_3$ is hydrogen and hydroxyl).

In certain cases it is possible to convert the carboxylic acid function of a prostaglandin congener into a terminal hydroxymethyl ketone function as shown in Flowsheet O hereinbelow wherein Z, $C_{13}$–$C_{14}$, and $R_2$ is as hereinabove defined. Treatment of a prostaglandin congener (155) in which the 11-hydroxy group and the hydroxy groups of the β-chain are protected with a suitable group such as acetate or a dimethyl-t-butylsilyl ether with oxalyl chloride in benzene or dichloromethane for 2 to 5 hours furnishes the acid chloride (156), wherein $R_3''$ is hydrogen or a protected oxygen group. The protected 11-hydroxyl-acid chloride compound may be prepared in the manner described above in Flowsheet K.

The prostaglandin congeners (155) may be prepared by the 1,4 conjugate addition of the suitably protected cyclopentenones (100) or (111) such as (cyclopentenone 112) and the lithiocuprate (148,149 or 150) by the procedures disclosed herein by the examples and Flowsheet N. Addition of the acid chloride (156), dissolved in ether, to an ether solution of at least three equivalents of diazomethane gives the diazoketone (157). Hydrolysis of the diazoketone using aqueous sulfuric acid and tetrahydrofuran at about 0°–55° C. gives the hydroxymethyl ketone analog (158). The acetate protecting group can be removed by refluxing with acidified methanol. The dimethyl-t-butylsilyl ether protecting group can be removed by treatment with aqueous hydrochloric acid in tetrahydrofuran at 25° to 60° C.

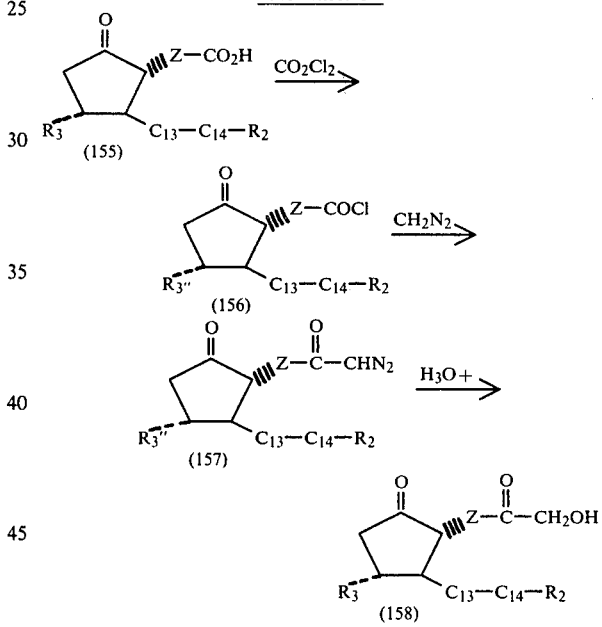

Flowsheet O

When the compounds of this invention are prepared from racemic starting compounds to racemates are obtained. In appropriate instances these racemates can be separated from each other by careful application of the usual chromatographic procedures. In the more difficult instances it may be necessary to apply high pressure liquid chromatography including recycling techniques. [See G. Fallick, *American Laboratory,* 19–27 (August, 1973) herein incorporated by reference, as well as references cited therein. Additional information concerning high speed liquid chromatography and the instruments necessary for its application is available from Waters Associate, Inc., Maple Street, Milford, Mass.]

It is also possible to prepare the compounds of this invention in their optically active forms by the conversion of the optically active 4-hydroxycyclopent-2-en-1-one carboxylic acids (159) to the optically active protected hydroxy ketone analog (160) using the methods outlined hereinabove in Flowsheet P.

Flowsheet P

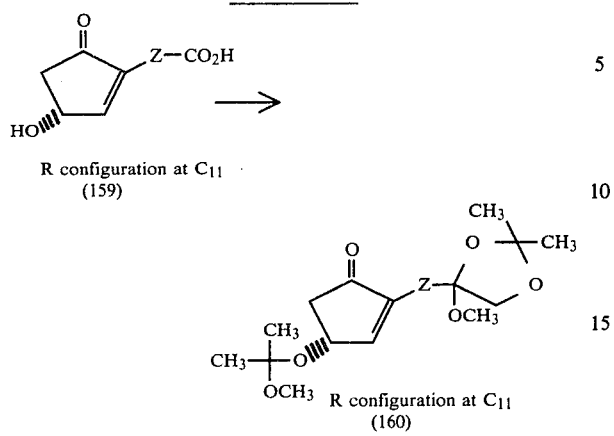

R configuration at C₁₁
(159)

R configuration at C₁₁
(160)

When one utilizes a racemic cyclopentenone (151) and a racemic vinyliodide (145) or racemic vinylstannane (146) the conjugate adduct isolated (154 or 155) consists of a mixture of 4-optical isomers. These four optical isomers are, in the case of the 15-deoxy-16-hydroxyprostaglandins, identified as nat. 16α, nat. 16β, ent 16α and ent 16β. Silica-gel chromatography of the 4 isomers (154 or 155) will provide two fractions consisting of nat. 16α and ent 16β and nat. 16β and ent 16α.

If one utilizes a resolved cyclopentenone (151) that contains the 4(R) configuration, and a racemic vinyliodide (145) or racemic vinylstannane (146), the conjugate adduct isolated (154 or 155) consists of a mixture of two-optical isomers. These two optical isomers are, in the case of the 15-deoxy-16-hydroxyprostaglandins, identified as nat. 16α and nat. 16β. Silica gel chromatography of the two isomers will provide separated nat. 16α and separated nat. 16β.

If one utilizes an optically active vinyliodide (145) or optically active vinylstannane (146) and a racemic cyclopentenone (151), then the conjugate adduct isolated (154 and 155) consists of two optical isomers. If the vinyliodide (145) or vinylstannane (146) used would provide the nat. 16α as one of the products, the other product will be ent 16α. Likewise, the products from a vinyliodide (145) or vinylstannane (146) of the opposite optical configuration will be nat 16α and ent 16β. Silica gel chromatography will separate nat. 16α from ent 16α and likewise, nat. 16β is separable from ent 16β.

If one utilizes a resolved cyclopentenone (151) that contains the 4(R) configuration and an optically active vinyliodide (145) or optically active vinylstannane (146), then the conjugate adduct (154 and 155) will consist of only one optical isomer, which will be either nat. 16α or nat. 16β, depending upon the configuration of the starting vinyliodide (145) or vinylstannane (146).

In accordance with the following reaction scheme prostanoids are prepared as described by Stork in J.A.C.S. 97, 474 (1975) and J.A.C.S. 97, 6260 (1975) which are incorporated by reference.

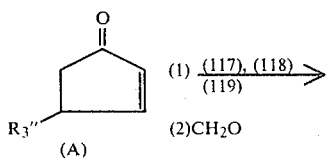

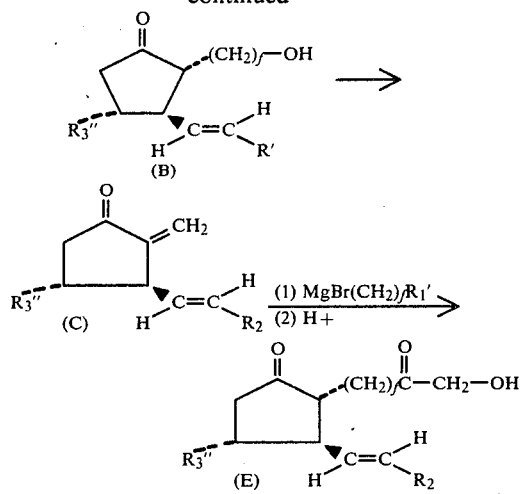

Treatment of the protected 4-oxycylcyclopentenone (A) with a cuprate such as (148), (149) or (150) as hereinabove defined, followed by quenching with formaldehyde to provide the hydroxymethyl analog (B) which is dehydrated with reagents such as excess methansulfonyl chloride in pyridine followed by treatment of the crude mesylate with diissopropylethylamine in ether overnight. R₃″, R₃ and R are as previously defined. Addition of the methylenecyclopentanone (C) to a solution of the grignard MgBr(CH₂)ƒR₁ wherein f is as previously defined and R₁' is a substituent selected from the group R₁ wherein the hydroxyl group of the substituent is protected by a suitable blocking group such as 2-methoxy-propyl-2-oxy, and a catalytic amount of Bu₃P-.CuI (Bu₃ is tertiary butyl) followed by mild hydrolysis of the adduct provides the product prostanoid (E) wherein f, R₃ and R₂ are as previously defined.

The bromide precursor to the grignard described above is prepared in accordance with the procedure of Flowsheet L.

Conjugate addition of the vinyl cuprates to (129) followed by deblocking as described hereinabove in Flowsheet N then gives the compounds of this invention in their optically active forms. Although in some cases two diastereoisomers will be formed, each optically active, they can be separated by chromotographic procedures as described hereinabove.

The preparation of optically active 4-hydroxycyclopent-2-en-1-ones such as (159) is described hereinbelow.

The 4-hydroxycyclopentenone racemates may be resolved into their component enantiomers (161) and (162) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride [to give (163)], (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (161) and (162). A useful procedure for the resolution of a 4-hydroxycyclopentenone racemate via an oxime such as (132) is described in the art [R. Pappo, P. Collins and C. Jung, *Tetrahedron Letters*, 943 (1973)], herein incorporated by reference.

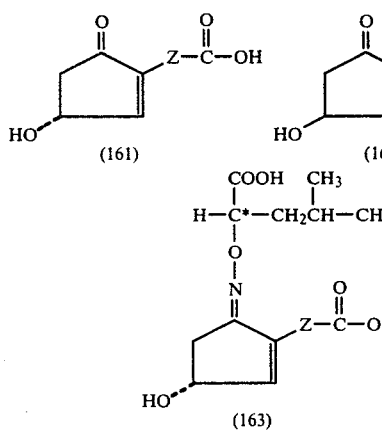

An alternate procedure for the preparation of the 4(R)-hydroxycyclopentenone enantiomers such as (161) involves as a key step the selective microbiological or chemical reduction of trione (164) to the 4(R)-hydroxycyclopentanedione (165). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcylohexylmethylphosphine)rhodium (I) tetrafluoroborate in the presence of one equivalent of organic base, such as triethylamine.

Conversion of hydroxycyclopentanedione (165) to an enol ether or enol ester, (166), E=alkyl, preferably iso-propyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (166) with excess sodium bis (2-methoxyethoxy)aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (167). The ester (167) can then be hydrolized to acid (161).

For a description of these procedures in the art see: C. J. Sih, et al., *J.A.C.S.*, 95, 1676 (1973); J. B. Heather, et al., *Tetrahedron Letters*, 2213 (1973); R. Pappo and P. W. Collins, *Tetrahedron Letters*, 2627 (1972); and R. Pappo, P. Collins, and C. Jung, *Ann. N. Y. Acad. Sci.*, 180, 64 (1971). All of these references are herein incorporated by reference.

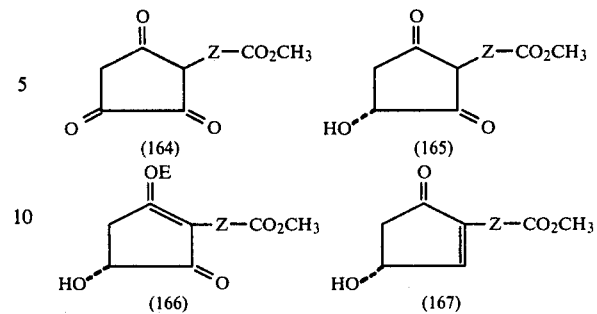

Procedures for the preparation of the requisite cycopentanetriones (164) are well-established in the art and generally involve the treatment of a ω-1-oxo long chain ester (168) with methyl or ethyl oxalate and a base such as sodium methoxide in methanol, followed by treatment with dilute hydrochloric acid in aqueous methanol to effect the dealkoxyalylation of the intermediate (169) See. J. Kutsube and M. Matsui, *Agr. Biol. Chem.*, 33 1078 (1969); P. Collins, C. J. Jung and R. Pappo, *Israel Journal of Chemistry*, 6, 839 (1968); R. Pappo, P. Collins and C. Jung, *Ann. N. Y. Acad. Sci.*, 180, 64 (1971); C. J. Sih, et al., *J. A. C. S.*, 95, 1676 (1973) (see reference 7); and J. B. Heather, et al., *Tetrahedron Letters*, 2313 (1973) for pertinent background literature.

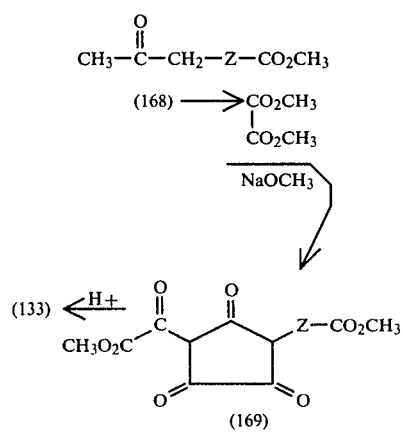

The intermediate keto esters (168) may be prepared by a variety of methods known to the art. One useful procedure is outlined below and involves alkylation of ethyl acetoacetate sodium salt (170) in the usual manner with the appropriate side-chain precursor (171), X=Cl, Br, I, preferably Br or I) followed by decarboethoxylation and reesterification, all in the usual manner.

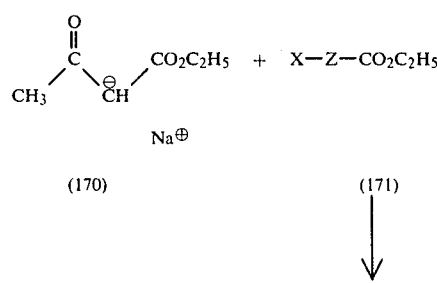

-continued

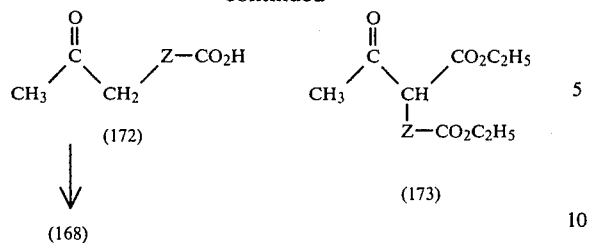

(168)

The side-chain precursors (171) are commercially available where Z is —$(CH_2)_p$—, and can be prepared as described in Belgian Patent 786,215 (granted and opened to inspection Jan. 15, 1974).

Those precursors wherein Z is —$(CH_2)_t$—O—$CH_2$— can be prepared by the transformation shown directly below starting with the mono-tetrahydropyranyl derivative (174). Thus, (143) is converted to the lithium alcoholate by treatment with butyl lithium, the alcoholate is then O-alkylated with ethyl bromoacetate to provide (171) which on de-O-tetrahydropyranylation, mesylation and reaction with lithium bromide gives the required (176) (These and all the above-described transformations can be effected in the usual manner well-established in the art; pertinent examples for most of the reactions can be found in the above-cited Belgian Pat. No. 786,215.)

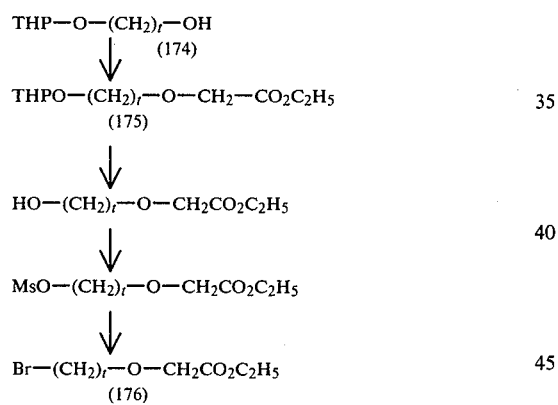

It is also possible to resolve the 4-hydroxycyclopentenone racemate (177) by microbiological means. Thus, treatment of the 4-O-alkanoyl or aroyl derivatives (178), $R_{18}$=aryl or alkyl) of racemate (177) (preferably the 4-O-acetyl and 4-O-propionyl derivatives) with an appropriate microorganism, preferably a Saccharomyces species e.g., 1375-143, affords preferential de-O-acylation of the 4(R)-enantiomer to give (178), which is then separated from the unreacted 4(S)-O-acyl enantiomer (180) by chromatographic procedures. After separation, mild hydrolysis of the 4(S) derivative (180) provides the 4(S)-hydroxycyclopentenone (181). [See N. J. Marsheck and M. Miyano, *Biochima et Biphysica Acta*, 316, 363 (1973) for related examples.]

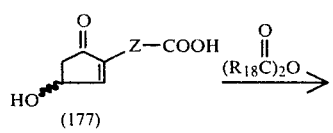

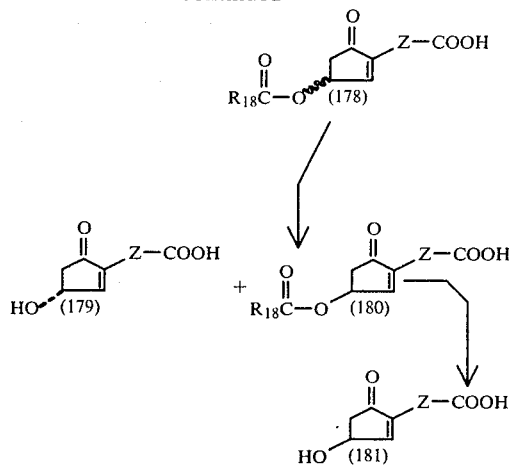

It is also possible to prepare the individual 4-hydroxycyclopentenones (179) and (181) directly by selective microbial hydroxylations of the corresponding 4-unsubstituted cyclopentenone (182). For example, with *Aspergillus niger* ATCC 9142; a selective 4(R)-hydroxylation of [151, Z=$(CH_2)_6$] has been reported; see S. Kurozumi, T. Tora and S. Ishimoto, *Tetrahedron Letters*, 4959 (1973). Other microorganisms can also accomplish this hydroxylation.

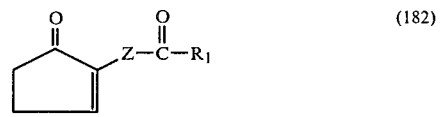

The ring system of the novel compounds of this invention allow them to be characterized as follows:

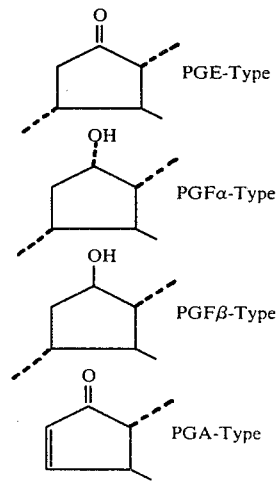

The 9α-hydroxy PGF compounds of this invention (154) are prepared by a conjugate addition reaction as described hereinabove in Flowsheet N. The initial conjugate addition product (152) (wherein Z, T′, $R_3''$ and R′ are as hereinabove defined) is not deblocked but dissolved in tetrahydrofuran. An excess of lithium perhydro-9b-borophenalyhydride (PBPH) in tetrahydrofuran is added at −78° C. After warming to 0° C., the reaction mixture is quenched with saturated ammonium chloride solution. The product (183) is isolated and deblocked with acetic acid-tetrahydrofuran-water 4:2:1 at 40° C. in the cases where T' is

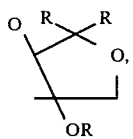

and with dilute hydrochlorid acid in the cases where T' is

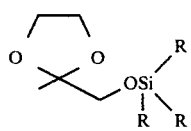

to give the 9α-hydroxy compounds of this invention (184). See Flowsheet P hereinbelow wherein Z, T', R"$_3$, R$_2$, R' and R$_3$ are as hereinabove defined.

FLOWSHEET P

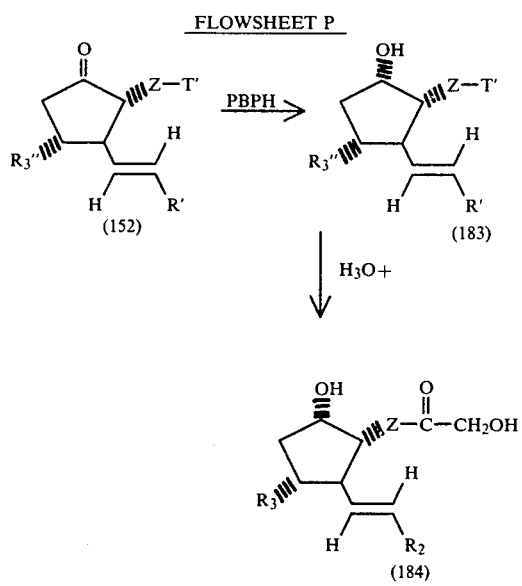

The 9β-hydroxy PGF compounds of this invention (156) are prepared by performing a conjugate addition as described hereinabove in Flowsheet N. The initial conjugate addition product (152) (wherein Z, T', R"$_3$, and R' are as hereinabove defined) is not deblocked but dissolved in ethanol and an excess of sodium borohydride is added. The mixture is stirred for 8 hours, poured into water and the reduced products (183) and (185) are obtained. These are deblocked with acetic acid-tetrahydrofuran-water 4:2:1 at 40° C. in the cases where T' is

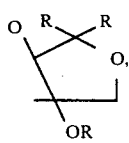

and with dilute hydrochloric acid in tetrahydrofuran in the cases where T' is

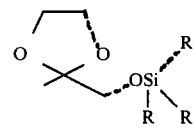

to give the 9α-hydroxy (184) and 9β-hydroxy (186) compounds of this invention which can be separated by silica gel chromatography. See Flowsheet Q hereinbelow wherein Z, T', R, R', R"$_3$, R$_2$ and R$_3$ are as defined hereinabove.

FLOWSHEET Q

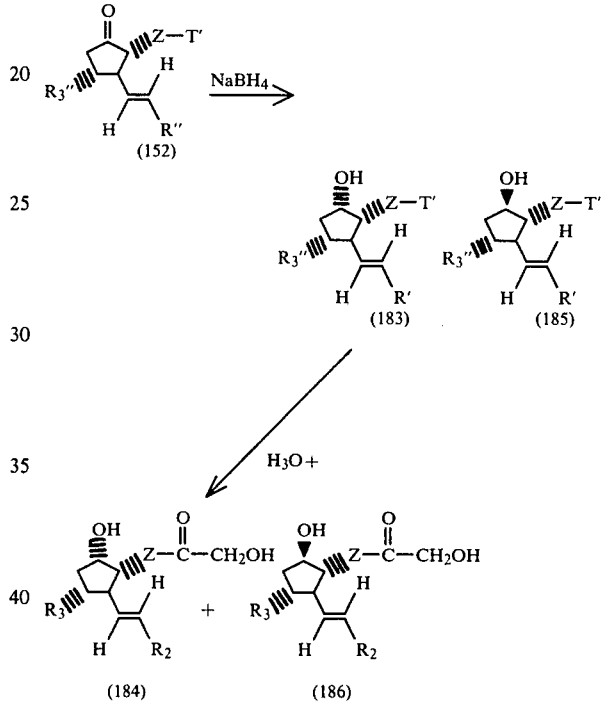

The 1-hydroxymethyl group of the PGE compounds of this invention can be selectively esterified by dissolving the compound (184) in pyridine and adding one equivalent of an anhydride (R$_{15}$-CO)$_2$O or the acid chloride

and allowing the mixture to stand overnight to give the desired esters (187).

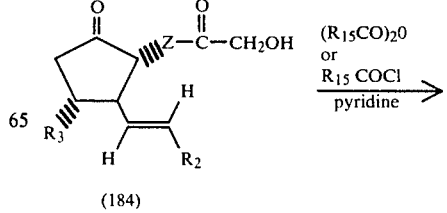

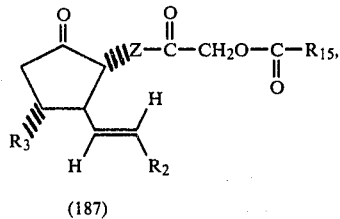

(187)

$R_{15}$ is phenyl or phenyl substituted with one or more groups such as alkyl ($C_1$–$C_4$), OR, SR, F, Cl; dialkylamino; or $C_1$–$C_4$ alkyl, $C_1$–$C_4$ alkoxy wherein R is $C_1$–$C_4$ alkyl.

The 1-hydroxymethyl group of the PGF compounds of this invention can be selectively esterified by dissolving the compound (184 or 186) in pyridine and adding one equivalent of an anhydride ($R_{15}$-CO)$_2$O or the acid chloride

and allowing the mixture to stand overnight to give the desired esters (188 and 189).

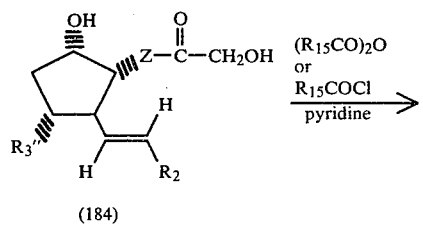

(184)

(188)

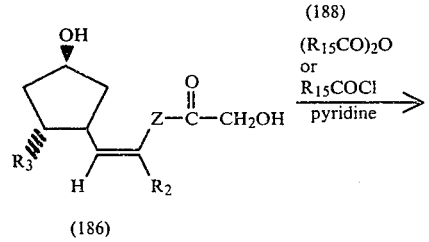

(186)

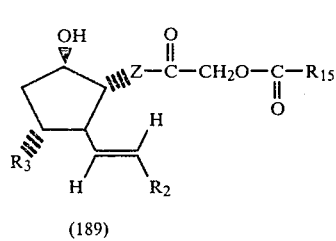

(189)

$R_{15}$ is phenyl or phenyl substituted with one or more groups such as alkyl ($C_1$–$C_4$), OR, SR, F, Cl; dialkylamino; or $C_1$–$C_4$ alkyl, $C_1$–$C_4$ alkoxy wherein R is $C_1$–$C_4$ alkyl.

FLOWSHEET R

PGA

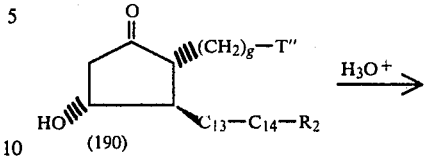

(190)

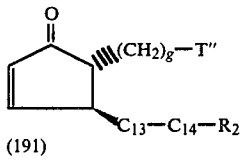

(191)

The PGA, compounds of this invention (191) are prepared from the corresponding 11-hydroxy analogs (190) by treatment of (190) with dilute hydrochloric acid in tetrahydrofuran for 2 to 4 days at room temperature as shown hereinabove in Flowsheet R, wherein $C_{13}$–$C_{14}$, $R_2$ and g are as hereinabove defined and T" is a moiety selected from a group consisting of:

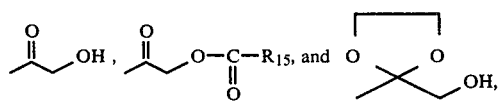

wherein $R_{15}$ is hereinabove defined.

As shown in Flowsheet S, hereinbelow, the compounds of this invention wherein R" is

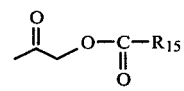

(195) can also be prepared by selective esterification of the terminal hydroxyl group of compound (192) which is also part of this invention.

This esterification can be accomplished by treatment of a pyridine solution of (192) with one equivalent of an anhydride (193) or acid chloride (194) at room temperature for 24 hours.

FLOWSHEET S

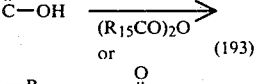

(192)

(193)

(194)

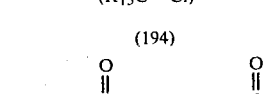

(195)

FLOWSHEET T

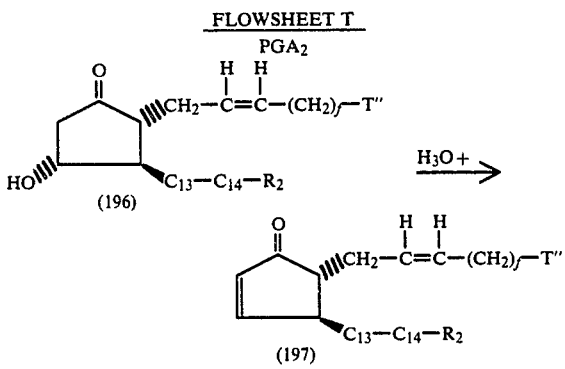

The PGA$_2$ compounds of this invention (197) are prepared from the corresponding 11-hydroxy analog (196) by treatment of (196) with dilute hydrochloric acid in tetrahydrofuran for 2 to 4 days at room temperature as shown hereinabove in Flowsheet T wherein C$_{13}$-C$_{14}$, R$_2$ and f are as hereinabove defined and T" is a moiety selected from a group consisting of:

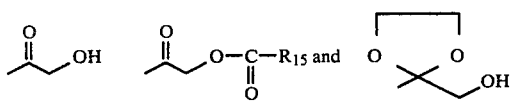

wherein R$_{15}$ is hereinabove defined

As shown in Flowsheet U hereinbelow, the compounds of this invention wherein T" is

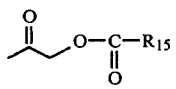

(201) can also be prepared by selective esterification of the terminal hydroxyl group of compounds (198) which is also part of this invention.

This esterification can be accomplished by treatment of a pyridine solution of (198) with one equivalent of an anhydride (199) or acid chloride (200) at room temperature for 24 hours.

FLOWSHEET U

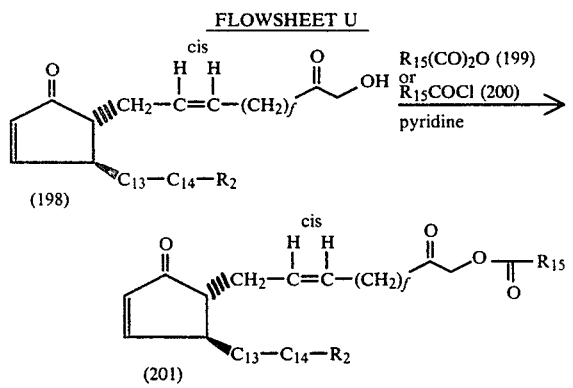

In accordance with the process of Bundy et al. J.A.C.S. 94, 2123 (1972) or E. J. Corey J.O.C. 38, 3187 (1973) which are incorporated by reference, the PGA$_1$, PGA$_0$ or PGA$_2$ series compounds of this invention may be converted to the corresponding PGE$_0$, PGE$_1$ or PGE$_2$ compound.

This conversion is accomplished by treating either the protected or unprotected PGA compounds (i.e. 191 or 197) with alkaline hydrogen peroxide to provide a mixture of isomeric 10,11-epoxides which, without separation is reduced with chromous acetate in acidic acid or by aluminum amalgum to provide after hydrolysis (if necessary) and silica gel chromatography, the 11α-hydroxy-PGE compounds and a lesser amount of the corresponding 11β-epimer.

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various nonsteroidal anti-inflammatory agents (e.g., indomethacin, aspirin, and phenylbutazone), bronchodilators, anti-inflammatory agents, abortifacients, agents for the induction of labor, agents for the induction of menses, fertility-controlling agents, oestrus regulators for use in animal husbandry with cattle and other domestic animals and central nervous system regulatory agents. Certain of the novel compounds of this invention possess utility as intermediates for the preparation of the other novel compounds of this invention.

The novel compounds of this invention possess the pharmacological activity described below as associated with the appropriate above-described prostaglandin types.

The known PGE, PGF$_\alpha$, PGF$_\beta$, PGA and PGD compounds are all potent in causing multiple biological responses even at low doses. For example, PGE$_1$, PGE$_2$, PGA$_1$ and PGA$_2$ are extremely potent in causing vasodepression and smooth muscle stimulation, and also are potent as antilipolytic agents. For example, the 11-deoxy-PGE compounds of this invention are selective in that they are at most relatively weak stimulants of smooth muscle. A further advantage of these novel compounds should be in their increased stabilities and lengthened self-lives.

Therefore, each of these novel prostaglandin analogs of this invention should be more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively orally, sublingualy, intravaginally, buccually, or rectally, in addition to the usual intravenous, instramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGE$_1$, PGE$_2$, PGE$_3$, dihydro-PGE$_1$, PGF$_\alpha$, PGF$_\beta$ and PGA compounds, their esters and pharmacologically acceptable salts, are extremely potent in causing various biological responses. For that reason, these compounds are useful for pharmacological purposes. See, for example, Bergstrome, et al., *Pharmacol. Rev.*, 20, 1 (1968), and references cited herein. A few of those biological responses are systemic arterial blood pressure lowering in the case of the PGA and PGE compounds as measured, for example, in anesthetized (sodium phenobarbital) pentolinium-treated rats with indewelling aortic and right heart cannulas; pressor activity, similarly measured, for the PGF compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of PGE compounds, as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen, and in the case of the PGE and PGA compounds, stimulation of epidermal proliferation and keratinization, as shown when they are applied in culture to embryonic chick and rat skin segments.

Because of these biological responses, these known prostaglandins are useful to study, prevent, control, or alleviate a wide variety of disease and undesirable physiological conditions in birds and mammals including humans, useful domestic animals, pets, and zoological specimens, and in laboratory animals, e.g., mice, rats, rabbits, and monkeys.

For example, these compounds are useful in mammals, including man, as nasal decongestants. For this purpose, the compounds are used in a dose range of about 0.01 mg. to about 10 mg per ml of a pharmacologically suitable liquid vehicle or as an aerosol spray, both for topical application.

PGA, PGF$_\beta$ and PGE compounds are useful as hypotensive agents to reduce blood pressure in mammals including man. For this purpose, the PGF$_\beta$ compounds are administered by intravenous infusion at the rate of about 0.01 mg to about 40 mg per Kg of body weight per minute, or in a single dosage or multiple doses of about 25 mg to 2500 mg per Kg of body weight total per day. The PGE and PGA compounds are administered by intravenous infusion at the rate of about 0.01 to about 50 mg per Kg of body weight per minute, or in a single dose or multiple doses of about 25 to 2500 mg per Kg of body weight total per day.

The PGE, PGF$_\alpha$ and PGF$_\beta$ compounds are useful in place of oxytocin to induce labor in pregnant female animals, including humans, cows, sheep and pigs, at or near term or in pregnant animals with intrauterine death of the fetus from about 20 weeks to term. For this purpose, the PGF compound is infused intravenously at a dose of 0.01 mg to 50 mg per Kg of body weight per minute until or near the termination of the second stage of labor, i.e., expulsion of the fetus. Similarly, the PGE compound is infused intravenously at a dose of 0.01 to 50 mg per Kg of body weight per minute until or near the expulsion of the fetus. These compounds are especially useful when the female is one or more weeks postmature and natural labor has not started, or 12 to 60 hours after the membranes have ruptured and natural labor has not yet started.

The PGE, PGF$_\alpha$ and PFG$_\beta$ compounds are useful for controlling the reproductive cycle in ovulating female mammals, including humans and other animals. For that purpose, PGF$_{2\alpha}$, for example, is administered systemically at a dose level in the range of 0.01 mg to about 20 mg per Kg of body weight, advantageously during a span of time starting approximately at the time of ovulation and ending approximately at the time of menses or just prior to menses. Likewise, a PGE compound is administered in the same fashion at a dose level of 0.01 mg to about 50 mg per Kg of body weight. Additionally, expulsion of an embryo or fetus is accomplished by similar administration of the compound during the first third or the second third of the normal mammalian gestation period. Accordingly, such compounds are useful as abortifacients. They are also useful for induction of menses during approximately the first two weeks of a missed menstrual period and thus, are useful as contraceptive anti-fertility agents.

11$\alpha$-hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore PGE$_2$, for example, is useful in place of or in combination with less than usual amounts of these known smooth muscle stimulators for example, to relieve the symptoms of paralytic ileus, to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 mg per Kg of body weight per minute until the desired effect is obtained. Subsequent doses are given by intravenous, subcutaneous, or intramuscular injection or infusion during puerperium in the range of 0.01 to 2 mg per Kg of body weight per day, the exact dose depending on the age, weight, and condition of the patient or animal.

The novel PGA, PGE and PGF$_\beta$ of this invention are also useful as bronchodilators for the treatment of asthma and chronic bronchitis. As such they may be conveniently administered by inhalation of aerosol sprays prepared in a dose range of about 10 $\mu$g to about 10 mg/ml of a pharmacologically suitable liquid vehicle. Relative to the natural prostaglandins, the PGA and PGE compounds in particular have the significant advantage of inducing prolonged effects.

The PGE and PGA compounds are also useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 mg to about 500 mg per Kg of body weight per minute, or in a total daily dose by injection or infusion in the range of about 0.1 to about 20 mg per Kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE and PGA compounds also stimulate epidermal proliferation and keratinization, and in such a capacity are useful to promote and accelerate healing of skin which has been damaged, for example, by burns, wounds, abrasions or surgery. The Vassopressor action of the PGA compounds makes them particularly useful in speeding the adherence and growth of skin autografts, especially small, deep (Davies) grafts which are intended to cover skinless areas by subsequent outward growth rather than initially, and in retarding rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion cream, or ointment in combination with the usual pharmaceutically acceptable diluents. In some instances, when there is substantial fluid loss as in the case of extensive burns or skin loss due to other causes, systemic administration of PGE is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Illustrative of a wet dressing for topical application to second and/or third degree burns of skin area 5 to 25 square centimeters is the use of an isotonic aqueous solution containing one to 500 mg/ml of the PGA compound or several times that concentration of the PGE compound. Especially for topical use, these prostaglandins are useful in combination with antibiotics such as gentamycin, neomycin, polymyxin B, bacitracin, spectinomycin, and oxytetracycline; with other antibacterials such as mafenide hydrochloride, sulfadiazine, furazolium chloride, and nitrofurazone; and with corticoid steroids, such as hydrocortisone, prednisolone, methylprednisolone, and fluoroprednisolone; each of those being used in the combination at the usual concentration suitable for its use alone.

The PGA compounds and derivatives and salts thereof increase the flow of blood in the mammalian kidney, thereby increasing the volume and electrolyte content of the urine. For that reason, PGA compounds are useful in managing cases of renal disfunction, especially in cases of severely impaired renal blood flow, for example, the hepatorena syndrome and early kidney transplant rejection. In case of excessive or inappropriate antidiuretic hormone ADH vasopressin secretion, the diuretic effect of these compounds is even greater. In anephretic states, the vasopressin action of these compounds is especially useful.

The PGE compounds of this invention are also useful as topical vasodilators.

The $PGE_1$ compounds of this invention are useful whenever it is desired to inhibit platelet aggregation, to reduce the adhesive character of platelets, and to remove or prevent the formation of thrombi in mammals including man, rabbits, and rats. For example, these compounds are useful to treat and prevent myocardial infarcts and post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg per Kg of body weight per day are used, the exact dose depending on the age, weight, and condition of the patient or animal, and on the frequency and route of administration.

It is well known that platelet aggregation inhibitors may be useful as anti-thrombotic drugs. Inhibition of platelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervals from animals given inhibitors by an oral or parenteral route.

The PGE compounds of the present invention exhibit the ability to inhibit platelet aggregation in vitro when tested by the following procedure.

Human protein rich plasma is incubated with modified Tyrode's solution in a proportion of 40-50% human protein rich plasma. The test compounds are added at varying concentrations and after 5 minutes incubation, an aagregating agent such as adenosine diphosphate or collagen is added. The change in optical density (light transmission) is monitored by eye and inhibition is recorded as a (−) or lack of inhibition is recorded as a (+). Test compounds are considered active if they inhibit adenosine diphosphate or collagen induced aggregation at a concentration of 0.025 mg/ml or less within 5-10 minutes.

The PGE compounds of this invention also have bronchodilator activity as determined in a test using dogs anesthetized, artificially ventilated and submitted to a continuous respiratory spasm induced by pilocarpine.

Mongrel dogs of either sex weighing between 5 and 10 kg are used. They are premedicated with morphone HCl by subcutaneous injection at 1.5 mg/Kg. An intravenous perfusion of 5%(W/V) chloralose is started ½ hour after the morphine injection in such a way that 60 mg/Kg are administered within 15 minutes. After completion, a continuous perfusion of 10 mg/Kg/hour is maintained throughout the experiment. The dogs are artificially ventilated by means of a Starling pump at a rate of 20 breaths/minute. The volume is adjusted according to the weight of the animal. [Kleinman and Radford, *J. Appl. Physiol.,* 19, 360 (1964)]. All the measurements are made with the dogs positioned supine in a heated, V-shaped table. Curarization is obtained by succinylcholine chloride using a starting injection of 3 mg/Kg lasting 3 minutes, followed by a continuous perfusion of 0.1 mg/Kg/minute.

The respiratory spasm is induced by a starting injection of 400 μg/Kg of pilocarpine HCl lasting 5 minutes. An increase or decrease in the dose of pilocarpine HCl may occur as a function of the observed effect on the airway's resistance. A 15 minute delay is observed before the start of a continuous perfusion of pilocarpine HCl at a dose of 4 μg/Kg/minute to maintain a constant spasm during the test.

A metallic cannula is inserted and fixed, after tracheotomy, into the upper part of the trachea. The two cephalic veins and the two femoral veins are catheterized to inject the various agents. The femoral artery is catheterized to measure the systemic blood pressure. An esophageal balloon (11 cm×2.5 cm) is inserted into the lower third of the oesophagus to measure the endothoracic pressure. The measurement of air flow is made with a Fleish pneumotachograph connected to the tracheal tube.

The transpulmonary pressure is measured as follows: The tracheal cannula is equipped with a stainless steel axial tube (1.5 mm) which is closed at its distal end and projected 2.5 cm beyond the end of the cannula. Three holes with a diameter of one mm are pierced on this latter segment. This tube, which is used to measure the tracheal pressure, is connected to one of the two chambers of a Sanborn 267 B/C differential transducer. The other chamber is connected to the esophageal balloon by means of a polyethylene catheter of the same length and characteristics as the balloon's.

The airflow is measured from the Fleish pneumotachograph by means of a Sanborn 270 differential transducer.

The tidal volume is obtained by electronic integration of the flow signal using an R.C. integrator.

The systemic and pulmonary blood pressures are gauged by means of a Sanborn 267 B/C or 1280B pressure transducer.

An electrocardiogram is taken in lead 2. Its use is to monitor a cardiac rate-meter.

All these parameters are recorded on a Sanborn polygraph. The transpulmonary pressure and the tidal volume are also displayed as rectangular coordinates on an oscilloscope.

The airway's resistance, expressed in cm of water/liter/second, is measured by subtracting from the electrical equivalent of the transpulmonary pressure, a voltage proportional to the flow so as to synchronize the pressure and volume signals on the oscilloscope [Mead and Whittenberger, *J. Appl. Physiol.*, 5,779 (1953)].

The value of the pulmonary elastance, expressed in cm of water/liter, is obtained by means of the same principle, i.e., an electrical signal proportioned to the volume is subtracted from the transpulmonary pressure signal, in order to optimize the pressure-flow loop on the oscilloscope.

The details of this method are described by Lulling, et al. [*Med. Pharmacol. Exp.*, 16, 481 (1967)].

The computing operations are carried out with an analogical computer which allows the direct reading, cycle to cycle, of the values of resistance and elastance.

The test compounds are administered by an Aerosol ® route. The micronebulizer of a Bird Mark 7 respirator is fitted on the metallic cannula just after the pneumotachograph. The "puff" of the test compound, in Aerosol ® is driven by a 2 Kg/cm$_2$ pressure, allowed into the micronebulizer just during one inspiration cycle. The micronebulizer is fitted on the respiratory tube only during the "puff." It is weighed just before and just after administration to determine the amount of test compound administered. Approximately 50 mg of the solution is administered to each dog. In accordance with the Pilocarpine Assay described herein, the compounds of this invention should exhibit bronchodilator activity.

The bronchodilator activity for representative compounds of this invention was determined in Guinea-Pigs against bronchospasms elicited by intravenous injections of serotonin, histamine, and acetylcholine, by the Konzett procedure the details of which are those discussed by J. Lulling, P Lievens, F. El Sayed and J. Prignot, *Arzeimittel-Forschung* 18, 995 (1968).

In the table which follows, bronchodilator activity for representative compounds of the invention against spasmogenic agents serotonin, histamine, and acetylcholine is expressed as an ED$_{50}$ determined from the results obtained with three logarithmic cumulative intravenous doses.

| KONZETT DATA COMPOUND | ED$_{50}$ mg/kg | | |
|---|---|---|---|
| | SEROTONIN | HISTAMINE | ACETYLCHOLINE |
| dl 1,9-dioxo-11α,16-dihydroxy-1-hydroxymethyl-17-methylene-5-cis,13-trans-prostadiene. | $12.5 \times 10^{-3}$ | $2.0 \times 10^{-3}$ | $8.0 \times 10^{-3}$ |
| dl 1,9-dioxo-11α,16-dihydroxy-1-hydroxymethyl-16-methyl-13-trans-19-prostadiene. | $60 \times 10^{-3}$ | $35 \times 10^{-3}$ | $22 \times 10^{-3}$ |
| dl 1,9-dioxo-11α,15-dihydroxy-1-hydroxymethyl-15-vinyl-13-trans-prostene. | $696 \times 10^{-6}$ | $134 \times 10^{-6}$ | $323 \times 10^{-6}$ |
| dl 1,9-dioxo-11α,16-dihydroxy-1-hydroxymethyl-16-trifluoromethyl-13-trans-prostene. | $13 \times 10^{-3}$ | $60 \times 10^{-3}$ | $19 \times 10^{-3}$ |
| dl 1,9-dioxo-11α,16-dihydroxy-1-hydroxymethyl-16-methyl-18,20-trinor-13-trans-prostene. | 6.68 | — | — |
| dl 1,9-dioxo-11α,16-dihydroxy-1-hydroxymethyl-16-chloromethyl-13-trans-prostene. | $11 \times 10^{-3}$ | $8.4 \times 10^{-3}$ | $16.6 \times 10^{-3}$ |
| dl 1,9-dioxo-11α,16-dihydroxy-1-hydroxymethyl-16-fluoromethyl-13-trans-prostene. | $1.7 \times 10^{-3}$ | $2.2 \times 10^{-3}$ | $6.3 \times 10^{-3}$ |
| dl 1,9-dioxo-11α,16-dihydroxy-2-hydroxymethyl-16-methyl-17-methylene-13-trans-prostene (less mobile epimer)* | $9.1 \times 10^{-3}$ | $5.4 \times 10^{-3}$ | $12.2 \times 10^{-3}$ |
| dl 1,9-dioxo-11α,16-dihydroxy-2-hydroxymethyl-16-methyl-17-methylene-13-trans-prostene (more mobile epimer)* | $2.0 \times 10^{-3}$ | $14.1 \times 10^{-3}$ | $509 \times 10^{-6}$ |
| dl 1,9-dioxo-11α,16-dihydroxy-2-hydroxymethyl-16-methyl-19-chloro-20-nor-13-trans-prostene. | $4.4 \times 10^{-3}$ | $2.1 \times 10^{-3}$ | $6.6 \times 10^{-3}$ |

*More mobile and less mobile refer to relation mobilities on silica gel tlc plates.

Reference Example 1

2-Methylene Valaraldehyde

A mixture of 200 g. of valaraldehyde. 208.8 g. of 37% formalin and 226.7 g. of dimethylamine hydrochloride is heated with stirring at 90° C. for 24 hours and then steam distilled until no organic material distills over. The distillate is saturated with sodium chloride and the organic layer is separated and dried over magnesium sulfate then distilled, giving the desired product in the fraction boiling at 43°–45° C., 0.52 mm.

Reference Example 2

4-Hydroxy-5-methylene-1-octyne

To a stirred mixture of 12.16 g. of magnesium in 120 ml. of ether containing 200 mg. of mercuric chloride is added 2 ml. of propargyl bromide and 0.5 ml. of 1,2-dibromoethane. This mixture is stirred under argon until the reaction begins. To this is added with stirring a solution of 41.57 g. of 2-methylene valaraldehyde and 64.95 g. of propargyl bromide in 90 ml. of ether, dropwise, at a rate to maintain reflux. After addition is complete the mixture is refluxed 15 minutes, stirred at room temperature one hour, cooled to 0° C. and saturated ammonium chloride solution is added dropwise until reflux stops. The mixture is filtered through Celite, dried over magnesium sulfate and the ether is removed giving the product as a light orange oil.

Reference Example 3

5-Methylene-4-triethylsilyloxy-1-octyne

To a solution of 30.0 g. of 4-hydroxy-5-methylene-1-octyne and 31.02 g. of imidazole in 80 ml of dimethylformamide at 0° C., is added 40.9 g. of triethychlorosilane. The mixture is stirred at room temperature for 30 minutes, poured into cold water and extracted with petroleum ether. The petroleum ether is removed and the residue is distilled. The product is recovered in the fraction boiling at 103°–106° C. (1.5 mm.).

Reference Example 4

5-Methylene-4-triethylsilyloxy-1-tri-n-butylstannyl-1-octene

A mixture of 20 g. of 5-methylene-4-triethylsilyloxy-1-octyne, 25.36 g. of tri-n-butylstannane and 0.1 g. of azobisisobutyrylnitrile is placed in an oil bath at 100° C. After 10 minutes an exotherm raises the temperature to 150° C. The mixture is then heated at 130°–140° C. for 1.5 hours. The excess tri-n-butylstannane is distilled off at 130° C. (1 mm.) and the residue is distilled in a Kugelrohr at 120°–140° C., 0.15–0.05 mm., giving the product as a colorless liquid.

Reference Example 5

3-Methylene-2-hexanone

A mixture of 100 g. of 2-hexanone, 90 g. of 30% formaline and 97.7 g. of dimethylamine hydrochloride is stirred at 85° C. for 24 hours. The mixture is then steam distilled. To the distillate is added 25 g. of potassium carbonate. The mixture is steam distilled. The organic layer is dried over magnesium sulfate and distilled in vacuo. The fraction boiling at 120°–126° C. is saved. To the residue is slowly added 46 g. of methyl iodide. The resulting paste is placed in an oil bath at 170° C. The distillate (120° C.) is collected, combined with the above distillate and redistilled in vacuo giving at 115°–119° C. the desired product.

Reference Example 6

4-Hydroxy-4-methyl-5-methylene-1-octyne

To a mixture of 5.0 g. of magnesium and 100 mg. of mercuric chloride in 10 ml. of ether is added with stirring, one ml. of dibromoethane. The mixture is stirred for 10 minutes and 0.5 ml. of propargyl bromide is added. An additional 50 ml. of ether is added, followed by a solution of 17.5 g. of 3-methylene-2-hexanone and 27.8 g. of propargyl bromide in 60 ml. of ether, dropwise at a rate to maintain vigorous reflux. The mixture is refluxed for ½ hour, cooled at 0° C. and saturated ammonium chloride solution is added dropwise. The mixture is filtered through Celite and the solids are washed with ether. The ether solution is dried over magnesium sulfate and the ether is removed giving the desired product.

Reference Example 7

4-Methyl-5-methylene-4-trimethylsilyloxy-1-octyne

To a solution of 25.77 g. of 4-hydroxy-4-methyl-5-methylene-1-octyne and 28.6 g. of imidazole in 50 ml. of dimethylformamide is added 22.9 g. of chlorotrimethylsilane. The mixture is stirred at room temperature for 40 minutes, poured into cold water and extracted with petroleum ether. The extract is washed with water and saturated sodium bicarbonate solution, dried over magnesium sulfate and the solvent is removed. The residue is distilled and the desired product recovered at 85°–87° C. (0.45 mm.) as a colorless liquid.

Reference Example 8

E-4-Methyl-5-methylene-4-trimethylsilyloxy-1-tri-n-butyl-stannyl-1-octyne

A mixture of 26 g. of 4-methyl-5-methylene-4-trimethylsilyloxy-1-octyne, 200 mg. of azoisobutyrylnitrile and 41.1 g. of tri-n-butylstannane is stirred under argon in an oil bath at 140° C. The mixture is stirred at 140°–150° C. for one hour under argon, then at 140°–150° C. for 1.5 hours under vacuum to remove excess tri-n-butylstannane. The residue is distilled via a Kugelrohr (150° C., 0.05 mm.) giving the desired product as a colorless liquid.

Reference Example 9

Treatment of the starting carbonyls of Table A with formalin by the procedure of Reference Examples 1 or 5 produces the α-methylenecarbonyl derivative which upon condensation with propargylic magnesium bromide by the procedure of Reference Examples 2 or 6 produces the hydroxy alkyne of Table A. Protection of the hydroxy alkynes of Table A with either chlorotriethylsilane according to the procedure of Reference Example 3 or chlorotrimethylsilane by the procedure of Example 6 produces the trialkylsilyloxy alkyne which upon treatment with tri-n-butylstannane by the procedure of Reference Examples 4 or 7 provides the trans-vinylstannanes of Table A.

TABLE A

| STARTING CARBONYL | α-METHYLENE CARBONYL COMPOUND | HYDROXY-ALKYNE | TRIALKYLSILYL-OXY ALKYNE | TRANS-VINYL STANNANE |
|---|---|---|---|---|
| butryaldehye | 2-methylene butyraldehyde | 5-methylene-4-hydroxy-1-heptyne | 5-methylene-triethylsiloxy-1 heptyne | 1-trans-tri-n-butyl-stannyl-5-methylene-4-triethylsiloxy-1-heptene |
| 2-pentanone | 3-methylene-2-pentanone | 4-methyl-5-methylene-4-hydroxy-1-heptyne | 4-methyl-5-methylene-4-trimethylsiloxy- | 1-trans-tri-n-butyl-stannyl-4-methyl-5-methylene-siloxy-1-heptene |

TABLE A-continued

| STARTING CARBONYL | α-METHYLENE CARBONYL COMPOUND | HYDROXY-ALKYNE | TRIALKYLSILYL-OXY ALKYNE | TRANS-VINYL STANNANE |
|---|---|---|---|---|
| 3-hexanone | 2-methylene-3-hexanone | 4-ethyl-5-methylene-4-hydroxy-1-heptyne | 4-ethyl-5-methylene-4-trimethyl siloxy-1-heptyne | 1-trans-tri-n-butyl-stannyl-4-ethyl-5-methylene-4-trimethylsiloxy-1-heptene |
| Hexaldehyde | 2-methylene-hexaldehyde | 5-methylene-4-hydroxy-1-nonyne | 5-methylene-4-triethylsiloxy-1-nonyne | 1-trans-tri-n-butyl-stannyl-5-methylene-4-triethylsiloxy-1-nonene |
| 2-heptanone | 3-methylene-2-heptanone | 4-methyl-5-methylene-4-hydroxy-1-nonyne | 4-methyl-5-methylene-4-trimethylsiloxy-1-nonyne | 1-trans-tri-n-butyl stannyl-4-methyl-5-methylene-4-trimethyl-siloxy-1-nonene |
| 3-Octanone | 4-methylene-3-octanone | 4-ethyl-5-methylene-4-hydroxy-1-nonyne | 4-ethyl-5-methylene-4-trimethyl-siloxy-1-nonyne | 1-trans-tri-n-butyl-stannyl-4-ethyl-5-methylene-4-trimethylsiloxy-1-nonene |
| heptaldehyde | 3-methylene-heptaldehyde | 5-methylene-4-hydroxy-1-decyne | 5-methylene-4-triethylsiloxy-1-decyne | 1-trans-tri-n-butyl stannyl-4-ethyl-5-methylene-4-triethylsiloxy-1-decene |
| 2-octanone | 3-methylene-1-octanone | 4-methyl-5-methylene-4-hydroxy-1-decyne | 4-methyl-5-methylene-4-trimethylsiloxy-1-decyne | 1-trans-tri-n-butyl stannyl-4-methyl-5-methylene-4-trimethylsiloxy-1-decene |
| 3-nonanone | 4-methylene-3-nonanone | 4-methyl-5-methylene-4-hydroxy-1-decyne | 4-ethyl-5-methylene-4-trimethylsiloxy-1-decyne | 1-trans-tri-n-butyl-stannyl-4-ethyl-5-methylene-4-trimethylsiloxy-1-decene |
| 3-heptanone | 4-methylene-3-heptanone | 4-ethyl-5-methylene-4-hydroxy-1-nonyne | 4-ethyl-5-methylene-4-trimethyl-siloxy-1-nonyne | 1-trans-tri-n-butyl stannyl-4-ethyl-5-methylene-4-trimethyl-siloxy-1-octene |

Reference Example 10

1,2-Octadien-4-one

To a stirred solution of 0.50 moles of propargyl-magnesium bromide in 340 ml. of ether at −78° C. is added a solution of 65.2 g. (0.50 moles) of ethyl valerate in 100 ml. of ether during 60 minutes. The solution is stirred at −78° C. for 30 minutes and then hydrolyzed by pouring onto a mixture of ice and ether. The ether layer is washed with brine, treated with hydroquinone, dried over magnesium sulfate, and concentrated.

To a stirred, ice-cold solution of the liquid concentrate (94 g.) in 1200 ml. of tetrahydrofuran is added 60 ml. of 10% potassium carbonate solution. The resulting mixture is stirred at 0° C. for 2 hours, treated with 15 ml. of 4 N hydrochloric acid, and diluted with ether. The organic layer is washed with brine, dried over magnesium sulfate, treated with hydroquinone and concentrated. The product is distilled to provide the title compound as a colorless liquid, b.p. ca 80° C. (15 mm.).

Reference Example 11

4-Hydroxy-propadienyl-1-octyne

To a stirred solution of 125 mmol. of propargyl-magnesium bromide in 85 ml. of ether at −20° C. is added a solution of 11.7 g. (95 mmol.) of 1,2-octadien-4-one in 30 ml. of ether during 30 minutes. After the addition, the solution is stirred at 25° C. overnight, cooled to 0° C., and treated dropwise with 18 ml. of saturated ammonium chloride solution. The mixture is filtered, and the filtrate is washed with brine, dried over magnesium sulfate, and concentrated. The product is distilled from anhydrous potassium carbonate to provide the title compound as a colorless liquid, b.p. 84°–87° C. (8 mm.).

Reference Example 11a

4-Propadienyl-4-trimethylsilyloxy-1-octyne

To a stirred, ice-cold solution of 10.85 g. (66.1 mmol.) of 4-hydroxy-4-propadienyl-1-octyne and 13.2 g. (194 mmol.) of imidazole in 50 ml. of dimethylformamide at 0° C. is added 9.5 ml. of chlorotrimethylsilane. The solution is kept at 0° C. for 70 hours and diluted with petroleum ether. The resulting mixture is shaken with water at 0° C. The organic layer is washed with water and brine, dried over magnesium sulfate and concentrated to give the title compound as a liquid.

Reference Example 12

1-Iodo-4-propadienyl-4-trimethylsilyloxy-trans-1-octene

To a stirred solution of 2.36 g. (10 mmol.) of 4-propadienyl-4-trimethylsilyloxy-1-octyne in 5 ml. of glyme is added a solution of 11 mmol. of bis-(3-methyl-2-butyl)-borane in 15 ml. of glyme at 0° C. The mixture is stirred at 25° C. for 90 minutes, cooled to 0° C., and treated portionwise with 3.0 g. of triethylamine oxide. The stirred mixture is maintained at 25°–30° C. for 45 minutes, diluted with 20 ml. of tetrahydrofuran and poured into 100 ml. of ice-cold 15% sodium hydroxide solution, followed immediately with a solution of 8.0 g. of iodine in 20 ml. of tetrahydrofuran. The mixture is stirred at ambient temperature for 30 minutes and then extracted with ether. The extract is washed successively with water, sodium thiosulfate solution and brine; dried over magnesium sulfate; and filtered. The residue obtained after solvent evaporation is subjected to chromatography on silica gel with heptane solvent to afford the title compound as a liquid.

Reference Example 13

Treatment of the ethyl esters of Table A with propargyl magnesium bromide by the procedure of Example 10 followed by treatment with propargyl magnesium bromide by the procedure of Reference Example 11 followed by silyl ether formation by the procedure of Reference Example 12 followed by iodo vinylation by the procedure of Reference Example 4 is productive of the iodoalkenes and intermediates listed in Table B.

TABLE B

| STARTING ESTER | DIENONE | HYDROXY ALKYNE | SILOXY ALKYNE | IODOALKENE |
| --- | --- | --- | --- | --- |
| ethyl hexanoate | 1,2-nonadien-4-one | 4-hydroxy-4-propadienyl-1-nonyne | 4-propaldienyl-4-trimethylsilyloxy-1-nonyne | 1-iodo-4-propadienyl-4-trimethylsilyloxy-trans-1-nonyne |
| ethyl heptanoate | 1,2-decadien-4-one | 4-hydroxy-4-propadienyl-1-decyne | 4-propadienyl-4-trimethylsilyloxy-1-decyne | 1-iodo-4-propadienyl-4-trimethylsilyloxy-trans-1-decene |
| ethyl butyrate | 1,2-heptadien-4-one | 4-hydroxy-4-propadienyl-1-heptyne | 4-propadienyl-4-trimethylsilyloxy-1-heptyne | 1-iodo-4-propadienyl-4-trimethylsilyloxy-trans-1-heptene |
| ethyl-4-chloro-butyrate | 7-chloro-1,2-heptadiene-4-one | 7-chloro-4-hydroxy-4-propadienyl-1-heptyne | 7-chloro-4-propadienyl-4-trimethylsilyloxy-1-heptyne | 1-iodo-7-chloro-4-propadienyl-4-trimethylsilyloxy-trans-1-heptyne |

Reference Example 14

1-Hydroxy-2-hexanone

To a stirred mixture of 25 g. of valeryl chloride and 122.6 g. of tris(trimethylsilyloxy)ethylene is added 9 drops of anhydrous stannic chloride. After stirring at room temperature for 1.5 hours, the mixture is poured slowly into a stirring mixture of 60 ml. of 0.6 N. hydrochloric acid and 120 ml. of tetrahydrofuran and stirred for one hour. Work up is by diluting with ether, washing with brine, saturated sodium bicarbonate and brine again, and drying over anhydrous sodium sulfate. The ether solution is evaporated to dryness to give 21.5 g. of liquid which is vacuum distilled to give 15.5 g. of colorless liquid at b.p. 70–77° C./9 mm.; PMR$\delta$ 4.28(s), 2.42 (t, J=6).

Reference Example 15

1-Chloro-2-hexanone

To a stirred solution of 11.5 g. of 1-hydroxy-2-hexanone in 110 ml. of dimethylformamide is added 35 ml. of methanesulfonyl chloride dropwise during 10 minutes. The mixture is heated and stirred at 85° C. for 3 hours, then cooled in a ice-water bath. To this is added 50 ml. of water dropwise and the mixture is extracted with ether. The ether solution is washed with water and brine, dried, and then distilled to give 10.8 g. of product as a colorless liquid at b.p. 30°-32° C./4 mm.; PMR≠ 4.12 (s), 2.60 (t, J=7).

Reference Example 16

4-Chloromethyl-4-hydroxy-1-octyne

To a stirred suspension of 2.1 g. of magnesium and 20 mg. of mercuric chloride in 25 ml. of ether is added 0.8 ml. of propargyl bromide. After a few minutes of vigorous stirring, to this is added a mixture of 10.75 g. of 1-chloro-2-hexanone and 7.2 ml. of propargyl bromide in 25 ml. of ether, at such a rate that the reaction mixture is maintained at 25°-28° C. After addition, the mixture is stirred at room temperature one hour, cooled in an ice-water bath and 30 ml. of saturated ammonium chloride is added dropwise. The mixture is filtered through celite and washed with ether. The ether solution is concentrated to give 11.0 g. of a yellow liquid which is vacuum distilled to give 6.9 g. of product as a colorless liquid at b.p. 60°-61° C./−4 mm.; PMR$\delta$ 3.62 (ABq, CH$_2$Cl), 2.53 (d, J=3, C≡C—CH$_2$), 2.06 (t, j=3, HC≡C).

Reference Example 17

4-Chloromethyl-4-trimethylsiloxy-1-octyne

To a stirred, ice-cold solution of 7.22 g. of 4-chloromethyl-4-hydroxy-1-octyne and 7.16 g. of imidazole in 28 ml. of dimethylformamide is added 6.5 ml. of trimethylchlorosilane via a syrine during 15 minutes. The resulting mixture is stirred at room temperature overnight, diluted with hexane and poured into a mixture of ice and saturated sodium bicarbonate solution. The hexane solution is separated, washed with saturated sodium bicarbonate, water and brine, dried over anhydrous sodium sulfate and concentrated in vacuo to give 11.8 g. of a colorless liquid which is vacuum distilled at b.p. 50°-57° C./3.5–4 mm. to give 9.7 g. of product as a colorless liquid; PMR$\delta$ 3.58 (s), 2.50 (d), 1.99 (t), 0.87 (s,OTMS).

Reference Example 18

1-Tri-n-butylstannyl-4-chloromethyl-4-trimethylsiloxy-trans-1-octene

A mixture of 9.27 g. of 4-chloromethyl-4-trimethyl-silyloxy-1-octyne, 40 mg. of azoisobutyronitrile, and 10.0 ml. of tri-n-butyltin hydride is heated and stirred at 125° C. for 1.5 hours, then vacuum distilled through a short path to give, after a forerun, 19.5 g. of product as a colorless liquid at b.p. 140°-160° C./0.1–0.2 mm.; PMR$\delta$ 5.98 (m, olefin), 3.40 (s, CH$_2$Cl), 2.40 (m, C=C—CH$_2$), 0.14 (s,OTMS).

Reference Examples 19 and 20

7-Chloro-4-hydroxy-4-methyl-1-heptyne

To a mixture of 6.69 g. of magnesium in 20 ml. of ether under argon, is added 0.1 g. of mercuric chloride and 0.1 g. of dibromoethane. The mixture is stirred for 10 minutes and 0.5 ml. of propargyl bromide is added. A 50 ml. portion of ether is added, followed by a solution of 30 g. of 5-chloro-2-pentanone and 32.55 g. of propargyl bromide in 45 ml. of ether with stirring, at a rate to maintain vigorous reflux. The mixture is stirred an additional 15 minutes, cooled to −5° C. and an ice cold saturated solution of ammonium chloride is added dropwise. The ether layer is decanted and filtered. The solids are washed with ether which is also filtered. The combined ether filtrates are washed with water, dried over magnesium sulfate and the solvent removed giving the product as an orange oil.

Reference Example 21

7-Chloro-4-methyl-4-trimethylsilyloxy-1-heptyne

To a solution of 7-chloro-4-hydroxy-4-methyl-1-heptyne in 80 ml. of dimethylformamide at 0° C., is added 43.8 g. (0.644 moles) of imidazole and 35.02 g. (0.322 moles of) chlorotrimethylsilane. The mixture is stirred at room temperature for 45 minutes, poured into water and extracted with hexane. The hexane solution is washed with dilute sodium bicarbonate solution, dried over magnesium sulfate and the solvent removed leaving an orange liquid. This liquid is distilled giving the desired product in the fraction boiling at 83°–88° C., 1.5 mm. as a colorless liquid.

Reference Example 22

E/Z-1-tri-n-butylstannyl-7-chloro-4-methyl-4-trimethylsilyloxy-1-heptyne

A stirred mixture of 15 g. of 7-chloro-4-methyl-4-trimethylsilyloxy-1-heptyne, 18.92 g. of tri-n-butylstannane 80 mg. of azobisisobutyrylnitrile, under argon is placed in a bath at 100° C. The mixture is heated at 140° C. for one hour. Excess tri-n-butylstannane is distilled off under vacuum. The residue is distilled via a Kugelrohr (130°–135° C., 0.03 mm.) to give the desired product as a colorless liquid.

Reference Example 23

E-7-Chloro-1-iodo-4-methyl-4-trimethylsilyoxy-1-heptene

To a solution of 9.1 g. of sodium borohydride and 44 g. of 2-methyl-2-butene in 390 ml. of tetrahydrofuran, at 0° C. under argon, is added dropwise with stirring 44.56 g. of boron trifluoride etherate. The mixture is stirred 1.5 hours at 0° C., 0.5 hour at room temperature, recooled to 0° C. and a mixture of 43 g. of 7-chloro-4-methyl-4-trimethylsilyloxy-1-heptene in 60 ml. of tetrahydrofuran is added over 10 minutes. The mixture is stirred 2 hours at room temperature, then 81.8 g. of trimethylamine oxide is added portionwise over 15 minutes at 0° C. The mixture is stirred 1.5 hours at room temperature, then filtered through Celite. To the filtrate is added simultaneously, a solution of 413.7 g. of sodium hydroxide in 2 liters of water and a solution of 211 g. of iodine in 350 ml. of tetrahydrofuran. The solution is stirred vigorously for 0.5 hour, the organic layer is separated and the aqueous layer is extracted with hexane. Most of the tetrahydrofuran is removed from the initial organic layer and it is combined with the hexane extract. The combined solution is washed twice with saturated sodium thiosulfate solution, brine, dried over magnesium sulfate and filtered through a pad of silica gel. The residue is distilled via a Kugelrohr at 115°–120° C., 0.15 mm. giving the desired product as a yellow oil.

Reference Example 24

Preparation of 7-Chloro-hept-1-en-2-one

To a suspension of 28 g. (0.21 mol) of aluminum trichloride in 75 ml. of $CH_2Cl_2$ at −20° C. is added with stirring a mixture of 20 g. (0.2 mol.) of vinyltrimethylsilane and 28.2 g. (0.2 mol.) of 4-chlorobutylchloride dropwise over 45 minutes. The mixture is stirred at −20° C. for 4 hours and kept at 0° for 18 hours. The mixture is poured into 300 g. of ice containing 50 g. $NH_4Cl$ and stirred until all solids are dissolved. The mixture is extracted with ether and the combined ether extracts are washed with saturated $NaHCO_3$ and dried ($MgSO_4$). The ether is removed in vacuo and the residue distilled (50°–60°, 0.125 mm.) to give a light yellow liquid (14.9 g.).

Reference Example 25

Preparation of 7-Chloro-4-hydroxy-4-vinyl-1-heptyne

To a suspension of 3.0 g. (0.12 mol.) of magnesium metal in 10 ml. ether containing 100 mg. $HgCl_2$ is added with stirring, under argon, 0.3 ml. of $CH_2CH_2B_2$. After 5 minutes a reaction is initiated and 0.5 g. of 80% propargylbromide in toluene is added. Upon evidence of a vigorous reaction, an additional 25 ml. of ether is introduced. A mixture of 13 g. (0.1 mol) of 7-chlorohept-1-en-2-one and 19.5 g. (0.12 mol.) of propargylbromide in 35 ml. ether is added at such a rate to maintain a vigorous reflux. After addition is complete, stirring is continued 10 minutes. The mixture is cooled to 0° C. and satd. $NH_4Cl$ is added slowly. The mixture is filtered through diatomaceous earth and the ether is removed in vacuo to provide the title product as an oil.

Reference Example 26

Preparation of 7 Chloro-4-trimethylsilyoxy-4-vinyl-1-heptyne

The alcohol from the previous example is dissolved in DMF (25 ml.) and 16.58 g. of imidazole and 13.3 g. of chlorotrimethylsilane is added. After stirring at ambient temperature for 1 hour, the reaction mixture is poured into ice water and extracted with petroleum ether. The organic extracts are washed with saturated $NaHCO_3$, and dried ($MgSO_4$), and concentrated in vacuo to provide an oil. This residue is distilled (76°–82°, 0.08 mm.) to afford 20.4 g. of the title product as a colorless oil.

Reference Example 27

Preparation of E-7-Chloro-4-trimethylylsiloxy 4-vinyl-1-tri-n-butylstannyl-1-heptane A mixture of 7-chloro-4 -trimethylsilyloxy-4vinyl-1-heptyne (17 g., 0.07 mol.) and 20.7 g. (0.071 mol.) of tri-n-butylstannane and 150 mg. of azobisisobutyrlnitrile (AIBN) is stirred under argon in a 140° oil bath behind a safety shield. After three minutes an exotherm occurs and the mixture is maintained at 140° C. for 1.5 hours. After cooling, air is admitted and the unreacted tri-n-butylstannane is removed by distillation via Kugelrohr (140°, 0.5–0.3 mm.) to give a very light yellow oil (30 g.). This oil consists of a mixture of the E and Z isomers.

Reference Example 28

4-Chloropropyl trimethylsilylethylnyl ketone

To a stirred solution of 16.8 grams of 4-chloro-butryl chloride and 20.4 grams of bis-trimethylsilylacetylene in 300 ml. of dry methylene chloride, cooled in an ice bath, is added powdered anhydrous aluminum chloride, portionwise over a period of 20 minutes. The mixture is stirred for 5 minutes, then the cooling bath is removed and the mixture stirred at room temperature for 4 hours. The mixture is poured into 500 ml. of ice water. The organic layer is separated, washed with water and brine, dried over anhydrous sodium sulfate and filtered through diatomaceous earth. The clear mother liquid is evaporated to dryness giving a brownish residue. The residue is Kugelrohr-distilled to give a colorless liquid.

Reference Example 29

7-Chloro-4-hydroxy-4-trimethylsilylethynyl-1-heptyne

To a stirred suspension of 1.29 grams of magnesium and 10 mg. of mercuric chloride in 12 ml. of ether is added 0.4 ml. of propargyl bromide. The reaction is initiated after stirring at room temperature for a few minutes. The solution of 11.2 grams of 3-chloropropyl trimethylsilylethynyl ketone and 3.51 ml. of propargyl bromide in 13 ml. of ether is added dropwise so that the mixture is very gently boiled during a period of about 40 minutes. After addition is complete, the cooling bath is removed and the mixture is stirred at room temperature for about 1.5 hours. The mixture is recooled in an ice bath and 10 ml. of saturated ammonium chloride solution is added. The resulting white mixture is filtered through diatomaceous earth. The clear mother liquid is washed with saturated sodium chloride solution and dried over anhydrous magnesium sulfate. The solvent is evaporated to dryness giving a red liquid. The liquid is Kugelrohr-distilled to afford the pale yellow liquid distillate which is the desired product.

Reference Example 30

7-Chloro-4-trimethylsilyloxy-4-trimethylsilylethynyl-1-heptyne

To a stirred mixture of 8.5 grams of 7-chloro-4-hydroxy-4-trimethylsilylethynyl-1-heptnye (Example 29) and 6.2 grams of imidazole in 24 ml. of dry dimethylformamide is added, under nitrogen, 5.7 ml. of chlorotrimethylsilane, in a slow stream, via a syringe. The mixture is stirred in an ice bath for one hour and then at room temperature overnight. The mixture is poured into hexane, washed with saturated sodium bicarbonate solution, water and then brine and dried over sodium sulfate. The solvents are evaporated to dryness yielding the desired product.

Reference Example 31

E-7-Chloro-4-trimethylsilylethynyl-4-trimethylsiloxy-4-trimethylsilylethynyl-1-tributyl stannyl-1-heptene To a mixture of 10 mg. of azobisisobutyronitrile and 2.94 grams of 7-chloro-4-trimethylsilyloxy-4-trimethylsilylethynyl-1-heptyne (Example 30) is added 2.65 ml. of tri-n-butyl stannane via a syringe. The mixture is stirred and heated under nitrogen in an oil bath at 130° C. for about 3 hours and then cooled to room temperature. The mixture is vacuum-distilled through a short-path distillation apparatus to remove a forerun of unreacted tri-n-butyl stannane. The yellow oil (pot residue) comprises the desired product as a mixture of E and Z isomers.

Reference Example 32

Preparation of E-7 Chloro-4-triethylsilyloxy-1-tri-n-butylstannyl-1-heptene

Treatment of 4-chlorobutyraldehyde by the procedures of Reference Examples 1 to 3 (utilizing chlorotriethylsilane) is productive of the title compound and the intermediates shown in Table D.

TABLE D

| STARTING CARBONYL | HYDROXYALKYNE | SILYLOXYALKYNE | VINYLSTANNANE |
|---|---|---|---|
| 4-chlorobutyr-aldekyde | 7-chloro-4-hydroxy-1-heptyne | 7-chloro-4-triehtylsilyloxy-1-heptyne | E-7-chloro-4-triethylsilyloxy-1-tri-n-butylstannyl-1-heptene and the corresponding Z isomer |

Reference Example 33

1,1-Dimethoxy-2-hexanone

A mixture of 36.9 g. of washed 50% sodium hydride dispersion (0.77 moles) and 600 ml. of dimethylsulfoxide is heated under argon at 65° C. for 2 hours. At 0° C. is added dropwise, 50 g. (0.38 moles) of ethyl valerate. The solution is stirred at room temperature for 2 hours, then diluted with 1400 ml. of water and 70 ml. of concentrated hydrochloric acid and 75 g. of sodium chloride is added. The mixture is extracted four times with chloroform and the solution is dried (magnesium sulfate charcoal). The solvent is removed. The residue is dissolved in 700 ml. of methanol. A 55.65 g. (0.22 moles) portion of iodine is added and the solution is refluxed 90 minutes. The solvent is removed, the residue is dissolved in chloroform and the solution is washed twice with water and once with saturated sodium thiosulfate. The solution is dried (magnesium sulfate charcoal). The solvent is removed and the residue is distilled twice. The fraction boiling at 64°–72° C., 5 mm. is collected to give 28.3 gm. of the title compound. [T. L. Moore *J. Org. Chem.*, 32 786 (1967).]

Reference Example 34

4-Dimethoxymethyl-4-trimethylsiloxy-1-octyne

To a suspension of 5.31 g. (0.22 moles) of magnesium in 15 ml. of ether is added 100 mg. of mercuric chloride and 1.5 ml. of 1,2-dibromoethane. After the reaction begins, another 45 ml. of ether is added followed by the dropwise addition of a solution of 25 g. (0.16 moles of 1,1-dimethoxy-2-hexanone and 27.3 g. (0.2 moles) of 85% propargyl bromide in 45 ml. of ether at a rate which maintains reflux. Midway through the addition 15 ml. of tetrahydrofuran is added. After complete addition of the solution, the mixture is refluxed for 40 minutes. The mixture is cooled to 0° C. and saturated ammonium chloride solution is added followed by magnesium sulfate. The mixture is filtered through Celite and the solvent is removed. The residue is dissolved in 53 ml. of dimethylformamide and at 0° C. is added 24.4 g. (0.36 moles) of imidazole and 21.19 g. (0.20 moles) of trimethylchlorosilane. After stirring at 25° C. for 70 minutes, the solution is poured into water and extracted with hexanes. The organic layer is dried over magnesium sulfate and the solvent is removed. Distillation (75°–95° C., 0.3 mm.) gives 17.4 g. of the title compound.

Reference Example 35

E-1-tri-Butylstannyl-4-dimethoxymethyl-4-trimethyl-siloxy-1-octene

A mixture of 10.0 g. (36.7 moles) of 4-dimethoxymethyl-4-trimethylsiloxy-1-octyne, 12.82 g. (44 moles) of tri-n-butylstannyl hydride and 100 mg. of azobisisobutyronitrile is heated to 140° C. under argon for 2 hours. The excess hydride is distilled off and the residue is purified by molecular distillation (bath temperature=170°-175° C., 0.2 mm.) to give 20.5 g. of the title compound.

Reference Example 36

Treatment of the esters of Table E by the successive procedures of Examples 33–35 is productive of the dimethoxymethyl vinylstannanes of the Table.

TABLE E

| STARTING ESTER | PRODUCT DIMETHOXYMETHYL VINYL STANNANE |
| --- | --- |
| Ethyl butyrate | E-1-tributylstannyl-4-dimethoxymethyl-4 trimethylsilyloxy-1-heptene |
| Ethyl hexanoate | E-1-tributylstannyl-4-dimethoxymethyl-4-trimethylsilyloxy-1-nonene |
| Ethyl heptanoate | E-1-tributylstannyl-4-dimethoxymethyl-4-trimethylsilyloxy-1-decene |

Reference Example 37

1-Fluoro-2-hexanone

A solution of 26.5 g. of ethyl fluoroacetate in 350 ml. of ether is cooled in a dry ice-ethanol bath under nitrogen. To this is added 250 ml. of a solution comprising 110 ml. of 2.67 M n-butylmagnesium chloride in tetrahydrofuran which has been diluted with 140 ml. of ether, dropwise through a dropping funnel over a period of one hour. During this addition, the temperature of the reaction mixture is maintained at −65° C. to −72° C. After complete addition, 100 ml. of 15% aqueous sulfuric acid is added and the mixture is stirred at room temperature for one hour. The ether portion of the mixture is separated, washed with water, then brine, dried and then concentrated on a rotary evaporator at about 15° C. The concentrated solution is distilled through a Vigorox column to remove a forerun (b.p. 40°-80° C./760 mm) and then the product is collected at 30°-35° C./14 mm.

Reference Example 38

4-Fluoromethyl-4-hydroxy-1-octyne

A 0.25 ml. portion of propargyl bromide is added to a stirred suspension of 0.73 g. of magnesium and 6 mg. of mercuric chloride in 7.5 ml. of ether. The reaction is initiated after a few minutes of vigorous stirring at room temperature. A mixture of 3 g. of 80% 1-fluoro-2-hexanone and 3.63 g. of propargyl bromide in 7.5 ml. of ether is added dropwise through a dropping funnel so that the reaction remains gently refluxing (25° C. to 32° C.). Cooling in a water bath is required. The reaction mixture is cooled in an ice bath, quenched with 8 ml. of cold saturated aqueous ammonium chloride, filtered through Celite and washed with ether. The mother liquor is evaporated to dryness giving a reddish oily residue, which is Kugelrohr-distilled at 45° C./-4 mm giving the product as a colorless liquid.

Reference Example 39

4-Fluoromethyl-4-trimethylsilyloxy-1-octyne

To a solution of 4.38 g. of 4-fluoromethyl-4-hydroxy-1-octyne and 4.8 g. of imidazole in 19 ml. of dimethylformamide, cooled in an ice bath under nitrogen is added 4.5 ml. of trimethylchlorosilane via a syringe during a few minutes. The mixture is stirred in the ice bath for 30 minutes and then at room temperature under nitrogen overnight. The solution is poured into hexane, washed with saturated aqueous sodium bicarbonate, water, then brine and dried over anhydrous sodium sulfate. The solvents are removed in vacuo giving the product as a colorless liquid.

Reference Example 40

4-Fluoromethyl-4-trimethylsilyloxy-1-tri-n-butylstannyl-trans-1-octene

A solution of 6.36 g. of 4-fluoromethyl-4-trimethylsilyloxy-1-octyne, 11.64 g. (10.6 ml.) of tributylstannane and 40 mg. of azobisisobutyronitrile is heated and stirred at 120° C. under nitrogen for 3 hours. The mixture is cooled, filtered through Celite and washed with hexanes. The hexanes are removed in vacuo and the residual liquid is vacuum distilled through a short path. The product is obtained at b.p. 110°-135° C./0.2-0.25 mm. (The product contains a minor amount of cis isomer.)

Reference Example 41

1,1-Difluoro-2-hexanone

To a 3 liter, three-neck, round bottom flask, equipped with a magnetic stirrer, a dropping funnel filled with 39.9 g. of difluoroacetic acid and 200 ml. of ether, and a rubber septum is added 1350 ml. of ether. After cooling in a dry ice-acetone bath under nitrogen, one mole of n-butyl lithium (2.2 M, hexane) is added via a double tip needle. The difluoroacetic acid solution is slowly added to the cooled n-butyl lithium solution via the dropping funnel over 3 hours. The thick mixture is stirred at −78° C. for one hour and then quenched by pouring into a mixture of one liter of 4 N hydrochloric acid and one liter of ice, divided into three flasks, with stirring. The organic layers are combined and washed with water and brine. The 1500 ml. of solution is distilled at atmospheric pressure in a water bath. After the forerun is collected, the residue is fractionally distilled giving 18.8 g. (b.p. 100°-110° C.) of product that is 75% real.

Reference Example 42

4-Difluoromethyl-4-hydroxy-1-octyne

To a stirred suspension of 3.6 g. of magnesium and 30 mg. of mercuric chloride in 0.33 ml. of ether is added 1.5 ml. of propargyl bromide. The mixture is stirred vigorously for several minutes to initiate reaction, then a solution of 15.5 g. of 1,1-difluoro-2-hexanone and 12.1 ml. of propargyl bromide in 33 ml. of ether is added slowly (dropwise) over a 1.5 hour period, so that the mixture remains gently refluxing (25°-30° C.). After addition, the mixture is stirred at room temperature for 30 minutes, then cooled in an ice bath to 0°-5° C. and quenched by adding 35 ml. of saturated ammonium chloride solution dropwise and then stirred for 30 minutes. The mixture is filtered through Celite and washed with ether. The filtrate is concentrated in vacuo giving a yellow oil. This oil is vacuum distilled at 71° C., 12 mm giving the product as 10.54 g. of colorless oil which becomes pale yellow on standing at room temperature.

Reference Example 43

4-Difluoromethyl-4-trimethylsiloxy-1-octyne

A solution of 11.5 g. of 4-difluoromethyl-4-hydroxy-1-octyne and 11.32 g. of imidazole in 45 ml. of dimethylformamide is cooled in an ice bath under nitrogen. A 10.3 ml. portion of trimethylchlorosilane is added using a syringe over a 15 minute period. The mixture is stirred in the ice bath for one hour and then overnight at room temperature. The solution is diluted with hexane and then poured into saturated aqueous sodium bicarbonate solution. The hexane solution is separated, washed with aqueous sodium bicarbonate solution and brine, dried over anhydrous sodium sulfate and the solvents are evaporated to dryness giving the desired product as a colorless liquid.

Reference Example 44 trans-4-Difluoromethyl-4-trimethylsiloxy-1-tri-n-butylstannyl-1-octene

A mixture of 13.0 g. of 4-difluoromethyl-4-trimethylsiloxy-1-octyne, 17.23 ml. of tri-n-butylstannane and 70 mg. of azobisisobutyronitrile is heated under nitrogen in an oil bath at 125°-135° C. for 2 hours. The reaction is cooled to room temperature and vacuum distilled through a short-path apparatus, giving, after a 5 ml. forerun, 35.6 g. of the product as an oil, containing a minor amount of the corresponding cis isomer.

Reference Example 45

1,1,1-Trifluoromethyl-2-hexanone

A mechanically stirred solution of 57 g. of trifluoroacetic acid in one liter of anhydrous ether, under argon, is cooled to −78° C. and treated with one mole of n-butyl lithium (2.2 M in hexane) over a 2¼ hour period. After an additional 1¼ hours, the reaction mixture becomes gelatinous and stirring is discontinued. The reaction mixture, on standing overnight under an argon atmosphere, becomes fluid and stirring is continued for 2 hours. The solution is then syphoned into an agitated mixture of 200 ml. of concentrated hydrochloric acid and approximately one liter of cracked ice. The ether layer is separated, washed with saturated saline solution, then saturated sodium bicarbonate solution and dried over anhydrous magnesium sulfate. The ether is distilled at atmospheric pressure and the residue is fractionally distilled, giving 7.8 g. of the desired product, b.p. 75°-85° C.

Reference Example 46

4-Trifluoromethyl-4-hydroxy-1-octyne

To a stirred mixture of 1.78 g. of magnesium and approximately 25 mg. of mercuric chloride in 10 ml. of dry ether is added 0.6 ml. of propargyl bromide. The reaction is initiated by gentle warming. The refluxing solution is cooled in an ice bath and treated with a solution of 4.8 ml. of propargyl bromide and 10.85 g. of 1,1,1-trifluoromethyl-2-hexanone in 7 ml. of dry ether by dropwise addition over an 80 minute period maintaining the reaction temperature between 10° and 15° C. The mixture is stirred for 1¾ hours at room temperature, then recooled and terminated with 10 ml. of saturated ammonium chloride solution. The mixture is filtered through Celite and washed copiously with ether. The filtrate is washed with saturated saline solution, dried over anhydrous potassium carbonate-magnesium sulfate and evaporated to an oil. Fractional distillation of the oil at 12 mm pressure afforded 5.5 g. of the desired product, b.p. 65°-70° C.

Reference Example 47

4-Trifluoromethyl-4-trimethylsiloxy-1-octyne

A stirred solution of 4.99 g. of 4-trifluoromethyl-4-hydroxy-1-octyne and 5.65 g. of imidazole in 28 ml. of dry dimethylformamide, under argon, is cooled in an ice bath and then treated with 5.2 ml. of trimethylsilyl chloride by dropwise addition over a period of about 20 minutes. After an additional 15 minutes at ice bath temperature, the reaction mixture is stirred at room temperature overnight. The mixture is then poured into approximately 150 ml. of hexane and washed with small portions of ice cold water and saturated saline solution. The solution is dried over anhydrous magnesium sulfate and evaporated under reduced pressure to give the desired product.

Reference Example 48 trans-4-Trifluoromethyl-4-trimethylsiloxy-1-tri n-butylstannyl-1-octene

A stirred mixture of 6.66 g. of 4-trifluoromethyl-4-trimethylsiloxy-1-octyne and 26 mg. of azobisisobutyronitrile, under argon, is treated with 6.95 ml. of tri-n-butyl tin hydride, via a syringe. After treatment, a condenser is attached to the reaction vessel and the reaction mixture, under argon, is slowly heated to 130°-135° C. and maintained at this temperature for 1.5 hours. Subsequent fractional distillation of the reaction mixture at approximately 0.07 mm pressure gives the desired product, b.p. 125°-135° C. (containing a minor amount of the corresponding cis isomer).

Reference Example 49

Treatment of the starting carbonyl of Table F with the alkyl lithium reagent indicated provides the fluoroketones of the table, which upon subsequent treatment with propargyl magnesium bromide, provides the indicated hydroxy-alkynes, which are treated with trimethylchlorosilane by the procedure indicated to provide the alkyne-trimethylsiloxy ethers which upon treatment with tri-n-butylstannane provide the corresponding trans-vinylstannanes of the table. (Each trans-vinylstannane contains 10-20% of the corresponding cis-vinylstannane.)

TABLE F

| STARTING CARBONYL | ALKYL-LITHIUM | FLUOROKETONE | HYDROXY-ALKYNE | ALKYNE-TRIMETHYLSILOXY-ETHER | TRANS-VINYL STANNAN |
|---|---|---|---|---|---|
| trifluoroacetic acid | n-propyl | 1,1,1-trifluoro-2-pentanone | 4-trifluoromethyl-4-hydroxy-1-heptyne | 4-trifluoromethyl-4-trimethylsiloxy-1-heptyne | 1-trans-tri-n-butyl stannyl-4-trifluoromethyl-4-trimethylsiloxy-1-heptene |

TABLE F-continued

| STARTING CARBONYL | ALKYL-LITHIUM | FLUOROKETONE | HYDROXY-ALKYNE | ALKYNE-TRI-METHYLSIL-OXY-ETHER | TRANS-VINYL STANNAN |
|---|---|---|---|---|---|
| difluoro-acetic acid | n-propyl | 1,1-difluoro-2-pentanone | 4-difluoromethyl-4-hydroxy-1-heptyne | 4-difluoro-methyl-4-trimethyl-siloxy-1-heptyne | 1-trans-tri-n-buty-stannyl-4-difluoro-methyl-4-trimethyl-siloxy-1-heptene |
| ethyl fluo-roacetate | n-propyl | 1-fluoro-2-pentanone | 4-fluoromethyl-4-hydroxy-1-heptyne | 4-fluoro-methyl-4-trimethyl-siloxy-1-heptyne | 1-trans-tri-n-buty-stannyl-4-fluoro-methyl-4-trimethyl-siloxy-1-heptene |
| trifluoro-acetic acid | n-pentyl | 1,1,1-trifluoro-2-heptanone | 4-trifluoromethyl-4-hydroxy-1-nonyne | 4-trifluoro-methyl-4-trimethyl-siloxy-1-nonyne | 1-trans-tri-n-buty-stannyl-4-trifluoro-methyl-4-trimethyl-siloxy-1-nonene |
| difluoro-acetic acid | n-pentyl | 1,1-difluoro-2-heptanone | 4-difluoromethyl-4-hydroxy-1-nonyne | 4-difluoro-methyl-4-trimethyl-siloxy-1-nonyne | 1-trans-tri-n-butyl-stannyl-4-difluoro-methyl-4-trimethyl-siloxy-1-nonene |
| ethyl fluo-roacetate | n-pentyl | 1-fluoro-2-heptanone | 4-fluoromethyl-4-hydroxy-1-nonyne | 4-fluoro-methyl-4-trimethyl-siloxy-1-nonyne | 1-trans-tri-n-butyl-stannyl-4-fluoro-methyl-4-trimethyl-siloxy-1-nonene |
| trifluoro-acetic acid | n-hexyl | 1,1,1-trifluoro-2-octanone | 4-trifluoromethyl-4-hydroxy-1-decyne | 4-trifluoro-methyl-4-trimethyl-siloxy-1-decyne | 1-trans-tri-n-butyl-stannyl-4-trifluoro-methyl-4-trimethyl-siloxy-1-decene |
| difluoro-acetic acid | n-hexyl | 1,1-difluoro-2-octanone | 4-difluoromethyl-4-hydroxy-1-decyne | 4-difluoro-methyl-4-trimethyl-siloxy-1-decyne | 1-trans-tri-n-butyl-stannyl-4-difluoro-methyl-4-trimethyl-siloxy-1-decene |
| ethyl fluo-roacetate | n-hexyl | 1-fluoro-2-octanone | 4-fluoromethyl-4-hydroxy-1-decyne | 4-fluoro-methyl-4-trimethyl-siloxy-1-decyne | 1-trans-tri-n-butyl-stannyl-4-fluoro-methyl-4-trimethyl-siloxy-1-decene |

Reference Example 50

4-hydroxy-4-methyl-7-oxo-1-octyne

To a stirred solution of propargylmagnesium bromide in 35 ml. of ether, prepared from 7.65 g. (0.3 moles) of magnesium, 170 mg. of mercuric chloride and 33.6 g. (0.28 moles) of propargyl bromide, is added dropwise under argon atmosphere a solution of 25 g. (0.245 moles) of 4-methoxy-2-butanone [L. R. Fedor, J. Am. Chem. Soc., 91:4, 908 (1969)] in 20 ml. of ether at a rate to maintain gentle refluxing. The resulting mixture is stirred at ambient temperature for an additional 30 minutes then quenched at 5° C. by the addition of 140 ml. of saturated ammonium chloride solution. After filtration the ether phase is separated; the aqueous phase is extracted twice with additional ether. The combined ether extracts are washed with saturated sodium chloride solution, dried with anhydrous magnesium sulfate and taken to dryness in vacuo. Distillation of the residual oil provided 13.7 g. (40%) of product; b.p. 84°-85° C. (13 mm.).

Reference Example 51

4-Methyl-4-trimethylsilyloxy-7-oxa-1-octyne

To a solution of 13 g. (0.091 moles) of 4-hydroxy-4-methyl-7-oxa-1-octyne and 16 g. (0.235 moles) of imidazole in 80 ml. of dry dimethylformamide is added dropwise, at 5° C. under nitrogen with stirring, 12.5 ml. (0.115 moles) of trimethylchlorosilane. After an additional 15 minutes at 5° C. the solution is stirred at ambient temperature for 18 hours then added to 450 ml. of hexane. The resulting solution is washed with ice-cold water, ice-cold saturated sodium chloride solution, dried with anhydrous magnesium sulfate and taken to dryness in vacuo. Distillation of the residual oil furnishes 16.8 g. (86%) of product; b.p. 87°-88° C. (7 mm.).

Reference Example 52

E-1-Tri-n-butylstannyl-4-methyl-4-tri-methylsilyloxy-7-oxa-1-octene

To a stirred solution of 15 g. (0.069 moles) of 4-methyl-4-trimethylsilyloxy-7-oxa-1-octyne and 75 mg. of azobisisobutyronitrile is added dropwise, under nitrogen atmosphere, 21.1 g. ( 0.073 moles) of tri-n-butyltin hydride. The solution is stirred at 130°-135° C. for 1½ hours, then cooled to ambient temperature. Distillation provides 29 g. (86%) of product as a colorless oil; b.p. 165°-167° C. (0.25 mm.).

Reference Example 53

4-Hydroxy-4-methyl-7-thia-1-octyne

To a stirred mixture of 6.6 g. (0.275 moles) of magnesium and 116 mg. of mercuric chloride in 35 ml. of ether is added, dropwise under argon atmosphere, 35.2 g. of propargyl bromide (80% solution in toluene) and 25 g. (0.21 moles) of methylmercaptobutane-3-one [D. B. Reisner, J. Am. Chem. Soc., 78, 2132 (1956)] in 100 ml. of ether at a rate to maintain gentle refluxing. After stirring at the reflux temperature for 35 minutes, the cooled mixture is quenched by dropwise addition of 140 ml. of saturated ammonium chloride solution. The ether phase is separated, washed with saturated sodium chloride solution, dried with anhydrous magnesium sulfate and taken to dryness. Distillation of the residual oil provides 27.4 g. (82%) of product as a colorless oil; b.p. 114°–115° C. (7–8 mm.).

Reference Example 54 n-butyl trimethylsilylethynyl ketone

To a stirred solution of 14.4 g. of valeryl chloride and 20.4 g. of bis-trimethylsilylacetylene in 300 ml. of dry methylene chloride, cooled in an ice bath, is added powdered anhydrous aluminum chloride, portionwise, over a period of 20 minutes. The mixture is stirred for 5 minutes, then the cooling bath is removed and the mixture is stirred at room temperature for 4 hours. The mixture is poured into 500 ml. of ice-water. The organic layer is separated, washed with water and brine, dried over anhydrous sodium sulfate and filtered through diatomaceous earth. The mother liquor is evaporated to dryness giving a brownish residue. This residue is Kugelrohr-distilled to give 16.56 g. of colorless liquid at 45° C./0.3 mm which is essentially identical with the authentic product.

Reference Example 55

4-Trimethylsilylethynyl-1-octyn-4-ol

To a stirred suspension of 1.29 g. of magnesium and 10 mg. of mercuric chloride in 12 ml. of ether is added 0.4 ml. of propargyl bromide. The reaction is initiated after stirring at room temperature for a few minutes. The stirred mixture is cooled in an ice-water bath and a solution of 9.64 g. of n-butyl trimethylsilylethynyl ketone and 3.51 ml. of propargyl bromide in 13 ml. of ether is added, dropwise so that the mixture is very gently boiling during 40 minutes. After addition, the cooling bath is removed and the mixture is stirred at room temperature for 1.5 hours. The mixture is re-cooled in an ice-bath and 10 ml. of saturated ammonium chloride solution is added. The resulting white mixture is filtered through diatomaceous earth. The clear mother liquor is washed with saturated sodium chloride solution and dried over anhydrous magnesium sulfate. The solvent is evaporated to dryness giving 10.5 g. of a red liquid. This liquid is Kugelrohr-distilled at 60° C./0.25–0.3 mm. The pale yellow liquid distillage which is the desired product weighs 8.5 g.

Reference Example 56

4-Trimethylsilylethynyl-1-octyn-4-ol trimethylsilyl ether

To a stirred mixture of 8.5 g. of 4-trimethylsilylethynyl-1-octyn-4-ol and 6.2 g. of imidazole in 24 ml. of dry dimethylformamide is added, under nitrogen, 5.7 ml. of chlorotrimethylsilane, in a slow stream, via a syringe. The mixture is stirred in an ice-bath for one hour and then at room temperature overnight. The mixture is poured into hexane, washed with saturated sodium bicarbonate solution, water and then brine and dried over sodium sulfate. The solvents are evaporated to dryness giving 11.1 g. of the desired product.

Reference Example 57

4-Trimethylsilylethynyl-4-trimethylsiloxy-1-octen-1-tri-n-butyl stannane

To a mixture of 10 mg. of azobisisobutyronitrile and 2.94 g. of 4-trimethylsilylethynyl-1-octyn-4-ol trimethylsilyl ether is added 2.65 ml. of tri-n-butyl stannane via a syringe. The mixture is stirred and heated under nitrogen in an oil bath at 130° C. for 3 hours and then cooled to room temperature. This mixture is vacuum-distilled through a short-path distillation apparatus to remove a forerun at 40° C./0.4 mm. The yellow oil (pot residue) comprises the desired product.

Reference Example 58

Treatment of the acid chlorides in Table G-1 with bistrimethylsilylacetylene, as described in Example 54, provides the trimethylsilylethynyl ketones of Table G, which upon treatment with propargylmagnesium bromide according to Example 55, provides the diacetyleneic ketones of Table G-1, which upon treatment with chlorotrimethylsilane by the procedure of Example 56 followed by treatment with tri-n-butylstannane according to Example 57, provide the vinylstannanes of Table G-1.

TABLE G-1

| STARTING ACID KOLIDE | TRIMETHYLSILYL-ETHYNYL KETONE | DIACETYLENIC KETONE | VINYLSTANNANE |
| --- | --- | --- | --- |
| 4-oxapentanoyl chloride | 3-oxo-6-oxa-1-trimethylsilyl-1-heptyne | 4-hydroxy-4-trimethylsilylethynyl-7-oxa-1-octyne | 4-trimethyl-silyloxy-4-trimethylsilyl-ethynyl-7-oxa-1-tri-n-butyl-stannyl trans-1-octene |
| 4-oxakeptanoyl chloride | 3-oxo-6-oxa-1-trimethylsilyl-1-nonyne | 4-hydroxy-4-trimethylsiyethynyl-7-oxa-1-decyne | 4-trimethyl-silyloxy-4-trimethylsilyl-ethynyl-7-oxa-1-tri-n-butyl-stannyl trans-1-decene |

Reference Example 59

Treatment of the aldehydes of Table G-2 with propargyl magnesium bromide by the procedure described in U.S. Pat. No. 4,061,670, herein incorporated by reference, provides the propargyl alcohol of the Table. Further transformations as illustrated in U.S. Pat. No. 4,061,670 provides the vinyliodides of Table G-2.

TABLE G-2

| STARTING ALDEHYDE | PROPARGYL ALCOHOL | VINYLIODIDE |
|---|---|---|
| 4-oxapentanol | 4-hydroxy-7-oxa-1-octyne | 4-trimethylsilyloxy-7-oxa-4-vinyl-1-iodo-trans-1-octene |
| 4-oxaheptanal | 4-hydroxy-7-oxa-1-deceyne | 4-trimethylsilyloxy-7-oxa-4-vinyl-1-iodo-trans-1-decene |

Reference Table 60 trans-1- Iodo-oct-1en-4one

To a solution of 6.4 g. of 4-hydroxy-1-iodo-trans-1-octene (U.S. Pat. No. 4,061,671, Ex. 4) in 25 ml. of ether, cooled in an ice-bath under argon, is added dropwise over 15 minutes, 25 ml. of a solution prepared by dissolving 100 g. of sodium dichromate dihydrate in 300 ml. of water, followed by 136 g. of sulfuric acid with ice-bath cooling and subsequent dilution to 500 ml. After addition, the mixture is stirred at room temperature for 2 hours and diluted with ether. The ether phase is separated and saved. The aqueous phase is extracted with ether. The ether solutions are combined, washed with saturated sodium chloride solution, 5% sodium thiosulfate solution, twice with saturated sodium chloride solution, dried over magnesium sulfate and taken to dryness, giving the product as an orange oil.

Reference Example 61

4-Deutero-4-hydroxy-1-iodo-trans-1-octene

To a solution of 5.93 g. of trans-1-iodo-oct-1-en-4one in 100 ml. of deuterium ethoxide cooled in an ice-salt bath (0° C.) under argon, is added with stirring, 2.0 g. of sodium borodeuteride portionwise over 10 minutes. The mixture is stirred at 0° to 5° C. for 1¾ hours and then diluted with 300 ml. of ice and water. Then 5% hydrochloric acid is slowly added at 0° to 5° C. until the mixture is acidic. Ether is added, the mixture is stirred for 5 minutes and the ether layer is separated and saved. The aqueous layer is extracted with ether. The ether solutions are combined, washed three times with saturated sodium chloride solution, dried over sodium sulfate, refrigerated overnight, filtered and taken to dryness, giving the product as a pale yellow oil.

Reference Example 62

4-Deutero-4-triethylsilyloxy-1-iodo-trans-1-octene

To a solution of 5 g. of 4-deutero-4-hydroxy-1-iodo-trans-1-octene in 40 ml. of dry dimethylformamide is added 3.4 g. of imidazole. This solution is cooled in an ice-bath, under argon and to it is added, with stirring, 4 g. of chlorotriethylsilane in a steady stream. The mixture is stirred in the ice-bath for 30 minutes and then at room temperature overnight and poured into a mixture of 80 ml. of hexane and 80 ml. of ice water. The hexane layer is separated, washed with saturated sodium chloride solution, dried over sodium sulfate and taken to drynes giving the desired product.

Reference Example 63

Treatment of trans-1-iodo-dec-1-en-4-one (U.S. Pat. No. 4,061,471) by the procedures of Examples 61 and 62 is productive of 4-deutero-4-triethylsilyloxy-1-iodo-trans-1-decene.

Reference Example 64

4-Hydroxy-4-methyl-oct-1-yn-7-ene

A mixture of 19.45 g. of magnesium, 0.15 g. of mercuric chloride and 0.5 ml. of 1,2-dibromoethane in 40 ml. of ether, under argon, is stirred for 5 minutes. A 0.5 ml. portion of propargylbromide is added followed by 160 ml. of ether. To the stirred mixture is added dropwise a solution of 60.0 g. of 5-oxo-1-hexene and 87.3 g. of propargyl bromide in 100 ml. of ether, at such a rate as to maintain a vigorous reflux. After addition is complete, the mixture is stirred for 20 minutes, cooled in an ice-bath and a saturated solution of ammonium chloride is added dropwise. The solid is removed by filtration through Celite and washing with ether. The solvent is removed from the filtrate giving the product as an orange liquid.

Reference Example 65

4-Methyl-4-trimethylsilyloxy-oct-1-yn-7-ene

To a mixture of 50 g. of 4-hydroxy-4-methyl-oct-1-yn-7-ene and 61.3 g. of imidazole in 100 ml. of dimethylformamide at 0° C., is added, with stirring, 49.1 g. of trimethylsilyloxy chloride. The mixture is stirred at room temperature overnight and poured into petroleum ether and water. The organic layer is washed with water and saturated sodium bicarbonate solution and dried over magnesium sulfate. The solvent is removed and the residue distilled (74°–78° C., 1.5 mm.) to give the product as a colorless liquid.

Reference Example 66

E-1-Tri-n-butylstannyl-4-methyl-4-trimethylsilyloxy-1,7-octadiene

A mixture of 30 g. of 4-methyl-4-trimethylsilyloxy-oct-1-yn-7-ene, 58.66 g. of tri-n-butylstannane and 200 mg. of azobisisobutyronitrile is placed in a bath at 95° C. and stirred under argon. The mixture is heated at 140° C. for one hour and then at 140° C. under vacuum for 1.5 hours. The mixture is distilled via a Kugelrohr at 140° C., 0.06 mm to give the product as a colorless liquid.

Reference Example 67

1-Hydroxy-hexan-2-one

To a mixture of 25 g. of valeryl chloride and 97.06 g. of tris-trimethylsilyloxyethylene is added 9 drops of stannic chloride. The mixture is stirred until the exotherm reaches 55° C., then placed in an ice-bath. The exotherm continues to about 70° C. When the temperature begins to fall, the mixture is removed from the ice-bath and stirred for 3.5 hours, then slowly poured into a mixture of 50 ml. of 0.6N hydrochloric acid and 100 ml. of tetrahydrofuran. This mixture is stirred for one hour, then saturated with sodium chloride and extracted with ether. The ether is washed with saturated sodium bicarbonate solution, dried over magnesium sulfate and evaporated, giving the desired product as a light yellow oil.

Reference Example 68

1-Triethylsilyloxy-hexan-2-one

To a solution of the crude 1-hydroxy-hexan-2-one (prepared in Example 1) in 80 ml. of dimethylformamide at 0° C. is added with stirring, 40.8 g. of imidazole and 45.21 g. of chlorotriethylsilane. The mixture is stirred at 0° C. for 5 minutes and then at room temperature overnight, then poured into cold water and extracted with petroleum ether. The petroleum ether solution is washed with water, then saturated sodium bicarbonate solution and then dried over magnesium sulfate. The solvent is removed and the residue is distilled. The fraction boiling at 95°-103° C. (0.7 mm.) is collected giving the desired product as a cloudy colorless liquid.

Reference Example 69

4-Hydroxy-4-triethylsilyloxymethyl-1-octyne

A mixture of 3.8 g. of magnesium and 50 mg. of mercuric chloride in 40 ml. of ether is stirred under argon. To this is added 10 drops of dibromoethane and 1 ml. of propargyl bromide. This mixture is stirred until the reaction is initiated (15 minutes), then a solution of 30.0 g. of 1-triethylsilyl-oxy-hexan-2-one and 18.55 g. of propargyl bromide in 30 ml. of ether is added dropwise, at a rate to maintain reflux. After addition is complete, the mixture is refluxed ½ hour, then cooled to −5° C. and a saturated solution of ammonium chloride is added. The mixture is filtered through Celite and the solids are washed with ether. The ether is filtered and then evaporated giving the desired product as a yellow oil.

Reference Example 70

4-Triethylsilyloxymethyl-4-trimethylsilyloxy-1-octyne

To a solution of the 4-hydroxy-4-triethylsilyloxymethyl-1-octyne (prepared in Example 3) and 23.9 g. of imidazole in 50 ml. of dimethylformamide at 0° C., is added with stirring, 21.2 g. of chlorotrimethylsilane. The mixture is stirred for 75 minutes, then poured into ice water and extracted with hexane. The hexane layer is washed with water, then saturated sodium bicarbonate solution, dried over magnesium sulfate and the hexane is removed. The residue is distilled. The fraction boiling at 133°-136° C. (1.2 mm.) is collected giving the desired product as a colorless liquid.

Reference Example 71

E-4-Triethylsilyloxymethyl-4-trimethylsilyloxy-1-tri-n-butylstannyl-1-octene

A mixture of 20.0 g. of 4-triethylsilyloxymethyl-4-trimethylsilyloxy-1-octyne, 18.18 g. of tri-n-butylstannane and 70 mg. of azobisisobutyronitrile is stirred under argon and placed in a bath at 100° C. After 5 minutes an exotherm ensues. The mixture is heated at 130°-140° C. for one hour and then the excess tri-n-butylstannane is removed at 130° C. and reduced pressure. The residue is distilled at 130°-140° C., 0.03 mm. in a Kugelrohr apparatus, giving the desired product as a colorless liquid.

Reference Example 72

Treatment of the carboxylic acid chlorides of Table H by the procedures of Examples 67, 68, 69 and 70 is productive of the intermediates and vinylstannanes of Table H.

TABLE H

| ACID CHLORIDE | HYDROXYMETHYL KETONE | SILYLOXY KETONE | HYDROXY ALKYNE | SLYLOXY ALKYNE | VINYL STANNANE |
|---|---|---|---|---|---|
| butryl chloride | 1-hydroxy-pentan-2-one | 1-trilethylsilyl-oxy-pentan-2-one | 4-hydroxy-4-triethylsilyl-oxymethyl-1-hyptyne | 4-triethyl-silyloxymethyl-4-trimethyl-silyloxy-1-heptyne | E-4-triethyl-silyloxymethyl-4-trimethyl-silyloxy-1-tributylstannyl-1-heptene |
| hexanoyl chloride | 1-hydroxy-heptan-2-one | 1-triethylsilyloxy-heptan-2-one | 4-hydroxy-4-triethylsilyl-oxymethyl-1-nonyne | 4-triethyl-silyloxymethyl-4-trimethyl-silyloxy-1-nonyne | E-4-triethyl-silyloxymethyl-4-trimethyl-silyloxy-1-tributylstannyl-1-nonene |
| heptanoyl chloride | 1-hydroxy-octan-2-one | 1-triethylsilyloxy-octan-2-one | 4-hydroxy-4-triethylsilyl-oxymethyl-1-decyne | 4-triethyl-silyloxy-methyl-4-trimethyl-silyloxy-1-decyne | E-4-triethyl-silyloxymethyl-4-trimethyl-silyloxy-1-tributylstannyl-1-decene |

Reference Example 73

Preparation of trimethylsilyl-2-trimethylsilyloxy acetate

To a solution of 15 g. (0.197 mol) of glycolic acid in 50 ml. of dry pyridine is poured 32.3 g. (0.2 mol) of 1,1,1,3,3,3-hexamethyldisilazine. After stirring 15 minutes, 10.86 g. (0.1 mol) of trimethylsilyl chloride is added dropwise. The mixture is stirred for one hour and then filtered from a white solid which is washed with petroleum ether. The filtrate and washings are concentrated at reduced pressure at 30° C. The residue is distilled (85°-86°, 15 minutes) to give 38 g. of the title compound.

Reference Example 74

Preparation of tris-trimethylsilyloxyethylene

To a solution of 50.98 g. (0.316 mol) of 1,1,1,3,3,3-hexamethyldisilazine in 250 ml. of tetrahydrofuran is added with stirring under argon at 0° C. dropwise 133.3 ml. (0.32 mol) of 2.4M n-butyl lithium in hexane. After addition is complete the solution is maintained at 45° C. for 30 minutes. The solution is cooled to −78° and 58.7 g. of trimethylsilyl-2-trimethylsilyloxy acetate (Example 73) is added dropwise. After stirring 30 minutes, 43.2 g. (0.4 mol) of trimethylsilylchloride is added over 10 minutes. The solution is allowed to warm to room temperature over 30 minutes. The solvent is removed at reduced pressure. The residue is mixed with an equal volume of petroleum ether and filtered from the suspended lithium chloride. The solvent is removed and the residue is distilled (70°–75° C., 1.4 minutes) to give 64.65 g. of the title compound.

Reference Example 75

Preparation of 2-[6-(chloroformyl)hexyl]cyclopent-2-en-1-one

To a suspension of 1.94 g. (0.08 mol) of sodium hydride in 100 ml. of tetrahydrofuran is added with stirring under argon dropwise a solution of 17 g. (0.08 mol) of 2-(6-carboxyhexyl)-cyclopent-2-en-1-one in 160 ml. of tetrahydrofuran. After the addition is complete, the mixture is stirred for 1 hour 15 minutes. The mixture is cooled to 0° C. and 13 ml. of oxalyl chloride is added. The mixture is stirred at 0° C. for 30 minutes and at room temperature for 30 minutes. The solution is diluted with 500 ml. of ether and filtered through Celite. The solvent is removed from the filtrate and the residue is extracted with hot hexane twice. The hexane is removed to give 16.0 g. of the title compound.

Reference Example 76

Preparation of 2-(8-hydroxy-7-oxo-octyl)cyclopent-2-en-1-one

A mixture of 6.3 g. of 2-[6-(chloroformyl)hexyl]-cyclopent-2-en-1-one (Example 75) and 16 g. of tris-trimethylsilyloxyethylene (Example 74) are stirred at 90° to 100° C. under argon for one hour. To this mixture is added 25 ml. of dioxane and 10 ml. of 0.6N hydrochloric acid. The mixture is heated at 80° C. for 30 minutes. The mixture is poured into brine and extracted with ether. The ether solution is washed with saturated sodium bicarbonate and dried over magnesium sulfate. The solvent is removed and the residue is chromatographed on a dry column of silica gel eluting with ether containing 2% acetic acid to give 1.7 g. of the title compound ($R_f$=0.45).

Reference Example 77

Preparation of 2-(6-carbodimethyl-t-butylsilyloxyhex-2-cis-en-yl)-4-dimethyl-t-butylsilyloxy-cyclopent-2-en-1-one To 5.0 g. of 2-(6-carboxyhex-2-cis-enyl)-4-hydroxycyclopent-2-en-1-one and 7.5 g. of imidazole in 24 ml. of dimethylformamide is added 10.2 g. of dimethyl-t-butylsilylchloride. The mixture is maintained at 37° C. for 4 hours. The mixture is poured into ice water and extracted with hexane. The hexane solution is washed with saturated sodium bicarbonate and dried over magnesium sulfate. The solvent is removed. Toluene is added and removed. The residue is distilled in a Kugelrohr apparatus (165° C., 0.5–0.1 mm) to give 4.56 g. of the title compound.

Reference Example 77-A

Preparation of 2-(8-hydroxy-7-oxo-2-cis-octenyl)-cyclopent-2-en-1-one

Treatment of 2-(6-carboxy-2-cis-hexenyl)-cyclopenten-1-one by the procedures described in Reference Example 75 and 76 is productive of the title compound.

Reference Example 78

Preparation of 1-(6-carboxyhex-2-cis-enyl)-4-dimethyl-t-butylsilyloxycyclopent-2-en-1-one A solution of 1-(6-carbodimethyl-t-butylsilyloxyhex-2-cis-enyl)-4-dimethyl-t-butylsilyloxycyclopent-2-en-1-one (Example 77) in 40 ml. of acetic acid - tetrahydrofuran - water (4:2:1) is stirred at room temperature for 1.5 hour. The solvents are removed at reduced pressure at 40° C. The residue is dissolved in ether. The ether solution is washed with water, brine, and dried over magnesium sulfate. The solvent is removed. Toluene is added and removed to give 3.1 g. of the title compound.

Reference Example 79

Preparation of 1-[6-(chloroformyl) hex-2-cis-enyl]-4-dimethyl-t-butylsilyloxycyclopent-2-en-1-one To 59.66 g. of 1-(6-carbodimethyl-t-butylsilyloxyhex-2-cis-enyl)-4-dimethyl-t-butylsilyloxycyclopent-2-en-1-one (Example 78) in 300 ml. of tetrahydrofuran containing 0.5 ml. of dimethylformamide at 0° C. under argon with stirring is added over 20 minutes 29.2 ml. of oxalyl chloride in 40 ml. of tetrahydrofuran. After 1.5 hours the solvent is removed at reduced pressure at 35° C. The residue is dissolved in petroleum ether and filtered through Celite. The solvent is removed to give the title compound.

Reference Example 80

Preparation of 1-(8-hydroxy-7-oxo-oct-2-cis-enyl)-4-hydroxy-cyclopent-2-en-1-one A mixture of 59.3 g. of 1-[6(chloroformyl)hex-2-cis-enyl]-4-dimethyl-t-butylsilyloxycyclopent-2-en-1-one (Example 79) and 101.5 g. of tris-trimethylsilyloxyethylene (Example 74) is heated under argon at 90°–95° C. for 3 hours 10 minutes. The reaction mixture is poured into a mixture of 300 ml. of tetrahydrofuran and 140 ml. of 0.6N hydrochloric acid and the resulting mixture is stirred at 70° C. for 2.5 hours. The mixture is poured in brine and extracted with ethyl acetate. The organic layer is washed with saturated sodium bicarbonate and dried over magnesium sulfate. The solvent is removed and the residue is chromatographed on a dry column of silica gel eluting with ethyl acetate. The product bond ($R_f$=0.4) is extracted to give 6.45 g. of the title compound.

Reference Example 81

Preparation of 5-bromopentanoylchloride

To a solution of 97 g. of 5-bromopentanoic acid in 240 ml. of methylene chloride containing 1 ml. of dimethylformamide is added dropwise 76.2 g. of oxalyl chloride. The mixture is stirred one hour at room temperature and 30 minutes at 50° C. The solvent is removed and the residue is distilled twice (75° C., 0.6 minutes) to give 88.2 g. of the title compound.

Reference Example 82

Preparation of 6-bromo-1-hydroxy-2-hexanone

To 191.4 g. of tris-trimethylsilyloxyethylene (Example 74) containing 15 drops of stannic tetrachloride under argon with stirring at 10° C. is added 87 g. of 5-bromopentanoyl chloride (Example 81) dropwise.

After one-half of the acid chloride is added, the mixture is stirred until an exotherm ensues. The remaining acid chloride is added dropwise maintaining the reaction exotherm at 65° C. The mixture is then stirred for 2.5 hours. The mixture is slowly poured into a stirred mixture of 100 ml. of 0.6N hydrochloric acid and 200 ml. of tetrahydrofuran. The mixture is stirred for 30 minutes and poured into brine. The mixture is extracted with ether. The ether solution is washed with saturated sodium bicarbonate and dried over magnesium sulfate. The solvent is removed. The residue is mixed with petroleum ether and cooled in dry ice acetone to induce crystallization. The petroleum ether is decanted and the solid is dried at reduced pressure to give 64.72 g. of the title compound.

Reference Example 83

Preparation of
6-bromo-1-dimethyl-t-butylsilyloxy-2-hexanone ethylene ketal

A mixture of 84 g. of 6-bromo-1-hydroxy-2-hexanone (Example 81), 240 ml. of ethylene glycol, and 1.7 g. of p-toluenesulfonic acid is refluxed in 1800 ml. of toluene using a Dean-Stark trap for 1 hour 45 minutes. The mixture is cooled to room temperature and washed with saturated sodium bicarbonate, water, and brine. The solvent is removed giving 75.17 g. of a yellow oil. To a 27.36 g. portion of this material and 16.2 g. of imidazole in 57 ml. of dimethylformamide at 0° with stirring is added 20.55 g. of dimethyl-t-butylchlorosilane. The mixture is stirred at room temperature for 1.5 hour and then poured into water. The mixture is extracted with petroleum ether. The organic phase is washed with dilute hydrochloric acid, saturated sodium bicarbonate and dried over magnesium sulfate. The solvent is removed and the residue is distilled in a Kugelrohr apparatus (0.5–0.2 mm., 100°–110° C.) to give 35.25 of the title compound.

Reference Examples 84

Preparation of 1-dimethyl-t-butylsilyloxy-2-hexanone ethylene ketal 6-triphenylphosphonium bromide A mixture of 35.25 g. of 6-bromo-1-dimethyl-t-butylsilyloxy-2-hexanone ethylene ketal (Example 83) and 26.2 g. of triphenylphosphine in 68 ml. of acetonitrile is refluxed 90 hours. The acetonitrile is removed at reduced pressure. The residue is washed three times with ether and dried at reduced pressure to give 53.8 g. of the title compound.

Reference Example 85

Preparation of
2,5-dihydro-2,5-dimethoxy-2-(9-dimethyl-t-butylsilyloxy-8-oxonon-3-cis-enyl) furan A suspension of 2.3 g. (0.096 mol) of oil-free sodium hydride is stirred under argon at 65° C. in 75 ml. of dimethylsulfoxide. After gas evolution ceased (1 hour), at 0° C., is added 53.8 g. (0.086 mol) of 1-dimethyl-t-butylsilyloxy-2-hexanone ethylene ketal 6-triphenylphosphonium bromide (Example 84) in 160 ml. of dimethylsulfoxide. After stirring 15 minutes at room temperature, 16.3 g. (0.037 mol) of 2,5-dihydro-2,5-dimethoxy-2-(3'-oxoprophyl) furan [U.S. Pat. No. 3,952,033] in 40 ml. of dimethylsulfoxide is added. After stirring one hour at room temperature, the solvent is removed at reduced pressure at 55° C. The solid residue is extracted with an ether-petroleum ether mixture. The solution is washed with water, saturated sodium bicarbonate and dried over magnesium sulfate. The solvent is removed and petroleum ether is added. After standing 30 minutes, the triphenylphosphine oxide is removed by filtration. The solvent is removed and the residue is chromatographed on a dry column of florisil eluting first with hexane and then with hexane-ether 5:1 to give 13.2 g. of the title compound.

Reference Example 86

Preparation of
2-(8-dimethyl-t-butylsilyloxy-7-oxo-oct-2-cis-enyl)-4-hydroxycyclopent-2-en-1-one,7-ethylene ketal A mixture of 66.08 g. of 2,5-dihydro-2,5-dimethoxy-2-(9-dimethyl-t-butylsilyloxy-8-oxonon-3-cis-enyl) furan (Example 85), 26.4 g. of sodium dihydrogen phosphate, 5.2 g. of sodium acetate and 0.5 g. of hydroquinone in 1320 ml. of dioxane and 660 ml. of water is stirred at reflux under argon for 22 hours. The mixture is cooled to room temperature, saturated with sodium chloride, and the organic layer is separated. The aqueous layer is extracted with ether. The combined organic solutions are washed with brine and dried over magnesium sulfate. The solvent is removed to give 57.5 g. of an oil. To this is added 300 ml. of ether, 300 ml. of petroleum ether and 22 g. of anhydrous chloral. The solution is stirred under argon and 23 g. of triethylamine is added. After 1 to 40 minutes, the solution is washed with water, dilute hydrochloric acid, saturated sodium bicarbonate, brine, and dried over magnesium sulfate. The solvent is removed and the residue is chromatographed on a dry column of silica gel eluting with ethylacetate-hexane 1:1 to give 14.55 g. of the title compound ($R_f$=0.4).

Reference Example 87

Preparation of
2-(8-dimethyl-t-butylsilyloxy-7-oxo-oct-2-cis-enyl)-4-trimethylsilyloxycyclopent-2-en-1-one, 7-ethylene ketan A mixture of 14.5 g. (0.0367 mol) of 2-(8-dimethyl-t-butylsilyloxy-7-oxo-oct-2-cis-enyl)-4-hydroxycyclopent-2-en-1-one, 7-ethylene ketal (Example 86) and 3.34 g. (0.04 mol) of imidazole in 30 ml. of dimethylformamide is stirred as 4.98 g. (0.047 mol) of timethylsilylchloride is added. After one hour, the mixture is poured into water and extracted with hexane. The hexane solution is washed with water, saturated sodium bicarbonate, and dried over magnesium sulfate. The solution is filtered through a pad of silica gel. The solvent is removed and the residue is dried at reduced pressure to give 12.5 g. of the title compound.

Reference Example 88

Preparation of
2-[6-(4-methoxy-2,2-dimethyl-1,3-dioxolan-4-yl)hex-2-cis-enyl]-4-(2-methoxypropyl-2-oxy) cyclopent-2-en-1-one A mixture of 2-(8-hydroxy-7-oxo-oct-2-cis-enyl)-4-hydroxycyclopent-2-en-1-one (Example 80), 14 ml. of 2 methoxypropene, and 0.23 g. of ammonium nitrate in 35 ml. of benzene is added 7 ml. of dimethoxypropane. P-toluenesulfonic acid is added in very small portions until TLC indicates the reaction is initiated. The mixture is stirred 1.5 hour at room temperature, 40° C. for 15 minutes, and another 30 minutes at room temperature. To the stirred solution is added 50 g. of crushed 4A molecular sieve. After 15 minutes, the solution is filtered, washed with saturated sodium bicarbonate, and dried over sodium sulfate. The solvent is removed and the residue is chromatographed on a dry column of silica gel eluting with ether-hexane 1:1. The product bond ($R_f$=0.5) is extracted to give 3.44 g. of the title compound.

Reference Example 89

By the sequence of reactions described hereinabove for Reference Examples 75 and 76 or 77 through 80, and the protection reaction described hereinabove in Reference Example 88, the protected cyclopent-2-en-1-one listed in Table I hereinbelow are prepared from the indicated carboxylic acids.

TABLE I

| Example | Carboxylic acid | Protected cyclopent-2-en-1-one |
|---|---|---|
| 89 | 2-(6-carboxyhexyl)cyclopent-2-en-1-one | 2-[6-(4-methoxy-2,2-dimethyl-1,3-dioxolan-4-yl)-hexyl]cyclopent-2-en-1-one |
| 90 | 2-(6-carboxyhex-2-cis-enyl)-cyclopent-2-en-1-one | 2-[6-(4-methoxy-2,2-dimethyl-1,3-dioxolan-4-yl)-hex-2-cis-enyl]cyclopent-2-en-1-one |
| 91 | 2-(6-carboxyhexyl)-4-hydroxy-cyclopent-2-en-1-one | 2-[6-(4-methoxy-2,2-dimethyl-1,3-dioxolan-4-yl)-hexyl]-4-(2-methoxypropyl-2-oxy)cyclopent-2-en-1-one |
| 92 | 2-(6-carboxyhex-2-cis-enyl)-4(R)-hydroxycyclopent-2-en-1-one | 2-[6-(4-methoxy-2,2-dimethyl-1,3-dioxolan-4-yl)-hex-2-cis-enyl]-4(R)-(2-methoxypropyl-2-oxy)cyclopent-2-en-1-one |
| 93 | 2-(6-carboxyhexyl)-4(R)-hydroxycyclopent-2-en-1-one | 2-[6-(4-methoxy-2,2-dimethyl-1,3-dioxolan-4-yl)-hexyl]-4(R)-(2-methoxypropyl-2-oxy)cyclopent-2-en-1-one |

Reference Example 94

Preparation of 2-(8-hydroxy-7-oxo-octyl)cyclopent-2-en-1-one-7-ethylene ketal

A solution of 5.5 g. of 2-(8-hydroxy-7-oxo-octyl)cyclopent-2-en-1-one (Example 88), 25 ml. of ethylene glycol, and 0.1 g. of P-toluenesulfonic acid in 200 ml. of toluene is refluxed for 40 minutes using a Dean-Stark trap. The solution is poured into saturated sodium bicarbonate. The mixture is extracted with benzene. The organic solution is washed three times with water and dried over magnesium sulfate. The solvent is removed to give 6.0 g. of the title compound.

Reference Example 95

Preparation of 2-(8-trimethylsilyloxy-7-oxo-octyl)cyclopent-2-en-1-one,7-ethylene ketal To a solution of 2.2 g. of 2-(8-hydroxy-7-oxo-octyl)-cyclopent-2-3n-1-one, 7-ethylene ketal (Example 94) in 20 ml. of pyridine is added 4.6 ml. of 1,1,1,3,3,3-hexamethyldisilazide and, dropwise, 2.3 ml. of trimethylsilylchloride. After 15 minutes, the excess reagents and solvent are removed at reduced pressure. The residue is taken up in ether and filtered through a short pad of silica gel. The solvent is removed. Toluene is added and removed. The residue is dried at reduced pressure to give 2.77 g. of the title compound.

Reference Example 96

Preparation of 2(8-hydroxy-7-oxo-2-cis-octenyl)-4-hydroxy-cyclopent-2-en-1-one, 7-ethylene ketal A mixture of 3.9 g. of 2-(8-hydroxy-7-oxo-2-cis-octenyl)-4-hydroxycyclopent-2-en-one, 33 ml. of ethylene glycol and 1.5 mg. of Amberlyst ® was stirred at room temperature for 3 hours. The mixture was filtered and the filtrate was treated with 1.5 g. of Amberlyst ® 15 and stirred at room temperature for two hours. At this point, an additional 1.0 g. of Amberlyst ® 15 was added and the mixture was stirred at room temperature for approximately another 12 hours. The mixture was diluted with ethylacetate and filtered. The filtrate was added to an equal volume of toluene and the mixture was well shaken. The organic extract was washed with sodium bicarbonate, water and brine and dried. Evaporation of the solvent in vacuo to dryness gave 2.5 g. of the title product as a yellow oil.

The aqueous phase was extracted three times with ethylacetate. The ethylacetate extract was diluted with approximately 50 ml. of toluene to separate out the ethylene glycol and washed with water and brine, and finally dried over anhydrous sodium sulfate. Evaporation of the solvent was productive of 1.8 gm. of the title product as a yellow oil.

Reference Examples 97-101

Treatment of the keto-cyclopentenones of Table J with ethylene glycol and Amberlyst ® 15 Ion Resin by the procedure described in Reference Example 96 is productive of the ketal-cyclopentenones of Table J.

TABLE J

| Example | Keto-cyclopentenones | Ketal-cyclopentenones |
|---|---|---|
| 97 | 2-(8-hydroxy-7-oxo-octyl)-4-hydroxycyclopent-2-en-1-one | 2-8(-hydroxy-7-oxo-octyl)-4-hydroxycyclopent-2-en-1-one, 7-ethylene ketal |
| 98 | 2-(8-hydroxy-7-oxo-octyl)-4(R)-hydroxycyclopent-2-en-1-one | 2-(8-hydroxy-7-oxo-octyl)-4(R)-hydroxycyclopent-2-en-1-one, 7-ethylene ketal |
| 99 | 2-(8-hydroxy-7-oxo-2-cis-octenyl)-4(R)-hydroxycyclopent-2-en-1-one | 2-(8-hydroxy-7-oxo-2-cis-octenyl)-4(R)-hydroxycyclopent-2-en-one, 7-ethylene ketal |
| 100 | 2-(8-hydroxy-7-oxo-octyl)-cyclopent-2-en-1-one | 2-(8-hydroxy-7-oxo-octyl)-cyclopent-2-en-1-one, 7-ethylene ketal |
| 101 | 2-(8-hydroxy-7-oxo-2-cis-octenyl)-cyclopent-2-en- | 2-(8-hydroxy-7-oxo-2-cis-octenyl)-cyclopent-2-en-1-one, 7-ethylene ketal |

TABLE J-continued

| Example | Keto-cyclopentenones | Ketal-cyclopentenones |
|---|---|---|
| | 1-one | |

Reference Example 102

Preparation of
2-[8-trimethylsilyloxy-7-(ethylenedioxy-2-cis-octenyl]-4-trimethylsilyloxy-cyclopent-2-en-1-one To stirred solution of 2[8-hydroxy-7-oxo-2-cis-octenyl]-4-hydroxycyclopent-2-en-1-one, 7 ethylene ketal, pyridine and hexamethyldisilazane cooled in an ice-water bath, was added trimethylsilylchloride dropwise via a syringe. Upon addition of the trimethylsilylchloride, white solid precipitated. The mixture was stirred at room temperature for about 15 hours. The mixture was then diluted with toluene and evaporated to dryness. The residue was then diluted with toluene and evaporated to dryness. The residue was finally treated with hexane and filtered through Celite, and the hexane solution was concentrated in vacuo to give 3.5 g. of the titled product as a yellow oil.

Reference Examples 103–107

Treatment of the ketal cyclopentenones of Table K with chlorotrimethylsilane by the procedure of Reference Example 102 is productive of the silylether-ketals of the Table.

After 30 min., TLC (ethyl acetate, 2,4-DNP) shows no starting material, minor spots at RF=0.5 and 0.6, and a major spot at $R_f$=0.78. After 1 hr. total time, another 0.1 ml. of dichloroacetic acid is added. After a total reaction time of 2 hrs., the solution is diluted with 650 ml. of hexane. The solution is washed with 50 ml. of saturated $NaHCO_3$ and brine, the solution is dried ($K_2CO_3$,$MgSO_4$) and 0.05 ml. of pyridine is added. The solvents are removed giving 48.4 g. (97% of Anal. Calcd for $C_{21}H_{36}O_6$: C, 65.60; H, 9.44. Found: C, 65.35; H, 9.45.

PMR: δ ($CDCl_3$), 7.06 (m, 1H, enone), 4.92 (m, 1H, C$\underline{H}$O), 4.00 (s. 2H, C$\underline{H}_2$O), 3.22 (s, 3H, $OCH_3$), 3.18 (s, 3H, $OCH_3$), 2.62, 2.40, 2.16 (m's, 6H, $CH_2$'s), 1.36 (m, 20H, $CH_2$'s, $CH_3$'s). IR: (neat) 5830 nm.

Reference Examples 109–113

In accordance with the reaction sequence of the Reference Examples 76–80 and the protective reaction of Reference Example 108, the protected cyclopent-2-en-1-ones listed in Table L hereinbelow are prepared from the indicated carboxylic acids.

TABLE L

| EXAMPLE | Carboxylic acid | Protected cyclopent-2-en-1-one |
|---|---|---|
| 109 | 2-(6-carboxyhexyl)cyclopent-2-en-1-one | 2-[8-(1-methoxy-1-methylethoxy)-7-oxo-octyl]cyclopent-2-en-1-one |
| 110 | 2-(6-carboxyhex-2-cis-enyl)-cyclopent-2-en-1-one | 2-[8-(1-methoxy-1-methylethoxy)-7-oxo-oct-2-cis-enyl]cyclopent-2-en-1-one |
| 111 | 2-(6-carboxyhex-2-cis-enyl)-4-(R)-hydroxycyclopent-2-en-1-one | 2-[8-(1-methoxy-1-methylethoxy)-7-oxo-oct-2-cis-enyl] 4R-(1-methoxy-1-methylethoxy)cyclopent-2-en-1-one |
| 112 | 2-(6-carboxyhexyl)-4-(R)-hydroxycyclopent-2-en-1-one | [8-(1-methoxy-1-methylethoxy)-7-oxo-octyl] 4R-(1-methoxy-1-methylethoxy)cyclopent-2-en-1-one |
| 113 | 2-(6-carboxyhexyl)-4-hydroxy-cyclopent-2-en-1-one | 2-[8-(1-methoxy-1-methylethoxy)-7-oxo-octyl] 4-(1-methoxy-1-methylethoxy)cyclopent-2-en-1-one |

TABLE K

| REFERENCE EXAMPLES | STARTING KETAL CYCLOPENT-2-EN-1-ONE | PRODUCT SILYLETHER KETAL |
|---|---|---|
| 103 | 97 | 2-[8-trimethylsilyloxy-7-(ethylene dioxy)-octyl] 4-trimethylsilyloxy cyclopent-2-en-1-one |
| 104 | 98 | 2-[8-trimethylsilyloxy-7-(ethylenedioxy)-octyl] 4(R)-trimethylsilyloxy cyclopent-2-en-1-one |
| 105 | 99 | 2-[8-trimethylsilyloxy-7-(ethylenedioxy)-2-cis-octenyl]-4(R)-trimethylsilyloxy cyclopent-2-en-1-one |
| 106 | 100 | 2-[8-trimethylsilyloxy-7-(ethylenedioxy)-octyl] cyclopent-2-en-1-one |
| 107 | 101 | 2-[8-trimethylsilyloxy-7-(ethylenedioxy)-2-cis-octenyl] cyclopent-2-en-1-one |

Reference Example 108

2-[8-(1-Methoxy-1-methylethoxy)-7-oxo-octyl]4-(1-methoxy-1-methylethoxy)cyclopent-2-en-1-one To a stirred solution of 31.2 g. (130 mmol) of 2-(8-hydroxy-7-oxo-octyl)-4-hydroxycyclopent-2-en-1-one (Example 76)—in 190 ml. of sieve dried $CH_2Cl_2$ is added 47 ml. of 2-methoxy propene (Eastman) followed by 0.1 ml. of dichloroacetic acid. The resulting mild exotherm is maintained at 25° C. by water bath cooling.

Reference Example 114

2-[8-(1-trimethylsilyloxy)-7-oxo-octyl]4-trimethylsilyloxy cyclopent-2-en-1-one

A mixture of 30 g. of 2-(8-hydroxy-7-oxo-octyl) 4-hydroxycyclopent-2-3n-1-one (Example 76), 20 g. of chlorotrimethylsilane and 25 g. of imidazole in 130 ml. dimethylformamide is stirred overnight, poured into water and extracted with petroleum ether. The organic solution is washed with water, then saturated sodium bicarbonate solution and dried over magnesium sulfate. The solvent is removed and the residue distilled via a Kugelrohr giving the desired product as a colorless oil.

References Examples 115–119

In accordance with the reaction sequence of Reference Examples 76–80, the protected cyclopent-2-en-1-ones listed in Table M are prepared from the indicated carboxylic acids.

ing 25 minutes. After stirring at −70° C. for 10 minutes, then at −35° C. for 1.5 hours, the mixture is recooled to −78° C. and added a solution of 1.5 g. of 1-pentynyl-copper and 4.1 ml. of hexamethylphosphorous triamide in 11 ml. of ether during 15 minutes. After stirring at −78° C. for 1.5 hours, to the resulting mixed cuprate solution is added a solution of 2.0 g. (5.2 mmol) of 4-(1methoxy-1-methylethoxy)-2-[8-(1-methoxy-1-methylethoxyl)-7-oxo-octyl]cyclopent-2-en-1-one in 5

TABLE M

| REFERENCE EXAMPLES | CARBOXYLIC ACID | PROTECTED CYCLOPENT-2-EN-1-ONE |
|---|---|---|
| 115 | 2-(6-carboxyhexyl)-4-hydroxy-cyclopent-2-en-1-one | 2-[8-(1-trimethylsilyloxy)-7-oxo-octyl] 4-trimethylsilyloxy cyclopent-2-en-1-one |
| 116 | 2-(6-carboxyhexyl)-4-(R)-hydroxy-cyclopent-2-en-1-one | 2-[8-(1-trimethylsilyloxy)-7-oxo-octyl] 4R-trimethylsilyloxy cyclopent-2-en-1-one |
| 117 | 2-(6-carboxyhex-2-cis-enyl)-4(R)-hydroxycyclopent-2-en-1-one | 2-[8-(1-trimethylsilyloxy)-7-oxo-oct-2-cis-enyl] 4R-trimethylsilyloxy cyclopent-2-en-1-one |
| 118 | 2-(6-carboxyhexyl) cyclopent-2-en-1-one | 2-[8-(1-trimethylsilyloxy)-7-oxo-octyl] cyclopent-2-en-1-one |
| 119 | 2-(6-carboxyhex-2-cis-enyl)-cyclopent-2-en-1-one | 2-[8-(1-trimethylsilyloxy)-7-oxo-oct-2-cis-enyl]] cyclopent-2-en-1-one |

Reference Example 120

1,9-Dioxo-11α,16-dihydroxy-1-hydroxymethyl-16-fluoromethyl-13-trans-prostene

To a stirred solution of 5.42 g. (10.4 mmol) of (E)-1-(tributylstannyl)-4-(fluoromethyl)-4-(trimethylsilyloxy)-1-octene in 5 ml. of dry tetrahydrofuran cooled to −78° C. under argon is added dropwise 4.16 ml. (8.34 mmol) of 2M n-butyllithium in hexane during 10 minutes. The solution is stirred at the same temperature for 10 minutes, then at −40° C. for 2 hours, recooled to −78° C. and then a solution of 1.36 g. (10.4 mmol) of 1-pentynyl-copper and 3.4 g. (20.8 mmol) of hexamethylphosphorous triamide in 15 ml. of ether is added dropwise. The solution is stirred for one hour at −78° C. and 2 g. (5.20 mmol) of 4-(1-methoxy-1-methylethoxy)-2-[8-(1-methoxy-1-methylethoxy)-7-oxo-octenyl]-cyclopent-2-en-1-one in 3 ml. of ether is added. The solution is stirred at −40° C. for one hour, allowed to warm slowly to −20° C. over 20 minutes, recooled to −50° C. and quenched by pouring it into 75 ml. of cold saturated ammonium chloride and 75 ml. of ether. The mixture is stirred for ½ hour, extracted twice with ether and the combined ether extracts are washed with dilute hydrochloric acid, brine, dried with anhydrous magnesium sulfate and taken to dryness furnishing an oil. The oil is treated with 70 ml. of a mixture of acetic acid:tetrahydrofuran:water (4:2:1) for one hour at 40° C., then diluted with toluene and taken to dryness. The residual oil is dissolved in 40 ml. of methanol and extracted with 2–40 ml. portions of heptane which are discarded. Evaporation of the methanol furnishes an oil which is chromatographed on a silica gel column. Elution with ethyl acetate provides the desired product.

Reference Example 121

Preparation of 1,9-dioxo-11α,16-dihydroxy-1-hydroxymethyl-16-trifluoromethyl-13-trans-prostene To a stirred solution of 5.36 g. (9.61 mmol) of E-1-tributylstannyl-4-trifluoromethyl-4-trimethylsilyloxy-1-octene in 5 ml. of THF, cooled in a dry ice-acetone bath, is added 4.8 ml. of n-BuLi (2.0 M in hexane) during ml. of ether during 20 minutes. After stirring at −70° C. for 10 minutes, then at −35° C. for 1.5 hours, the mixture is poured into a cold mixture of 200 ml. of saturated NH4Cl, 200 ml. of ether and 3 ml. of acetic acid and stirred vigorously for 30 minutes. The aqueous phase is separated and extracted with ethyl acetate. The combined organic extract was washed with oil. HCl, water and brine and concentrated in vacuo to give a yellow liquid. This liquid is heated and stirred with 30 ml. of acetic acid, 15 ml. of THF and 7.5 ml. of water at 40° C. for one hour. The mixture is diluted with toluene and concentrated in vacuo to give a greenish liquid. This liquid is applied to 25 g. of silica gel and washed with 200 ml. of hexane followed by 200 ml. of ethylacetate. The ethylacetate solution is concentrated in vacuo to give 3.38 g. of oil. This oil is purified by silica gel dry column chromatography eluting with 60% EtoAc, 0.5% HoAc in hexane. From the column segments is isolated 1.6 g. of 1,9-dioxo-1-hydroxymethyl-11α-hydroxy-16-trimethylsilyloxy-16-trifluoromethyl-13-trans-prostene. This material is heated and stirred with 30 ml. of acetic acid, 15 ml. of THF, 7.5 ml. of water and 5 drops of 4NHCl at 45° C. for 4 hours. The mixture is diluted with toluene and concentrated in vacuo. The concentrate is diluted with ether and washed thoroughly with water and brine and concentrated in vacuo to give an amber oil. This oil is purified by silica gel dry column chromatography eluting with 60% EtoAc, 0.5% HoAc in hexane. From the column segments is isolated 0.9 g. of product 1; Anal. Calcd for $C_{22}H_{35}F_3O_5$: C60.53,H8.08.Found: C60.70,H7.98.

Reference Example 122

1,9-Dioxo-1-hydroxymethyl-11α,16α-dihydroxy-16-chloromethyl-13-trans-prostene and 1,9-dioxo-1-hydroxymethyl-11α,16β-dihydroxy-16-chloromethyl-13-trans-prostene To a stirred solution of 5.56 g. of E-1-tri-n-butylstannyl-4-trimethylsilyloxy-4-chloromethyl-1-octene in 6 ml. of tetrahydrofuran, cooled in a dry ice-acetone bath, is added 4.7 ml. of n-butyllithium (2.2 M. in hexane) during 30 minutes. After stirring at −45° C. for 45 minutes, then at −30° C. for 30 minutes, it is recooled to −78° C. and there is added a solution of 1.35 g. of 1-pentynyl copper and 3.7 ml. of hexamethylphosphoroustriamid in 10 ml. of ether. After stirring at −78° C. for 1.5 hours the resulting mixed cuprate solution is added to a solution of 2.0 g. of 4-(1-methoxy-1-methylethoxy)-2-[8-(1-methoxy-1-methylethoxy)-7-oxo-octenyl]-cyclopent-2-en-1-one in 5 ml. of ether during 20 minutes. After stirring at −45° C. for one hour, then at −30° C. for 20 minutes, it is recooled to −70° C. and quenched by pouring into a cold mixture of 200 ml. of saturated ammonium chloride, 3 ml. of acetic acid and 200 ml. of ether. The organic phase is separated and washed with dilute hydrochloric acid, water and brine and concentrated to give a liquid. The liquid is treated with 30 ml. of acetic acid, 15 ml. of tetrahydrofuran and 7.5 ml. of water and stirred at 40° C. for one hour. It is diluted with toluene and rotary evaporated to dryness to give an amber oil. The oil is applied to a pad of silica gel (25 g. of silic ARCC-7) and washed with 200 ml. of hexane followed by 200 ml. of ethyl acetate. The ethyl acetate solution is concentrated to give 3.7 g. of amber oil which is purified by dry column chromatography (870 g. silica gel) to give 0.98 g. of pure product as a yellow oil: PMR δ5.56 (m, olefin), 4.24 (s, $CH_2OH$), 4.06 (q, J=6, 11-H).

Reference Example 123

1,9-Dioxo-11α,16-dihydroxy-1-hydroxymethyl-16-methyl-17-methylene-13-trans-prostene and the separation of the more polar (L) and less polar (U) isomers To a solution of 6.47 g. of E-4-methyl-5-methylene-4-trimethylsilyloxy-1-tri-n-butylstannyl-1-octene in 5 ml. of tetrahydrofuran at −78° C. under argon is added with stirring 5.78 ml. of 1.8 M. n-butyllithium. After 2.45 hours the solution is cooled to −78° C. and a solution of 1.4 g. of pentynyl copper and 3.39 g. of hexamethylphosphoramide in 30 ml. of ether is added. After one hour 2 g. of 4-(1-methoxy-1-methylethoxy)-2-[8-(1-methoxy-1-methylethoxy)-7-oxo-octenyl] cyclopent-2-en-1-one in 5 ml. of ether is added. The mixture is stirred at −50° C. to −40° C. for ¾ hour, then at −40° to −20° C. for ½ hour and saturated ammonium chloride is added. The mixture is stirred for 15 minutes and then extracted with ether. The ether extract is washed with dilute hydrochloric acid and then with a mixture of saturated ammonium chloride and sodium bicarbonate. The solvent is removed and the residue is stirred for one hour in 50 ml. of a mixture of acetic acid:tetrahydrofuran:water (4:2:1), in a water bath at 45° to 25° C. The solvents are removed at reduced pressure. The residue is partitioned between heptane and methanol. The methanol is removed. The heptane layer is subjected to high pressure liquid chromatography, eluting with ethyl acetate (0.1% acetic acid), giving the desired product in two isomeric forms.

Reference Example 124

1,9-Dioxo-11α,16-dihydroxy-1-hydroxymethyl-17-methylene-5-cis-13-trans-prostadiene To a solution of 4.79 g. of E-5-methylene-4-triethylsilyloxy-1-tri-n-butylstannyl-1-octene in 5 ml. of tetrahydrofuran under argon at −78° C., is added with stirring, 4.0 ml. of 2.2 M. n-butyllithium. After 2 hours at −30° to −20° C. the mixture is recooled to −78° C., and a solution of 1.23 g. of pentynyl copper and 3.2 g. of hexamethylphosphoramide in 25 ml. of ether is added. After one hour at −78° C., there is added 1.63 g. of 4-tetrahydropyranyloxy-2-(8-tetrahydropyranyloxy-7-oxo-2-cis-octenyl)cyclopent-2-en-1-one in 5 ml. of ether. The mixture is maintained at −40° to −30° C. for one hour, then at −25° C. for 10 minutes and then at −20° C. for one hour. The mixture is cooled to −35° C. and 3 ml. of acetic acid followed by saturated ammonium chloride solution are added. The mixture is extracted with ether. The extract is washed with dilute hydrochloric acid, saturated sodium bicarbonate solution and saturated ammonium chloride solution. The ether is removed and the residue is dissolved in 50 ml. of acetic acid:tetrahydrofuran:water(4:2:1) containing 2 drops of concentrated hydrochloric acid, then stirred, under argon at 45° C. for 5 hours and at room temperature overnight. The solvents are removed at 50° C. and reduced pressure. The residue is chromatographed as described in Reference Example 123, giving the desired product as a yellow oil.

Reference Example 125

1,9-Dioxo-11α,16-dihydroxy-1-hydroxymethyl-16-methyl-13-trans-19-prostadiene

To a solution of 5.2 g. of E-1-tri-n-butylstannyl-4-methyl-4-trimethylsilyloxy-1,7-octadiene in 5 ml. of tetrahydrofuran, under argon, is added with stirring, 5.8 ml. of 1.8 M. n-butyllithium at −50° C. The solution is maintained at −20° to −10° C. for 2.5 hours and then cooled to −78° C. A solution of 1.37 g. of pentynyl copper and 3.4 g. of tri-n-butyl phosphine in 30 ml. of ether is added. After one hour, 2 g. of 4-(1-methoxy-1-methylethoxy)-2-[7-oxo-8-(1-methoxy-1-methylethoxy)octyl]cyclopent-2-en-1-one in 5 ml. of ether is added. The solution is stirred at −50° to −30° C. for ½ hour, then at −30° to −20° C. for ½ hour, saturated ammonium chloride is added and the mixture is extracted with ether. The ether layer is washed with dilute hydrochloric acid, saturated sodium bicarbonate solution and saturated ammonium chloride solution. The solvent is removed and the residue is stirred in 50 ml. of a mixture of acetic acid:tetrahydrofuran:water (4:2:1) for two hours. The solvents are removed at reduced pressure at 30° C. and the residue is purified by high pressure liquid chromatography eluting with ethyl acetate: heptane (4:1) and ethyl acetate. The desired product is recovered in purified form.

Reference Example 126

1,9-Dioxo-11α,16-dihydroxy-1-hydroxymethyl-16-methyl-19-chloro-20-nor-13-trans-prostene To a stirred solution of 1.3 g. of E-7-chloro-1-iodo-4-methyl-4-trimethylsilyloxy-1-heptene in 2 ml. of dry toluene at −78° C. under argon is added 1.5 ml. of 2 M. n-butyllithium, dropwise over 5 minutes. The mixture is stirred at −40° C. for 1.5 hours, recooled to −78° C. and a mixture of 0.4 g. of pentynyl copper and 1.0 g. of hexamethylphosphoramide in 9 ml. of ether is added dropwise over 5 minutes. The mixture is stirred for one hour at −78° C. and 1.5 g. of 4-(1-methoxy-1-methylethoxy)-2-[8-(1-methoxy-1-methoxyethyl)-7-oxo-octenyl]cyclopent-2-en-1-one in 5 ml. of ether is added. The mixture is stirred at −50° C. for one hour, allowed to warm slowly to 31 22° to −20° C. over 45 minutes, recooled to −40° C. and 40 ml. of cold saturated ammonium chloride solution and 20 ml. of ether are added. The mixture is stirred ½ hour, extracted twice with ether and the combined ether extracts are washed with two 30 ml. portions of cold dilute hydrochloric acid, 40 ml. of saturated sodium bicarbonate solution and sodium chloride solution, dried over magnesium sulfate, concentrated and stored in a freezer overnight. The resulting oil is stirred with 20 ml. of a mixture of acetic acid:-tetrahydrofuran:water (4:2:1) for one hour at 40° C., and then concentrated on a rotary evaporator, adding toluene frequently to remove the acetic acid. The mixture is diluted with ethyl acetate, washed with saturated sodium bicarbonate solution, dried over magnesium sulfate and chromatographed on a silica gel column, eluting with ethyl acetate;heptane (4:1) to give the desired prouct.

Reference Example 127

11α,16-Dihydroxy-9-oxo-16-dimethoxymethyl-13-trans-prostenoic acid

To a solution of 10.2 g. (18.2 mmol) of 1-tri-n-butyl-stannyl-4-dimethoxymethyl-4-trimethylsiloxy-1-octene in 10 ml. of tetrahydrofuran is added at $-78°$ C. under argon with stirring 8.1 ml. of 2.0 M. n-butyllithium in hexanes. The solution is maintained at $-40°$ to $-35°$ C. for 2 hours. The solution is cooled to $-78°$ C. and a solution of 2.13 g. pentynyl copper and 6.55 g. of tri-n-butyl phosphine in 70 ml. of ether is added. After 45 minutes, a solution of 2-(6-carbotrimethylsiloxyhexyl)-4-trimethylsiloxycyclopent-2-en-1-one in 5 ml. of ether is added. After 0.5 hours at $-45°$ C. and 0.5 hours at $-45°$ to $-20°$ C., the solution is quenched by adding saturated ammonium chloride solution. The mixture is stirred for 30 minutes and extracted with ether. The ether solution is washed with dilute hydrochloric acid. The ether is removed and the residue is stirred in a mixture of acetic acid:tetrahydrofuran:water (4:2:1) for 2 hours. The solvents are removed and the residue is chromatographed on a dry column of silica gel eluting with ethyl acetate:hexane (4:1) 1% acetic acid to give 2.07 g. of the title compound.

Reference Example 128

11α,16-Dihydroxy-9-oxo-16-formyl-13-trans-prostenoic acid

A solution of 1.5 g. of 11α,16-dihydroxy-9-16-dimethoxymethyl-13-trans-prostenoic acid in 40 ml. of acetic acid:tetrahydrofuran:water (4:2:1) containing 5 drops of 4N hydrochloric acid is heated to 45° C. under argon for 2.5 hours. Another 5 drops of 4N hydrochloric acid is added and the mixture is heated one hour. The mixture is diluted with toluene and the solvents are removed at reduced pressure. Toluene is added and removed twice. The residue is chromatographed on a dry column of silica gel eluting with ethyl acetate:hexane (4:1) containing 1% acetic acid to give 0.7 g. of the title compound.

Reference Example 129

Preparation of dl-11α,16-dihydroxy-1-hydroxymethyl-1-(ethylenedioxy)-9-oxo-16-vinyl-5-cis-13-trans-prostadiene To a stirred solution of E-4-trimethylsilyloxy-1-tributylstannyl-4-vinyl-octene in THF, n-butyllithium (2.9 ml., 2.5 M in hexane was added over a 20 minute period. After addition, the mixture was stirred at $-70°$ C. for 15 minutes then at $-40°$ C. to $-50°$ C. for one hour, then at $-30°$ C. to $-40°$ C. for 30 minutes. The mixture was recooled to $-78°$ C. and a solution of copperpentyne 0.93 g. (7.15 mmol), 2.4 ml. of HMPTA (2.4 ml.) and ether 8 ml. was added over a 15 minute period. A yellowish mixture resulted which was stirred in a dry-ice acetone bath for 1½ hours and a solution of 2-[8-trimethylsilyloxy-7-(ethylenedioxy)-2-cis-octenyl]-4-trimethylsilyloxy-cyclopent-2-en-1-one. 1.32 g. (3.1 mmol) in 5 ml. of ether was added over a 15 minute period. The mixture was stirred at $-70°$ C. for 15 minutes, then for one hour at about from 40 to $-50°$ C., and finally at about $-30°$ C. to $-40°$ C. for ½ hour. The mixture was cooled to $-70°$ C. and quenched by pouring the mixture into a cold mixture of 200 ml. of saturated $NH_4Cl$, 100 ml. of ether and 3 ml. of acetic acid. After vigorous stirring for 20 minutes, the aqueous layer was separated and extracted twice with 100 ml. of ethyl acetate. The combined organic extract was with dilute HCl, $H_2O$ and brine and evaporated to dryness. The residue was treated with 20 ml. of acetic acid, 10 ml. of THF and 5 ml. of water and stirred at room temperature for 40 minutes. This mixture was then diluted with toluene and rotary evaporated to dryness. This residue was treated in accordance with the residue treatment steps mentioned above.

Following the second residue treatment steps, the residue was soaked on 15 g. of silica gel and washed with 200 ml. of hexane followed by 200 ml. of ethyl acetate. The hexane extract was discarded. The residue from the ethylacetate extract was purified by dry column silica gel chromatography eluting with ethyl acetate. The product was washed off the silica gel with ethyl acetate, and the solvent evaporated to provide 510 mg. of the title product.

Reference Example 130

Hydrolysis of dl-11α,16-dihydroxy-1-hydroxymethyl-(1-ethylenedioxy)-9-oxo-16-vinyl-5-cis-13-trans-prostadiene to provide dl-1,9-dioxo-11α,16-dihydroxy-1-hydroxymethyl-16-vinyl-5-cis,13-trans-prostadiene A mixture of 14 mg. of 11α,16-dihydroxy-1-hydroxymethyl-(1-ethylenedioxy)-9-oxo-16-vinyl-5-cis, 13-trans-prostadiene, 4 ml. of acetic acid, 2 ml. of THF, 1 ml. of water and one drop of HCl is stirred for 6.5 hours at 48° C. The solution is concentrated and dissolved in ether-ethylacetate. The solution is washed with saturated $NaHCO_3$ and brine. The solution is dried and the solvent is removed to give the title compound.

Reference Example 131

Preparation of dl-9α,11α,16-trihydroxy-1-hydroxymethyl-2-(ethylenedioxy)-16-vinyl-5-cis, 13-trans-prostadiene To a stirred solution of dl-11α,16-dihydroxy-1-hydroxymethyl-1-(ethylenedioxy)-9-oxo-16-vinyl-5-cis,13-trans-prostadiene in THF cooled in an ice bath, Li-selectride$^R$ (Aldrich, 1 m. solution in THF) was added dropwise over a 15 minute period. After stirring the mixture for one hour, 3.7 ml. of 2.5 N NaOH was added dropwise and the mixture was then allowed to warm to 0° C. gradually over a 20 minute period. The mixture was then placed in an ice-water bath and 3 ml. of 30% $H_2O_2$ was added dropwise, and the mixture was stirred in the ice-water bath for 20 minutes. The mixture was then diluted with water and concentrated to remove as much THF as possible. The concentrate was added to ethylacetate. The aqueous phase was then separated and extracted with ethylacetate. The ethylacetate extracts were combined and washed with partially saturated sodium chloride, saturated sodium chloride and then dried. The solvent was evaporated in vacuo to provide 400 mg. of the title product.

Reference Example 132

1,1-Dimethoxy-2-hexanone

A mixture of 36.9 g of washed 50% sodium hydride dispersion (0.77 moles) and 600 ml. of dimethylsulfoxide is heated under argon at 65° C. for 2 hours. At 0° C. is added dropwise, 50 g. (0.38 moles) of ethyl valerate. The solution is stirred at room temperature for 2 hours, then diluted with 1400 ml. of water and 70 ml. of concentrated hydrochloric acid and 75 g. of sodium chloride is added. The mixture is extracted four times with chloroform and the solution is dried (magnesium sulfate charcoal). The solvent is removed. The residue is dissolved in 700 ml. of methanol. A 55.65 g. (0.22 moles) portion of iodine is added and the solution is refluxed 90 minutes. The solvent is removed, the residue is dissolved in chloroform and the solution is washed twice with water and once with saturated sodium thiosulfate. The solution is dried (magnesium sulfate charcoal). The solvent is removed and the residue is distilled twice. The fraction boiling at 64°-72° C., 5 mm. is collected to give 28.3 gm. of the title compound. [T. L. Moore *J. Org. Chem.*, 32 786 (1967)].

Reference Example 133

4-Dimethoxymethyl-4-trimethylsiloxy-1-octyne

To a suspension of 5.31 g. (0.22 moles) of magnesium in 15 ml. of ether is added 100 mg. of mercuric chloride and 1.5 ml. of 1,2-dibromoethane. After the reaction begins, another 45 ml. of ether is added followed by the dropwise addition of a solution of 25 g. (0.16 moles) of 1,1-dimethoxy-2-hexanone and 27.3 g. (0.2 moles) of 85% propargyl bromide in 45 ml. of ether at a rate which maintains reflux. Midway through the addition 15 ml. of tetrahydrofuran is added. After complete addition of the solution, the mixture is refluxed for 40 minutes. The mixture is cooled to 0° C. and saturated ammonium chloride solution is added followed by magnesium sulfate. The mixture is filtered through Celite and the solvent is removed. The residue is dissolved in 53 ml. of dimethylformamide and at 0° C. is added 24.4 g. (0.36 moles) of imidazole and 21.19 g. (0.20 moles) of trimethylchlorosilane. After stirring at 25° C. for 70 minutes, the solution is poured into water and extracted with hexanes. The organic layer is dried over magnesium sulfate and the solvent is removed. Distillation (75°-95° C., 0.3 mm.) gives 17.4 g. of the title compound.

Reference Example 134

E-1-tri-n-Butylstannyl-4-dimethoxymethyl-4-trimethylsiloxy-1-octene

A mixture of 10.0 g. (36.7 mmoles) of 4-dimethoxymethyl-4-trimethylsiloxy-1-octyne, 12.82 g. (44 mmoles) of tri-n-butylstannyl hydride 100 mg. of azobisisobutyronitrile is heated to 140° C. under argon for 2 hours. The excess hydride is distilled off and the residue is purified by molecular distillation (bath temperature = 170°-175° C., 0.2mm.) to give 20.5 g. of the title compound.

TABLE N

| Starting Ester | β-keto-sulfonide | ketoacetal | Trimethylsilyloxy alkyne | trans vinyl stannane |
| --- | --- | --- | --- | --- |
| ethyl butyrate | 4-oxo-2-sulfinyl-neptane | 1,1-dimethoxy-2-pentanone | 4-dimethoxymethyl-4-trimethylsilyloxy-1-heptyne | 1-trans-tri-n-butyl-stannyl-4-dimethoxymethyl-4-trimethyl-siloxy-1-heptene |
| ethyl hexanoate | 4-oxo-2-sulfinyl-nonane | 1,1-dimethoxy-2-heptanone | 4-dimethoxymethyl-4-trimethylsilyloxy-1-nonyne | 1-trans-tri-n-butyl-stannyl-4-dimethoxymethyl-4-trimethyl-siloxy-1-nonene |
| ethyl heptanoate | 4-oxo-2-sulfinyl-decene | 1,1-dimethoxy-2-octanone | 4-dimethoxymethyl-4-trimethylsilyloxy-1-decyne | 1-trans-tri-n-butyl-stannyl-4-dimethoxymethyl-4-trimethyl-siloxy-1-decene |

Reference Example 135

Treatment of the ethyl esters of Table N by the procedure of Reference Example 1 provides the β-ketosulfoxides of the table which are converted to the ketoacetals. Treatment of the ketoacetals of the table with propargyl magnesium bromide, provides the hydroxyalkyne that is protected as the TMS-alkyne of the table by the procedure of Reference Example 2. Hydrostannation by the procedure of Reference Example 3 provides the trans vinylstannanes of Table N.

Reference Example 136

TABLE O

To a solution of the listed vinyltin of Table O in THF (1 ml. per gm.) at −78° C. under argon, with stirring, is added 1.1 equivalents of a 2 molar solution of n-butyllithium in hexane. After 2 hours at −30° C. the solution is recooled to −78° C. and 1 equivalent of copperpentyne and hexamethylphosphoroustriamide (HMPTA) (2.7 ml. per gm. of copperpentyne) in ether (20 ml. per gm. of copperpentyne) are added. After stirring for 45 minutes at −78° C. one-half equivalent of 4-(1-methoxy-1-methylethoxy)-2-[8-(1-methoxy-1-methylethoxy-7-oxo-octyl]cyclopent-2-en-1-one in ether is added. After stirring for one hour at −40° C., the solution is allowed to warm to −20° C. over a 30 minute period. To the stirred mixture is added acetic acid (1 ml. per gm. of the vinyltin) followed by a saturated solution of ammonium chloride.

The mixture is extracted with ether, the ether solution is washed with dilute hydrochloric acid solution followed by saturated sodium bicarbonate solution. The ether layer is separated and the solvent is removed. The residue is stirred in a mixture of THF;H₂O:acetic acid (2:1:4) at 40° C. for one hour. The solvents are removed at reduced pressure. The residue is chromatographed on a dry column of silica gel eluting with ether-ethylacetate 4:1 to provide the listed product of Table O.

TABLE O

| VINYLTIN | PRODUCT COMPOUND |
|---|---|
| E-1-tri-N-butylstannyl-4-methyl-4-trimethylsilyloxy-7-oxa-1-octene (Example 52) | 1,9-dioxo-11α,16-dihydroxy-1-hydroxymethyl-16-methyl-19-oxa-13-trans-prostene |
| E-1-tri-N-butylstannyl-4-dimethoxymethyl-4-trimethyl-siloxy-1-octene | 1,9-dioxo-11α,16-dihydroxy-1-hydroxymethyl-16-dimethoxymethyl-13-trans-prostene |

Reference Example 137

TABLE P

To a solution of the vinyliodide listed in Table P, in ether (3 ml. per gm.) at −78° C. under argon is added with stirring 2 equivalents of 1.6 M t-butyllithium in hexane. After 1½ hours at −78° C. and 30 minutes at −40° C. and 1 equivalent of copperpentyne and hexamethylphosphoroustriamide (HMPTA) (2.7 ml. per gm. of copperpentyne) in ether (20 ml. per gm. of copperpentyne). After stirring for 45 minutes at −78° C. one-half equivalent of 4-(1-methoxy-1-methylethoxy)-2-[8-(1-methoxy-1-methylethoxy-7-oxo-octyl]cyclopent-2-en-1-one in ether is added. After stirring for one hour at −40° C., the solution is allowed to warm to −20° C. over a 30 minute period. To the stirred mixture is added acetic acid (1 ml. per gm. of the vinyltin) followed by a saturated solution of ammonium chloride.

The mixture is extracted with ether, the ether solution is washed with dilute hydrochloric acid solution followed by saturated sodium bicarbonate solution. The ether layer is separated and the solvent is removed. The residue is stirred in a mixture of THF:H₂O:acetic acid (2:1:4) at 40° C. for one hour. The solvents are removed at reduced pressure. The residue is chromatographed on a dry column of silica gel eluting with ether-ethylacetate 4:1 to provide the listed product of Table P.

TABLE P

| VINYLIODIDE | PRODUCT COMPOUND |
|---|---|
| 1-iodo-4-propadienyl-4-trimethylsilyloxy-trans-1-octene (Example 12) | 1,9-dioxo-11α,16-dihydroxy-1-hydroxymethyl-16-allenyl-13-trans-prostene |
| 4-deutero-4-triethylsilyloxy-1-iodo-trans-1-octene (Example 62) | 1,9-dioxo-11α,16-dihydroxy-1-hydroxymethyl-16-deutero-13-trans-prostene |

Reference Example 138

1,2-Dibromo-2-ethoxyethane

To 143 ml. of ethylvinyl ether at −25° C., is added, dropwise with stirring, during 2 hours, 82 ml. of bromine, at such a rate as to maintain the temperature at −10° C. The excess bromine is titrated with a few ml. of ethylvinyl ether. The product is distilled directly from the reaction vessel. After a 30 g. forerun, the main fraction of 266 g. of colorless liquid is collected, b.p. 55°–57° C., 10 mm.

Reference: Zhur. Org. Khim., 2, 1569 (1966). Reference Example 139

1-Bromo-2-ethoxyhexane

To a stirred solution of 1.68 moles of n-butylmagnesium bromide, as a 1.7 M solution in ether, is added dropwise a solution of 300 g. of 1,2-dibromo-2-ethoxyethane in 750 ml. of ether during a period of 2 hours at −15° C. The resulting mixture is stirred for one hour while warming to 20° C., then cooled to 0° C., and treated while stirring with 500 ml. of water, followed by 100 ml. of 4N hydrochloric acid. The organic layer is washed with brine, dried over magnesium sulfate and concentrated. The residue is distilled to provide a colorless liquid, b.p. 83°–84° C., 18 mm.

Reference Example 140

2-Ethoxy-1-hexene

A 17.3 g. portion of 50% sodium hydride in mineral oil is washed free of the mineral oil under a nitrogen atmosphere with three 150 ml. portions of petroleum ether. This sodium hydride is then suspended in 300 ml. of dry dimethylformamide. A solution of 62.7 g. of 1-bromo-2-ethoxyhexane in 150 ml. of dimethylformamide is added followed by one ml. of isopropanol. The mixture is stirred and heated cautiously using an oil bath, starting at 25° C. Upon reaching an internal temperature of 82° C., a vigorous exothermic reaction begins. This reaction is maintained by a water bath at 85° C. to 90° C. When the reaction slows, the mixture is heated externally at 85° C. to 90° C. for 45 minutes. The reaction mixture is cooled to 0° C., treated cautiously with a total of 1.5 liters of water and then extracted with three 400 ml. portions of ether. The organic extracts are combined, washed with three 250 ml. portions of water, then two 250 ml. portions of brine and dried over potassium carbonate. To the organic solution is added 6 drops of pyridine and 100 mg. of hydroquinone. This mixture is filtered and concentrated in vacuo, giving an orange liquid. Distillation of this crude product gives 21 g. of the desired product, b.p. 83°–85° C., 140 mm.

Reference: Chem. Abstr., 54, 8595f.

Reference Example 141

2-Butyl-1-chloro-2-ethoxy-1-fluoro cyclopropane

To a solution of 61.0 g. of 2-ethoxy-1-hexene, 135 ml. of 13.5 M potassium hydroxide and 217 g. of "18-crown -6" ether at −15° C. is added dropwise over 30 minutes at 0°, a 90 ml. portion of dichlorofluoromethene. After the addition, the mixture is placed in an ice bath. An exotherm raises the temperature to 20° C., whereupon the mixture is placed in a dry-ice/carbon tetrachloride bath to matintain the temperature at −5° C. to 0° C. After three hours at this temperature, the reaction mixture is diluted with water and extracted with ether. The ether extracts are combined, washed with water, then brine, dried over potassium carbonate and concentrated in vacuo to an oil. This oil is distilled through a 6 inch Vigreux column to provide 82 g. of the desired compound as a colorless liquid, b.p. 70°–71° C., 16 mm.

Reference Example 142

3,3-Diethoxy-2-fluoro-1-hexene

A stirred solution of 58.4 g. of 2-butyl-1-chloro-2-ethoxy-1-fluorocyclopropane and 166 g. of anhydrous potassium carbonate in 400 ml. of absolute ethanol is heated at reflux for 18 hours. The solution is cooled and the bulk of the ethanol is removed in vacuo. The residue is partitioned with 500 ml. of water and 750 ml. of ether. The ether phase is washed with three 100 ml. portions of brine, dried over potassium carbonate and concentrated in vacuo to provide 54 g. of a pale yellow oil. A 4.45 g. portion of this oil is distilled through a 6 inch Vigreux column giving 2.5 g. of the desired product as a colorless liquid, b.p. 80°-81° C., 24 mm.

Reference Example 143

2-Fluorohex-1-en-2-one

A solution comprising 49 g. of 3,3-diethoxy-2-fluoro-1-hexene, 60 ml. of 4N hydrochloric acid, 720 ml. of tetrahydrofuran and 0.25 g. of hydroquinone is allowed to stand at room temperature for 17 hours. The solution is then concentrated in vacuo to 150 ml. and diluted with ether and brine. The ether layer is washed with brine, dried over magnesium sulfate and concentrated in vacuo giving 28 g. of a light yellow liquid. This liquid is distilled giving 19 g. of the desired compound. (This ketone should be used immediately in the procedure of Example 7 and hydroquinone should be added to the distillate to prevent polymerization.)

Reference Example 144

4-Hydroxy-4-(1'-fluorovinyl)-1-octyne

The grignard reaction is accomplished according to the procedure disclosed in U.S. Pat. No. 4,061,670 which is incorporated herein by reference.

To a stirred suspension of 62 mg. of mercuric chloride and 4.97 g. of magnesium metal shavings in 30 ml. of ether, at room temperature, is added a solution of 29.1 g. of 80% propargyl bromide in toluene in 90 ml. of ether. After the grignard formation is complete, the grignard solution is cooled to −20° C. and a solution of 18.9 g. of 2-fluorohex-1-en-2-one in 65 ml. of ether is added. The reaction mixture is stirred at room temperature for 1.5 hours, recooled to 0° C., quenched cautiously with 5 ml. of saturated ammonium chloride and diluted with 50 ml. of ether. The ether phase is washed with brine, filtered through diatomaceous earth, dried over a mixture of potassium carbonate and magnesium sulfate and concentrated in vacuo, giving 30 g. of an oil. A small amount of potassium carbonate is added to this oil which is then distilled through a 6 inch Vigreux column giving 14 g. of the desired product as a colorless liquid, b.p. 70°-73° C., 14 mm.

Reference Example 145

4-(1'-Fluorovinyl)-4-trimethylsilyloxy-1-octyne

To a stirred 0° C. solution of 13.7 g. of 4-(1-fluorovinyl)-4-hydroxy-1-octyne and 16.1 g. of imidazole in 60 ml. of anhydrous dimethylformamide is added, via a syringe over a 3 minute period, 11.6 ml. of chlorotrimethylsilane. The resulting solution is stirred at room temperature for 18 hours, cooled to 0° C., diluted with 350 ml. of petroleum ether and shaken with 150 ml. of water. The organic phase is separated, washed with six 50 ml. portions of water, then 50 ml. of brine, dried over magnesium sulfate and concentrated in vacuo giving 18.9 g. of the desired product as a colorless liquid.

Reference Example 146

E-4-(1'-Fluorovinyl)-1-tributylstannyl-4-trimethylsilyloxy-1-octene

A mixture of 21.4 ml. of tributylstannane, 18.3 g. of 4-(1'-fluorovinyl)-4-trimethylsilyloxy-1-octyne and azobisisobutyronitrile is heated under an inert atmosphere on an oil bath. Upon reaching 85° C., a rapid exotherm occurs which is moderated to maintain 140° C. using a water bath. After the exotherm the mixture is heated at 135° C. for one hour, then cooled to room temperature. The resulting oil is distilled via a Kugelrohr to give the desired product as 33.68 g. of a light yellow liquid (air bath 160° C., 0.15 mm.).

Reference Example 147 dl-11α,16-Dihydroxy-9-oxo-16-(1-fluorovinyl)-13-trans-prostene

To a stirred solution of 5.39 g. of (E)-1-(tri-n-butylstannyl)-4-(1'-fluorovinyl)-4-(trimethylsilyloxy)-1-octene in 5 ml. of dry tetrahydrofuran, cooled to −78° C. in an argon atmosphere, is added dropwise, during 10 minutes, 5.06 ml. of 1.92M n-butyllithium in hexane. The resulting solution is stirred at −78° C. for 10 minutes, then at −35° C. for 2½ hours. The solution is recooled to −78° C. and a solution of 1.32 g. of 1-pentynylcopper and 5.04 ml. of tri-n-butylphosphine in 15 ml. of ether is added during 10 minutes. The resulting solution, containing lithiopentynyl [(E)-4-(1'-fluorovinyl)-4-(trimethylsilyloxy)-1-octenyl]cuprate is stirred at −78° C. for one hour at which time 3 g. of 4-(trimethylsilyloxy)-2-(6'-carbotrimethylsilyloxyhexenyl)-cyclopent-2-en-1-one in 3 ml. of ether is added during 10 minutes. The solution is stirred at −78° C. for 10 minutes, then at −35° C. for 2 hours, recooled to −55° C. and quenched by pouring into 100 ml. of cold saturated ammonium chloride solution and 100 ml. of ether.

The ether layer is separated and saved. The aqueous layer is extracted twice with ether. The combined organic extracts are washed with dilute hydrochloric acid, then brine, dried with anhydrous sodium sulfate and taken to dryness, leaving an oil. This oil is treated with 60 ml. of acetic acid, 30 ml. of tetrahydrofuran and 15 ml. of water, stirred at room temperature for one hour, then diluted with toluene and taken to dryness.

The residual oil is dissolved in 45 ml. of methanol and the resulting solution is extracted twice with 45 ml. portions of heptane. The extracts are discarded. The methanol solution is taken to dryness leaving 5.64 g. of oil. This oil is applied to a 2 inch flat dry column containing 750 g. of silica gel and developed with ethyl acetate:hexane:acetic acid (60:40:1). The bottom 20 inches of the column is removed and discarded. The remainder of the column is divided into one inch segments. Segments 20-25 are combined to provide 392 mg. of the desired product as an oil.

Reference Example 148 dl-11α,16-dihydroxy-9-oxo-16-(1-fluorovinyl)-5-cis,13-trans-prostadiene

To a stirred solution of 8.7 g. of (E)-1-tri-n-butylstannyl)-4-(1'-fluorovinyl)-4-trimethylsilyloxy-1-octene in 10 ml. of dry tetrahydrofuran, cooled to −78° C. under an argon atmosphere, is added dropwise over a period of 15 minutes, 7.7 ml. of 1.92M n-butyllithium. The resulting solution is stirred at −78° C. for 20 minutes, then at −45° C. to −35° C. for 2½ hours. The solution is recooled to −78° C., and a chilled solution of 2.9 g. of pentynylcopper and 9.0 g. of tri-n-butylphosphine in 20 ml. of dry ether is added dropwise over a period of 5 minutes. This turbid solution is stirred at −78° C. for 1½ hours. A solution of 4.0 g. of 4-(trimethylsiloxy)-2-(6'-carbotrimethylsiloxy-2'-(cis)-hexenyl)cyclopent-2-en-1-one in 10 ml. of dry ether is chilled in a dry-ice/acetone bath and added dropwise during a period of 5 minutes. This solution is stirred at −78° C. for 20 minutes, then at −45° C. to −35° C. for one hour, then slowly allowed to warm to −23° C. over a period of 45 minutes. The solution is recooled to −78° C. and the reaction is quenched by pouring the solution into an ice cold mixture of 200 ml. of saturated ammonium chloride solution and 200 ml. of ether. The mixture is stirred rapidly for 20 minutes, then stored in a refrigerator overnight.

The layers are separated and the aqueous layer is extracted with two 250 ml. portions of ethyl acetate. The combined organic layers are washed with 250 ml. of cold dilute hydrochloric acid and then twice with 250 ml. of a solution of 50% saturated ammonium chloride and 50% saturated sodium bicarbonate, dried over magnesium sulfate and concentrated in vacuo. The resulting oil is treated with 80 ml. of glacial acetic acid, 40 ml. of tetrahydrofuran and 20 ml. of water and stirred in an argon atmosphere at room temperature for one hour. A 75 ml. portion of toluene is added and the mixture is concentrated in vacuo, using a water bath at 34°–35° C. to one-half its volume. Another 50 ml. of toluene is added and the above concentration is repeated. Toluene (25 ml.) is added twice more, the mixture, however, being concentrated to an oil after each addition. The remaining oil is partitioned between 50 ml. of heptane and 50 ml. of methanol. The methanol layer is saved and the heptane layer is extracted with an additional 10 ml. of methanol. The combined methanol layers are concentrated in vacuo to an oil. This oil is dissolved in 10 ml. of a mixture of ethyl acetate:hexane:acetic acid (80:20:0.1) and put on a Waters Co. preparative high pressure liquid chromatograph (model 500) via a syringe. The instrument is loaded with a pre-packed silica gel column (Waters Co.). The above described solvent mixture is pumped through the column at a rate of 250 ml. per minute, collecting 500 ml. fractions. The product starts to come off after 800 ml. has been eluted and after an additional 2 liters, the elution of the product is essentially complete. This includes some less and more polar impurities. Some toluene is added to each fraction. The fractions are then concentrated giving a total of 0.5 g. of crude oil. This oil is recolumned on 750 g. of dry column silica gel using a 2 inch flexible dry column tube and a solvent mixture of 70 parts ethyl acetate, 30 parts heptane and one part acetic acid. The oil is dissolved in 5 ml. of solvent and transferred to the column. The solvent is allowed to elute to the bottom of the column. The bottom 6 inches of the 62 inch column is cut off and discarded. The remainder of the column is cut into one inch segments. The product, (290 mg.) a mixture of two epimers, is collected in fractions 21–28. It is shown by C-13 n.m.r. spectroscopy to be a 40:60 mixture of upper to lower epimers.

Reference Example 150

Preparation of 3-vinyl-3-trimethylsilyloxy-1-tri-n-butylstannyl-1-octene

A mixture of the product of reference example 149, tin hydride and azobisisobutyronitrile was stirred under argon and placed in a bath at 100° C. After about 10 minutes an exotherm ensued. The mixture was stirred for 1.5 hours at 140° C. The excess tin hydride was removed by stirring at 130° under vacuum. The residue was distilled via Kugelrohr (0.04 mm 145°–155°) to provide 24.9 gms of title product as a colorless liquid.

Reference Example 149

Preparation of 3-vinyl-3-trimethylsilyloxy-1-octyne

Acetylene (dried using $H_2SO_4$ & KOH) was bubbled into 300 ml. of THF at 0° while a solution of the n-butylmagnesium chloride was added dropwise over 1.5 hr. After addition was complete a solution of the 3-oxo-1-octene in 100 ml. of THF was added dropwise over 15 min. The ice in the bath was allowed to melt slowly and the solution was stirred at room temperature overnight.

The mixture was cooled to 0° and 50 ml. of saturated $NH_4Cl$ was added dropwise with stirring. The mixture was filtered through celite, dried over magnesium sulfate and filtered again through Celite. The solvent was removed and the residue was stirred in 75 ml. of DMF containing the imidazole at 0° as the trimethylsilylchloride was slowly poured in. After 10 min. at 0° and 2.5 hr. at room temperature, the mixture was poured into $H_2O$ and extracted with petether. The organic layer was worked with water and $NaHCO_3$ and dried ($MgSO_4$). The solvent was removed and the residue was distilled (0.3 mm 63°–67°) to give the product as a colorless liquid.

Reference Example 151

Preparation of 1,9-dioxo-11α,15-dihydroxy-1-hydroxymethyl-15-vinyl-13-trans-Prostene To a solution of the product of Reference Example 150 in THF at −78° C. was added n-butyllithium. The solution was stirred at −50° C. to −10° C. over a 2 hr. 20 min. period. Copper pentyne and hexamethylphorphoroustriamide was added in 30 ml. of ether at −78° C. The solution turned dark green and then dark brown and the solution was stirred for 1 hr. The enone (Example 108) was added in 5 ml. of ether. The solution was stirred at −55° C. to −20° C. over 1.5 hours. The mixture was recooled to −30° C. and saturated $NH_4Cl$ was added. The mixture was stirred at room temperature for 30 minutes and extracted with ether. The solution was washed rapidly with dilute HCL followed by saturated $NaHCO_3$ and saturated $NH_4Cl$. The ether was removed. The residue was stirred in 50 ml. of acetic acid-THF-water for 1.5 hours. The solvents were removed at room temperature under vacuo. The residue was worked with saturated $NH_4$ (and saturated $NaHCO_3$ and dried $MgSO_4$). The solvent was removed giving a two phase oil. This oil was chromatographed on a dry silica column eluting with ethylacetate-hexame (4:1) cuts and combined of similar giving the title compound.

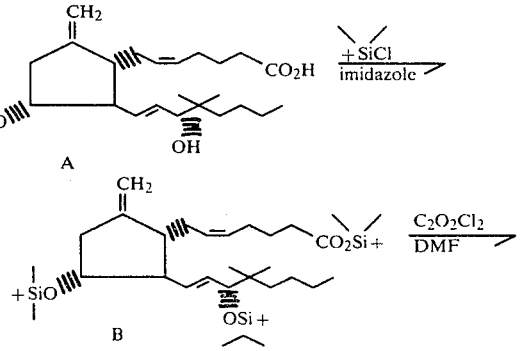

Flowsheet X

Flowsheet X

-continued

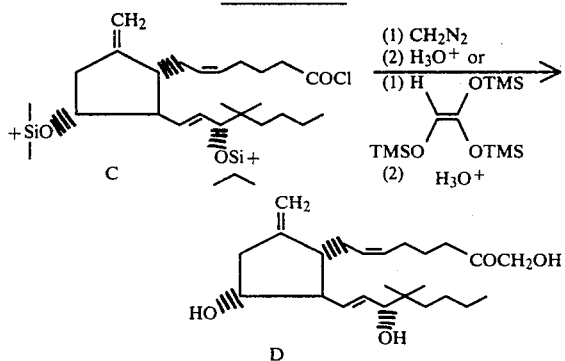

In accordance with Flowsheet X the prostaglandins of this invention containing the 9-methylene feature (D) are prepared starting with the corresponding carboxylic acid (A) the preparation of which has been described (G. L. Bundy, *Tetrahedron Lett.* 1957 (1975) and G. L. Bundy, *International Prostaglandin Conference*, Washington, D.C. May 27–31, 1979) by the reaction of (A) which at least three equivalents of dimethyl-t-butyl chlorosilane and imidazole in dimethylformamide to give (B). The reaction of (B) with one equivalent of oxalyl chloride in the presence of a catalytic amount of dimethylformamide in methylene chloride or tetrahydrofuran gives the carboxylic and chloride (C) which can be converted to the desired compound (D) by one of two methods. The reaction of (C) with an etheral solution of diazomethane followed by hydrolysis of the resulting diazoketone using aqueous sulfuric acid and an ether solvent such as diethylether, dioxane, or tetrahydrofuran at reflux gives the desired 9-methylene analogs (D) of this invention. Alternatively (D) can be prepared by the reaction of (C) with two equivalents of tris-trimethylsilyloxyethylene either by heating the mixture neat or in chlorobenzene or by allowing the neat mixture to react in the presence of a Lewis acid such as stannic chloride followed by hydrolysis in a mixture of dilute hydrochloric acid and dioxane.

The compounds of this invention containing a trans double bond between the $C_2$ and $C_3$ carbon atoms are prepared as illustrated in Flowsheet Y hereinbelow. Displacement of the bromide atom of compound (G) with a thiophenoxide group is accomplished by the reaction of (G) with at least one equivalent of thiophenol and sodium ethoxide in ethanol. The less hindered carboxylate group can be hydrolyzed using one equivalent of sodium hydroxide in aqueous ethanol to give (H). Compound (H) is converted to the mixed anhydride by the reaction with trifluoracetic anhydride in methylene chloride. The reaction of this anhydride with furan then gives (J). Hydrolysis of (J) with KOH in aqueous ethanol followed by reduction using sodium borohydride in ethanol gives alcohol (K) which on hydrolysis first in aqueous formic acid and then on aqueous sulfuric acid give compound (L). The reaction of (L) with at least two equivalents of dimethyl-t-butylchlorosilane using imidazole and DMF followed by the reaction of the resulting bis-silylated compound with one equivalent of oxalyl chloride in the presence of a catalytic amount of DMF then gives the acid chloride (M). The reaction of (M) with two equivalents of tris-trimethylsilyloxyethylene followed by hydrolysis in a mixture of dilute hydrochloric acid and THF gives compound (N) which can be silylated using 1,1,1,3,3,3-hexamethyldisilazane and trimethylsilylchloride in pyridine to give (O). The reaction of (O) with the cuprate reagent (P) followed by hydrolysis in acetic acid, $H_2O$, THF (4:1:2) gives compounds (O) and (R) which can be separated by silica gel chromatography the reaction of (Q) with m-chloroperbenzoic acid at $-78°$ C. to $0°$ C. followed by isolation and thermolysis of the resulting sulfoxide gives compound (S) which is a subject of this invention.

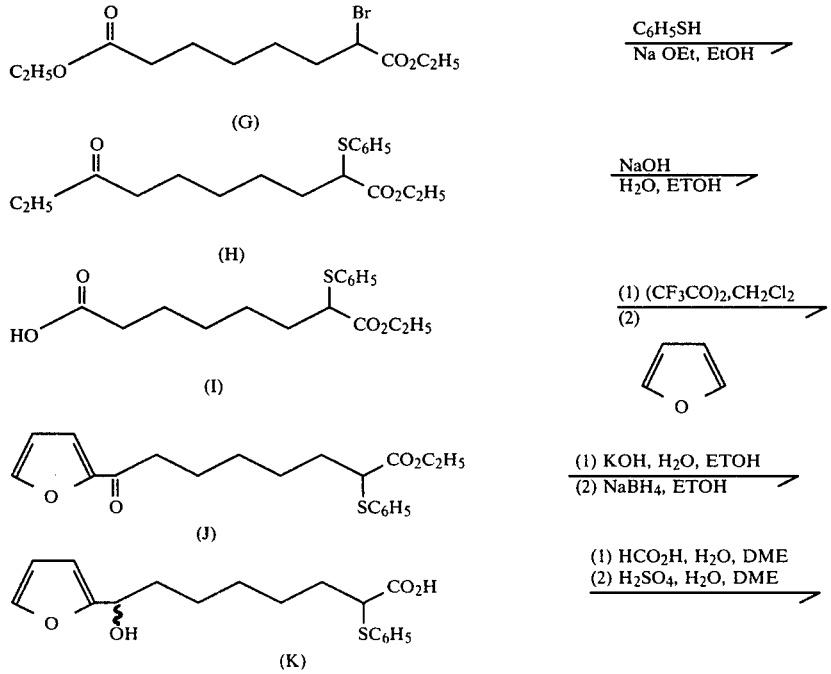

Flowsheet Y

-continued
Flowsheet Y

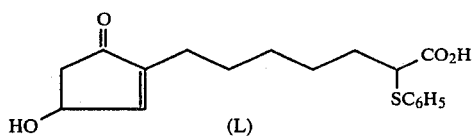

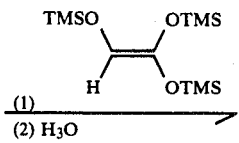
(1) SiCl, imidazole, DMF
(2) C₂O₂Cl₂, DMF, THF

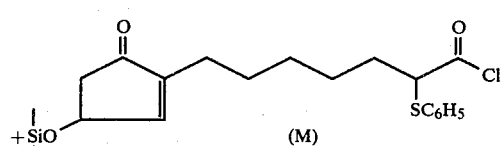

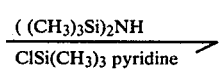
(1)
(2) H₃O

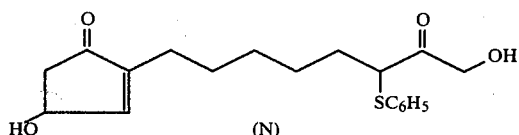

((CH₃)₃Si)₂NH / ClSi(CH₃)₃ pyridine

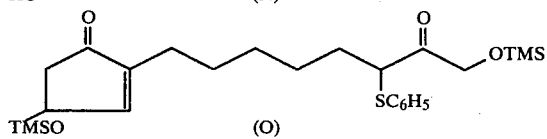

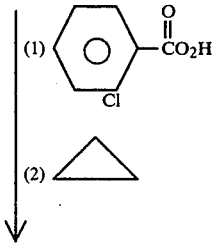
(1) Li–Cu
(P)
(2) H₃Ot

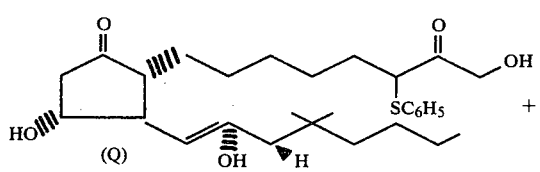

(1) chlorobenzoic acid
(2) cyclopropane

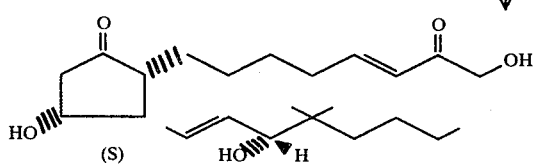

TABLES I and II

Treatment of the listed cyclopentenone with the listed vinylstannane in accordance with the procedure of Reference Example 136 is productive of the named PGE₁ product of Table I and the named PGE₂ product of Table II.

Although Tables I and II which follow the listed product is the dl-racemic product, as discussed above when the product is prepared from an optically active cyclopentenone (such as structure 151), the application of HPLC, column or thin layer chromatography will provide the individual nat.16α and nat. 16β compounds.

In the tables which follow an 11, 15, 16 substituent followed by the designation "a" or α indicates a substituent below the plane of the paper.

TABLE I

| EXAMPLE | VINYL TIN | CYCLOPENTENONE | PRODUCT PROSTAGLANDIN OF THE PGE1 SERIES |
|---|---|---|---|
| 1 | 1-trans-tri-n-butylstannyl-4-fluoromethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-fluoromethyl-20-nor-2-nor-13-trans prostene |
| 2 | 1-trans-tri-n-butylstannyl-4-difluoromethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-difluoromethyl-20-nor-2-nor-13-trans prostene |
| 3 | 1-trans-tri-n-butylstannyl-4-trifluoromethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-trifluoromethyl-20-nor-2-nor-13-trans prostene |
| 4 | 1-trans-tri-n-butylstannyl-4-chloromethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-chloromethyl-20-nor-2-nor-13-trans prostene |
| 5 | 1-trans-tri-n-butylstannyl-4-bromomethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-bromomethyl-20-nor-2-nor-13-trans prostene |
| EXAMPLE | VINYL IODIDE | CYCLOPENTENONE | PRODUCT PROSTAGLANDIN OF THE PGE1 SERIES |
| 6 | 1-trans-iodo-4-allenyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-allenyl-20-nor-2-nor-13-trans prostene |
| EXAMPLE | VINYL TIN | CYCLOPENTENONE | PRODUCT PROSTAGLANDIN OF THE PGE1 SERIES |
| 7 | 1-trans-tri-n-butylstannyl-5-methylene-4-triethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-17-methylene-20-nor-2-nor-13-trans prostene |
| 8 | 1-trans-tri-n-butylstannyl-4-methyl-5-methylene-4-trimethylsiloxy-1-heptene | 2-[5-4(methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-17-methylene-20-nor-2-nor-13-trans prostene |
| 9 | | | 20-nor-2-nor-13-trans prostene |
| 12 | 1-trans-tri-n-butylstannyl-7-oxa-4-triethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-19-oxa-2-nor-13-trans prostene |
| 13 | 1-trans-tri-n-butylstannyl-4-methyl-7-oxa-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-19-oxa-2-nor-13-trans prostene |
| 14 | 1-trans-tri-n-butylstannyl-7-thia-4-triethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-19-thia-2-nor-13-trans prostene |
| 15 | 1-trans-tri-n-butylstannyl-4-methyl-7-thia-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-19-thia-2-nor-13-trans prostene |
| EXAMPLE | VINYL IODIDE | CYCLOPENTENONE | PRODUCT PROSTAGLANDIN OF THE PGE1 SERIES |
| 16 | 1-trans-iodo-7-chloro-4-triethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-19-chloro-2-nor-20-nor-13-trans prostene |
| 17 | 1-trans-iodo-4-methyl-7-chloro-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-19-chloro-2-nor-20-nor-13-trans prostene |
| EXAMPLE | VINYL TIN | CYCLOPENTENONE | PRODUCT PROSTAGLANDIN OF THE PGE1 SERIES |

TABLE I-continued

| EXAMPLE | VINYL IODIDE | CYCLOPENTENONE | PRODUCT PROSTAGLANDIN OF THE PGE1 SERIES |
|---|---|---|---|
| 18 | 1-trans-tri-n-butylstannyl-4-fluoromethyl-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-fluoromethyl-2-nor-13-trans prostene |
| 19 | 1-trans-tri-n-butylstannyl-4-difluoromethyl-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-difluoromethyl-2-nor-13-trans prostene |
| 20 | 1-trans-tri-n-butylstannyl-4-trifluoromethyl-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-trifluoromethyl-2-nor-13-trans prostene |
| 21 | 1-trans-tri-n-butylstannyl-4-chloromethyl-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-chloromethyl-2-nor-13-trans prostene |
| 22 | 1-trans-tri-n-butylstannyl-4-bromomethyl-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-bromomethyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 23 | 1-iodo-4-allenyl-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-allenyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 24 | 1-trans-tri-n-butylstannyl-5-methylene-4-triethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-17-methylene-2-nor-13-trans prostene |
| 25 | 1-trans-tri-n-butylstannyl-4-methyl-5-methylene-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-methyl-17-methylene-2-nor-13-trans prostene |
| 26 | 1-trans-tri-n-butylstannyl-4-dimethoxymethyl-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-formyl-2-nor-13-trans prostene |
| 27 | 1-trans-tri-n-butylstannyl-4-deutero-4-triethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-deutero-2-nor-13-trans prostene |
| 28 | 1-trans-tri-n-butylstannyl-4-triethylsilyloxymethyl-4-trimethylsiloxy-1-octene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-hydroxymethyl-2-nor-13-trans prostene |
| 29 | 1-trans-tri-n-butylstannyl-4-fluoromethyl-4-trimethylsiloxy-1-nonene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-fluoromethyl-20-methyl-2-nor-13-trans prostene |
| 30 | 1-trans-tri-n-butylstannyl-4-difluoromethyl-4-trimethylsiloxy-1-nonene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-difluoromethyl-20-methyl-2-nor-13-trans prostene |
| 31 | 1-trans-tri-n-butylstannyl-4-trifluoromethyl-4-trimethylsiloxy-1-nonene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-trifluoromethyl-20-methyl-2-nor-13-trans prostene |
| 32 | 1-trans-tri-n-butylstannyl-4-chloromethyl-4-trimethylsiloxy-1-nonene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-chloromethyl-20-methyl-2-nor-13-trans prostene |
| 33 | 1-trans-tri-n-butylstannyl-4-bromomethyl-4-trimethylsiloxy-1-nonene | 2-[5-(4-methoxy-2,2-dimethyl-1,3-dioxolan-4-yl)pentyl]-4-(2-methoxypropyl)-2-oxy)cyclopent-2-en-1-one | dl-11a,16-dihydroxy-1-hydroxymethyl-1,9-dioxo-16-bromomethyl-20-methyl-2-nor-13-trans prostene |

TABLE I-continued

| EXAMPLE | VINYL IODIDE | CYCLPENTENONE | PRODUCT PROSTAGLANDIN OF THE PGE1 SERIES |
|---|---|---|---|
| 34 | 1-trans-iodo-4-allenyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-20-methyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 35 | 1-trans-tri-n-butylstannyl-5-methylene-4-triethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-17-methylene-20-methyl-2-nor-13-trans prostene |
| 36 | 1-trans-tri-n-butylstannyl-4-methyl-5-methylene-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-17-methylene-20-methyl-2-nor-13-trans prostene |
| 37 | 1-trans-tri-n-butylstannyl-4-dimethoxymethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-formyl-20-methyl-2-nor-13-trans prostene |
| 38 | 1-trans-tri-n-butylstannyl-4-deutro-4-triethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-deutro-20-methyl-2-nor-13-trans prostene |
| 39 | 1-trans-tri-n-butylstannyl-4-triethylsilyloxymethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-hydroxymethyl-20-methyl-2-nor-13-trans prostene |
| 40 | 1-trans-tri-n-butylstannyl-4-fluoromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-fluoromethyl-20-ethyl-2-nor-13-trans prostene |
| 41 | 1-trans-n-butylstannyl-4-difluoromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-difluoromethyl-20-ethyl-2-nor-13-trans prostene |
| 42 | 1-trans-tri-n-butylstannyl-4-trifluoromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-trifluoromethyl-20-ethyl-2-nor-13-trans prostene |
| 43 | 1-trans-tri-n-butylstannyl-4-chloromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-chloromethyl-20-ethyl-2-nor-13-trans prostene |
| 44 | 1-trans-tri-n-butylstannyl-4-bromomethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-bromomethyl-20-ethyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 45 | 1-trans-iodo-4-allenyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-allenyl-20-ethyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 46 | 1-trans-tri-n-butylstannyl-5-methylene-4-triethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-17-methylene-20-ethyl-2-nor-13-trans prostene |
| 47 | 1-trans-tri-n-butylstannyl-4-methyl-5-methylene-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-17-methylene-20-ethyl-2-nor-13-trans prostene |
| 48 | 1-trans-tri-n-butylstannyl-4-dimethoxymethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-formyl-20-ethyl-2-nor-13-trans prostene |
| 49 | 1-trans-tri-n-butylstannyl-4-deutro- | 2-[5-(4-methoxy-2,2-dimethyl-1,3-dioxolan- | dl-11a,16-dihydroxy-1-hydroxymethyl-1,9-dioxo-16-deutro- |

TABLE I-continued

| | | | |
|---|---|---|---|
| | | 4-triethylsiloxy-1-decene | 4-yl)pentyl]-4-(2-methoxypropyl-1,3-dioxolan-2-oxy)cyclopent-2-en-1-one | 20-ethyl-2-nor-13-trans prostene |
| 50 | | 1-trans-tri-n-butylstannyl-4-triethylsilyloxymethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-hydroxymethyl-20-ethyl-2-nor-13-trans prostene |
| 51 | | 1-trans-tri-n-butylstannyl-4-fluoromethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-fluoromethyl-20-nor-13-trans prostene |
| 52 | | 1-trans-tri-n-butylstannyl-4-difluoromethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-difluoromethyl-20-nor-13-trans prostene |
| 53 | | 1-trans-tri-n-butylstannyl-4-trifluoromethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-trifluoromethyl-20-nor-13-trans prostene |
| 54 | | 1-trans-tri-n-butylstannyl-4-chloromethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-chloromethyl-20-nor-13-trans prostene |
| 55 | | 1-trans-tri-n-butylstannyl-4-bromomethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-bromomethyl-20-nor-13-trans prostene |
| EXAMPLE | VINYL IODIDE | | CYCLOPENTENONE | PRODUCT PROSTAGLANDIN OF THE PGE1 SERIES |
| 56 | | 1-trans-iodo-4-allenyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-allenyl-20-nor-13-trans prostene |
| EXAMPLE | VINYL TIN | | CYCLOPENTENONE | PRODUCT PROSTAGLANDIN OF THE PGE1 SERIES |
| 57 | | 1-trans-tri-n-butylstannyl-5-methylene-4-triethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-17-methylene-20-nor-13-trans prostene |
| 58 | | 1-trans-tri-n-butylstannyl-4-methyl-5-methylene-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-17-methylene-20-nor-13-trans prostene |
| 59 | | 1-trans-tri-n-butylstannyl-4-dimethoxymethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-formyl-20-nor-13-trans prostene |
| 60 | | 1-trans-tri-n-butylstannyl-4-deutro-4-triethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-deutro-20-nor-13-trans prostene |
| 61 | | 1-trans-tri-n-butylstannyl-4-triethylsilyloxymethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-hydroxymethyl-20-nor-13-trans prostene |
| 62 | | 1-trans-tri-n-butylstannyl-7-oxa-4-triethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-19-oxa-13-trans prostene |
| 63 | | 1-trans-tri-n-butylstannyl-4-methyl-7-oxa-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-19-oxa-13-trans prostene |
| 64 | | 1-trans-tri-n-butylstannyl-7-thia-4-triethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-19-thia-13-trans prostene |
| 65 | | 1-trans-tri-n-butylstannyl-4-methyl-7-thia-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-19-thia-13-trans prostene |

TABLE I-continued

| EXAMPLE | VINYL IODIDE | CYCLOPENTENONE | PRODUCT PROSTAGLANDIN OF THE PGE1 SERIES |
|---|---|---|---|
| 66 | 1-trans-iodo-7-chloro-4-triethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-19-chloro-20-nor-13-trans prostene |
| 67 | 1-trans-iodo-4-methyl-7-chloro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-19-chloro-20-nor-13-trans prostene |

| EXAMPLE | VINYL TIN | CYCLOPENTENONE | PRODUCT PROSTAGLANDIN OF THE PGE1 SERIES |
|---|---|---|---|
| 68 | 1-trans-tri-n-butylstannyl-4-fluoromethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-fluoromethyl-13-trans prostene |
| 69 | 1-trans-tri-n-butylstannyl-4-difluoromethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-difluoromethyl-13-trans prostene |
| 70 | 1-trans-tri-n-butylstannyl-4-trifluoromethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-trifluoromethyl-13-trans prostene |
| 71 | 1-trans-tri-n-butylstannyl-4-chloromethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-chloromethyl-13-trans prostene |
| 72 | 1-trans-tri-n-butylstannyl-4-bromomethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-bromomethyl-13-trans prostene |

| EXAMPLE | VINYL IODIDE | CYCLOPENTENONE | PRODUCT PROSTAGLANDIN OF THE PGE1 SERIES |
|---|---|---|---|
| 73 | 1-trans-iodo-4-allenyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-allenyl-13-trans prostene |

| EXAMPLE | VINYL TIN | CYCLOPENTENONE | PRODUCT PROSTAGLANDIN OF THE PGE1 SERIES |
|---|---|---|---|
| 74 | 1-trans-tri-n-butylstannyl-5-methylene-4-triethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-17-methylene-13-trans prostene |
| 75 | 1-trans-tri-n-butylstannyl-4-methyl-5-methylene-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-17-methylene-13-trans prostene |
| 76 | 1-trans-tri-n-butylstannyl-4-dimethoxymethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-formyl-13-trans prostene |
| 77 | 1-trans-tri-n-butylstannyl-4-deutro-4-triethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-deutro-13-trans prostene |
| 78 | 1-trans-tri-n-butylstannyl-4-triethylsilyloxymethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-hydroxymethyl-13-trans prostene |
| 79 | 1-trans-tri-n-butylstannyl-4-fluoromethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-fluoromethyl-20-methyl-13-trans prostene |
| 80 | 1-trans-tri-n-butylstannyl-4-difluoromethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-difluoromethyl-20-methyl-13-trans prostene |

TABLE I-continued

| EXAMPLE | VINYL IODIDE | CYCLOPENTENONE | PRODUCT PROSTAGLANDIN OF THE PGE1 SERIES |
|---|---|---|---|
| 81 | 1-trans-tri-n-butylstannyl-4-trifluoromethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-trifluoromethyl-20-methyl-13-trans prostene |
| 82 | 1-trans-tri-n-butylstannyl-4-chloromethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-chloromethyl-20-methyl-13-trans prostene |
| 83 | 1-trans-tri-n-butylstannyl-4-bromomethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-bromomethyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 84 | 1-trans-iodo-4-allenyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-allenyl-20-methyl-13-trans prostene |

| EXAMPLE | VINYL TIN | CYCLOPENTENONE | PRODUCT PROSTAGLANDIN OF THE PGE1 SERIES |
|---|---|---|---|
| 85 | 1-trans-tri-n-butylstannyl-5-methylene-4-triethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-17-methylene-20-methyl-13-trans prostene |
| 86 | 1-trans-tri-n-butylstannyl-4-methyl-5-methylene-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-17-methylene-20-methyl-13-trans prostene |
| 87 | 1-trans-tri-n-butylstannyl-4-dimethoxymethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-formyl-20-methyl-13-trans prostene |
| 88 | 1-trans-tri-n-butylstannyl-4-deutro-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-deutro-20-methyl-13-trans prostene |
| 89 | 1-trans-tri-n-butylstannyl-4-triethylsilyloxymethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-hydroxmethyl-20-methyl-13-trans prostene |
| 90 | 1-trans-tri-n-butylstannyl-4-fluoromethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-fluoromethyl-20-ethyl-13-trans prostene |
| 91 | 1-trans-tri-n-butylstannyl-4-difluoromethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-difluoromethyl-20-ethyl-13-trans prostene |
| 92 | 1-trans-tri-n-butylstannyl-4-trifluoromethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-trifluoromethyl-20-ethyl-13-trans prostene |
| 93 | 1-trans-tri-n-butylstannyl-4-chloromethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-chloromethyl-20-ethyl-13-trans prostene |
| 94 | 1-trans-tri-n-butylstannyl-4-bromomethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-bromomethyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 95 | 1-trans-iodo-4-allenyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-allenyl-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 96 | 1-trans-tri-n-butylstannyl-5-methylene-4-triethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-17-methylene-20-ethyl-13-trans prostene |
| 97 | 1-trans-tri-n-butylstannyl-4-methyl-5-methylene-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-17-methylene-20-ethyl-13-trans prostene |
| 98 | 1-trans-tri-n-butylstannyl-4-dimethoxymethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-formyl-20-ethyl-13-trans prostene |
| 99 | 1-trans-tri-n-butylstannyl-4-deutro-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-deutro-20-ethyl-13-trans prostene |
| 100 | 1-trans-tri-n-butylstannyl-4-triethylsilylyloxymethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-hydroxymethyl-20-ethyl-13-trans prostene |
| 101 | 1-trans-tri-n-butylstannyl-4-fluoromethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-fluoromethyl-20-nor-2-homo-13-trans prostene |
| 102 | 1-trans-tri-n-butylstannyl-4-difluoromethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-difluoromethyl-20-nor-2-homo-13-trans prostene |
| 103 | 1-trans-tri-n-butylstannyl-4-trifluoromethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-trifluoromethyl-20-nor-2-homo-13-trans prostene |
| 104 | 1-trans-tri-n-butylstannyl-4-chloromethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-chloromethyl-20-nor-2-homo-13-trans prostene |
| 105 | 1-trans-tri-n-butylstannyl-4-bromomethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-bromomethyl-20-nor-2-homo-13-trans prostene |

| EXAMPLE | VINYL IODIDE | CYCLOPENTENONE | PRODUCT PROSTAGLANDIN OF THE PGE1 SERIES |
|---|---|---|---|
| 106 | 1-trans-iodo-4-allenyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a, 16-dihydroxy-1-hydroxymethyl-1,9-dioxo-16-allenyl-20-nor-1-13-trans prostene |

| EXAMPLE | VINYL TIN | CYCLOPENTENONE | PRODUCT PROSTAGLANDIN OF THE PGE1 SERIES |
|---|---|---|---|
| 107 | 1-trans-butylstannyl-5-methylene-4-triethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-17-methylene-20-nor-2-homo-13-trans prostene |
| 108 | 1-trans-tri-n-butylstannyl-4-methyl-5-methylene-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-methyl-17-methylene-20-nor-2-homo-13-trans prostene |
| 109 | 1-trans-tri-n-butylstannyl-4-dimethoxymethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-formyl-20-nor-2-homo-13-trans prostene |
| 110 | 1-trans-tri-n-butylstannyl-4-deutro-4-triethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-deutro-20-nor-2-homo-13-trans prostene |
| 111 | 1-trans-tri-n-butylstannyl-4-triethylsilylyloxymethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-hydroxymethyl-20-nor-2-homo-13-trans prostene |

TABLE I-continued

| | | | |
|---|---|---|---|
| 112 | 1-trans-tri-n-butylstannyl-7-oxa-4-triethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-19-oxa-2-homo-13-trans prostene |
| 113 | 1-trans-tri-n-butylstannyl-4-methyl-7-oxa-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-methyl-19-oxa-2-homo-13-trans prostene |
| 114 | 1-trans-tri-n-butylstannyl-7-thia-4-triethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-19-thia-2-homo-13-trans prostene |
| 115 | 1-trans-tri-n-butylstannyl-4-methy-7-thia-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-methyl-19-thia-2-homo-13-trans prostene |
| EXAMPLE | VINYL IODIDE | CYCLOPENTENONE | PRODUCT PROSTAGLANDIN OF THE PGE1 SERIES |
| 116 | 1-trans-iodo-7-chloro-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-19-chloro-2-homo-20-nor-13-trans prostene |
| 117 | 1-trans-iodo-4-methyl-7-chloro-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-methyl-19-chloro-2-homo-20-nor-13-trans prostene |
| EXAMPLE | VINYL TIN | CYCLOPENTENONE | PRODUCT PROSTAGLANDIN OF THE PGE1 SERIES |
| 118 | 1-trans-tri-n-butylstannyl-4-fluoromethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-fluoromethyl-2-homo-13-trans prostene |
| 119 | 1-trans-tri-n-butylstannyl-4-difluoromethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-difluoromethyl-2-homo-13-trans prostene |
| 120 | 1-trans-tri-n-butylstannyl-4-trifluoromethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-trifluoromethyl-2-homo-13-trans prostene |
| 121 | 1-trans-tri-n-butylstannyl-4-chloromethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-chloromethyl-2-homo-13-trans prostene |
| 122 | 1-trans-tri-n-butylstannyl-4-bromomethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-bromomethyl-2-homo-13-trans prostene |
| EXAMPLE | VINYL IODIDE | CYCLOPENTENONE | PRODUCT PROSTAGLANDIN OF THE PGE1 SERIES |
| 123 | 1-trans-iodo-4-allenyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-allenyl-2-homo-13-trans prostene |
| EXAMPLE | VINYL TIN | CYCLOPENTENONE | PRODUCT PROSTAGLANDIN OF THE PGE1 SERIES |
| 124 | 1-trans-tri-n-butylstannyl-5-methylene-4-triethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-17-methylene-2-homo-13-trans prostene |
| 125 | 1-trans-tri-n-butylstannyl-4-methyl-5-methylene-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-methyl-17-methylene-2-homo-13-trans prostene |
| 126 | 1-trans-tri-n-butylstannyl-4-dimethoxymethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-formyl-2-homo-13-trans prostene |

TABLE I-continued

| | | | |
|---|---|---|---|
| 127 | 1-trans-tri-n-butylstannyl-4-deutro-4-triethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-deutro-2-homo-13-trans prostene |
| 128 | 1-trans-tri-n-butylstannyl-4-triethylsilyoxymethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-hydroxymethyl-2-homo-13-trans prostene |
| 129 | 1-trans-tri-n-butylstannyl-4-fluoromethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-fluoromethyl-20-methyl-2-homo-13-trans prostene |
| 130 | 1-trans-tri-n-butylstannyl-4-difluoromethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-difluoromethyl-20-methyl-2-homo-13-trans prostene |
| 131 | 1-trans-tri-n-butylstannyl-4-trifluoromethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-trifluoromethyl-20-methyl-2-homo-13-trans prostene |
| 132 | 1-trans-tri-n-butylstannyl-4-chloromethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-chloromethyl-20-methyl-2-homo-13-trans prostene |
| 133 | 1-trans-tri-n-butylstannyl-4-bromomethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-bromomethyl-20-methyl-2-homo-13-trans prostene |
| EXAMPLE | VINYL IODIDE | CYCLOPENTENONE | PRODUCT PROSTAGLANDIN OF THE PGE1 SERIES |
| 134 | 1-trans-iodo-4-allenyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-allenyl-20-methy-2-homo-13-trans prostene |
| EXAMPLE | VINYL TIN | CYCLOPENTENONE | PRODUCT PROSTAGLANDIN OF THE PGE1 SERIES |
| 135 | 1-trans-tri-n-butylstannyl-5-methylene-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-17-methylene-20-methyl-2-homo-13-trans prostene |
| 136 | 1-trans-tri-n-butylstannyl-4-methyl-5-methylene-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-methyl-17-methylene-20-methyl-2-homo-13-trans prostene |
| 137 | 1-trans-tri-n-butylstannyl-4-dimethoxymethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-formyl-20-methyl-2-homo-13-trans prostene |
| 138 | 1-trans-tri-n-butylstannyl-4-deutro-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-deutro-20-methyl-2-homo-13-trans prostene |
| 139 | 1-trans-tri-n-butylstannyl-4-triethylsilyoxymethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-hydroxymethyl-20-methyl-2-homo-13-trans prostene |
| 140 | 1-trans-tri-n-butylstannyl-4-fluoromethyl-4-trimethylsiloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-fluoromethyl-20-ethyl-2-homo-13-trans prostene |
| 141 | 1-trans-tri-n-butylstannyl-4-difluoromethyl-4-trimethylsiloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-difluoromethyl-20-ethyl-2-homo-13-trans prostene |
| 142 | 1-trans-tri-n-butylstannyl-4-trifluoromethyl-4-trimethylsiloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-trifluoromethyl-20-ethyl-2-homo-13-trans prostene |
| 143 | 1-trans-tri-n-butylstannyl-4-chloromethyl-4-trimethylsiloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-chloromethyl- |

TABLE I-continued

| | VINYL IODIDE | CYCLOPENTENONE | PRODUCT PROSTAGLANDIN OF THE PGE1 SERIES |
|---|---|---|---|
| | 4-trimethylsiloxy-1-decene | 4-y)]heptyl]-4-(2-methoxypropyl-1,3-dioxolan-2-oxy)cyclopent-2-en-1-one | 20-ethyl-2-homo-13-trans prostene |
| 144 | 1-trans-tri-n-butylstannyl-4-bromomethyl-4-trimethylsiloxy-1-decene | 2-[7-(4-methoxy-2,2-dimethyl-1,3-dioxolan-4-y)]heptyl]-4-(2-methoxypropyl-1,3-dioxolan-2-oxy)cyclopent-2-en-1-one | dl-11a,16-dihydroxy-1-hydroxymethyl-1,9-dioxo-16-bromomethyl-20-ethyl-2-homo-13-trans prostene |
| EXAMPLE | VINYL IODIDE | CYCLOPENTENONE | PRODUCT PROSTAGLANDIN OF THE PGE1 SERIES |
| 145 | 1-trans-iodo-4-allenyl-4-trimethylsiloxy-1-decene | 2[7-(4-methoxy-2,2-dimethyl-1,3-dioxolan-4-y)]heptyl]-4-(2-methoxypropyl-1,3-dioxolan-2-oxy)cyclopent-2-en-1-one | dl-11a,16-dihydroxy-1-hydroxymethyl-1,9-dioxo-16-allenyl-20-ethyl-2-homo-13-trans prostene |
| EXAMPLE | VINYL TIN | CYCLOPENTENONE | PRODUCT PROSTAGLANDIN OF THE PGE1 SERIES |
| 146 | 1-trans-tri-n-butylstannyl-5-methylene-4-triethylsiloxy-1-decene | 2-[7-(4-methoxy-2,2-dimethyl-1,3-dioxolan-4-y)]heptyl]-4-(2-methoxypropyl-1,3-dioxolan-2-oxy)cyclopent-2-en-1-one | dl-11a,16-dihydroxy-1-hydroxymethyl-1,9-dioxo-17-methylene-20-ethyl-2-homo-13-trans prostene |
| 147 | 1-trans-tri-n-butylstannyl-4-methyl-5-methylene-4-trimethylsiloxy-1-decene | 2-[7-(4-methoxy-2,2-dimethyl-1,3-dioxolan-4-y)]heptyl]-4-(2-methoxypropyl-1,3-dioxolan-2-oxy)cyclopent-2-en-1-one | dl-11a,16-dihydroxy-1-hydroxymethyl-1,9-dioxo-16-methyl-17-methylene-20-ethyl-2-homo-13-trans prostene |
| 148 | 1-trans-tri-n-butylstannyl-4-dimethoxymethyl-4-trimethylsiloxy-1-decene | 2-[7-(4-methoxy-2,2-dimethyl-1,3-dioxolan-4-y)]heptyl]-4-(2-methoxypropyl-1,3-dioxolan-2-oxy)cyclopent-2-en-1-one | dl-11a,16-dihydroxy-1-hydroxymethyl-1,9-dioxo-16-formyl-20-ethyl-2-homo-13-trans-prostene |
| 149 | 1-trans-tri-n-butylstannyl-4-deutero-4-triethylsiloxy-1-decene | 2-[7-(4-methoxy-2,2-dimethyl-1,3-dioxolan-4-y)]heptyl]-4-(2-methoxypropyl-1,3-dioxolan-2-oxy)cyclopent-2-en-1-one | dl-11a,16-dihydroxy-1-hydroxymethyl-1,9-dioxo-16-deutro-20-ethyl-2-homo-13-trans prostene |
| 150 | 1-trans-tri-n-butylstannyl-4-triethylsilyloxymethyl-4-trimethylsiloxy-1-decene | 2-[7-(4-methoxy-2,2-dimethyl-1,3-dioxolan-4-y)]heptyl]-4-(2-methoxypropyl-1,3-dioxolan-2-oxy)cyclopent-2-en-1-one | dl-11a,16-dihydroxy-1-hydroxymethyl-1,9-dioxo-16-hydroxymethyl-20-ethyl-2-homo-13-trans prostene |
| 151 | 1-trans-tri-n-butylstannyl-4-fluoromethyl-4-trimethylsiloxy-1-heptene | 2-[6-(4-methoxy-2,2-dimethyl-1,3-dioxolan-4-y)]hexyl]-4R-(2-methoxypropyl-1,3-dioxolan-2-oxy)cyclopent-2-en-1-one | nat-11a,16-dihydroxy-1-hydroxymethyl-1,9-dioxo-16-fluoromethyl-20-nor-13-trans prostene |
| 152 | 1-trans-tri-n-butylstannyl-4-difluoromethyl-4-trimethylsiloxy-1-heptene | 2-[6-(4-methoxy-2,2-dimethyl-1,3-dioxolan-4-y)]hexyl]-4R-(2-methoxypropyl-1,3-dioxolan-2-oxy)cyclopent-2-en-1-one | nat-11a,16-dihydroxy-1-hydroxymethyl-1,9-dioxo-16-difluoromethyl-20-nor-13-trans prostene |
| 153 | 1-trans-tri-n-butylstannyl-4-trifluoromethyl-4-trimethylsiloxy-1-heptene | 2-[6-(4-methoxy-2,2-dimethyl-1,3-dioxolan-4-y)]hexyl]-4R-(2-methoxypropyl-1,3-dioxolan-2-oxy)cyclopent-2-en-1-one | nat-11a,16-dihydroxy-1-hydroxymethyl-1,9-dioxo-16-trifluoromethyl-20-nor-13-trans prostene |
| 154 | 1-trans-tri-n-butylstannyl-4-chloromethyl-4-trimethylsiloxy-1-heptene | 2-[6-(4-methoxy-2,2-dimethyl-1,3-dioxolan-4-y)]hexyl]-4R-(2-methoxypropyl-1,3-dioxolan-2-oxy)cyclopent-2-en-1-one | nat-11a,16-dihydroxy-1-hydroxymethyl-1,9-dioxo-16-chloromethyl-20-nor-13-trans prostene |
| 155 | 1-trans-tri-n-butylstannyl-4-bromomethyl-4-trimethylsiloxy-1-heptene | 2-[6-(4-methoxy-2,2-dimethyl-1,3-dioxolan-4-y)]hexyl]-4R-(2-methoxypropyl-1,3-dioxolan-2-oxy)cyclopent-2-en-1-one | nat-11a,16-dihydroxy-1-hydroxymethyl-1,9-dioxo-16-bromomethyl-20-nor-13-trans prostene |
| EXAMPLE | VINYL IODIDE | CYCLOPENTENONE | PRODUCT PROSTAGLANDIN OF THE PGE1 SERIES |
| 156 | 1-trans-iodo-4-allenyl-4-trimethylsiloxy-1-heptene | 2-[6-(4-methoxy-2,2-dimethyl-1,3-dioxolan-4-y)]hexyl]-4R-(2-methoxypropyl-1,3-dioxolan-2-oxy)cyclopent-2-en-1-one | nat-11a,16-dihydroxy-1-hydroxymethyl-1,9-dioxo-16-allenyl-20-nor-13-trans-prostene |
| EXAMPLE | VINYL TIN | CYCLOPENTENONE | PRODUCT PROSTAGLANDIN OF THE PGE1 SERIES |
| 157 | 1-trans-tri-n-butylstannyl-5-methylene-4-triethylsiloxy-1-heptene | 2-[6-(4-methoxy-2,2-dimethyl-1,3-dioxolan-4-y)]hexyl]-4R-(2-methoxypropyl-1,3-dioxolan-2-oxy)cyclopent-2-en-1-one | nat-11a,16-dihydroxy-1-hydroxymethyl-1,9-dioxo-17-methylene-20-nor-13-trans prostene |
| 158 | 1-trans-tri-n-butylstannyl-4-methyl-5-methylene | 2-[6-(4-methoxy-2,2-dimethyl-1,3-dioxolan- | nat-11a,16-dihydroxy-1-hydroxymethyl-1,9-dioxo-16-methyl- |

| | | TABLE I-continued | |
|---|---|---|---|
| | | CYCLOPENTENONE | |
| 159 | 1-trans-tri-n-butylstannyl-4-dimethoxymethyl-4-trimethylsiloxy-1-heptene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-formyl-20-nor-13-trans prostene |
| 160 | 1-trans-tri-n-butylstannyl-4-deutro-4-triethylsiloxy-1-heptene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-deutro-20-nor-13-trans prostene |
| 161 | 1-trans-tri-n-butylstannyl-4-triethylsilyloxymethyl-4-trimethylsiloxy-1-heptene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-hydroxymethyl-20-nor-13-trans prostene |
| 162 | 1-trans-tri-n-butylstannyl-7-oxa-4-triethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-19-oxa-13-trans prostene |
| 163 | 1-trans-tri-n-butylstannyl-4-methyl-7-oxa-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-19-oxa-13-trans prostene |
| 164 | 1-trans-tri-n-butylstannyl-7-thia-4-triethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-19-thia-13-trans prostene |
| 165 | 1-trans-tri-n-butylstannyl-4-methyl-7-thia-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-methyl-19-thia-13-trans prostene |
| EXAMPLE | VINYL IODIDE | CYCLOPENTENONE | PRODUCT PROSTAGLANDIN OF THE PGE1 SERIES |
| 166 | 1-trans-iodo-7-chloro-4-triethylsiloxy-1-heptene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-19-chloro-20-nor-13-trans prostene |
| 167 | 1-trans-iodo-4-methyl-7-chloro-4-trimethylsiloxy-1-heptene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-methyl-19-chloro-20-nor-13-trans prostene |
| EXAMPLE | VINYL TIN | CYCLOPENTENONE | PRODUCT PROSTAGLANDIN OF THE PGE1 SERIES |
| 168 | 1-trans-tri-n-butylstannyl-4-fluoromethyl-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-fluoromethyl-13-trans prostene |
| 169 | 1-trans-tri-n-butylstannyl-4-difluoromethyl-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-difluoromethyl-13-trans prostene |
| 170 | 1-trans-tri-n-butylstannyl-4-trifluoromethyl-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-trifluoromethyl-13-trans prostene |
| 171 | 1-trans-tri-n-butylstannyl-4-chloromethyl-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-chloromethyl-13-trans prostene |
| 172 | 1-trans-tri-n-butylstannyl-4-bromomethyl-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-bromomethyl-13-trans prostene |
| EXAMPLE | VINYL IODIDE | CYCLOPENTENONE | PRODUCT PROSTAGLANDIN OF THE PGE1 SERIES |
| 173 | 1-trans-iodo-4-allenyl-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-allenyl-13-trans prostene |

TABLE I-continued

| EXAMPLE | VINYL TIN | CYCLOPENTENONE | PRODUCT PROSTAGLANDIN OF THE PGE1 SERIES |
|---|---|---|---|
| 174 | 1-trans-tri-n-butylstannyl-5-methylene 4-triethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-17-methylene-13-trans prostene |
| 175 | 1-trans-tri-n-butylstannyl-4-methyl-5-methylene 4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-methyl-17-methylene-13-trans prostene |
| 176 | 1-trans-tri-n-butylstannyl-4-dimethoxymethyl-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-formyl-13-trans prostene |
| 177 | 1-trans-tri-n-butylstannyl-4-deutro-4-triethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-deutro-13-trans prostene |
| 178 | 1-trans-tri-n-butylstannyl-4-triethylsilyloxymethyl-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-hydroxymethyl-13-trans prostene |
| 179 | 1-trans-tri-n-butylstannyl-4-fluoromethyl-4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-fluoromethyl-20-methyl-13-trans prostene |
| 180 | 1-trans-tri-n-butylstannyl-4-difluoromethyl-4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-difluoromethyl-20-methyl-13-trans prostene |
| 181 | 1-trans-tri-n-butylstannyl-4-trifluoromethyl-4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-trifluoromethyl-20-methyl-13-trans prostene |
| 182 | 1-trans-tri-n-butylstannyl-4-chloromethyl-4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-chloromethyl-20-methyl-13-trans prostene |
| 183 | 1-trans-tri-n-butylstannyl-4-bromomethyl-4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-bromomethyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 184 | 1-trans-iodo-4-allenyl-4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-allenyl-20-methyl-13-trans prostene |

| EXAMPLE | VINYL TIN | CYCLOPENTENONE | PRODUCT PROSTAGLANDIN OF THE PGE1 SERIES |
|---|---|---|---|
| 185 | 1-trans-tri-n-butylstannyl-5-methylene 4-triethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-17-methylene-20-methyl-13-trans prostene |
| 186 | 1-trans-tri-n-butylstannyl-4-methyl-5-methylene 4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-methyl-17-methylene-20-methyl-13-trans prostene |
| 187 | 1-trans-tri-n-butylstannyl-4-dimethoxymethyl-4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-formyl-20-methyl-13-trans prostene |
| 188 | 1-trans-tri-n-butylstannyl-4-deutro-4-triethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-deutro-20-methyl-13-trans prostene |
| 189 | 1-trans-tri-n-butylstannyl-4-triethylsilyloxymethyl-4-trimethylsiloxy-1-nonene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-hydroxymethyl-20-methyl-13-trans prostene |

TABLE I-continued

| | VINYL IODIDE | CYCLOPENTENONE | PRODUCT PROSTAGLANDIN OF THE PGE1 SERIES |
|---|---|---|---|
| 190 | 1-trans-tri-n-butylstannyl-4-fluoromethyl-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-fluoromethyl-20-ethyl-13-trans prostene |
| 191 | 1-trans-tri-n-butylstannyl-4-difluoromethyl-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-difluoromethyl-20-ethyl-13-trans prostene |
| 192 | 1-trans-tri-n-butylstannyl-4-trifluoromethyl-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-trifluoromethyl-20-ethyl-13-trans prostene |
| 193 | 1-trans-tri-n-butylstannyl-4-chloromethyl-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-chloromethyl-20-ethyl-13-trans prostene |
| 194 | 1-trans-tri-n-butylstannyl-4-bromomethyl-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-bromomethyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 195 | 1-trans-iodo-4-allenyl-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-allenyl-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 196 | 1-trans-tri-n-butylstannyl-5-methyl-5-methylene-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-17-methylene-20-methyl-13-trans prostene |
| 197 | 1-trans-tri-n-butylstannyl-4-methyl-5-methylene-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-methyl-17-methylene-20-ethyl-13-trans prostene |
| 198 | 1-trans-tri-n-butylstannyl-4-dimethoxymethyl-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-formyl-20-ethyl-13-trans prostene |
| 199 | 1-trans-tri-n-butylstannyl-4-deutro-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-deutro-20-ethyl-13-trans prostene |
| 200 | 1-trans-tri-n-butylstannyl-4-triethylsilyloxymethyl-4-trimethylsiloxy-1-decene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-hydroxymethyl-20-ethyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 201 | 1-trans-tri-n-butylstannyl-4-fluoromethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-fluoromethyl-20-nor-2-nor-13-trans prostene |
| 202 | 1-trans-tri-n-butylstannyl-4-difluoromethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-difluoromethyl-20-nor-2-nor-13-trans prostene |
| 203 | 1-trans-tri-n-butylstannyl-4-trifluoromethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-trifluoromethyl-20-nor-2-nor-13-trans prostene |
| 204 | 1-trans-tri-n-butylstannyl-4-chloromethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-chloromethyl-20-nor-2-nor-13-trans prostene |
| 205 | 1-trans-tri-n-butylstannyl-4-bromomethyl-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-bromomethyl-20-nor-2-nor-13-trans prostene |

TABLE I-continued

| EXAMPLE | VINYL IODIDE | CYCLOPENTENONE | PRODUCT PROSTAGLANDIN OF THE 11-DEOXY PGE1 SERIES |
|---|---|---|---|
| 206 | 1-trans-iodo-4-allenyl-4-trimethylsiloxy-1-heptene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-16-allenyl 20-nor-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 207 | 1-trans-tri-n-butylstannyl-5-methylene-4-triethylsiloxy-1-heptene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-17-methylene-20-nor-2-nor-13-trans prostene |
| 208 | 1-trans-tri-n-butylstannyl-4-methyl-5-methylene-4-triethylsiloxy-1-heptene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-16-methyl-17-methylene-20-nor-2-nor-13-trans prostene |
| 209 | 1-trans-tri-n-butylstannyl-4-dimethoxymethyl-4-triethylsiloxy-1-heptene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-16-formyl-20-nor-2-nor-13-trans prostene |
| 210 | 1-trans-tri-n-butylstannyl-4-deutro-4-triethylsiloxy-1-heptene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-16-deutro-20-nor-2-nor-13-trans 19-chloro-2-nor-20-nor-13-trans |
| 211 | 1-trans-tri-n-butylstannyl-4-triethylsilyloxymethyl-4-triethylsiloxy-1-heptene | 2-[5-(4-methoxy-2,2-dimethyl-1,3-dioxolan-4-yl)pentyl]-4-(2-methoxypropyl)-cyclopent-2-en-1-one | dl-16-dihydroxy-1-hydroxymethyl-1,9-dioxo-16-hydroxymethyl-20-nor-2-nor-13-trans prostene |
| 212 | 1-trans-tri-n-butylstannyl-7-oxa-4-triethylsiloxy-1-octene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-19-oxa-2-nor-13-trans prostene |
| 213 | 1-trans-tri-n-butylstannyl-4-methyl-7-oxa-4-triethylsiloxy-1-octene | 2-[5-(4-methoxy-2,2-dimethyl-1,3-dioxolan-4-yl)dl-16-hydroxy-1-hydroxymethyl-1,9-dioxo-16-fluoromethyl-cyclopent-2-en-1-one | dl-16-hydroxy-1-hydroxymethyl-1,9-dioxo-19-oxa-2-nor-20-nor-13-trans prostene |
| 214 | 1-trans-tri-n-butylstannyl-7-thia-4-triethylsiloxy-1-octene | 2-[5-(4-methoxy-2,2-dimethyl-1,3-dioxolan-4-yl)pentyl]dl-16-hydroxy-1-hydroxymethyl-1,9-dioxo-16-difluoromethyl-cyclopent-2-en-1-one | dl-16-hydroxy-1-hydroxymethyl-1,9-dioxo-19-thia-2-nor-13-trans prostene |
| 215 | 1-trans-tri-n-butylstannyl-4-methyl-7-thia-4-trimethylsiloxy-1-octene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-16-methyl-19-thia-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 216 | 1-trans-iodo-7-chloro-4-triethylsiloxy-1-heptene | 2-[ 5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-19-chloro-2-nor-13-trans prostene |
| 217 | 1-trans-iodo-4-methyl-7-chloro-4-triethylsiloxy-1-heptene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-16-methyl-19-chloro-2-nor-20-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 218 | 1-trans-tri-n-butylstannyl-4-fluoromethyl-4-trimethylsiloxy-1-octene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-16-fluoromethyl-2-nor-13-trans prostene |
| 219 | 1-trans-tri-n-butylstannyl-4-difluoromethyl-4-trimethylsiloxy-1-octene | 2-[5-(4-methoxy-2,2-dimethyl-1,3-dioxolan-4-yl)pentyl]-4-(2-methoxypropyl)-cyclopent-2-en-1-one | dl-16-hydroxy-1-hydroxymethyl-1,9-dioxo-16-difluoromethyl-2-nor-13-trans prostene |

TABLE I-continued

| | VINYL IODIDE | CYCLOPENTENONE | PRODUCT PROSTAGLANDIN OF THE 11-DEOXY PGE1 SERIES |
|---|---|---|---|
| 220 | 1-trans-tri-n-butylstannyl-4-trifluoromethyl-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-trifluoromethyl-2-nor-13-trans prostene |
| 221 | 1-trans-tri-n-butylstannyl-4-chloromethyl-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-chloromethyl-2-nor-13-trans prostene |
| 222 | 1-trans-tri-n-butylstannyl-4-bromomethyl-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-bromomethyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 223 | 1-trans-iodo-4-allenyl-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-allenyl-2-nor-13-trans prostene |
| EXAMPLE | VINYL TIN | CYCLOPENTENONE | PRODUCT PROSTAGLANDIN OF THE 11-DEOXY PGE1 SERIES |
| 224 | 1-trans-tri-n-butylstannyl-5-methylene-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-17-methylene-2-nor-13-trans prostene |
| 225 | 1-trans-tri-n-butylstannyl-4-methyl-5-methylene-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-methyl-17-methylene-2-nor-13-trans prostene |
| 226 | 1-trans-tri-n-butylstannyl-4-dimethyoxymethyl-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-formyl-2-nor-13-trans prostene |
| 227 | 1-trans-tri-n-butylstannyl-4-deutro-4-triethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-deutro-2-nor-13-trans prostene |
| 228 | 1-trans-tri-n-butylstannyl-4-triethylsilyloxymethyl-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-hydroxymethyl-2-nor-13-trans prostene |
| 229 | 1-trans-tri-n-butylstannyl-4-fluoromethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-fluoromethyl-20-methyl-2-nor-13-trans prostene |
| 230 | 1-trans-tri-n-butylstannyl-4-difluoromethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-difluoromethyl-20-methyl-2-nor-13-trans prostene |
| 231 | 1-trans-tri-n-butylstannyl-4-trifluoromethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-trifluoromethyl-20-methyl-2-nor-13-trans prostene |
| 232 | 1-trans-tri-n-butylstannyl-4-chloromethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-chloromethyl-20-methyl-2-nor-13-trans prostene |
| 233 | 1-trans-tri-n-butylstannyl-4-bromomethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-bromomethyl-20-methyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 234 | 1-trans-iodo-4-allenyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-allenyl-20-methyl-2-nor-13-trans prostene |
| EXAMPLE | VINYL TIN | CYCLOPENTENONE | PRODUCT PROSTAGLANDIN OF THE 11-DEOXY PGE1 SERIES |

TABLE I-continued

| | | | |
|---|---|---|---|
| 235 | 1-trans-tri-n-butylstannyl-5-methylene-4-triethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-17-methylene-20-methyl-2-nor-13-trans prostene |
| 236 | 1-trans-tri-n-butylstannyl-4-methyl-5-methylene-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-methyl-17-methylene-20-methyl-2-nor-13-trans prostene |
| 237 | 1-trans-tri-n-butylstannyl-4-dimethoxymethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-formyl-20-methyl-2-nor-13-trans prostene |
| 238 | 1-trans-tri-n-butylstannyl-4-deutro-4-triethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-deutro-20-methyl-2-nor-13-trans prostene |
| 239 | 1-trans-tri-n-butylstannyl-4-triethylsilyloxymethyl-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-hydroxymethyl-20-methyl-2-nor-13-trans prostene |
| 240 | 1-trans-tri-n-butylstannyl-4-fluoromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-fluoromethyl-20-ethyl-2-nor-13-trans prostene |
| 241 | 1-trans-tri-n-butylstannyl-4-difluoromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-difluoromethyl-20-ethyl-2-nor-13-trans prostene |
| 242 | 1-trans-tri-n-butylstannyl-4-trifluoromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-trifluoromethyl-20-ethyl-2-nor-13-trans prostene |
| 243 | 1-trans-tri-n-butylstannyl-4-chloromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-chloromethyl-20-ethyl-2-nor-13-trans prostene |
| 244 | 1-trans-tri-n-butylstannyl-4-bromomethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-bromomethyl-20-ethyl-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 245 | 1-trans-iodo-4-allenyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-allenyl-20-ethyl-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 246 | 1-trans-tri-n-butylstannyl-5-methylene-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-17-methylene-20-ethyl-2-nor-13-trans prostene |
| 247 | 1-trans-tri-n-butylstannyl-4-methyl-5-methylene-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-methyl-17-methylene-20-ethyl-2-nor-13-trans prostene |
| 248 | 1-trans-tri-n-butylstannyl-4-dimethoxymethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-formyl-20-ethyl-2-nor-13-trans prostene |
| 249 | 1-trans-tri-n-butylstannyl-4-deutro-4-triethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-deutro-20-ethyl-2-nor-13-trans prostene |
| 250 | 1-trans-tri-n-butylstannyl-4-triethylsilyloxymethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-hydroxymethyl-20-ethyl-2-nor-13-trans prostene |
| 251 | 1-trans-tri-n-butylstannyl-4-fluoromethyl-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-fluoromethyl- |

TABLE I-continued

| EXAMPLE | VINYL IODIDE | CYCLOPENTENONE | PRODUCT PROSTAGLANDIN OF THE 11-DEOXY PGE1 SERIES |
|---|---|---|---|
| 252 | 1-trans-tri-n-butylstannyl-4-difluoromethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-difluoromethyl-20-nor-13-trans prostene |
| 253 | 1-trans-tri-n-butylstannyl-4-trifluoromethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-trifluoromethyl-20-nor-13-trans prostene |
| 254 | 1-trans-tri-n-butylstannyl-4-chloromethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-chloromethyl-20-nor-13-trans prostene |
| 255 | 1-trans-tri-n-butylstannyl-4-bromomethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-bromomethyl-20-nor-13-trans prostene |
| EXAMPLE | VINYL IODIDE | CYCLOPENTENONE | PRODUCT PROSTAGLANDIN OF THE 11-DEOXY PGE1 SERIES |
| 256 | 1-trans-iodo-4-allenyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-allenyl-20-nor-13-trans prostene |
| EXAMPLE | VINYL TIN | CYCLOPENTENONE | PRODUCT PROSTAGLANDIN OF THE 11-DEOXY PGE1 SERIES |
| 257 | 1-trans-tri-n-butylstannyl-5-methylene-4-triethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-17-methylene-20-nor-13-trans prostene |
| 258 | 1-trans-tri-n-butylstannyl-4-methyl-5-methylene-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-methyl-17-methylene-20-nor-13-trans prostene |
| 259 | 1-trans-tri-n-butylstannyl-4-dimethoxymethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-formyl-20-nor-13-trans prostene |
| 260 | 1-trans-tri-n-butylstannyl-4-deutro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-deutro-20-nor-13-trans prostene |
| 261 | 1-trans-tri-n-butylstannyl-4-triethylsilyloxymethyl-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-hydroxymethyl-20-nor-13-trans prostene |
| 262 | 1-trans-tri-n-butylstannyl-7-oxa-4-triethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-19-oxa-13-trans prostene |
| 263 | 1-trans-tri-n-butylstannyl-4-methyl-7-oxa-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-methyl-19-oxa-13-trans prostene |
| 264 | 1-trans-tri-n-butylstannyl-7-thia-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-19-thia-13-trans prostene |
| 265 | 1-trans-tri-n-butylstannyl-4-methyl-7-thia-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-methyl-19-thia-13-trans prostene |
| EXAMPLE | VINYL IODIDE | CYCLOPENTENONE | PRODUCT PROSTAGLANDIN OF THE 11-DEOXY PGE1 SERIES |
| 266 | 1-trans-iodo-7-chloro-4-triethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-19-chloro-20-nor-13-trans prostene |

TABLE I-continued

| | | | |
|---|---|---|---|
| 267 | 1-trans-iodo-4-methyl-7-chloro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-methyl-19-chloro-20-nor-13-trans prostene |
| EXAMPLE | VINYL TIN | CYCLOPENTENONE | PRODUCT PROSTAGLANDIN OF THE 11-DEOXY PGE1 SERIES |
| 268 | 1-trans-tri-n-butylstannyl-4-fluoromethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-fluoromethyl-13-trans prostene |
| 269 | 1-trans-tri-n-butylstannyl-4-difluoromethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-difluoromethyl-13-trans prostene |
| 270 | 1-trans-tri-n-butylstannyl-4-trifluoromethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-trifluoromethyl-13-trans prostene |
| 271 | 1-trans-tri-n-butylstannyl-4-chloromethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-chloromethyl-13-trans prostene |
| 272 | 1-trans-tri-n-butylstannyl-4-bromomethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-bromomethyl-13-trans prostene |
| EXAMPLE | VINYL IODIDE | CYCLOPENTENONE | PRODUCT PROSTAGLANDIN OF THE 11-DEOXY PGE1 SERIES |
| 273 | 1-trans-iodo-4-allenyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-allenyl-13-trans prostene |
| EXAMPLE | VINYL TIN | CYCLOPENTENONE | PRODUCT PROSTAGLANDIN OF THE 11-DEOXY PGE1 SERIES |
| 274 | 1-trans-tri-n-butylstannyl-5-methylene-4-triethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-17-methylene-13-trans prostene |
| 275 | 1-trans-tri-n-butylstannyl-4-methyl-5-methylene-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-methyl-17-methylene-13-trans prostene |
| 276 | 1-trans-tri-n-butylstannyl-4-dimethoxymethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-formyl-13-trans prostene |
| 277 | 1-trans-tri-n-butylstannyl-4-deutro-4-triethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-deutro-13-trans prostene |
| 278 | 1-trans-tri-n-butylstannyl-4-triethylsilyloxymethyl-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-dihydroxy-1-hydroxymethyl-1,9-dioxo-16-hydroxymethyl-13-trans prostene |
| 279 | 1-trans-tri-n-butylstannyl-4-fluoromethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-fluoromethyl-20-methyl-13-trans prostene |
| 280 | 1-trans-tri-n-butylstannyl-4-difluoromethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-difluoromethyl-20-methyl-13-trans prostene |
| 281 | 1-trans-tri-n-butylstannyl-4-trifluoromethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-trifluoromethyl-20-methyl-13-trans prostene |
| 282 | 1-trans-tri-n-butylstannyl-4-chloromethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-chloromethyl-20-methyl-13-trans prostene |

TABLE I-continued

| EXAMPLE | VINYL IODIDE / VINYL TIN | CYCLOPENTENONE | PRODUCT PROSTAGLANDIN |
|---|---|---|---|
| 283 | 1-trans-tri-n-butylstannyl-4-bromomethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-bromomethyl-20-methyl-13-trans prostene |
| EXAMPLE | VINYL IODIDE | CYCLOPENTENONE | PRODUCT PROSTAGLANDIN OF THE 11-DEOXY PGE1 SERIES |
| 284 | 1-trans-iodo-4-allenyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-allenyl-20-methyl-13-trans prostene |
| EXAMPLE | VINYL TIN | CYCLOPENTENONE | PRODUCT PROSTAGLANDIN OF THE 11-DEOXY PGE1 SERIES |
| 285 | 1-trans-tri-n-butylstannyl-5-methylene-4-triethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-17-methylene-20-methyl-13-trans prostene |
| 286 | 1-trans-tri-n-butylstannyl-4-methyl-5-methylene-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-methyl-17-methylene-20-methyl-13-trans prostene |
| 287 | 1-trans-tri-n-butylstannyl-4-dimethoxymethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-formyl-20-methyl-13-trans prostene |
| 288 | 1-trans-tri-n-butylstannyl-4-deutro-4-triethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-deutro-20-methyl-13-trans prostene |
| 289 | 1-trans-tri-n-butylstannyl-4-triethylsilyloxymethyl-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-hydroxymethyl-20-methyl-13-trans prostene |
| 290 | 1-trans-tri-n-butylstannyl-4-fluoromethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-fluoromethyl-20-ethyl-13-trans prostene |
| 291 | 1-trans-tri-n-butylstannyl-4-difluoromethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-difluoromethyl-20-ethyl-13-trans prostene |
| 292 | 1-trans-tri-n-butylstannyl-4-trifluoromethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-trifluoromethyl-20-ethyl-13-trans prostene |
| 293 | 1-trans-tri-n-butylstannyl-4-chloromethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-chloromethyl-20-ethyl-13-trans prostene |
| 294 | 1-trans-tri-n-butylstannyl-4-bromomethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-bromomethyl-20-ethyl-13-trans prostene |
| EXAMPLE | VINYL IODIDE | CYCLOPENTENONE | PRODUCT PROSTAGLANDIN OF THE 11-DEOXY PGE1 SERIES |
| 295 | 1-trans-iodo-4-allenyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-allenyl-20-ethyl-13-trans prostene |
| EXAMPLE | VINYL TIN | CYCLOPENTENONE | PRODUCT PROSTAGLANDIN OF THE 11-DEOXY PGE1 SERIES |
| 296 | 1-trans-tri-n-butylstannyl-5-methylene-4-triethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-17-methylene-20-ethyl-13-trans prostene |
| 297 | 1-trans-tri-n-butylstannyl-4-methyl-5-methylene-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-methyl-17-methylene-20-ethyl-13-trans prostene |

TABLE I-continued

| | | | PRODUCT |
|---|---|---|---|
| 298 | 1-trans-tri-n-butylstannyl-4-dimethoxymethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-formyl-20-ethyl-13-trans prostene |
| 299 | 1-trans-tri-n-butylstannyl-4-deutro-4-triethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-deutro-20-ethyl-13-trans prostene |
| 300 | 1-trans-tri-n-butylstannyl-4-triethylsilyloxymethyl-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-hydroxymethyl-20-ethyl-13-trans prostene |
| 301 | 1-trans-tri-n-butylstannyl-4-fluoromethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-fluoromethyl-20-nor-2-homo-13-trans prostene |
| 302 | 1-trans-tri-n-butylstannyl-4-difluoromethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-difluoromethyl-20-nor-2-homo-13-trans prostene |
| 303 | 1-trans-tri-n-butylstannyl-4-trifluoromethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-trifluoromethyl-20-nor-2-homo-13-trans prostene |
| dl-304 hydroxy-1-hydroxymethyl-1,9-dioxo-16-chloromethyl | 1-trans-tri-n-butylstannyl-4-chloromethyl-4-trimethylsiloxy-1-heptene | 2-[(4-methoxy-2,2-dimethyl-1,3-dioxolan-4-yl)heptyl]-4-(2-methoxypropyl-2-oxy)cyclopent-2-en-1-one | 4-trimethylsiloxy-1-heptene |
| 305 | 1-trans-tri-n-butylstannyl-4-bromomethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | 20-nor-2-homo-13-trans prostene |
| | | | dl-16-hydroxy-1-hydroxymethyl-1,9-dioxo-16-bromomethyl-20-nor-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 306 | 1-trans-iodo-4-allenyl-4-trimethylsiloxy-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-allenyl-20-nor-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 307 | 1-trans-tri-n-butylstannyl-5-methylene-4-triethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-17-methylene-20-nor-2-homo-13-trans prostene |
| 308 | 1-trans-tri-n-butylstannyl-4-methyl-5-methylene-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-methyl-17-methylene-20-nor-2-homo-13-trans prostene |
| 309 | 1-trans-tri-n-butylstannyl-4-dimethoxymethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-formyl-20-nor-2-homo-13-trans prostene |
| 310 | 1-trans-tri-n-butylstannyl-4-deutro-4-triethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-deutro-20-nor-2-homo-13-trans prostene |
| 311 | 1-trans-tri-n-butylstannyl-4-triethylsilyloxymethyl-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-hydroxymethyl-20-nor-2-homo-13-trans prostene |
| 312 | 1-trans-tri-n-butylstannyl-7-oxa | 2-[(4-methoxy-2,2-dimethyl-1,3-dioxolan- | dl-16-hydroxy-1-hydroxymethyl-1,9-dioxo- |

TABLE I-continued

| EXAMPLE | VINYL | CYCLOPENTENONE | PRODUCT PROSTAGLANDIN OF THE 11-DEOXY PGE1 SERIES |
|---|---|---|---|
| | 4-triethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | 19-oxa-2-homo-13-trans prostene |
| 313 | 1-trans-tri-n-butylstannyl-4-methyl-7-oxa-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-methyl-19-oxa-2-homo-13-trans prostene |
| 314 | 1-trans-tri-n-butylstannyl-7-thia-4-triethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-19-thia-2-homo-13-trans prostene |
| 315 | 1-trans-tri-n-butylstannyl-4-methyl-7-thia-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-methyl-19-thia-2-homo-13-trans prostene |
| EXAMPLE | VINYL IODIDE | CYCLOPENTENONE | PRODUCT PROSTAGLANDIN OF THE 11-DEOXY PGE1 SERIES |
| 316 | 1-trans-iodo-7-chloro-4-triethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-19-chloro-2-homo-20-nor-13-trans prostene |
| 317 | 1-trans-iodo-4-methyl-7-chloro-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-methyl-19-chloro-2-homo-20-nor-13-trans prostene |
| EXAMPLE | VINYL TIN | CYCLOPENTENONE | PRODUCT PROSTAGLANDIN OF THE 11-DEOXY PGE1 SERIES |
| 318 | 1-trans-tri-n-butylstannyl-4-fluoromethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-fluoromethyl-2-homo-13-trans prostene |
| 319 | 1-trans-tri-n-butylstannyl-4-difluoromethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-difluoromethyl-2-homo-13-trans prostene |
| 320 | 1-trans-tri-n-butylstannyl-4-trifluoromethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-trifluoromethyl-2-homo-13-trans prostene |
| 321 | 1-trans-tri-n-butylstannyl-4-chloromethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-chloromethyl-2-homo-13-trans prostene |
| 322 | 1-trans-tri-n-butylstannyl-4-bromomethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-bromomethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 323 | 1-trans-iodo-4-allenyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-allenyl-2-homo-13-trans prostene |
| EXAMPLE | VINYL TIN | CYCLOPENTENONE | PRODUCT PROSTAGLANDIN OF THE 11-DEOXY PGE1 SERIES |
| 324 | 1-trans-tri-n-butylstannyl-5-methylene-4-triethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-17-methylene-2-homo-13-trans prostene |
| 325 | 1-trans-tri-n-butylstannyl-4-methyl-5-methylene-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-methyl-17-methylene-2-homo-13-trans prostene |
| 326 | 1-trans-tri-n-butylstannyl-4-dimethoxymethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-formyl-2-homo-13-trans prostene |
| 327 | 1-trans-tri-n-butylstannyl-4-deutro- | 2-[7-(4-methoxy-2,2-dimethyl-1,3-dioxolan- | dl-16-hydroxy-1-hydroxymethyl-1,9-dioxo-16-deutro- |

TABLE I-continued

| | | |
|---|---|---|
| | 4-triethylsiloxy-1-octene | 2-homo-13-trans prostene |
| | | 4-yl)heptyl]-4-(2-methoxypropyl-1,3-dioxolan-2-oxy)cyclopent-2-en-1-one | |
| 328 | 1-trans-tri-n-butylstannyl-4-triethylsilyloxymethyl-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-hydroxymethyl-2-homo-13-trans prostene |
| 329 | 1-trans-tri-n-butylstannyl-4-fluoromethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-fluoromethyl-20-methyl-2-homo-13-trans prostene |
| 330 | 1-trans-tri-n-butylstannyl-4-difluoromethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-difluoromethyl-20-methyl-2-homo-13-trans prostene |
| 331 | 1-trans-tri-n-butylstannyl-4-trifluoromethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-trifluoromethyl-20-methyl-2-homo-13-trans prostene |
| 332 | 1-trans-tri-n-butylstannyl-4-chloromethyl-4-trimethylsiloxy-1-nonene | 2-[(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-chloromethyl-20-methyl-2-homo-13-trans prostene |
| 333 | 1-trans-tri-n-butylstannyl-4-bromomethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-bromomethyl-20-methyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 334 | 1-trans-iodo-4-allenyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-allenyl-20-methyl-2-homo-13-trans prostene |
| EXAMPLE | VINYL TIN | CYCLOPENTENONE | PRODUCT PROSTAGLANDIN OF THE 11-DEOXY PGE1 SERIES |
| 335 | 1-trans-tri-n-butylstannyl-5-methyl-5-methylene-4-triethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-17-methylene-20-methyl-2-homo-13-trans prostene |
| 336 | 1-trans-tri-n-butylstannyl-4-methyl-5-methylene-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-methyl-17-methylene-20-methyl-2-homo-13-trans prostene |
| 337 | 1-trans-tri-n-butylstannyl-4-dimethoxymethyl-4-trimethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-formyl-20-methyl-2-homo-13-trans prostene |
| 338 | 1-trans-tri-n-butylstannyl-4-deutro-4-triethylsiloxy-1-nonene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-deutro-20-methyl-2-homo-13-trans prostene |
| 339 | 1-trans-tri-n-butylstannyl-4-triethylsilyloxymethyl-4-trimethylsiloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-hydroxymethyl-20-ethyl-2-homo-13-trans prostene |
| 340 | 1-trans-tri-n-butylstannyl-4-fluoromethyl-4-trimethylsiloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-fluoromethyl-20-ethyl-2-homo-13-trans prostene |
| 341 | 1-trans-tri-n-butylstannyl-4-difluoromethyl-4-trimethylsiloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-difluoromethyl-20-ethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 345 | 1-trans-iodo-4-allenyl- | 2-[7-(4-methoxy-2,2-dimethyl-1,3-dioxolan- | dl-16-hydroxy-1-hydroxymethyl-1,9-dioxo-16-allenyl- |

TABLE I-continued

| EXAMPLE | VINYL TIN | CYCLOPENTENONE | PRODUCT PROSTAGLANDIN OF THE 11-DEOXY PGE1 SERIES |
|---|---|---|---|
| | 4-trimethylsilyloxy-1-decene | 4-yl]heptyl]-4-(2-methoxypropyl-2-oxy)cyclopent-2-en-1-one | 20-ethyl-2-homo-13-trans prostene |
| 346 | 1-trans-tri-n-butylstannyl-5-methylene-4-triethylsilyloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-17-methylene-20-ethyl-2-homo-13-trans prostene |
| 347 | 1-trans-tri-n-butylstannyl-4-methyl-5-methylene-4-trimethylsilyloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-methyl-17-methylene-20-ethyl-2-homo-13-trans prostene |
| 348 | 1-trans-tri-n-butylstannyl-4-dimethoxymethyl-4-trimethylsilyloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-formyl-20-ethyl-2-homo-13-trans prostene |
| 349 | 1-trans-tri-n-butylstannyl-4-deutero-4-triethylsilyloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-deutro-20-ethyl-2-homo-13-trans prostene |
| 350 | 1-trans-tri-n-butylstannyl-4-triethylsilyloxymethyl-4-trimethylsilyloxy-1-decene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-hydroxymethyl-20-ethyl-2-homo-13-trans prostene |

| EXAMPLE | VINYL TIN | CYCLOPENTENONE | PRODUCT PROSTAGLANDIN OF THE PGE1 SERIES |
|---|---|---|---|
| 351 | 1-trans-tri-n-butylstannyl-4-(1-fluorovinyl)-4-trimethylsilyloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-(1-fluorovinyl)-20-nor-2-nor-13-trans prostene |
| 352 | 1-trans-tri-n-butylstannyl-3-vinyl-3-trimethylsilyloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,15a-dihydroxy-1-hydroxymethyl-1,9-dioxo-16-vinyl-20-nor-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 353 | 1-iodo-4-vinyl-7-chloro-4-trimethylsilyloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-vinyl-19-chloro-2-nor-20-nor-13-trans prostene |
| 354 | 1-iodo-4-methyl-7-chloro-4-trimethylsilyloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-19-chloro-2-nor-20-nor-13-trans prostene |

| EXAMPLE | VINYL TIN | CYCLOPENTENONE | PRODUCT PROSTAGLANDIN OF THE PGE1 SERIES |
|---|---|---|---|
| 355 | 1-trans-tri-n-butylstannyl-4-methyl-4-trimethylsilyloxy-1-pentene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-2-nor-18,19,20-trinor-13-trans prostene |
| 356 | 1-trans-tri-n-butylstannyl-4-(1-fluorovinyl)-4-trimethylsilyloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-(1-fluorovinyl)-2-nor-13-trans prostene |
| 357 | 1-trans-tri-n-butylstannyl-3-vinyl-3-trimethylsilyloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-11a,15a-dihydroxy-1-hydroxymethyl-1,9-dioxo-15-vinyl-2-nor-13-trans prostene |
| 358 | 1-trans-tri-n-butylstannyl-4-(1-fluorovinyl)-4-trimethylsilyloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-(1-fluorovinyl)-20-methyl-2-nor-13-trans prostene |
| 359 | 1-trans-tri-n-butylstannyl-3-vinyl-3-trimethylsilyloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-11a,15a-dihydroxy-1-hydroxymethyl-1,9-dioxo-15-vinyl-20-methyl-2-nor-13-trans prostene |
| 360 | 1-trans-tri-n-butylstannyl-4-(1-fluorovinyl)- | 2-[5-(4-methoxy-2,2-dimethyl-1,3-dioxolan- | dl-11a,16-dihydroxy-1-hydroxymethyl-1,9-dioxo-16-(1-fluorovinyl)- |

| EXAMPLE | VINYL IODIDE | CYCLOPENTENONE | PRODUCT PROSTAGLANDIN OF THE PGE1 SERIES |
|---|---|---|---|
| | 4-trimethylsiloxy-1-decene | 4-yl)pentyl]-4-(2-methoxypropyl-2-oxy)cyclopent-2-en-1-one | 20-ethyl-2-nor-13-trans prostene |
| 361 | 1-trans-tri-n-butylstannyl-3-vinyl-3-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-11a,15a-dihydroxy-1-hydroxymethyl-1,9-dioxo-15-vinyl-20-ethyl-2-nor-13-trans prostene |
| 362 | 1-trans-tri-n-butylstannyl-4-(1-fluorovinyl)-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-(1-fluorovinyl)-20-nor-13-trans prostene |
| 363 | 1-trans-tri-n-butylstannyl-3-vinyl-3-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,15a-dihydroxy-1-hydroxymethyl-1,9-dioxo-15-vinyl-20-nor-13-trans prostene |
| EXAMPLE | VINYL IODIDE | CYCLOPENTENONE | PRODUCT PROSTAGLANDIN OF THE PGE1 SERIES |
| 364 | 1-trans-iodo-4-vinyl-7-chloro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-19-chloro-20-nor-13-trans prostene |
| 365 | 1-trans-iodo-4-methyl-7-chloro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-19-chloro-20-nor-13-trans prostene |
| EXAMPLE | VINYL TIN | CYCLOPENTENONE | PRODUCT PROSTAGLANDIN OF THE PGE1 SERIES |
| 366 | 1-trans-tri-n-butylstannyl-4-methyl-4-trimethylsiloxy-1-pentene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-18,19,20-trinor-13-trans prostene |
| 367 | 1-trans-tri-n-butylstannyl-4-(1-fluorovinyl)-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-(1-fluorovinyl)-13-trans prostene |
| 368 | 1-trans-tri-n-butylstannyl-3-vinyl-3-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,15a-dihydroxy-1-hydroxymethyl-1,9-dioxo-15-vinyl-13-trans prostene |
| 369 | 1-trans-tri-n-butylstannyl-4-(1-fluorovinyl)-4-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-(1-fluorovinyl)-20-methyl-13-trans prostene |
| 370 | 1-trans-tri-n-butylstannyl-3-vinyl-3-trimethylsiloxy-1-nonene | 2-[6-(4-methoxy-2,2-dimethyl-1,3-dioxolan-4-yl)hexyl]-4-(2-methoxypropyl-2-oxy)cyclopent-2-en-1-one | dl-11a,15a-dihydroxy-1-hydroxymethyl-1,9-dioxo-15-vinyl-20-methyl-13-trans prostene |
| 371 | 1-trans-tri-n-butylstannyl-4-(1-fluorovinyl)-4-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-(1-fluorovinyl)-20-ethyl-13-trans prostene |
| 372 | 1-trans-tri-n-butylstannyl-3-vinyl-3-trimethylsiloxy-1-decene | 2-[6-(4-methoxy-2,2-dimethyl-1,3-dioxolan-4-yl)hexyl]-4-(2-methoxypropyl-2-oxy)cyclopent-2-en-1-one | dl-11a,15a-dihydroxy-1-hydroxymethyl-1,9-dioxo-15-vinyl-20-ethyl-13-trans prostene |
| 373 | 1-trans-tri-n-butylstannyl-4-(1-fluorovinyl)-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-(1-fluorovinyl)-20-nor-2-homo-13-trans prostene |
| 374 | 1-trans-tri-n-butylstannyl-3-vinyl-3-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,15a-dihydroxy-1-hydroxymethyl-1,9-dioxo-15-vinyl-20-nor-2-homo-13-trans prostene |
| EXAMPLE | VINYL IODIDE | CYCLOPENTENONE | PRODUCT PROSTAGLANDIN OF THE PGE1 SERIES |
| 375 | 1-trans-iodo-4-vinyl-7-chloro-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-vinyl-19-chloro-2-homo-20-nor-13-trans prostene |

| | VINYL TIN | CYCLOPENTENONE | PRODUCT PROSTAGLANDIN OF THE PGE1 SERIES |
|---|---|---|---|
| 376 | 1-trans-iodo-4-methyl-7-chloro-4-trimethylsiloxy-1-heptene | 2-[7-(4-methoxy-2,2-dimethyl-1,3-dioxolan-4-yl)heptyl]-4-(2-methoxypropyl)-2-oxy)cyclopent-2-en-1-one | dl-11a,16-dihydroxy-1-hydroxymethyl-1,9-dioxo-16-methyl-19-chloro-2-homo-20-nor-13-trans prostene |
| EXAMPLE | VINYL TIN | CYCLOPENTENONE | PRODUCT PROSTAGLANDIN OF THE PGE1 SERIES |
| 377 | 1-trans-tri-n-butylstannyl-4-methyl-4-trimethylsiloxy-1-pentene | 2-[7-(4-methoxy-2,2-dimethyl-1,3-dioxolan-4-yl)heptyl]-4-(2-methoxypropyl)-2-oxy)cyclopent-2-en-1-one | dl-11a,16-dihydroxy-1-hydroxymethyl-1,9-dioxo-16-methyl-2-homo-18,19,20-trinor-13-trans prostene |
| 378 | 1-trans-tri-n-butylstannyl-4-(1-fluorovinyl)-4-trimethylsiloxy-1-octene | 2-[7-(4-methoxy-2,2-dimethyl-1,3-dioxolan-4-yl)heptyl]-4-(2-methoxypropyl)-2-oxy)cyclopent-2-en-1-one | dl-11a,16-dihydroxy-1-hydroxymethyl-1,9-dioxo-16-(1-fluorovinyl)-2-homo-13-trans prostene |
| 379 | 1-trans-tri-n-butylstannyl-3-vinyl-3-trimethylsiloxy-1-octene | 2-[7-(4-methoxy-2,2-dimethyl-1,3-dioxolan-4-yl)heptyl]-4-(2-methoxypropyl)-2-oxy)cyclopent-2-en-1-one | dl-11a,15a-dihydroxy-1-hydroxymethyl-1,9-dioxo-15-vinyl-2-homo-13-trans prostene |
| 380 | 1-trans-tri-n-butylstannyl-4-(1-fluorovinyl)-4-trimethylsiloxy-1-nonene | 2-[7-(4-methoxy-2,2-dimethyl-1,3-dioxolan-4-yl)heptyl]-4-(2-methoxypropyl)-2-oxy)cyclopent-2-en-1-one | dl-11a,16-dihydroxy-1-hydroxymethyl-1,9-dioxo-16-(1-fluorovinyl)-20-methyl-2-homo-13-trans prostene |
| 381 | 1-trans-tri-n-butylstannyl-3-vinyl-3-trimethylsiloxy-1-nonene | 2-[7-(4-methoxy-2,2-dimethyl-1,3-dioxolan-4-yl)heptyl]-4-(2-methoxypropyl)-2-oxy)cyclopent-2-en-1-one | dl-11a,15a-dihydroxy-1-hydroxymethyl-1,9-dioxo-15-vinyl-20-methyl-2-homo-13-trans prostene |
| 382 | 1-trans-tri-n-butylstannyl-4-(1-fluorovinyl)-4-trimethylsiloxy-1-decene | 2-[7-(4-methoxy-2,2-dimethyl-1,3-dioxolan-4-yl)heptyl]-4-(2-methoxypropyl)-2-oxy)cyclopent-2-en-1-one | dl-11a,16-dihydroxy-1-hydroxymethyl-1,9-dioxo-16-(1-fluorovinyl)-20-ethyl-2-homo-13-trans prostene |
| 383 | 1-trans-tri-n-butylstannyl-3-vinyl-3-trimethylsiloxy-1-decene | 2-[7-(4-methoxy-2,2-dimethyl-1,3-dioxolan-4-yl)heptyl]-4-(2-methoxypropyl)-2-oxy)cyclopent-2-en-1-one | dl-11a,15a-dihydroxy-1-hydroxymethyl-1,9-dioxo-15-vinyl-20-ethyl-2-homo-13-trans prostene |
| 384 | 1-trans-tri-n-butylstannyl-4-(1-fluorovinyl)-4-trimethylsiloxy-1-heptene | 2-[6-(4-methoxy-2,2-dimethyl-1,3-dioxolan-4-yl)hexyl]-4R-(2-methoxypropyl)-2-oxy)cyclopent-2-en-1-one | nat-11a,16-dihydroxy-1-hydroxymethyl-1,9-dioxo-16-(1-fluorovinyl)-20-nor-13-trans prostene |
| 385 | 1-trans-tri-n-butylstannyl-3-vinyl-3-trimethylsiloxy-1-heptene | 2-[6-(4-methoxy-2,2-dimethyl-1,3-dioxolan-4-yl)hexyl]-4R-(2-methoxypropyl)-2-oxy)cyclopent-2-en-1-one | nat-11a,15a-dihydroxy-1-hydroxymethyl-1,9-dioxo-15-vinyl-20-nor-13-trans prostene |
| EXAMPLE | VINYL IODIDE | CYCLOPENTENONE | PRODUCT PROSTAGLANDIN OF THE PGE1 SERIES |
| 386 | 1-trans-iodo-4-vinyl-7-chloro-4-trimethylsiloxy-1-heptene | 2-[6-(4-methoxy-2,2-dimethyl-1,3-dioxolan-4-yl)hexyl]-4R-(2-methoxypropyl)-2-oxy)cyclopent-2-en-1-one | nat-11a,16-dihydroxy-1-hydroxymethyl-1,9-dioxo-16-vinyl-19-chloro-20-nor-13-trans prostene |
| 387 | 1-trans-iodo-4-methyl-7-chloro-4-trimethylsiloxy-1-heptene | 2-[6-(4-methoxy-2,2-dimethyl-1,3-dioxolan-4-yl)hexyl]-4R-(2-methoxypropyl)-2-oxy)cyclopent-2-en-1-one | nat-11a,16-dihydroxy-1-hydroxymethyl-1,9-dioxo-16-methyl-19-chloro-20-nor-13-trans prostene |
| EXAMPLE | VINYL TIN | CYCLOPENTENONE | PRODUCT PROSTAGLANDIN OF THE PGE1 SERIES |
| 388 | 1-trans-tri-n-butylstannyl-4-methyl-4-trimethylsiloxy-1-pentene | 2-[6-(4-methoxy-2,2-dimethyl-1,3-dioxolan-4-yl)hexyl]-4R-(2-methoxypropyl)-2-oxy)cyclopent-2-en-1-one | nat-11a,16-dihydroxy-1-hydroxymethyl-1,9-dioxo-16-methyl-18,19,20-trinor-13-trans prostene |
| 389 | 1-trans-tri-n-butylstannyl-4-(1-fluorovinyl)-4-trimethylsiloxy-1-octene | 2-[6-(4-methoxy-2,2-dimethyl-1,3-dioxolan-4-yl)hexyl]-4R-(2-methoxypropyl)-2-oxy)cyclopent-2-en-1-one | nat-11a,16-dihydroxy-1-hydroxymethyl-1,9-dioxo-16-(1-fluorovinyl)-13-trans prostene |
| 390 | 1-trans-tri-n-butylstannyl-3-vinyl-3-trimethylsiloxy-1-octene | 2-[6-(4-methoxy-2,2-dimethyl-1,3-dioxolan-4-yl)hexyl]-4R-(2-methoxypropyl)-2-oxy)cyclopent-2-en-1-one | nat-11a,15a-dihydroxy-1-hydroxymethyl-1,9-dioxo-15-vinyl-13-trans prostene |
| 391 | 1-trans-tri-n-butylstannyl-4-(1-fluorovinyl)-4-trimethylsiloxy-1-nonene | 2-[6-(4-methoxy-2,2-dimethyl-1,3-dioxolan-4-yl)hexyl]-4R-(2-methoxypropyl)-2-oxy)cyclopent-2-en-1-one | nat-11a,16-dihydroxy-1-hydroxymethyl-1,9-dioxo-16-(1-fluorovinyl)-20-methyl-13-trans prostene |

TABLE I-continued

| EXAMPLE | | | PRODUCT PROSTAGLANDIN OF THE 11-DEOXY PGE1 SERIES |
|---|---|---|---|
| 392 | 1-trans-tri-n-butylstannyl-3-vinyl-3-trimethylsiloxy-1-nonene | 2[6-(4-methoxy-2,2-dimethyl-1,3-dioxolan-4-yl)hexyl]-4R-(2-methoxypropyl-2-oxy)cyclopent-2-en-1-one | nat-11a,15a-dihydroxy-1-hydroxymethyl-1,9-dioxo-15-vinyl-20-methyl-13-trans prostene |
| 393 | 1-trans-tri-n-butylstannyl-4-(1-fluorovinyl)-4-trimethylsiloxy-1-decene | 2[6-(4-methoxy-2,2-dimethyl-1,3-dioxolan-4-yl)hexyl]-4R-(2-methoxypropyl-2-oxy)cyclopent-2-en-1-one | nat-11a,18-dihydroxy-1-hydroxymethyl-1,9-dioxo-16-(1-fluorovinyl)-20-ethyl-13-trans prostene |
| 394 | 1-trans-tri-n-butylstannyl-3-vinyl-3-trimethylsiloxy-1-decene | 2[6-(4-methoxy-2,2-dimethyl-1,3-dioxolan-4-yl)hexyl]-4R-(2-methoxypropyl-2-oxy)cyclopent-2-en-1-one | nat-11a,15a-dihydroxy-1-hydroxymethyl-1,9-dioxo-15-vinyl-20-ethyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 395 | 1-trans-tri-n-butylstannyl-4-(1-fluorovinyl)-4-trimethylsiloxy-1-heptene | 2[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-(fluorovinyl)-20-nor-2-nor-13-trans prostene |
| 396 | 1-trans-tri-n-butylstannyl-3-vinyl-3-trimethylsiloxy-1-heptene | 2[5-(4-methoxy-2,2-dimethyl-1,3-dioxolan-4-yl)pentyl]-4-(2-methoxypropyl-2-oxy)cyclopent-2-en-1-one | dl-15a-hydroxy-1-hydroxymethyl-1,9-dioxo-15-vinyl-20-nor-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 397 | 1-iodo-4-vinyl-7-chloro-4-trimethylsiloxy-1-heptene | 2[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-vinyl-19-chloro-2-nor-20-nor-13-trans prostene |
| 398 | 1-iodo-4-methyl-7-chloro-4-trimethylsiloxy-1-heptene | 2[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-methyl-19-chloro-2-nor-20-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 399 | 1-trans-tri-n-butylstannyl-4-methyl-4-trimethylsiloxy-1-pentene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-methyl-2-nor-18,19,20-trinor-13-trans prostene |
| 400 | 1-trans-tri-n-butylstannyl-4-(1-fluorovinyl)-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-(1-fluorovinyl)-2-nor-13-trans prostene |
| 401 | 1-trans-tri-n-butylstannyl-3-vinyl-3-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-15a-hydroxy-1-hydroxymethyl-1,9-dioxo-15-vinyl-2-nor-13-trans prostene |
| 402 | 1-trans-tri-n-butylstannyl-4-(1-fluorovinyl)-4-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-(1-fluorovinyl)-20-methyl-2-nor-13-trans prostene |
| 403 | 1-trans-tri-n-butylstannyl-3-vinyl-3-trimethylsiloxy-1-nonene | 2-[5-(4-methoxy-2,2-dimethyl-1,3-dioxolan-4-yl)pentyl]-4-(2-methoxypropyl-2-oxy)cyclopent-2-en-1-one | dl-15a-hydroxy-1-hydroxymethyl-1,9-dioxo-15-vinyl-20-methyl-2-nor-13-trans prostene |
| 404 | 1-trans-tri-n-butylstannyl-4-(1-fluorovinyl)-4-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-(1-fluorovinyl)-20-ethyl-2-nor-13-trans prostene |
| 405 | 1-trans-tri-n-butylstannyl-3-vinyl-3-trimethylsiloxy-1-decene | 2-[5-(4-methoxy-2,2-dimethyl-1,3-dioxolan-4-yl)pentyl]-4-(2-methoxypropyl-2-oxy)cyclopent-2-en-1-one | dl-15a-hydroxy-1-hydroxymethyl-1,9-dioxo-15-vinyl-20-ethyl-2-nor-13-trans prostene |
| 406 | 1-trans-tri-n-butylstannyl-4-(1-fluorovinyl)-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-(1-fluorovinyl)-20-nor-13-trans prostene |
| 407 | 1-trans-tri-n-butylstannyl-3-vinyl-3-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-15a-hydroxy-1-hydroxymethyl-1,9-dioxo-15-vinyl- |

TABLE I-continued

| EXAMPLE | VINYL IODIDE | CYCLOPENTENONE | PRODUCT PROSTAGLANDIN OF THE 11-DEOXY PGE1 SERIES |
|---|---|---|---|
| | 3-trimethylsiloxy-1-heptene | 4-yl)hexyl]-4-(2-methoxypropyl-2-oxy) cyclopent-2-en-1-one | 20-nor-13-trans prostene |
| 408 | 1-trans-iodo-4-vinyl-7-chloro 4-trimethylsiloxy-1-heptene | 2-[6-(4-methoxy-2,2-dimethyl-1,3-dioxolan-4-yl)hexyl]-4-(2-methoxypropyl-2-oxy) cyclopent-2-en-1-one | dl-16-hydroxy-1-hydroxymethyl-1,9-dioxo-16-vinyl-19-chloro-20-nor-13-trans prostene |
| 409 | 1-trans-iodo-4-methyl-7-chloro 4-trimethylsiloxy-1-heptene | 2-[6-(4-methoxy-2,2-dimethyl-1,3-dioxolan-4-yl)hexyl]-4-(2-methoxypropyl-2-oxy) cyclopent-2-en-1-one | dl-16-hydroxy-1-hydroxymethyl-1,9-dioxo-16-methyl-19-chloro-20-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 410 | 1-trans-tri-n-butylstannyl-4-methyl-4-trimethylsiloxy-1-pentene | 2-[6-(4-methoxy-2,2-dimethyl-1,3-dioxolan-4-yl)hexyl]-4-(2-methoxypropyl-2-oxy) cyclopent-2-en-1-one | dl-16-hydroxy-1-hydroxymethyl-1,9-dioxo-16-methyl-18,19,20-trinor-13-trans prostene |
| 411 | 1-trans-tri-n-butylstannyl-4-(1-fluorovinyl)-4-trimethylsiloxy-1-octene | 2-[6-(4-methoxy-2,2-dimethyl-1,3-dioxolan-4-yl)hexyl]-4-(2-methoxypropyl-2-oxy) cyclopent-2-en-1-one | dl-16-hydroxy-1-hydroxymethyl-1,9-dioxo-16-(1-fluorovinyl)-13-trans prostene |
| 412 | 1-trans-tri-n-butylstannyl-3-vinyl-3-trimethylsiloxy-1-octene | 2-[6-(4-methoxy-2,2-dimethyl-1,3-dioxolan-4-yl)hexyl]-4-(2-methoxypropyl-2-oxy) cyclopent-2-en-1-one | dl-15a-hydroxy-1-hydroxymethyl-1,9-dioxo-15-vinyl-13-trans prostene |
| 413 | 1-trans-tri-n-butylstannyl-4-(1-fluorovinyl)-4-trimethylsiloxy-1-nonene | 2-[6-(4-methoxy-2,2-dimethyl-1,3-dioxolan-4-yl)hexyl]-4-(2-methoxypropyl-2-oxy) cyclopent-2-en-1-one | dl-16-hydroxy-1-hydroxymethyl-1,9-dioxo-16-(1-fluorovinyl)-20-methyl-13-trans prostene |
| 414 | 1-trans-tri-n-butylstannyl-3-vinyl-3-trimethylsiloxy-1-nonene | 2-[6-(4-methoxy-2,2-dimethyl-1,3-dioxolan-4-yl)hexyl]-4-(2-methoxypropyl-2-oxy) cyclopent-2-en-1-one | dl-15a-hydroxy-1-hydroxymethyl-1,9-dioxo-15-vinyl-20-methyl-13-trans prostene |
| 415 | 1-trans-tri-n-butylstannyl-4-(1-fluorovinyl)-4-trimethylsiloxy-1-decene | 2-[6-(4-methoxy-2,2-dimethyl-1,3-dioxolan-4-yl)hexyl]-4-(2-methoxypropyl-2-oxy) cyclopent-2-en-1 one | dl-16-hydroxy-1-hydroxymethyl-1,9-dioxo-16-(1-fluorovinyl)-20-ethyl-13-trans prostene |
| 416 | 1-trans-tri-n-butylstannyl-3-vinyl-3-trimethylsiloxy-1-decene | 2-[6-(4-methoxy-2,2-dimethyl-1,3-dioxolan-4-yl)hexyl]-4-(2-methoxypropyl-2-oxy) cyclopent-2-en-1-one | dl-15a-hydroxy-1-hydroxymethyl-1,9-dioxo-15-vinyl-20-ethyl-13-trans prostene |
| 417 | 1-trans-tri-n-butylstannyl-4-(1-fluorovinyl)-4-trimethylsiloxy-1-heptene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-16-(1-fluorovinyl)-20-nor-2-homo-13-trans prostene |
| 418 | 1-trans-tri-n-butylstannyl-3-vinyl-3-trimethylsiloxy-1-heptene | 2-[7-(4-methoxy-2,2-dimethyl-1,3-dioxolan-4-yl)heptyl]-4-(2-methoxypropyl-2-oxy) cyclopent-2-en-1-one | dl-15a-hydroxy-1-hydroxymethyl-1,9-dioxo-15-vinyl-20-nor-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 419 | 1-trans-iodo-4-vinyl-7-chloro 4-trimethylsiloxy-1-heptene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-16-vinyl-19-chloro-2-homo-20-nor-13-trans prostene |
| 420 | 1-trans-iodo-4-methyl-7-chloro 4-trimethylsiloxy-1-heptene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-16-methyl-19-chloro-2-homo-20-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 421 | 1-trans-tri-n-butylstannyl-4-methyl-4-trimethylsiloxy-1-pentene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-16-methyl-2-homo-18,19,20-trinor-13-trans prostene |
| 422 | 1-trans-tri-n-butylstannyl-4-(1-fluorovinyl)- | 2-[7-(4-methoxy-2,2-dimethyl-1,3-dioxolan- | dl-16-hydroxy-1-hydroxymethyl-1,9-dioxo-16-(1-fluorovinyl)- |

TABLE I-continued

| | | | PRODUCT |
|---|---|---|---|
| | 4-yl)heptyl]-4-(2-methoxypropyl-1,3-dioxolan-2-oxy)cyclopent-2-en-1-one | 4-trimethylsiloxy-1-octene | 2-homo-13-trans prostene |
| 423 | 2-[7-(4-methoxy-2,2-dimethyl-1,3-dioxolan-4-yl)heptyl]-4-(2-methoxypropyl-2-oxy)cyclopent-2-en-1-one | 1-trans-tri-n-butylstannyl-3-vinyl-3-trimethylsiloxy-1-octene | dl-15a-hydroxy-1-hydroxymethyl-1,9-dioxo-15-vinyl-2-homo-13-trans prostene |
| 424 | 2-[7-(4-methoxy-2,2-dimethyl-1,3-dioxolan-4-yl)heptyl]-4-(2-methoxypropyl-2-oxy)cyclopent-2-en-1-one | 1-trans-tri-n-butylstannyl-4-(1-fluorovinyl)-4-trimethylsiloxy-1-nonene | dl-16-hydroxy-1-hydroxymethyl-1,9-dioxo-16-(1-fluorovinyl)-20-methyl-2-homo-13-trans prostene |
| 425 | 2-[7-(4-methoxy-2,2-dimethyl-1,3-dioxolan-4-yl)heptyl]-4-(2-methoxypropyl-2-oxy)cyclopent-2-en-1-one | 1-trans-tri-n-butylstannyl-3-vinyl-3-trimethylsiloxy-1-nonene | dl-15a-hydroxy-1-hydroxymethyl-1,9-dioxo-15-vinyl-20-methyl-2-homo-13-trans prostene |
| 426 | 2-[7-(4-methoxy-2,2-dimethyl-1,3-dioxolan-4-yl)heptyl]-4-(2-methoxypropyl-2-oxy)cyclopent-2-en-1-one | 1-trans-tri-n-butylstannyl-4-(1-fluorovinyl)-4-trimethylsiloxy-1-decene | dl-16-hydroxy-1-hydroxymethyl-1,9-dioxo-16-(1-fluorovinyl)-20-ethyl-2-homo-13-trans prostene |
| 427 | 2-[7-(4-methoxy-2,2-dimethyl-1,3-dioxolan-4-yl)heptyl]-4-(2-methoxypropyl-2-oxy)cyclopent-2-en-1-one | 1-trans-tri-n-butylstannyl-3-vinyl-3-trimethylsiloxy-1-decene | dl-15a-hydroxy-1-hydroxymethyl-1,9-dioxo-15-vinyl-20-ethyl-2-homo-13-trans prostene |
| EXAMPLE | VINYL TIN | CYCLOPENTENONE | PRODUCT PROSTAGLANDIN OF THE PGE1 SERIES |
| 428 | 1-trans-tri-n-butylstannyl-4-methyl-4-trimethylsiloxy-1,7-octadiene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-methyl-2-nor-13-trans-19 prostadiene |
| 429 | 1-trans-tri-n-butylstannyl-4-methyl-4-trimethylsiloxy-1,7-octadiene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-methyl-13-trans-19 prostadiene |
| 430 | 1-trans-tri-n-butylstannyl-4-methyl-4-trimethylsiloxy-1,7-octadiene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-methyl-2-homo-13-trans-19 prostadiene |
| 431 | 1-trans-tri-n-butylstannyl-4-methyl-4-trimethylsiloxy-1,7-octadiene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-methyl-13-trans-19 prostadiene |
| EXAMPLE | VINYL TIN | CYCLOPENTENONE | PRODUCT PROSTAGLANDIN OF THE 11-DEOXY PGE1 SERIES |
| 432 | 1-trans-tri-n-butylstannyl-4-methyl-4-trimethylsiloxy-1,7-octadiene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-methyl-2-nor-13-trans-19 prostadiene |
| 433 | 1-trans-tri-n-butylstannyl-4-methyl-4-trimethylsiloxy-1,7-octadiene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-methyl-13-trans-19 prostadiene |
| 434 | 1-trans-tri-n-butylstannyl-4-methyl-4-trimethylsiloxy-1,7-octadiene | 2-[7-(4-methoxy-2,2-dimethyl-1,3-dioxolan-4-yl)heptyl]-4-(2-methoxypropyl-2-oxy)cyclopent-2-en-1-one | dl-16-hydroxy-1-hydroxymethyl-1,9-dioxo-16-methyl-2-homo-13-trans-19 prostadiene |
| EXAMPLE | VINYL IODIDE | CYCLOPENTENONE | PRODUCT PROSTAGLANDIN OF THE PGE1 SERIES |
| 435 | 1-trans-iodo-4-vinyl-7-chloro-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-vinyl-19-chloro-2-nor-20-nor-13-trans prostene |
| 436 | 1-trans-iodo-7-chloro-4-triethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-19-chloro-2-nor-20-nor-13-trans prostene |
| 437 | 1-trans-iodo-4-allenyl-7-chloro-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-allenyl-19-chloro-2-nor-20-nor-13-trans-19 prostene |

TABLE I-continued

| EXAMPLE | VINYL TIN | CYCLOPENTENONE | PRODUCT PROSTAGLANDIN OF THE PGE1 SERIES |
|---|---|---|---|
| 438 | 1-trans-tri-n-butylstannyl-4-trimethylsilylethynyl-7-oxa-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-ethynyl-19-oxa-2-nor-13-trans-19 prostene |
| EXAMPLE | VINYL IODIDE | CYCLOPENTENONE | PRODUCT PROSTAGLANDIN OF THE PGE1 SERIES |
| 439 | 1-trans-iodo-4-vinyl-7-oxa-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-11a,16-dihydroxy-1-hydroxymethyl-1,9-dioxo-16-vinyl-19-oxa-2-nor-13-trans prostene |
| 440 | 1-trans-iodo-4-vinyl-7-chloro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-vinyl-19-chloro-20-nor-13-trans prostene |
| 441 | 1-trans-iodo-7-chloro-4-triethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-19-chloro-20-nor-13-trans prostene |
| 442 | 1-trans-iodo-4-allenyl-7-chloro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-allenyl-19-chloro-20-nor-13-trans prostene |
| EXAMPLE | VINYL TIN | CYCLOPENTENONE | PRODUCT PROSTAGLANDIN OF THE PGE1 SERIES |
| 443 | 1-trans-tri-n-butylstannyl-4-trimethylsilylethynyl-7-oxa-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-ethynyl-19-oxa-13-trans prostene |
| EXAMPLE | VINYL IODIDE | CYCLOPENTENONE | PRODUCT PROSTAGLANDIN OF THE PGE1 SERIES |
| 444 | 1-trans-iodo-4-vinyl-7-oxa-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-11a,16-dihydroxy-1-hydroxymethyl-1,9-dioxo-16-vinyl-19-oxa-13-trans prostene |
| 445 | 1-trans-iodo-4-vinyl-7-chloro-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-vinyl-19-chloro-2-homo-20-nor-13-trans prostene |
| 446 | 1-trans-iodo-7-chloro-4-triethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-19-chloro-2-homo-20-nor-13-trans prostene |
| 447 | 1-trans-iodo-4-allenyl-7-chloro-4-trimethylsiloxy-1-heptene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-allenyl-19-chloro-2-homo-20-nor-13-trans prostene |
| EXAMPLE | VINYL TIN | CYCLOPENTENONE | PRODUCT PROSTAGLANDIN OF THE PGE1 SERIES |
| 448 | 1-trans-tri-n-butylstannyl-4-trimethylsilylethynyl-7-oxa-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-ethynyl-19-oxa-2-homo-13-trans prostene |
| EXAMPLE | VINYL IODIDE | CYCLOPENTENONE | PRODUCT PROSTAGLANDIN OF THE PGE1 SERIES |
| 449 | 1-trans-iodo-4-vinyl-7-oxa-4-trimethylsiloxy-1-octene | 2-[7-(4-methoxy-2,2-dimethyl-1,3-dioxolan-4-yl)heptyl]-4-(2-methoxypropyl-2-oxy)cyclopent-2-en-1-one | dl-11a,16-dihydroxy-1-hydroxymethyl-1,9-dioxo-16-vinyl-19-oxa-2-homo-13-trans prostene |
| 450 | 1-trans-iodo-4-vinyl-7-chloro-4-trimethylsiloxy-1-heptene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-vinyl-19-chloro-20-nor-13-trans prostene |
| 451 | 1-trans-iodo-7-chloro-4-triethylsiloxy-1-heptene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-19-chloro-20-nor-13-trans prostene |

TABLE I-continued

| EXAMPLE | VINYL | CYCLOPENTENONE | PRODUCT PROSTAGLANDIN |
|---|---|---|---|
| 452 | 1-trans-iodo-4-allenyl-7-chloro-4-trimethylsiloxy-1-heptene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-allenyl-19-chloro-20-nor-13-trans prostene |
| EXAMPLE | VINYL TIN | CYCLOPENTENONE | PRODUCT PROSTAGLANDIN OF THE PGE1 SERIES |
| 453 | 1-trans-tri-n-butylstannyl-4-trimethylsilylethynyl-7-oxa-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-ethynyl-19-oxa-13-trans prostene |
| EXAMPLE | VINYL IODIDE | CYCLOPENTENONE | PRODUCT PROSTAGLANDIN OF THE PGE1 SERIES |
| 454 | 1-trans-iodo-4-vinyl-7-oxa-4-trimethylsiloxy-1-octene | 2-[6-(4-methoxy-2,2-dimethyl-1,3-dioxolan-4-yl)hexyl]-4R-(2-methoxypropyl-2-oxy)cyclopent-2-en-1-one | nat-11a,16-dihydroxy-1-hydroxymethyl-1,9-dioxo-16-vinyl-19-oxa-13-trans prostene |
| EXAMPLE | VINYL IODIDE | CYCLOPENTENONE | PRODUCT PROSTAGLANDIN OF THE 11-DEOXY PGE1 SERIES |
| 455 | 1-trans-iodo-4-vinyl-7-chloro-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-vinyl-19-chloro-2-nor-20-nor-13-trans prostene |
| 456 | 1-trans-iodo-7-chloro-4-triethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-19-chloro-2-nor-20-nor-13-trans prostene |
| 457 | 1-trans-iodo-4-allenyl-7-chloro-4-trimethylsiloxy-1-heptene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-allenyl-19-chloro-2-nor-20-nor-13-trans prostene |
| EXAMPLE | VINYL TIN | CYCLOPENTENONE | PRODUCT PROSTAGLANDIN OF THE 11-DEOXY PGE1 SERIES |
| 458 | 1-trans-tri-n-butylstannyl-4-trimethylsilylethynyl-7-oxa-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-ethynyl-19-oxa-2-nor-13-trans prostene |
| EXAMPLE | VINYL IODIDE | CYCLOPENTENONE | PRODUCT PROSTAGLANDIN OF THE 11-DEOXY PGE1 SERIES |
| 459 | 1-trans-iodo-4-vinyl-7-oxa-4-trimethylsiloxy-1-octene | 2-[5-(4-methoxy-2,2-dimethyl-1,3-dioxolan-4-yl)pentyl]-4-(2-methoxypropyl-2-oxy)cyclopent-2-en-1-one | dl-16-hydroxy-1-hydroxymethyl-1,9-dioxo-16-vinyl-19-oxa-2-nor-13-trans prostene |
| 460 | 1-trans-iodo-4-vinyl-7-chloro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-vinyl-19-chloro-20-nor-13-trans prostene |
| 461 | 1-trans-iodo-7-chloro-4-triethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-19-chloro-20-nor-13-trans prostene |
| 462 | 1-trans-iodo-4-allenyl-7-chloro-4-trimethylsiloxy-1-heptene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-allenyl-19-chloro-20-nor-13-trans prostene |
| EXAMPLE | VINYL TIN | CYCLOPENTENONE | PRODUCT PROSTAGLANDIN OF THE 11-DEOXY PGE1 SERIES |
| 463 | 1-trans-tri-n-butylstannyl-4-trimethylsilylethynyl-7-oxa-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-ethynyl-19-oxa-13-trans prostene |
| EXAMPLE | VINYL IODIDE | CYCLOPENTENONE | PRODUCT PROSTAGLANDIN OF THE 11-DEOXY PGE1 SERIES |
| 464 | 1-trans-iodo-4-vinyl-7-oxa-4-trimethylsiloxy-1-octene | 2-[6-(4-methoxy-2,2-dimethyl-1,3-dioxolan-4-yl)hexyl]-4-(2-methoxypropyl-2-oxy)cyclopent-2-en-1-one | dl-16-hydroxy-1-hydroxymethyl-1,9-dioxo-16-vinyl-19-oxa-13-trans prostene |

TABLE 1-continued

| | | | |
|---|---|---|---|
| 465 | 1-trans-iodo-4-vinyl-7-chloro 4-trimethylsiloxy-1-heptene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-16-vinyl-19-chloro-2-homo-20-nor-13-trans prostene |
| 466 | 1-trans-iodo-7-chloro 4-triethylsiloxy-1-heptene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-19-chloro-2-homo-20-nor-13-trans prostene |
| 467 | 1-trans-iodo-4-allenyl-7-chloro 4-trimethylsiloxy-1-heptene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-16-allenyl-19-chloro-2-homo-20-nor-13-trans prostene |
| EXAMPLE | VINYL TIN | CYCLOPENTENONE | PRODUCT PROSTAGLANDIN OF THE 11-DEOXY PGE1 SERIES |
| 468 | 1-trans-tri-n-butylstannyl-4-trimethylsilylethynyl-7-oxa 4-trimethylsiloxy-1-octene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-16-ethynyl-19-oxa-2-homo-13-trans prostene |
| EXAMPLE | VINYL IODIDE | CYCLOPENTENONE | PRODUCT PROSTAGLANDIN OF THE 11-DEOXY PGE1 SERIES |
| 469 | 1-trans-iodo-4-vinyl-7-oxa 4-trimethylsiloxy-1-octene | 2-[7-(4-methoxy-2,2-dimethyl-1,3-dioxolan-4-yl)heptyl]-4-(2-methoxypropyl-2-oxy) cyclopent-2-en-1-one | dl-16-hydroxy-1-hydroxymethyl-1,9-dioxo-16-vinyl-19-oxa-2-homo-13-trans prostene |

TABLE II

| EXAMPLE | VINYL TIN | CYCLOPENTENONE | PRODUCT PROSTAGLANDIN OF THE PGE2 SERIES |
|---|---|---|---|
| 1 | 1-trans-tri-n-butylstannyl-4-fluoromethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-fluoromethyl-20-nor-2-nor-5-cis-13-trans prostadiene |
| 2 | 1-trans-tri-n-butylstannyl-4-difluoromethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-difluoromethyl-20-nor-2-nor-5-cis-13-trans prostadiene |
| 3 | 1-trans-tri-n-butylstannyl-4-trifluoromethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-20-nor-2-nor-5-cis-13-trans prostadiene |
| 4 | 1-trans-tri-n-butylstannyl-4-chloromethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-chloromethyl-20-nor-2-nor-5-cis-13-trans prostadiene |
| 5 | 1-trans-tri-n-butylstannyl-4-bromomethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-bromomethyl-20-nor-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 6 | 1-trans-iodo-4-allenyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-allenyl-20-nor-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 7 | 1-trans-tri-n-butylstannyl-5-methylene-4-triethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-17-methylene-20-nor-2-nor-5-cis-13-trans prostadiene |
| 8 | 1-trans-tri-n-butylstannyl-4-methyl-5-methylene-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-20-nor-2-nor-5-cis-13-trans prostadiene |
| 9 | 1-trans-tri-n-butylstannyl-4-dimethoxymethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-formyl-20-nor-2-nor-5-cis-13-trans prostadiene |
| 10 | 1-trans-tri-n-butylstannyl-4-deutro-4-triethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-deutro-20-nor-2-nor-5-cis-13-trans prostadiene |
| 11 | 1-trans-tri-n-butylstannyl-4-triethylsilyloxymethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-hydroxymethyl-20-nor-2-nor-5-cis-13-trans prostadiene |
| 12 | 1-trans-tri-n-butylstannyl-7-oxa-4-triethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-19-oxa-2-nor-2-nor-5-cis-13-trans prostadiene |
| 13 | 1-trans-tri-n-butylstannyl-4-methyl-7-oxa-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-methyl-19-oxa-2-nor-2-nor-5-cis-13-trans prostadiene |
| 14 | 1-trans-tri-n-butylstannyl-7-thia-4-triethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-19-thia-2-nor-5-cis-13-trans prostadiene |
| 15 | 1-trans-tri-n-butylstannyl-4-methyl-7-thia-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-methyl-19-thia-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 16 | 1-trans-iodo-7-chloro | 2-[5-(4-methoxy-2,2-dimethyl-1,3-dioxolan- | dl-11a,16-dihydroxy-1-hydroxymethyl-1,9-dioxo- |

TABLE II-continued

| | | | PRODUCT |
|---|---|---|---|
| 17 | 4-triethylsiloxy-1-heptene | 4-yl]pent-2-cis-enyl]π-4-(2-methoxypropyl-2-oxy)cyclopent-2-en-1-one | 19-chloro-2-nor-20-nor-5-cis-13-trans prostadiene |
| | 1-trans-iodo-4-methyl-7-chloro-4-trimethylsiloxy-1-heptene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-methyl-19-chloro-2-nor-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 18 | 1-trans-tri-n-butylstannyl-4-fluoromethyl-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-fluoromethyl-2-nor-5-cis-13-trans prostadiene |
| 19 | 1-trans-tri-n-butylstannyl-4-difluoromethyl-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-difluoromethyl-2-nor-5-cis-13-trans prostadiene |
| 20 | 1-trans-tri-n-butylstannyl-4-trifluoromethyl-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-2-nor-5-cis-13-trans prostadiene |
| 21 | 1-trans-tri-n-butylstannyl-4-chloromethyl-4-trimethylsiloxy-1-octene | 2-[5-(4-methoxy-2,2-dimethyl-1,3-dioxolan-4-yl]pent-2-cis-enyl]-4-(2-methoxy-2-oxy)cyclopent-2-en-1-one | dl-11a,16-dihydroxy-1-hydroxymethyl-1,9-dioxo-16-chloromethyl-2-nor-5-cis-13-trans prostadiene |
| 22 | 1-trans-tri-n-butylstannyl-4-bromomethyl-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-bromomethyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 23 | 1-trans-iodo-4-allenyl-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-allenyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 24 | 1-trans-tri-n-butylstannyl-5-methylene-4-triethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-17-methylene-2-nor-5-cis-13-trans prostadiene |
| 25 | 1-trans-tri-n-butylstannyl-4-methyl-5-methylene-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-2-nor-5-cis-13-trans prostadiene |
| 26 | 1-trans-tri-n-butylstannyl-4-dimethoxymethyl-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-6-formyl-2-nor-5-cis-13-trans prostadiene |
| 27 | 1-trans-tri-n-butylstannyl-4-deutero-4-triethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-deutero-2-nor-5-cis-13-trans prostadiene |
| 28 | 1-trans-tri-n-butylstannyl-4-triethylsilyloxymethyl-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-hydroxymethyl-2-nor-5-cis-13-trans prostadiene |
| 29 | 1-trans-tri-n-butylstannyl-4-fluoromethyl-4-trimethylsiloxy-1-nonene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-fluoromethyl-20-methyl-2-nor-5-cis-13-trans prostadiene |
| 30 | 1-trans-tri-n-butylstannyl-4-difluoromethyl-4-trimethylsiloxy-1-nonene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-difluoromethyl-20-methyl-2-nor-5-cis-13-trans prostadiene |
| 31 | 1-trans-tri-n-butylstannyl-4-trifluoromethyl-4-trimethylsiloxy-1-nonene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-20-methyl-2-nor-5-cis-13-trans prostadiene |

TABLE II-continued

| EXAMPLE | VINYL IODIDE / VINYL TIN | CYCLOPENTENONE | PRODUCT PROSTAGLANDIN OF THE PGE2 SERIES |
|---|---|---|---|
| 32 | 1-trans-tri-n-butylstannyl-4-chloromethyl-4-trimethylsiloxy-1-nonene | 2-[5-(4-methoxy-2,2-dimethyl)-1,3-dioxolan-4-yl]pent-2-cis-enyl]-4-(2-methoxypropyl-2-oxy)cyclopent-2-en-1-one | dl-11a,16-dihydroxy-1-hydroxymethyl-1,9-dioxo-16-chloromethyl-20-methyl-2-nor-5-cis-13-trans prostadiene |
| 33 | 1-trans-tri-n-butylstannyl-4-bromomethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-bromomethyl-20-methyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 34 | 1-trans-iodo-4-allenyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-allenyl-20-methyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 35 | 1-trans-tri-n-butylstannyl-5-methylene-4-triethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-17-methylene-20-methyl-2-nor-5-cis-13-trans prostadiene |
| 36 | 1-trans-tri-n-butylstannyl-4-methyl-5-methylene-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-20-methyl-2-nor-5-cis-13-trans prostadiene |
| 37 | 1-trans-tri-n-butylstannyl-4-dimethoxymethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-formyl-20-methyl-2-nor-5-cis-13-trans prostadiene |
| 38 | 1-trans-tri-n-butylstannyl-4-deutro-4-triethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-deutro-20-methyl-2-nor-5-cis-13-trans prostadiene |
| 39 | 1-trans-tri-n-butylstannyl-4-triethylsilyloxymethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-hydroxymethyl-20-methyl-2-nor-5-cis-13-trans prostadiene |
| 40 | 1-trans-tri-n-butylstannyl-4-fluoromethyl-4-trimethylsiloxy-1-decene | 2-[5-(4-methoxy-2,2-dimethyl-1,34-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-fluoromethyl-20-ethyl-2-nor-5-cis-13-trans prostadiene |
| 41 | 1-trans-tri-n-butylstannyl-4-difluoromethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-difluoromethyl-20-ethyl-2-nor-5-cis-13-trans prostadiene |
| 42 | 1-trans-tri-n-butylstannyl-4-trifluoromethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-20-ethyl-2-nor-5-cis-13-trans prostadiene |
| 43 | 1-trans-tri-n-butylstannyl-4-chloromethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-chloromethyl-20-ethyl-2-nor-5-cis-13-trans prostadiene |
| 44 | 1-trans-tri-n-butylstannyl-4-bromomethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-bromomethyl-20-ethyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 45 | 1-trans-iodo-4-allenyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-allenyl-20-ethyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 46 | 1-trans-tri-n-butylstannyl-5-methylene-4-triethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-17-methylene-20-ethyl-2-nor-5-cis-13-trans prostadiene |

TABLE II-continued

| | | | |
|---|---|---|---|
| 47 | 1-trans-tri-n-butylstannyl-4-methyl-5-methylene 4-trimethylsiloxy-1-decene | 2-[5-(4-methoxy-2,2-dimethyl-1,3-dioxolan-4-yl]pent-2-cis-enyl]-4-(2-methoxypropyl-2-oxy) cyclopent-2-en-1-one | dl-11a,16-dihydroxy-1-hydroxymethyl-1,9-dioxo-16-methyl-17-methylene-20-ethyl-2-nor-5-cis-13-trans prostadiene |
| 48 | 1-trans-tri-n-butylstannyl-4-dimethoxymethyl-4-trimethylsiloxy-1-decene | 2-[5-(4-methoxy-2,2-dimethyl-1,3-dioxolan-4-yl]pent-2-cis-enyl]-4-(2-methoxypropyl-2-oxy) cyclopent-2-en-1-one | dl-11a,16-dihydroxy-1-hydroxymethyl-1,9-dioxo-16-formyl-20-ethyl-2-nor-5-cis-13-trans prostadiene |
| 49 | 1-trans-tri-n-butylstannyl-4-deutro-4-triethylsiloxy-1-decene | 2-[5-(4-methoxy-2,2-dimethyl-1,3-dioxolan-4-yl]pent-2-cis-enyl]-4-(2-methoxypropyl-2-oxy) cyclopent-2-en-1-one | dl-11a,16-dihydroxy-1-hydroxymethyl-1,9-dioxo-16-deutro-20-ethyl-2-nor-5-cis-13-trans prostadiene |
| 50 | 1-trans-tri-n-butylstannyl-4-triethylsilyloxymethyl-4-trimethylsiloxy-1-decene | 2-[5-(4-methoxy-2,2-dimethyl-1,3-dioxolan-4-yl]pent-2-cis-enyl]-4-(2-methoxypropyl-2-oxy) cyclopent-2-en-1-one | dl-11a,16-dihydroxy-1-hydroxymethyl-1,9-dioxo-16-hydroxymethyl-20-ethyl-2-nor-5-cis-13-trans prostadiene |
| 51 | 1-trans-tri-n-butylstannyl-4-fluoromethyl-4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-fluoromethyl-20-nor-5-cis-13-trans prostadiene |
| 52 | 1-trans-tri-n-butylstannyl-4-difluoromethyl-4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-difluoromethyl-20-nor-5-cis-13-trans prostadiene |
| 53 | 1-trans-tri-n-butylstannyl-4-trifluoromethyl-4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-trifluoromethyl-20-nor-5-cis-13-trans prostadiene |
| 54 | 1-trans-tri-n-butylstannyl-4-chloromethyl-4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-chloromethyl-20-nor-5-cis-13-trans prostadiene |
| 55 | 1-trans-tri-n-butylstannyl-4-bromomethyl-4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-bromomethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 56 | 1-iodo-4-allenyl-4-trimethylsiloxy-1-heptene | 2-[6-(4-methoxy-2,2-dimethyl-1,3-dioxolan-4-yl]hex-6-cis-enyl]-4-(2-methoxypropyl-2-oxy) cyclopent-2-en-1-one | dl-11a,16-dihydroxy-1-hydroxymethyl-1,9-dioxo-16-allenyl-20-nor-5-cis-13-trans prostadiene |
| EXAMPLE | VINYL TIN | CYCLOPENTENONE | PRODUCT PROSTAGLANDIN OF THE PGE2 SERIES |
| 57 | 1-trans-tri-n-butylstannyl-5-methylene 4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-17-methylene-20-nor-5-cis-13-trans prostadiene |
| 58 | 1-trans-tri-n-butylstannyl-4-methyl-5-methylene 4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-methyl-17-methylene-20-nor-5-cis-13-trans prostadiene |
| 59 | 1-trans-tri-n-butylstannyl-4-dimethoxymethyl-4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-formyl-20-nor-5-cis-13-trans prostadiene |
| 60 | 1-trans-tri-n-butylstannyl-4-deutro-4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-deutro-20-nor-5-cis-13-trans prostadiene |
| 61 | 1-trans-tri-n-butylstannyl-4-triethylsilyloxymethyl-4-trimethylsiloxy-1-heptene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-16-hydroxymethyl-20-nor-5-cis-13-trans prostadiene |
| 62 | 1-trans-tri-n-butylstannyl-7-oxa-4-triethylsiloxy-1-octene | 2-[6-(4-methoxy-2,2-dimethyl-1,3-dioxolan-4-yl]hex-2-cis-enyl]-4-(2-methoxypropyl-2-oxy) cyclopent-2-en-1-one | dl-11a,16-dihydroxy-1-hydroxymethyl-1,9-dioxo-19-oxa-5-cis-13-trans prostadiene |
| 63 | 1-trans-tri-n-butylstannyl-4-methyl-7-oxa | 2-[6-(4-methoxy-2,2-dimethyl-1,3-dioxolan | dl-11a,16-dihydroxy-1-hydroxymethyl-1,9-dioxo-16-methyl- |

TABLE II-continued

| EXAMPLE | VINYL IODIDE / VINYL TIN | CYCLOPENTENONE | PRODUCT PROSTAGLANDIN OF THE PGE2 SERIES |
|---|---|---|---|
| | 4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | 19-oxa-5-cis-13-trans prostadiene |
| 64 | 1-trans-tri-n-butylstannyl-7-thia 4-triethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-19-thia-5-cis-13-trans prostadiene |
| 65 | 1-trans-tri-n-butylstannyl-4-methyl-7-thia 4-trimethylsilyoxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-methyl-19-thia-5-cis-13-trans prostadiene |
| EXAMPLE | VINYL IODIDE | CYCLOPENTENONE | PRODUCT PROSTAGLANDIN OF THE PGE2 SERIES |
| 66 | 1-trans-iodo-7-chloro 4-triethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-19-chloro-20-nor-5-cis-13-trans prostadiene |
| 67 | 1-trans-iodo-4-methyl-7-chloro 4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-methyl-19-chloro-20-nor-5-cis-13-trans prostadiene |
| EXAMPLE | VINYL TIN | CYCLOPENTENONE | PRODUCT PROSTAGLANDIN OF THE PGE2 SERIES |
| 68 | 1-trans-tri-n-butylstannyl-4-fluoromethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-fluoromethyl-5-cis-13-trans prostadiene |
| 69 | 1-trans-tri-n-butylstannyl-4-difluoromethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-difluoromethyl-5-cis-13-trans prostadiene |
| 70 | 1-trans-tri-n-butylstannyl-4-trifluoromethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-5-cis-13-trans prostadiene |
| 71 | 1-trans-tri-n-butylstannyl-4-chloromethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-chloromethyl-5-cis-13-trans prostadiene |
| 72 | 1-trans-tri-n-butylstannyl-4-bromomethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-bromomethyl-5-cis-13-trans prostadiene |
| EXAMPLE | VINYL IODIDE | CYCLOPENTENONE | PRODUCT PROSTAGLANDIN OF THE PGE2 SERIES |
| 73 | 1-trans-iodo-4-allenyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-allenyl-5-cis-13-trans prostadiene |
| EXAMPLE | VINYL TIN | CYCLOPENTENONE | PRODUCT PROSTAGLANDIN OF THE PGE2 SERIES |
| 74 | 1-trans-tri-n-butylstannyl-5-methylene 4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-17-methylene-5-cis-13-trans prostadiene |
| 75 | 1-trans-tri-n-butylstannyl-4-methyl-5-methylene 4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-5-cis-13-trans prostadiene |
| 76 | 1-trans-tri-n-butylstannyl-4-dimethoxymethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-formyl-5-cis-13-trans prostadiene |
| 77 | 1-trans-tri-n-butylstannyl-4-deutero-4-triethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-deutero-5-cis-13-trans prostadiene |
| 78 | 1-trans-tri-n-butylstannyl-4-triethylsilyloxymethyl- | 2-[6-(4-methoxy-2,2-dimethyl-1,3-dioxolan-4-yl)(hex-2-cis-enyl]-4-(2-methoxypropyl-2-oxy)cyclopent-2-en-1-one | dl-11a,16-dihydroxy-1-hydroxymethyl-1,9-dioxo-16-hydroxymethyl- |

TABLE II-continued

| | | | |
|---|---|---|---|
| | | 4-trimethylsilyloxy-1-octene | 4-yl)hex-2-cis-enyl]-4-(2-methoxypropyl-2-oxy)cyclopent-2-en-1-one | 5-cis-13-trans prostadiene |
| 79 | | 1-trans-tri-n-butylstannyl-4-fluoromethyl-4-trimethylsilyloxy-1-nonene | 2-[6-(4-methoxy-2,2-dimethyl-1,3-dioxolan-4-yl)hex-2-cis-ethyl]-4-(2-methoxypropyl-2-oxy)cyclopent-2-en-1-one | dl-11a,16-dihydroxy-1-hydroxymethyl-1,9-dioxo-16-fluoromethyl-20-methyl-5-cis-13-trans prostadiene |
| 80 | | 1-trans-tri-n-butylstannyl-4-difluoromethyl-4-trimethylsilyloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-difluoromethyl-20-methyl-5-cis-13-trans prostadiene |
| 81 | | 1-trans-tri-n-butylstannyl-4-trifluoromethyl-4-trimethylsilyloxy-1-nonene | 2-[6-(4-methoxy-2,2-dimethyl-1,3-dioxolan-4-yl)hex-2-cis-enyl] -4-(2-methoxypropyl-2-oxy)cyclopent-2-en-1-one | dl-11a,16-dihydroxy-1-hydroxymethyl-1,9-dioxo-16-trifluoromethyl-20-methyl-5-cis-13-trans prostadiene |
| 82 | | 1-trans-tri-n-butylstannyl-4-chloromethyl-4-trimethylsilyloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-chloromethyl-20-methyl-5-cis-13-trans prostadiene |
| 83 | | 1-trans-tri-n-butylstannyl-4-bromomethyl-4-trimethylsilyloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-bromomethyl-20-methyl-5-cis-13-trans prostadiene |
| EXAMPLE | VINYL IODIDE | | CYCLOPENTENONE | PRODUCT PROSTAGLANDIN OF THE PGE2 SERIES |
| 84 | | 1-trans-iodo-4-allenyl-4-trimethylsilyloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-allenyl-20-methyl-5-cis-13-trans prostadiene |
| EXAMPLE | VINYL TIN | | CYCLOPENTENONE | PRODUCT PROSTAGLANDIN OF THE PGE2 SERIES |
| 85 | | 1-trans-tri-n-butylstannyl-5-methylene-4-trimethylsilyloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-17-methylene-20-methyl-5-cis-13-trans prostadiene |
| 86 | | 1-trans-tri-n-butylstannyl-4-methyl-5-methylene-4-trimethylsilyloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-20-methyl-5-cis-13-trans prostadiene |
| 87 | | 1-trans-tri-n-butylstannyl-4-dimethoxymethyl-4-trimethylsilyloxy-1-nonene | 2-[6-(4-methoxy-2,2-dimethyl-1,3-dioxolan-4-yl)hex-2-cys-enyl] -4-(2-methoxypropyl-2-oxy)cyclopent-2-en-1-one | dl-11a,16-dihydroxy-1-hydroxymethyl-1,9-dioxo-16-formyl-20-methyl-5-cis-13-trans prostadiene |
| 88 | | 1-trans-tri-n-butylstannyl-4-deutro-4-trimethylsilyloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-deutro-20-methyl-5-cis-13-trans prostadiene |
| 89 | | 1-trans-tri-n-butylstannyl-4-triethylsilyloxymethyl-4-trimethylsilyloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-hydroxymethyl-20-methyl-5-cis-13-trans prostadiene |
| 90 | | 1-trans-tri-n-butylstannyl-4-fluoromethyl-4-trimethylsilyloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-fluoromethyl-20-ethyl-5-cis-13-trans prostadiene |
| 91 | | 1-trans-tri-n-butylstannyl-4-difluoromethyl-4-trimethylsilyloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-difluoromethyl-20-ethyl-5-cis-13-trans prostadiene |
| 92 | | 1-trans-tri-n-butylstannyl-4-trifluoromethyl-4-trimethylsilyloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-20-ethyl-5-cis-13-trans prostadiene |
| 93 | | 1-trans-tri-n-butylstannyl-4-chloromethyl-4-trimethylsilyloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-chloromethyl-20-ethyl-5-cis-13-trans prostadiene |
| 94 | | 1-trans-tri-n-butylstannyl-4-bromomethyl-4-trimethylsilyloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-bromomethyl-20-ethyl-5-cis-13-trans prostadiene |

TABLE II-continued

| EXAMPLE | VINYL IODIDE | CYCLOPENTENONE | PRODUCT PROSTAGLANDIN OF THE PGE2 SERIES |
|---|---|---|---|
| 95 | 1-trans-iodo-4-allenyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-allenyl-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 96 | 1-trans-tri-n-butylstannyl-5-methylene-4-triethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-17-methylene-20-ethyl-5-cis-13-trans prostadiene |
| 97 | 1-trans-tri-n-butylstannyl-4-methyl-5-methylene-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-20-ethyl-5-cis-13-trans prostadiene |
| 98 | 1-trans-tri-n-butylstannyl-4-dimethoxymethyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-formyl-20-ethyl-5-cis-13-trans prostadiene |
| 99 | 1-trans-tri-n-butylstannyl-4-deutro-4-triethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-deutro-20-ethyl-5-cis-13-trans prostadiene |
| 100 | 1-trans-tri-n-butylstannyl-4-triethylsilyloxymethyl-4-trimethylsiloxy-1-decene | 2-[6-84-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-hydroxymethyl-20-ethyl-5-cis-13-trans prostadiene |
| 101 | 1-trans-tri-n-butylstannyl-4-fluoromethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-fluoromethyl-20-nor-2-homo-5-cis-13-trans prostadiene |
| 102 | 1-trans-tri-n-butylstannyl-4-difluoromethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-difluoromethyl-20-nor-2-homo-5-cis-13-trans prostadiene |
| 103 | 1-trans-tri-n-butylstannyl-4-trifluoromethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-20-nor-2-homo-5-cis-13-trans prostadiene |
| 104 | 1-trans-tri-n-butylstannyl-4-chloromethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-chloromethyl-20-nor-2-homo-5-cis-13-trans prostadiene |
| 105 | 1-trans-tri-n-butylstannyl-4-bromomethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-bromomethyl-20-nor-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 106 | 1-trans-iodo-4-allenyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-allenyl-20-nor-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 107 | 1-trans-tri-n-butylstannyl-5-methylene-4-triethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-17-methylene-20-nor-2-homo-5-cis-13-trans prostadiene |
| 108 | 1-trans-tri-n-butylstannyl-4-methyl-5-methylene-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-20-nor-2-homo-5-cis-13-trans prostadiene |
| 109 | 1-trans-tri-n-butylstannyl-4-dimethoxymethyl- | 2-[7-(4-methoxy-2,2-dimethyl-1,3-dioxolan- | dl-11a,16-dihydroxy-1-hydroxymethyl-1,9-dioxo-16-formyl- |

TABLE II-continued

| | | | |
|---|---|---|---|
| 110 | 1-trans-tri-n-butylstannyl-4-deutro-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-deutro-20-nor-2-homo-5-cis-13-trans prostadiene |
| 111 | 1-trans-tri-n-butylstannyl-4-triethylsilyloxymethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-hydroxymethyl-20-nor-2-homo-5-cis-13-trans prostadiene |
| 112 | 1-trans-tri-n-butylstannyl-7-oxa-4-triethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-19-oxa-2-homo-5-cis-13-trans prostadiene |
| 113 | 1-trans-tri-n-butylstannyl-4-methyl-7-oxa-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-methyl-19-oxa-2-homo-5-cis-13-trans prostadiene |
| 114 | 1-trans-tri-n-butylstannyl-7-thia-4-triethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-19-thia-2-homo-5-cis-13-trans prostadiene |
| 115 | 1-trans-tri-n-butylstannyl-4-methyl-7-thia-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-methyl-19-thia-2-homo-5-cis-13-trans prostadiene |
| EXAMPLE | VINYL IODIDE | CYCLOPENTENONE | PRODUCT PROSTAGLANDIN OF THE PGE2 SERIES |
| 116 | 1-trans-iodo-7-chloro-4-triethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-19-chloro-2-homo-20-nor-5-cis-13-trans prostadiene |
| 117 | 1-trans-iodo-4-methyl-7-chloro-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-19-chloro-2-homo-20-nor-5-cis-13-trans prostadiene |
| EXAMPLE | VINYL TIN | CYCLOPENTENONE | PRODUCT PROSTAGLANDIN OF THE PGE2 SERIES |
| 118 | 1-trans-tri-n-butylstannyl-4-fluoromethyl-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-fluoromethyl-2-homo-5-cis-13-trans prostadiene |
| 119 | 1-trans-tri-n-butylstannyl-4-difluoromethyl-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-difluoromethyl-2-homo-5-cis-13-trans prostadiene |
| 120 | 1-trans-tri-n-butylstannyl-4-trifluoromethyl-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-2-homo-5-cis-13-trans prostadiene |
| 121 | 1-trans-tri-n-butylstannyl-4-chloromethyl-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-chloromethyl-2-homo-5-cis-13-trans prostadiene |
| 122 | 1-trans-tri-n-butylstannyl-4-bromomethyl-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-bromomethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 123 | 1-trans-iodo-4-allenyl-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-allenyl-2-homo-5-cis-13-trans prostadiene |
| EXAMPLE | VINYL TIN | CYCLOPENTENONE | PRODUCT PROSTAGLANDIN OF THE PGE2 SERIES |
| 124 | 1-trans-tri-n-butylstannyl-5-methylene | 2-[7-(4-methoxy-2,2-dimethyl-1,3-dioxolan- | dl-11a,16-dihydroxy-1-hydroxymethyl-1,9-dioxo- |

TABLE II-continued

| | | | |
|---|---|---|---|
| | | 4-triethylsilyloxy-1-octene | 4-yl)hept-2-cis-enyl]-4-(2-methoxypropyl-2-oxy)cyclopent-2-en-1-one | 17-methylene-2-home-5-cis-13-trans prostadiene |
| 125 | | 1-trans-tri-n-butylstannyl-4-methyl-5-methylene-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-2-homo-5-cis-13-trans prostadiene |
| 126 | | 1-trans-tri-n-butylstannyl-4-dimethoxymethyl-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-formyl-2-homo-5-cis-13-trans prostadiene |
| 127 | | 1-trans-tri-n-butylstannyl-4-deutero-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-deutro-2-homo-5-cis-13-trans prostadiene |
| 128 | | 1-trans-tri-n-butylstannyl-4-triethylsilyloxymethyl-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-hydroxymethyl-2-homo-5-cis-13-trans prostadiene |
| 129 | | 1-trans-tri-n-butylstannyl-4-fluoromethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-fluoromethyl-20-methyl-2-homo-5-cis-13-trans prostadiene |
| 130 | | 1-trans-tri-n-butylstannyl-4-difluoromethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-difluoromethyl-20-methyl-2-homo-5-cis-13-trans prostadiene |
| 131 | | 1-trans-tri-n-butylstannyl-4-trifluoromethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-20-methyl-2-homo-5-cis-13-trans prostadiene |
| 132 | | 1-trans-tri-n-butylstannyl-4-chloromethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-chloromethyl-20-methyl-2-homo-5-cis-13-trans prostadiene |
| 133 | | 1-trans-tri-n-butylstannyl-4-bromomethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-bromomethyl-20-methyl-2-homo-5-cis-13-trans prostadiene |
| EXAMPLE | VINYL IODIDE | | CYCLOPENTENONE | PRODUCT PROSTAGLANDIN OF THE PGE2 SERIES |
| 134 | | 1-trans-iodo-4-allenyl-4-trimethylsiloxy-1-nonene | 2-[7-(-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-allenyl-20-methyl-2-homo-5-cis-13-trans prostadiene |
| EXAMPLE | VINYL TIN | | CYCLOPENTENONE | PRODUCT PROSTAGLANDIN OF THE PGE2 SERIES |
| 135 | | 1-trans-tri-n-butylstannyl-5-methylene-4-triethylsiloxy-1-nonnen | 2-[7-(-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-17-methylene-20-methyl-2-homo-5-cis-13-trans prostadiene |
| 136 | | 1-trans-tri-n-butylstannyl-4-methyl-5-methylene-4-trimethylsiloxy-1-nonene | 2-[7-(-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-methyl-17-methylene-20-methyl-2-homo-5-cis-13-trans prostadiene |
| 137 140 | | 1-trans-tri-n-butylstannyl-4-dimethoxymethyl-1-trans-tri-n-butylstannyl-4-fluoromethyl-4-trimethylsiloxy-1-decene | 2-[7-(-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-fluoromethyl-20-ethyl-2-homo-5-cis-13-trans prostadiene |
| 141 | | 1-trans-tri-n-butylstannyl-4-difluoromethyl-4-trimethylsiloxy-1-decene | 2-[7-(-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-difluoromethyl-20-ethyl-2-homo-5-cis-13-trans prostadiene |
| 142 | | 1-trans-tri-n-butylstannyl-4-trifluoromethyl-4-trimethylsiloxy-1-decene | 2-[7-(-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-trifluoromethyl-20-ethyl-2-homo-5-cis-13-trans prostadiene |
| 143 | | 1-trans-tri-n-butylstannyl-4-chloromethyl- | 2-[7-(-methoxy-2,2-dimethyl-1,3-dioxolan- | dl-11a,16-dihydroxy-1-hydroxymethyl-1,9-dioxo-16-chloromethyl- |

TABLE II-continued

| EXAMPLE | VINYL IODIDE / VINYL TIN | CYCLOPENTENONE | PRODUCT PROSTAGLANDIN OF THE PGE2 SERIES |
|---|---|---|---|
| 144 | 1-trans-tri-n-butylstannyl-4-bromomethyl-4-trimethylsiloxy-1-decene | 2-[7-(-methoxy-2,2-dimethyl-1,3-dioxolan-4-yl)hept-2-cis-enyl]-4-(2-methoxypropyl-2-oxy) cyclopent-2-en-1-one | dl-11a,16-dihydroxy-1-hydroxymethyl-1,9-dioxo-16-bromomethyl-20-ethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 145 | 1-trans-iodo-4-allenyl-4-trimethylsiloxy-1-decene | 2-[7-(-methoxy-2,2-dimethyl-1,3-dioxolan-4-yl)hept-2-cis-enyl]-4-(2-methoxypropyl-2-oxy) cyclopent-2-en-1-one | dl-11a,16-dihydroxy-1-hydroxymethyl-1,9-dioxo-16-allenyl-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 146 | 1-trans-tri-n-butylstannyl-5-methylene-4-triethylsiloxy-1-decene | 2-[7-(-methoxy-2,2-dimethyl-1,3-dioxolan-4-yl)hept-2-cis-enyl]-4-(2-methoxypropyl-2-oxy) cyclopent-2-en-1-one | dl-11a,16-dihydroxy-1-hydroxymethyl-1,9-dioxo-17-methylene-20-ethyl-2-homo-5-cis-13-trans prostadiene |
| 147 | 1-trans-tri-n-butylstannyl-4-methyl-5-methylene-4-trimethylsiloxy-1-decene | 2-[7-(-methoxy-2,2-dimethyl-1,3-dioxolan-4-yl)hept-2-cis-enyl]-4-(2-methoxypropyl-2-oxy) cyclopent-2-en-1-one | dl-11a,16-dihydroxy-1-hydroxymethyl-1,9-dioxo-16-methyl-17-methylene-20-ethyl-2-homo-5-cis-13-trans prostadiene |
| 148 | 1-trans-tri-n-butylstannyl-4-dimethoxymethyl-4-trimethylsiloxy-1-decene | 2-[7-(-methoxy-2,2-dimethyl-1,3-dioxolan-4-yl)hept-2-cis-enyl]-4-(2-methoxypropyl-2-oxy) cyclopent-2-en-1-one | dl-11a,16-dihydroxy-1-hydroxymethyl-1,9-dioxo-16-formyl-20-ethyl-2-homo-5-cis-13-trans prostadiene |
| 149 | 1-trans-tri-n-butylstannyl-4-deutro-4-triethylsiloxy-1-decene | 2-[7-(-methoxy-2,2-dimethyl-1,3-dioxolan-4-yl)hept-2-cis-enyl]-4-(2-methoxypropyl-2-oxy) cyclopent-2-en-1-one | dl-11a,16-dihydroxy-1-hydroxymethyl-1,9-dioxo-16-deutro-20-ethyl-2-homo-5-cis-13-trans prostadiene |
| 150 | 1-trans-tri-n-butylstannyl-4-triethylsilyloxymethyl-4-trimethylsiloxy-1-decene | 2-[7-(-methoxy-2,2-dimethyl-1,3-dioxolan-4-yl)hept-2-cis-enyl]-4-(2-methoxypropyl-2-oxy) cyclopent-2-en-1-one | dl-11a,16-dihydroxy-1-hydroxymethyl-1,9-dioxo-16-hydroxymethyl-20-ethyl-2-homo-5-cis-13-trans prostadiene |
| 151 | 1-trans-tri-n-butylstannyl-4-fluoromethyl-4-trimethylsiloxy-1-heptene | 2-[6-(-methoxy-2,2-dimethyl-1,3-dioxolan-4-yl)hex-2-cis-enyl]-4-(2-methoxypropyl-2-oxy) cyclopent-2-en-1-one | nat-11a,16-dihydroxy-1-hydroxymethyl-1,9-dioxo-16-fluoromethyl-20-nor-5-cis-13-trans prostadiene |
| 152 | 1-trans-tri-n-butylstannyl-4-difluoromethyl-4-trimethylsiloxy-1-heptene | 2-[6-(-methoxy-2,2-dimethyl-1,3-dioxolan-4-yl)hex-2-cis-enyl]-4-(2-methoxypropyl-2-oxy) cyclopent-2-en-1-one | nat-11a,16-dihydroxy-1-hydroxymethyl-1,9-dioxo-16-difluoromethyl-20-nor-5-cis-13-trans prostadiene |
| 153 | 1-trans-tri-n-butylstannyl-4-trifluoromethyl-4-trimethylsiloxy-1-heptene | 2-[6-(-methoxy-2,2-dimethyl-1,3-dioxolan-4-yl)hex-2-cis-enyl]-4-(2-methoxypropyl-2-oxy) cyclopent-2-en-1-one | nat-11a,16-dihydroxy-1-hydroxymethyl-1,9-dioxo-16-trifluoromethyl-20-nor-5-cis-13-trans prostadiene |
| 154 | 1-trans-tri-n-butylstannyl-4-chloromethyl-4-trimethylsiloxy-1-heptene | 2-[6-(-methoxy-2,2-dimethyl-1,3-dioxolan-4-yl)hex-2-cis-enyl]-4-(2-methoxypropyl-2-oxy) cyclopent-2-en-1-one | nat-11a,16-dihydroxy-1-hydroxymethyl-1,9-dioxo-16-chloromethyl-20-nor-5-cis-13-trans prostadiene |
| 155 | 1-trans-tri-n-butylstannyl-4-bromomethyl-4-trimethylsiloxy-1-heptene | 2-[6-(-methoxy-2,2-dimethyl-1,3-dioxolan-4-yl)hex-2-cis-enyl]-4-(2-methoxypropyl-2-oxy) cyclopent-2-en-1-one | nat-11a,16-dihydroxy-1-hydroxymethyl-1,9-dioxo-16-bromomethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 156 | 1-trans-iodo-4-allenyl-4-trimethylsiloxy-1-heptene | 2-[6-(4-methoxy-2,2-dimethyl-1,3-dioxolan-4-yl)hex-2-cis-enyl]-4r-(2-methoxypropyl-2-oxy) cyclopent-2-en-1-one | nat-11a,16-dihydroxy-1-hydroxymethyl-1,9-dioxo-16-allenyl-20-nor-5-cis-13-trans prostadiene |
| EXAMPLE | VINYL TIN | CYCLOPENTENONE | PRODUCT PROSTAGLANDIN OF THE PGE2 SERIES |
| 157 | 1-trans-tri-n-butylstannyl-5-methylene-4-triethylsiloxy-1-heptene | 2-[6-(-methoxy-2,2-dimethyl-1,3-dioxolan-4-yl)hex-2-cis-enyl]-4r-(2-methoxypropyl-2-oxy) cyclopent-2-en-1-one | nat-11a,16-dihydroxy-1-hydroxymethyl-1,9-dioxo-17-methylene-20-nor-5-cis-13-trans prostadiene |
| 158 | 1-trans-tri-n-butylstannyl-4-methyl-5-methylene | 2-[6-(-methoxy-2,2-dimethyl-1,3-dioxolan- | nat-11a,16-dihydroxy-1-hydroxymethyl-1,9-dioxo-16-methyl- |

TABLE II-continued

| EXAMPLE | VINYL IODIDE | CYCLOPENTENONE | PRODUCT PROSTAGLANDIN OF THE PGE2 SERIES |
|---|---|---|---|
| 159 | 1-trans-tri-n-butylstannyl-4-dimethoxymethyl-4-trimethylsiloxy-1-heptene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-formyl-20-nor-5-cis-13-trans prostadiene |
| 160 | 1-trans-tri-n-butylstannyl-4-deutro-4-triethylsiloxy-1-heptene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-deutro-20-nor-5-cis-13-trans prostadiene |
| 161 | 1-trans-tri-n-butylstannyl-4-triethylsilyloxymethyl-4-trimethylsiloxy-1-heptene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-hydroxymethyl-20-nor-5-cis-13-trans prostadiene |
| 162 | 1-trans-tri-n-butylstannyl-7-oxa-4-triethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-19-oxa-5-cis-13-trans prostadiene |
| 163 | 1-trans-tri-n-butylstannyl-4-methyl-7-oxa-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-methyl-19-oxa-5-cis-13-trans prostadiene |
| 164 | 1-trans-tri-n-butylstannyl-7-thia-4-triethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-19-thia-5-cis-13-trans ppostadiene |
| 165 | 1-trans-tri-n-butylstannyl-4-methyl-7-thia-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-methyl-19-thia-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 166 | 1-trans-iodo-7-chloro-4-triethylsiloxy-1-heptene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-19-chloro-20-nor-5-cis-13-trans prostadiene |
| 167 | 1-trans-iodo-4-methyl-7-chloro-4-trimethylsiloxy-1-heptene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-methyl-19-chloro-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 168 | 1-trans-tri-n-butylstannyl-4-fluoromethyl-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-fluoromethyl-5-cis-13-trans prostadiene |
| 169 | 1-trans-tri-n-butylstannyl-4-difluoromethyl-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-difluoromethyl-5-cis-13-trans prostadiene |
| 170 | 1-trans-tri-n-butylstannyl-4-trifluoromethyl-4-trimethylsiloxy-1-octene | 2-[6-(4-methoxy-2,2-dimethyl-1,3-dioxolan-4-yl)hex-2-cis-enyl]-4yl(hex-2-cis-enyl]-4r-(2-methoxypropyl-2-oxy)cyclopent-2-en-1-one | nat-11a,16-dihydroxy-1-hydroxymethyl-1,9-dioxo-16-trifluoromethyl-5-cis-13-trans prostadiene |
| 171 | 1-trans-tri-n-butylstannyl-4-chloromethyl-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-chloromethyl-5-cis-13-trans prostadiene |
| 172 | 1-trans-tri-n-butylstannyl-4-bromomethyl-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-bromomethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 173 | 1-trans-iodo-4-allenyl-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-allenyl-5-cis-13-trans prostadiene |

TABLE II-continued

| EXAMPLE | VINYL TIN | CYCLOPENTENONE | PRODUCT PROSTAGLANDIN OF THE PGE2 SERIES |
|---|---|---|---|
| 174 | 1-trans-tri-n-butylstannyl-5-methylene-4-triethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-17-methylene-5-cis-13-trans prostadiene |
| 175 | 1-trans-tri-n-butylstannyl-4-methyl-5-methylene-4-trimethylsiloxy-1-octene | 2-[6-(4-methoxy-2,2-dimethyl-1,3-dioxolan-4-yl)hex-2-cis-enyl]-4r-82-methoxypropyl-2-oxy)cyclopent-2-en-1-one | nat-11a,16-dihydroxy-1-hydroxymethyl-1,9-dioxo-16-methyl-17-methylene-5-cis-13-trans prostadiene |
| 176 | 1-trans-tri-n-butylstannyl-4-dimethoxymethyl-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-formyl-5-cis-13-trans prostadiene |
| 177 | 1-trans-tri-n-butylstannyl-4-deutro-4-triethylsiloxy-1-octene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-deutro-5-cis-13-trans prostadiene |
| 178 | 1-trans-tri-n-butylstannyl-4-triethylsilyloxymethyl-4-trimethylsiloxy-1-octene | 2-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-hydroxymethyl-5-cis-13-trans prostadiene |
| 179 | 1-trans-tri-n-butylstannyl-4-fluoromethyl-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-fluoromethyl-20-methyl-5-cis-13-trans prostadiene |
| 180 | 1-trans-tri-n-butylstannyl-4-difluoromethyl-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-difluoromethyl-20-methyl-5-cis-13-trans prostadiene |
| 181 | 1-trans-tri-n-butylstannyl-4-trifluoromethyl-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-trifluoromethyl-20-methyl-5-cis-13-trans prostadiene |
| 182 | 1-trans-tri-n-butylstannyl-4-chloromethyl-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-chloromethyl-20-methyl-5-cis-13-trans prostadiene |
| 183 | 1-trans-tri-n-butylstannyl-4-bromomethyl-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-bromomethyl-20-methyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 184 | 1-iodo-4-allenyl-4-trimethylsiloxy-1-nonene | 2-[6-(4-methoxy-2,2-dimethyl-1,3-dioxolan-4-yl)hex-2-cis-enyl]-4R-(2-methylpropyl-2-oxy)cyclopent-2-en-one | nat-11a,16-dihydroxy-1-hydroxymethyl-1,9-dioxo-16-allenyl-20-methyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 185 | 1-trans-tri-n-butylstannyl-5-methylene-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-17-methylene-20-methyl-5-cis-13-trans prostadiene |
| 186 | 1-trans-tri-n-butylstannyl-4-methyl-5-methylene-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-methyl-17-methylene-20-methyl-5-cis-13-trans prostadiene |
| 187 | 1-trans-tri-n-butylstannyl-4-dimethoxymethyl-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-formyl-20-methyl-5-cis-13-trans prostadiene |
| 188 | 1-trans-tri-n-butylstannyl-4-deutro-4-triethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-deutro-20-methyl-5-cis-13-trans prostadiene |
| 189 | 1-trans-tri-n-butylstannyl-4-triethylsilyloxymethyl-4-trimethylsiloxy-1-nonene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-hydroxymethyl-20-methyl-5-cis-13-trans prostadiene |

TABLE II-continued

| EXAMPLE | VINYL TIN | CYCLOPENTENONE | PRODUCT PROSTAGLANDIN OF THE PGE2 SERIES |
|---|---|---|---|
| 190 | 1-trans-tri-n-butylstannyl-4-fluoromethyl-4-trimethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-fluoromethyl-20-ethyl-5-cis-13-trans prostadiene |
| 191 | 1-trans-tri-n-butylstannyl-4-difluoromethyl-4-trimethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-difluoromethyl-20-ethyl-5-cis-13-trans prostadiene |
| 192 | 1-trans-tri-n-butylstannyl-4-trifluoromethyl-4-trimethylsiloxy-1-decene | 2[5-(4-methyoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-trifluoromethyl-20-ethyl-5-cis-13-trans prostadiene |
| 193 | 1-trans-tri-n-butylstannyl-4-chloromethyl-4-trimethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-chloromethyl-20-ethyl-5-cis-13-trans prostadiene |
| 194 | 1-trans-tri-n-butylstannyl-4-bromomethyl-4-trimethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-bromomethyl-20-ethyl-5-cis-13-trans prostadiene |
| EXAMPLE | VINYL IODIDE | CYCLOPENTENONE | PRODUCT PROSTAGLANDIN OF THE PGE2 SERIES |
| 195 | 1-trans-iodo-4-allenyl-4-trimethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-allenyl-20-ethyl-5-cis-13-trans prostadiene |
| EXAMPLE | VINYL TIN | CYCLOPENTENONE | |
| 196 | 1-trans-tri-n-butylstannyl-5-methylene-4-trimethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-17-methylene-20-ethyl-5-cis-13-trans prostadiene |
| 197 | 1-trans-tri-n-butylstannyl-4-methyl-5-methylene-4-trimethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-methyl-17-methylene-20-ethyl-5-cis-13-trans prostadiene |
| 198 | 1-trans-tri-n-butylstannyl-4-dimethoxymethyl-4-trimethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-formyl-20-ethyl-5-cis-13-trans prostadiene |
| 199 | 1-trans-tri-n-butylstannyl-4-deutro-4-triethylsiloxy-1-decene | 2[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-deutro-20-ethyl-5-cis-13-trans prostadiene |
| 200 | 1-trans-tri-n-butylstannyl-4-triethylsilyloxymethyl-4-trimethylsiloxy-1-decene | 2[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-hydroxymethyl-20-ethyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 201 | 1-trans-tri-n-butylstannyl-4-fluoromethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-fluoromethyl-20-nor-2-nor-5-cis-13-trans prostadiene |
| 202 | 1-trans-tri-n-butylstannyl-4-difluoromethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-difluoromethyl-20-nor-2-nor-5-cis-13-trans prostadiene |
| 203 | 1-trans-tri-n-butylstannyl-4-trifluoromethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-trifluoromethyl-20-nor-2-nor-5-cis-13-trans prostadiene |
| 204 | 1-trans-tri-n-butylstannyl-4-chloromethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-chloromethyl-20-nor-2-nor-5-cis-13-trans prostadiene |
| 205 | 1-trans-tri-n-butylstannyl-4-bromomethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-bromomethyl-20-nor-2-nor-5-cis-13-trans prostadiene |

TABLE II-continued

PRODUCT PROSTAGLANDIN OF THE 11-DEOXY PGE2 SERIES

| EXAMPLE | VINYL IODIDE | CYCLOPENTENONE | PRODUCT PROSTAGLANDIN OF THE 11-DEOXY PGE2 SERIES |
|---|---|---|---|
| 206 | 1-trans-iodo-4-allenyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-allenyl-20-nor-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 207 | 1-trans-tri-n-butylstannyl-4-methyl-5-methylene-4-triethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-17-methylene-20-nor-2-nor-5-cis-13-trans prostadiene |
| 208 | 1-trans-tri-n-butylstannyl-4-methyl-5-methylene-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-methyl-17-methylene-20-nor-2-nor-5-cis-13-trans prostadiene |
| 209 | 1-trans-tri-n-butylstannyl-4-dimethoxymethyl-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-formyl-20-nor-2-nor-5-cis-13-trans prostadiene |
| 210 | 1-trans-tri-n-butylstannyl-4-deutro-4-triethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-deutro-20-nor-2-nor-5-cis-13-trans prostadiene |
| 211 | 1-trans-tri-n-butylstannyl-4-triethylsilyloxymethyl-4-triethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-hydroxymethyl-20-nor-2-nor-5-cis-13-trans prostadiene |
| 212 | 1-trans-tri-n-butylstannyl-7-oxa-4-triethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-19-oxa-2-nor-2-nor-5-cis-13-trans prostadiene |
| 213 | 1-trans-tri-n-butylstannyl-4-methyl-7-oxa-4-triethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-methyl-19-oxa-2-nor-2-nor-5-cis-13-trans prostadiene |
| 214 | 1-trans-tri-n-butylstannyl-7-thia-4-triethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-19-thia-2-nor-5-cis-13-trans prostadiene |
| 215 | 1-trans-tri-n-butylstannyl-4-methyl-7-thia-4-triethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-methyl-19-thia-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 216 | 1-iodo-7-chloro-4-triethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-19-chloro-2-nor-20-nor-5-cis-13-trans prostadiene |
| 217 | 1-iodo-4-methyl-7-chloro-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-methyl-19-chloro-2-nor-20-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 218 | 1-trans-tri-n-butylstannyl-4-fluoromethyl-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-fluoromethyl-2-nor-5-cis-13-trans prostadiene |
| 219 | 1-trans-tri-n-butylstannyl-4-difluoromethyl-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-difluoromethyl-2-nor-5-cis-13-trans prostadiene |
| 220 | 1-trans-tri-n-butylstannyl-4-trifluoromethyl-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-trifluoromethyl-2-nor-5-cis-13-trans prostadiene |

TABLE II-continued

| EXAMPLE | VINYL IODIDE / VINYL TIN | CYCLOPENTENONE | PRODUCT PROSTAGLANDIN |
|---|---|---|---|
| 221 | 1-trans-tri-n-butylstannyl-4-chloromethyl-4-trimethylsiloxy-1-octene | 2-[5-(4-methoxy-2,2-dimethyl-1,3-dioxolan-4-yl)pent-2-cis-enyl] -4-(2-methoxypropyl-2-oxy)cyclopent-2-en-1-one | dl-16-hydroxy-1-hydroxymethyl-1,9-dioxo-16-chloromethyl-2-nor-5-cis-13-trans prostadiene |
| 222 | 1-trans-tri-n-butylstannyl-4-bromomethyl-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-bromomethyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 223 | 1-trans-iodo-4-allenyl-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-allenyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 224 | 1-trans-tri-n-butylstannyl-5-methylene-4-triethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-17-methylene-2-nor-5-cis-13-trans prostadiene |
| 225 | 1-trans-tri-n-butylstannyl-4-methyl-5-methylene-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-methyl-17-methylene-2-nor-5-cis-13-trans prostadiene |
| 226 | 1-trans-tri-n-butylstannyl-4-dimethoxymethyl-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-formyl-2-nor-5-cis-13-trans prostadiene |
| 227 | 1-trans-tri-n-butylstannyl-4-deutro-4-triethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-deutro-2-nor-5-cis-13-trans prostadiene |
| 228 | 1-trans-tri-n-butylstannyl-4-triethylsilyloxymethyl-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-hydroxymethyl-2-nor-5-cis-13-trans prostadiene |
| 229 | 1-trans-tri-n-butylstannyl-4-fluoromethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-fluoromethyl-20-methyl-2-nor-5-cis-13-trans prostadiene |
| 230 | 1-trans-tri-n-butylstannyl-4-difluoromethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-difluoromethyl-20-methyl-2-nor-5-cis-13-trans prostadiene |
| 231 | 1-trans-tri-n-butylstannyl-4-trifluoromethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-trifluoromethyl-20-methyl-2-nor-5-cis-13-trans prostadiene |
| 232 | 1-trans-tri-n-butylstannyl-4-chloromethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-chloromethyl-20-methyl-2-nor-5-cis-13-trans prostadiene |
| 233 | 1-trans-tri-n-butylstannyl-4-bromomethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-bromomethyl-20-methyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 234 | 1-trans-iodo-4-allenyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-allenyl-20-methyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 235 | 1-trans-tri-n-butylstannyl-5-methylene-4-triethylsiloxy-1-nonene | 2-[5-(4-methoxy-2,2-dimethyl-1,3-dioxolan-4-yl)pent-2-cis-enyl]-4-(2-methoxypropyl-2-oxy) | dl-16-hydroxy-1-hydroxymethyl-1,9-dioxo-17-methylene-20-methyl-2-nor-5-cis-13-trans prostadiene |

TABLE II-continued

| | VINYL TIN | CYCLOPENTENONE | PRODUCT PROSTAGLANDIN OF THE 11-DEOXY PGE2 SERIES |
|---|---|---|---|
| 236 | 1-trans-tri-n-butylstannyl-4-methyl-5-methylene-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-methyl-17-methylene-20-methyl-2-nor-5-cis-13-trans prostadiene |
| 237 | 1-trans-tri-n-butylstannyl-4-dimethoxymethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-formyl-20-methyl-2-nor-5-cis-13-trans prostadiene |
| 238 | 1-trans-tri-n-butylstannyl-4-deutro-4-triethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-deutro-20-methyl-2-nor-5-cis-13-trans prostadiene |
| 239 | 1-trans-tri-n-butylstannyl-4-triethylsilyloxymethyl-4-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-hydroxymethyl-20-methyl-2-nor-5-cis-13-trans prostadiene |
| 240 | 1-trans-tri-n-butylstannyl-4-fluoromethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-fluoromethyl-20-ethyl-2-nor-5-cis-13-trans prostadiene |
| 241 | 1-trans-tri-n-butylstannyl-4-difluoromethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-difluoromethyl-20-ethyl-2-nor-5-cis-13-trans prostadiene |
| 242 | 1-trans-tri-n-butylstannyl-4-trifluoromethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-trifluoromethyl-20-ethyl-2-nor-5-cis-13-trans prostadiene |
| 243 | 1-trans-tri-n-butylstannyl-4-chloromethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-chloromethyl-20-ethyl-2-nor-5-cis-13-trans prostadiene |
| 244 | 1-trans-tri-n-butylstannyl-4-bromomethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-bromomethyl-20-ethyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 245 | 1-trans-iodo-4-allenyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-allenyl-20-ethyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 246 | 1-trans-tri-n-butylstannyl-5-methylene-4-triethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-17-methylene-20-ethyl-2-nor-5-cis-13-trans prostadiene |
| 247 | 1-trans-tri-n-butylstannyl-4-methyl-5-methylene-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-methyl-17-methylene-20-ethyl-2-nor-5-cis-13-trans prostadiene |
| 248 | 1-trans-tri-n-butylstannyl-4-dimethoxymethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-formyl-20-ethyl-2-nor-5-cis-13-trans prostadiene |
| 249 | 1-trans-tri-n-butylstannyl-4-deutro-4-triethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-deutro-20-ethyl-2-nor-5-cis-13-trans prostadiene |
| 250 | 1-trans-tri-n-butylstannyl-4-triethylsilyloxymethyl-4-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-hydroxymethyl-20-ethyl-2-nor-5-cis-13-trans prostadiene |
| 251 | 1-trans-tri-n-butylstannyl-4-fluoromethyl-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-fluoromethyl-20-nor-5-cis-13-trans prostadiene |

TABLE II-continued

| | | | PRODUCT PROSTAGLANDIN OF THE 11-DEOXY PGE2 SERIES |
|---|---|---|---|
| 252 | 1-trans-tri-n-butylstannyl-4-difluoromethyl-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-difluoromethyl-20-nor-5-cis-13-trans prostadiene |
| 253 | 1-trans-tri-n-butylstannyl-4-trifluoromethyl-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-trifluoromethyl-20-nor-5-cis-13-trans prostadiene |
| 254 | 1-trans-tri-n-butylstannyl-4-chloromethyl-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-chloromethyl-20-nor-5-cis-13-trans prostadiene |
| 255 | 1-trans-tri-n-butylstannyl-4-bromomethyl-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-bromomethyl-20-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 256 | 1-trans-iodo-4-allenyl-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-allenyl-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 257 | 1-trans-tri-n-butylstannyl-5-methylene-4-triethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-17-methylene-20-nor-5-cis-13-trans prostadiene |
| 258 | 1-trans-tri-n-butylstannyl-4-methyl-5-methylene-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-17-methylene-20-nor-5-cis-13-trans prostadiene |
| 259 | 1-trans-tri-n-butylstannyl-4-dimethoxymethyl-4-trimethylsiloxy-1-heptene | 2-[6-(4-methoxy-2,2-dimethyl-1,3-dioxolan-4-yl)hex-2-cis-enyl-9-4-(2-methoxypropyl-2-oxy)cyclopent-2-en-1-one | dl-16-hydroxy-1-hydroxymethyl-1,9-dioxo-16-formyl-20-nor-5-cis-13-trans prostadiene |
| 260 | 1-trans-tri-n-butylstannyl-4-deutro-4-trimethylsiloxy-1-heptene | 2-[6-(4-methoxy-2,2dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-deutro-20-nor-5-cis-13-trans prostadiene |
| 261 | 1-trans-tri-n-butylstannyl-4-triethylsilyloxymethyl-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-hydroxymethyl-20-nor-5-cis-13-trans prostadiene |
| 262 | 1-trans-tri-n-butylstannyl-7-oxa-4-triethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-19-oxa-5-cis-13-trans prostadiene |
| 263 | 1-trans-tri-n-butylstannyl-4-methyl-7-oxa-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-methyl-19-oxa-5-cis-13-trans prostadiene |
| 264 | 1-trans-tri-n-butylstannyl-7-thia-4-triethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-19-thia-5-cis-13-trans prostadiene |
| 265 | 1-trans-tri-n-butylstannyl-4-methyl-7-thia-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-methyl-19-thia-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 266 | 1-trans-iodo-7-chloro-4-triethylsiloxy-1-heptene | 2-[6-(methoxy-2,2-dimethyl-1,3-dioxolan-4-yl)hex-2-cis-enyl]-4-methoxypropyl-2-oxy)cyclopent-2-en-1-one | dl-16-hydroxy-1-hydroxymethyl-1,9-dioxo-19-chloro-20-nor-5-cis-13-trans prostadiene |
| 267 | 1-trans-iodo-4-methyl-7-chloro-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-methyl-19-chloro-20-nor-5-cis-13-trans prostadiene |

TABLE II-continued

| EXAMPLE | VINYL TIN | CYCLOPENTENONE | PRODUCT PROSTAGLANDIN OF THE 11-DEOXY PGE2 SERIES |
|---------|-----------|----------------|---------------------------------------------------|
| 268 | 1-trans-tri-n-butylstannyl-4-fluoromethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-fluoromethyl-5-cis-13-trans prostadiene |
| 269 | 1-trans-tri-n-butylstannyl-4-difluoromethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-difluoromethyl-5-cis-13-trans prostadiene |
| 270 | 1-trans-tri-n-butylstannyl-4-trifluoromethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-trifluoromethyl-5-cis-13-trans prostadiene |
| 271 | 1-trans-tri-n-butylstannyl-4-chloromethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-chloromethyl-5-cis-13-trans prostadiene |
| 272 | 1-trans-tri-n-butylstannyl-4-bromomethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-bromomethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---------|--------------|----------------|---------------------------------------------------|
| 273 | 1-trans-iodo-4-allenyl-4-trimethylsiloxy-1-octene | 2-[6-(4-methoxy-2,2-dimethyl-1,3-dioxolan-4-yl)hex-2-cis-enyl-9-4-(2-methoxypropyl-2-oxy)cyclopent-2-en-1-one | dl-16-hydroxy-1-hydroxymethyl-1,9-dioxo-16-allenyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---------|-----------|----------------|---------------------------------------------------|
| 274 | 1-trans-tri-n-butylstannyl-5-methylene-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-17-methylene-5-cis-13-trans prostadiene |
| 275 | 1-trans-tri-n-butylstannyl-4-methyl-5-methylene-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-methyl-17-methylene-5-cis-13-trans prostadiene |
| 276 | 1-trans-tri-n-butylstannyl-4-dimethoxymethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-formyl-5-cis-13-trans prostadiene |
| 277 | 1-trans-tri-n-butylstannyl-4-deutro-4-triethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-deutro-5-cis-13-trans prostadiene |
| 278 | 1-trans-tri-n-butylstannyl-4-triethylsilyloxymethyl-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-hydroxymethyl-5-cis-13-trans prostadiene |
| 279 | 1-trans-tri-n-butylstannyl-4-fluoromethyl-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-fluoromethyl-20-methyl-5-cis-13-trans prostadiene |
| 280 | 1-trans-tri-n-butylstannyl-4-difluoromethyl-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-difluoromethyl-20-methyl-5-cis-13-trans prostadiene |
| 281 | 1-trans-tri-n-butylstannyl-4-trifluoromethyl-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-trifluoromethyl-20-methyl-5-cis-13-trans prostadiene |
| 282 | 1-trans-tri-n-butylstannyl-4-chloromethyl-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-chloromethyl-20-methyl-5-cis-13-trans prostadiene |
| 283 | 1-trans-tri-n-butylstannyl-4-bromomethyl- | 2-[6-(4-methoxy-2,2-dimethyl-1,3-dioxolan- | dl-16-hydroxy-1-hydroxymethyl-1,9-dioxo-16-bromomethyl- |

TABLE II-continued

| EXAMPLE | VINYL IODIDE | CYCLOPENTENONE | PRODUCT PROSTAGLANDIN OF THE 11-DEOXY PGE2 SERIES |
|---|---|---|---|
| | 4-trimethylsiloxy-1-nonene | 4-yl)hex-2-cis-enyl]-4-(2-methoxypropyl-2-ocy)cyclopent-2-en-1-one | 20-methyl-5-cis-13-trans prostadiene |
| 284 | 1-trans-iodo-4-allenyl-4-trimethylsiloxy-1-nonene | 2-[6-(4-methoxy-2,2-dimethyl-1,3-dioxolan-4-yl)hex-2-cis-enyl]4-(2-methoxypropyl-2-oxy)cyclopent-2-en-1-one | dl-16-hydroxy-1-hydroxymethyl-1,9-dioxo-16-allenyl-20-methyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 285 | 1-trans-tri-n-butylstannyl-5-methylene-4-triethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-17-methylene-20-methyl-5-cis-13-trans prostadiene |
| 286 | 1-trans-tri-n-butylstannyl-4-methyl-5-methylene-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-methyl-17-methylene-20-methyl-5-cis-13-trans prostadiene |
| 287 | 1-trans-tri-n-butylstannyl-4-dimethoxymethyl-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-formyl-20-methyl-5-cis-13-trans prostadiene |
| 288 | 1-trans-tri-n-butylstannyl-4-deutro-4-triethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-deutro-20-methyl-5-cis-13-trans prostadiene |
| 289 | 1-trans-tri-n-butylstannyl-4-triethylsilyloxymethyl-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxy-1-hydroxymethyl-1,9-dioxo-16-hydroxymethyl-20-methyl-5-cis-13-trans prostadiene |
| 290 | 1-trans-tri-n-butylstannyl-4-fluoromethyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-fluoromethyl-20-ethyl-5-cis-13-trans prostadiene |
| 291 | 1-trans-tri-n-butylstannyl-4-difluoromethyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-difluoromethyl-20-ethyl-5-cis-13-trans prostadiene |
| 292 | 1-trans-tri-n-butylstannyl-4-trifluoromethyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9l-dioxo-16-trifluoromethyl-20-ethyl-5-cis-13-trans prostadiene |
| 293 | 1-trans-tri-n-butylstannyl-4-chloromethyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-chloromethyl-20-ethyl-5-cis-13-trans prostadiene |
| 294 | 1-trans-tri-n-butylstannyl-4-bromomethyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-bromomethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 295 | 1-trans-iodo-4-allenyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-allenyl-20-ethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 296 | 1-trans-tri-n-butylstannyl-5-methylene-4-triethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-17-methylene-20-ethyl-5-cis-13-trans prostadiene |
| 297 | 1-trans-tri-n-butylstannyl-4-methyl-5-methylene-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-methyl-17-methylene-20-ethyl-5-cis-13-trans prostadiene |
| 298 | 1-trans-tri-n-butylstannyl-4-dimethoxymethyl- | 2-[6-(4-methoxy-2,2-dimethyl-1,3-dioxolan- | dl-16-hydroxy-1-hydroxymethyl-1,9-dioxo-16-formyl- |

TABLE II-continued

| | | | |
|---|---|---|---|
| | | 4-trimethylsiloxy-1-decene | 4-yl)hex-2-cis-enyl]-4-(2-methoxypropyl-2-oxy)cyclopent-2-en-1-one | 20-ethyl-5-cis-13-trans prostadiene |
| 299 | | 1-trans-tri-n-butylstannyl-4-deutro-4-triethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-deutro-20-ethyl-5-cis-13-trans prostadiene |
| 300 | | 1-trans-tri-n-butylstannyl-4-triethylsilyloxymethyl-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-hydroxymethyl-20-ethyl-5-cis-13-trans prostadiene |
| 301 | | 1-trans-tri-n-butylstannyl-4-fluoromethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-fluoromethyl-20-nor-2-homo-5-cis-13-trans prostadiene |
| 302 | | 1-trans-tri-n-butylstannyl-4-difluoromethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-difluoromethyl-20-nor-2-homo-5-cis-13-trans prostadiene |
| 303 | | 1-trans-tri-n-butylstannyl-4-trifluoromethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-trifluoromethyl-20-nor-2-homo-5-cis-13-trans prostadiene |
| 304 | | 1-trans-tri-n-butylstannyl-4-chloromethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-chloromethyl-20-nor-2-homo-5-cis-13-trans prostadiene |
| 305 | | 1-trans-tri-n-butylstannyl-4-bromomethyl-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-bromomethyl-20-nor-2-homo-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 306 | 1-trans-iodo-4-allenyl-4-trimethylsiloxy-1-heptene | | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-allenyl-20-nor-2-homo-5-cis-13-trans prostadiene |
| EXAMPLE | VINYL TIN | | CYCLOPENTENONE | PRODUCT PROSTAGLANDIN OF THE 11-DEOXY PGE2 SERIES |
| 307 | 1-trans-tri-n-butylstannyl-5-methylene-4-triethylsiloxy-1-heptene | | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-17-methylene-20-nor-2-homo-5-cis-13-trans prostadiene |
| 308 | 1-trans-tri-n-butylstannyl-4-methyl-5-methylene-4-triethylsiloxy-1-heptene | | 2-[7-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-17-methylene-20-nor-2-homo-5-cis-13-trans prostadiene |
| 309 | 1-trans-tri-n-butylstannyl-4-dimethoxymethyl-4-triethylsiloxy-1-heptene | | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-formyl-20-nor-2-homo-5-cis-13-trans prostadiene |
| 310 | 1-trans-tri-n-butylstannyl-4-deutro-4-triethylsiloxy-1-heptene | | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-deutro-20-nor-2-homo-5-cis-13-trans prostadiene |
| 311 | 1-trans-tri-n-butylstannyl-4-triethylsilyloxymethyl-4-triethylsiloxy-1-heptene | | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-hydroxymethyl-20-nor-2-homo-5-cis-13-trans prostadiene |
| 312 | 1-trans-tri-n-butylstannyl-7-oxa-4-triethylsiloxy-1-octene | | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-19-oxa-2-homo-5-cis-13-trans prostadiene |
| 313 | 1-trans-tri-n-butylstannyl-4-methyl-7-oxa-4-triethylsiloxy-1-octene | | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-19-oxa-2-homo-5-cis-13-trans prostadiene |
| 314 | 1-trans-tri-n-butylstannyl-7-thia-4-triethylsiloxy-1-octene | | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-19-thia-2-homo-5-cis-13-trans prostadiene |

TABLE II-continued

| | | | PRODUCT PROSTAGLANDIN |
|---|---|---|---|
| 315 | 1-trans-tri-n-butylstannyl-4-methyl-7-thia-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-19-thia-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 316 | 1-trans-iodo-7-chloro-4-triethylsilyloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-19-chloro-2-homo-20-nor-5-cis-13-trans prostadiene |
| 317 | 1-trans-iodo-4-methyl-7-chloro-4-trimethylsilyloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-19-chloro-2-homo-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 318 | 1-trans-tri-n-butylstannyl-4-fluoromethyl-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-fluoromethyl-2-homo-5-cis-13-trans prostadiene |
| 319 | 1-trans-tri-n-butylstannyl-4-difluoromethyl-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-difluoromethyl-2-homo-5-cis-13-trans prostadiene |
| 320 | 1-trans-tri-n-butylstannyl-4-trifluoromethyl-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-trifluoromethyl-2-homo-5-cis-13-trans prostadiene |
| 321 | 1-trans-tri-n-butylstannyl-4-chloromethyl-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-chloromethyl-2-homo-5-cis-13-trans prostadiene |
| 322 | 1-trans-tri-n-butylstannyl-4-bromomethyl-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-bromomethyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 323 | 1-trans-iodo-4-allenyl-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-allenyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 324 | 1-trans-tri-n-butylstannyl-5-methylene-4-triethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-17-methylene-2-homo-5-cis-13-trans prostadiene |
| 325 | 1-trans-tri-n-butylstannyl-4-methyl-5-methylene-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-17-methylene-2-homo-5-cis-13-trans prostadiene |
| 326 | 1-trans-tri-n-butylstannyl-4-dimethoxymethyl-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-formyl-2-homo-5-cis-13-trans prostadiene |
| 327 | 1-trans-tri-n-butylstannyl-4-deutro-4-triethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-deutro-2-homo-5-cis-13-trans prostadiene |
| 328 | 1-trans-tri-n-butylstannyl-4-triethylsilyloxymethyl-4-trimethylsilyloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-hydroxymethyl-2-homo-5-cis-13-trans prostadiene |
| 329 | 1-trans-tri-n-butylstannyl-4-fluoromethyl-4-trimethylsilyloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-fluoromethyl-20-methyl-2-homo-5-cis-13-trans prostadiene |

TABLE II-continued

| EXAMPLE | VINYL IODIDE / VINYL TIN / CYCLOPENTENONE | CYCLOPENTENONE | PRODUCT PROSTAGLANDIN |
|---|---|---|---|
| 330 | 1-trans-tri-n-butylstannyl-4-difluoromethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-difluoromethyl-20-methyl-2-homo-5-cis-13-trans prostadiene |
| 331 | 1-trans-tri-n-butylstannyl-4-trifluoromethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-trifluoromethyl-20-methyl-2-homo-5-cis-13-trans prostadiene |
| 332 | 1-trans-tri-n-butylstannyl-4-chloromethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-chloromethyl-20-methyl-2-homo-5-cis-13-trans prostadiene |
| 333 | 1-trans-tri-n-butylstannyl-4-bromomethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-bromomethyl-20-methyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 334 | 1-trans-iodo-4-allenyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-allenyl-20-methyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 335 | 1-trans-tri-n-butylstannyl-5-methylene-4-triethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-17-methylene-20-methyl-2-homo-5-cis-13-trans prostadiene |
| 336 | 1-trans-tri-n-butylstannyl-4-methyl-5-methylene-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-17-methylene-20-methyl-2-homo-5-cis-13-trans prostadiene |
| 337 | 1-trans-tri-n-butylstannyl-4-dimethoxymethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-formyl-20-methyl-2-homo-5-cis-13-trans prostadiene |
| 338 | 1-trans-tri-n-butylstannyl-4-deutro-4-triethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-deutro-20-methyl-2-homo-5-cis-13-trans prostadiene |
| 339 | 1-trans-tri-n-butylstannyl-4-triethylsilyloxymethyl-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-hydroxymethyl-20-methyl-2-homo-5-cis-13-trans prostadiene |
| 340 | 1-trans-tri-n-butylstannyl-4-fluoromethyl-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-fluoromethyl-20-ethyl-2-homo-5-cis-13-trans prostadiene |
| 341 | 1-trans-tri-n-butylstannyl-4-difluoromethyl-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-difluoromethyl-20-ethyl-2-homo-5-cis-13-trans prostadiene |
| 342 | 1-trans-tri-n-butylstannyl-4-trifluoromethyl-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-trifluoromethyl-20-ethyl-2-homo-5-cis-13-trans prostadiene |
| 343 | 1-trans-tri-n-butylstannyl-4-chloromethyl-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-chloromethyl-20-ethyl-2-homo-5-cis-13-trans prostadiene |
| 344 | 1-trans-tri-n-butylstannyl-4-bromomethyl-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-bromomethyl-20-ethyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 345 | 1-trans-iodo-4-allenyl- | 2-[7-(4-methoxy-2,2-dimethyl-1,3-dioxolan- | dl-16-hydroxy-1-hydroxymethyl-1,9-dioxo-16-allenyl- |

TABLE II-continued

| EXAMPLE | VINYL TIN | CYCLOPENTENONE | PRODUCT PROSTAGLANDIN OF THE 11-DEOXY PGE2 SERIES |
|---|---|---|---|
| | 4-trimethylsiloxy-1-decene | 4-yl)hept-2-cis-enyl]-4-(2-methoxypropyl-2-oxy)cyclopent-2-en-1-one | 20-ethyl-2-homo-5-cis-13-trans prostadiene |
| 346 | 1-trans-tri-n-butylstannyl-5-methylene-4-triethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-17-methylene-20-ethyl-2-homo-5-cis-13-trans prostadiene |
| 347 | 1-trans-tri-n-butylstannyl-4-methyl-5-methylene-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-17-methylene-20-ethyl-2-homo-5-cis-13-trans prostadiene |
| 348 | 1-trans-tri-n-butylstannyl-4-dimethoxymethyl-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-formyl-20-ethyl-2-homo-5-cis-13-trans prostadiene |
| 349 | 1-trans-tri-n-butylstannyl-4-deutro-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-deutro-20-ethyl-2-homo-5-cis-13-trans prostadiene |
| 350 | 1-trans-tri-n-butylstannyl-4-triethylsilyloxymethyl-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-hydroxymethyl-20-ethyl-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 351 | 1-trans-tri-n-butylstannyl-4-(1-fluorovinyl)-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-20-nor-2-nor-5-cis-13-trans prostadiene |
| 352 | 1-trans-tri-n-butylstannyl-3-vinyl-3-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,15a-dihydroxy-1-hydroxymethyl-1,9-dioxo-15-vinyl-20-nor-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 353 | 1-iodo-4-vinyl-7-chloro-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-vinyl-19-chloro-2-nor-20-nor-5-cis-13-trans prostadiene |
| 354 | 1-iodo-4-methyl-7-chloro-4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-methyl-19-chloro-2-nor-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 355 | 1-trans-tri-n-butylstannyl-4-methyl-4-trimethylsiloxy-1-pentene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-methyl-2-nor-18,19,20-trinor-5-cis-13-trans prostadiene |
| 356 | 1-trans-tri-n-butylstannyl-4-(1-fluorovinyl)-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-2-nor-5-cis-13-trans prostadiene |
| 357 | 1-trans-tri-n-butylstannyl-3-vinyl-3-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,15a-dihydroxy-1-hydroxymethyl-1,9-dioxo-15-vinyl-2-nor-5-cis-13-trans prostadiene |
| 358 | 1-trans-tri-n-butylstannyl-4-(1-fluorovinyl)-4-trimethylsiloxy-1-nonene | 2-[5-(4-methoxy-2,2-dimethyl-1,3-dioxglan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-20-methyl-2-nor-5-cis-13-trans prostadiene |
| 359 | 1-trans-tri-n-butylstannyl-3-vinyl-3-trimethylsiloxy-1-nonene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,15a-dihydroxy-1-hydroxymethyl-1,9-dioxo-15-vinyl-20-methyl-2-nor-5-cis-13-trans prostadiene |
| 360 | 1-trans-tri-n-butylstannyl-4-(1-fluorovinyl)- | 2-[5-(4-methoxy-2,2-dimethyl-1,3-dioxolan- | dl-11a,16-dihydroxy-1-hydroxymethyl-1,9-dioxo-16-(1-fluorovinyl)- |

TABLE II-continued

| EXAMPLE | VINYL IODIDE / VINYL TIN | CYCLOPENTENONE | PRODUCT PROSTAGLANDIN OF THE PGE2 SERIES |
|---|---|---|---|
|  | 4-trimethylsiloxy-1-decene | 4-yl)pent-2-cis-enyl]-4-(2-methoxypropyl-2-oxy)cyclopent-2-en-1-one | 20-ethyl-2-nor-5-cis-13-trans prostadiene |
| 361 | 1-trans-tri-n-butylstannyl-3-vinyl-3-trimethylsiloxy-1-decene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,15a-dihydroxy-1-hydroxymethyl-1,9-dioxo-15-vinyl-20-ethyl-2-nor-5-cis-13-trans prostadiene |
| 362 | 1-trans-tri-n-butylstannyl-4-(1-fluorovinyl)-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-20-nor-5-cis-13-trans prostadiene |
| 363 | 1-trans-tri-n-butylstannyl-3-vinyl-3-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,15a-dihydroxy-1-hydroxymethyl-1,9-dioxo-15-vinyl-20-nor-5-cis-13-trans prostadiene |
| EXAMPLE | VINYL IODIDE | CYCLOPENTENONE | PRODUCT PROSTAGLANDIN OF THE PGE2 SERIES |
| 364 | 1-trans-iodo-4-vinyl-7-chloro-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-vinyl-19-chloro-20-nor-5-cis-13-trans prostadiene |
| 365 | 1-trans-iodo-4-methyl-7-chloro-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-methyl-19-chloro-20-nor-5-cis-13-trans prostadiene |
| EXAMPLE | VINYL TIN | CYCLOPENTENONE | PRODUCT PROSTAGLANDIN OF THE PGE2 SERIES |
| 366 | 1-trans-tri-n-butylstannyl-4-methyl-4-trimethylsiloxy-1-pentene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-methyl-18,19,20-trinor-5-cis-13-trans prostadiene |
| 367 | 1-trans-tri-n-butylstannyl-4-(1-fluorovinyl)-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-5-cis-13-trans prostadiene |
| 368 | 1-trans-tri-n-butylstannyl-3-vinyl-3-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,15a-dihydroxy-1-hydroxymethyl-1,9-dioxo-15-vinyl-5-cis-13-trans prostadiene |
| 369 | 1-trans-tri-n-butylstannyl-4-(1-fluorovinyl)-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-20-methyl-5-cis-13-trans prostadiene |
| 370 | 1-trans-tri-n-butylstannyl-3-vinyl-3-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,15a-dihydroxy-1-hydroxymethyl-1,9-dioxo-15-vinyl-20-methyl-5-cis-13-trans prostadiene |
| 371 | 1-trans-tri-n-butylstannyl-4-(1-fluorovinyl)-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-20-ethyl-5-cis-13-trans prostadiene |
| 372 | 1-trans-tri-n-butylstannyl-3-vinyl-3-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,15a-dihydroxy-1-hydroxymethyl-1,9-dioxo-15-vinyl-20-ethyl-5-cis-13-trans prostadiene |
| 373 | 1-trans-tri-n-butylstannyl-4-(1-fluorovinyl)-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-20-nor-2-homo-5-cis-13-trans prostadiene |
| 374 | 1-trans-tri-n-butylstannyl-3-vinyl-3-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,15a-dihydroxy-1-hydroxymethyl-1,9-dioxo-15-vinyl-20-nor-2-homo-5-cis-13-trans prostadiene |
| EXAMPLE | VINYL IODIDE | CYCLOPENTENONE | PRODUCT PROSTAGLANDIN OF THE PGE2 SERIES |
| 375 | 1-trans-iodo-4-vinyl-7-chloro-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-vinyl-19-chloro-2-homo-20-nor-5-cis-13-trans prostadiene |

TABLE II-continued

| EXAMPLE | VINYL IODIDE / VINYL TIN | CYCLOPENTENONE | PRODUCT PROSTAGLANDIN OF THE PGE2 SERIES |
|---|---|---|---|
| 376 | 1-trans-iodo-4-methyl-7-chloro-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-methyl-19-chloro-2-homo-2-nor-5-cis-13-trans prostadiene |
| EXAMPLE | VINYL TIN | CYCLOPENTENONE | PRODUCT PROSTAGLANDIN OF THE PGE2 SERIES |
| 377 | 1-trans-tri-n-butylstannyl-4-methyl-4-trimethylsiloxy-1-pentene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-methyl-2-homo-18,19,20-trinor-5-cis-13-trans prostadiene |
| 378 | 1-trans-tri-n-butylstannyl-4-(1-fluorovinyl)-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-2-homo-5-cis-13-trans prostadiene |
| 379 | 1-trans-tri-n-butylstannyl-3-vinyl-3-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,15a-dihydroxy-1-hydroxymethyl-1,9-dioxo-15-vinyl-2-homo-5-cis-13-trans prostadiene |
| 380 | 1-trans-tri-n-butylstannyl-4-(1-fluorovinyl)-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-20-methyl-2-homo-5-cis-13-trans prostadiene |
| 381 | 1-trans-tri-n-butylstannyl-3-vinyl-3-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,15a-dihydroxy-1-hydroxymethyl-1,9-dioxo-15-vinyl-20-methyl-2-homo-5-cis-13-trans prostadiene |
| 382 | 1-trans-tri-n-butylstannyl-4-(1-fluorovinyl)-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-(1-fluorovinyl)-20-ethyl-2-homo-5-cis-13-trans prostadiene |
| 383 | 1-trans-tri-n-butylstannyl-3-vinyl-3-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,15a-dihydroxy-1-hydroxymethyl-1,9-dioxo-15-vinyl-20-ethyl-2-homo-5-cis-13-trans prostadiene |
| 384 | 1-trans-tri-n-butylstannyl-4-(1-fluorovinyl)-4-trimethylsiloxy-1-heptene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-(1-fluorovinyl)-20-nor-5-cis-13-trans prostadiene |
| 385 | 1-trans-tri-n-butylstannyl-3-vinyl-3-trimethylsiloxy-1-heptene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,15a-dihydroxy-1-hydroxymethyl-1,9-dioxo-15-vinyl-20-nor-5-cis-13-trans prostadiene |
| EXAMPLE | VINYL IODIDE | CYCLOPENTENONE | PRODUCT PROSTAGLANDIN OF THE PGE2 SERIES |
| 386 | 1-trans-iodo-4-vinyl-7-chloro-4-trimethylsiloxy-1-heptene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-vinyl-19-chloro-20-nor-5-cis-13-trans prostadiene |
| 387 | 1-trans-iodo-4-methyl-7-chloro-4-trimethylsiloxy-1-heptene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-methyl-19-chloro-20-nor-5-cis-13-trans prostadiene |
| EXAMPLE | VINYL TIN | CYCLOPENTENONE | PRODUCT PROSTAGLANDIN OF THE PGE2 SERIES |
| 388 | 1-trans-tri-n-butylstannyl-4-methyl-4-trimethylsiloxy-1-pentene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-methyl-18,19,20-trinor-5-cis-13-trans prostadiene |
| 389 | 1-trans-tri-n-butylstannyl-4-(1-fluorovinyl)-4-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-(1-fluorovinyl)-5-cis-13-trans prostadiene |
| 390 | 1-trans-tri-n-butylstannyl-3-vinyl-3-trimethylsiloxy-1-octene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,15a-dihydroxy-1-hydroxymethyl-1,9-dioxo-15-vinyl-5-cis-13-trans prostadiene |
| 391 | 1-trans-tri-n-butylstannyl-4-(1-fluorovinyl)-4-trimethylsiloxy-1-nonene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-(1-fluorovinyl)-20-methyl-5-cis-13-trans prostadiene |

TABLE II-continued

| EXAMPLE | VINYL TIN | CYCLOPENTENONE | PRODUCT PROSTAGLANDIN OF THE 11-DEOXY PGE2 SERIES |
|---|---|---|---|
| 392 | 1-trans-tri-n-butylstannyl-3-vinyl-3-trimethylsiloxy-1-nonene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,15a-dihydroxy-1-hydroxymethyl-1,9-dioxo-15-vinyl-20-methyl-5-cis-13-trans prostadiene |
| 393 | 1-trans-tri-n-butylstannyl-4-(1-fluorovinyl)-4-trimethylsiloxy-1-decene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,16-dihydroxy-1-hydroxymethyl-1,9-dioxo-16-(1-fluorovinyl)-20-ethyl-5-cis-13-trans prostadiene |
| 394 | 1-trans-tri-n-butylstannyl-3-vinyl-3-trimethylsiloxy-1-decene | 2-[6-(4-methoxy-2,2-dimethyl-1,3-dioxolan-4-yl)hex-2-cis-enyl]-4r-(2-methoxypropyl-2-oxy)cyclopent-2-en-1-one | nat-11a,15a-dihydroxy-1-hydroxymethyl-1,9-dioxo-15-vinyl-20-ethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 395 | 1-trans-tri-n-butylstannyl-4-(1-fluorovinyl)-4-trimethylsiloxy-1-heptene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-16-hydroxy-1-hydroxymethyl-1,9-dioxo-16-(1-fluorovinyl)-20-nor-2-nor-5-cis-13-trans prostadiene |
| 396 | 1-trans-tri-n-butylstannyl-3-vinyl-3-trimethylsiloxy-1-heptene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-15a-hydroxy-1-hydroxymethyl-1,9-dioxo-15-vinyl-20-nor-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 397 | 1-trans-iodo-4-vinyl-7-chloro-4-trimethylsiloxy-1-heptene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-16-hydroxy-1-hydroxymethyl-1,9-dioxo-16-vinyl-19-chloro-2-nor-20-nor-5-cis-13-trans prostadiene |
| 398 | 1-trans-iodo-4-methyl-7-chloro-4-trimethylsiloxy-1-heptene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-16-hydroxy-1-hydroxymethyl-1,9-dioxo-16-methyl-19-chloro-2-nor-20-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 399 | 1-trans-tri-n-butylstannyl-4-methyl-4-trimethylsilozy-1-pentene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-16-hydroxy-1-hydroxymethyl-1,9-dioxo-16-methyl-2-nor-18,19,20-trinor-5-cis-13-trans prostadiene |
| 400 | 1-trans-tri-n-butylstannyl-4-(1-fluorovinyl)-4-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-16-hydroxy-1-hydroxymethyl-1,9-dioxo-16-(1-fluorovinyl)-2-nor-5-cis-13-trans prostadiene |
| 401 | 1-trans-tri-n-butylstannyl-3-vinyl-3-trimethylsiloxy-1-octene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-15a-hydroxy-1-hydroxymethyl-1,9-dioxo-15-vinyl-2-nor-5-cis-13-trans prostadiene |
| 402 | 1-trans-tri-n-butylstannyl-4-(1-fluorovinyl)-4-trimethylsiloxy-1-nonene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-16-hydroxy-1-hydroxymethyl-1,9-dioxo-16-(1-fluorovinyl)-20-methyl-2-nor-5-cis-13-trans prostadiene |
| 403 | 1-trans-tri-n-butylstannyl-3-vinyl-3-trimethylsiloxy-1-nonene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-15a-hydroxy-1-hydroxymethyl-1,9-dioxo-15-vinyl-20-methyl-2-nor-5-cis-13-trans prostadiene |
| 404 | 1-trans-tri-n-butylstannyl-4-(1-fluorovinyl)-4-trimethylsiloxy-1-decene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-16-hydroxy-1-hydroxymethyl-1,9-dioxo-16-(1-fluorovinyl)-20-ethyl-2-nor-5-cis-13-trans prostadiene |
| 405 | 1-trans-tri-n-butylstannyl-3-vinyl-3-trimethylsiloxy-1-decene | 2-[5-(4-methoxy-2,2-dimethyl-1,3-dioxolan-4-yl]pent-2-cis-enyl]-4-(2-methoxypropyl-2-oxy)cyclopent-2-en-1-one | dl-15a-hydroxy-1-hydroxymethyl-1,9-dioxo-15-vinyl-20-ethyl-2-nor-5-cis-13-trans prostadiene |
| 406 | 1-trans-tri-n-butylstannyl-4-(1-fluorovinyl)-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-(1-fluorovinyl)-20-nor-5-cis-13-trans prostadiene |
| 407 | 1-trans-tri-n-butylstannyl-3-vinyl- | 2-[6-(4-methoxy-2,2-dimethyl-1,3-dioxolan- | dl-15a-hydroxy-1-hydroxymethyl-1,9-dioxo-15-vinyl- |

TABLE II-continued

| EXAMPLE | VINYL IODIDE | CYCLOPENTENONE | PRODUCT PROSTAGLANDIN OF THE 11-DEOXY PGE2 SERIES |
|---|---|---|---|
|  | 3-trimethylsiloxy-1-heptene | 4-yl)hex-2-cis-enyl]-4-(2-methoxypropyl-2-oxy)cyclopent-2-en-1-one | 20-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 408 | 1-trans-iodo-4-vinyl-7-chloro-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-vinyl-19-chloro-20-nor-5-cis-13-trans prostadiene |
| 409 | 1-trans-iodo-4-methyl-7-chloro-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-methyl-19-chloro-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 410 | 1-trans-tri-n-butylstannyl-4-methyl-4-trimethylsiloxy-1-pentene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-methyl-18,19,20-trinor-5-cis-13-trans prostadiene |
| 411 | 1-trans-tri-n-butylstannyl-4-(1-fluorovinyl)-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-(1-fluorovinyl)-5-cis-13-trans prostadiene |
| 412 | 1-trans-tri-n-butylstannyl-3-vinyl-3-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-15a-hydroxy-1-hydroxymethyl-1,9-dioxo-15-vinyl-5-cis-13-trans prostadiene |
| 413 | 1-trans-tri-n-butylstannyl-4-(1-fluorovinyl)-4-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-(1-fluorovinyl)-20-methyl-5-cis-13-trans prostadiene |
| 414 | 1-trans-tri-n-butylstannyl-3-vinyl-3-trimethylsiloxy-1-nonene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-15a-hydroxy-1-hydroxymethyl-1,9-dioxo-15-vinyl-20-methyl-5-cis-13-trans prostadiene |
| 415 | 1-trans-tri-n-butylstannyl-4-(1-fluorovinyl)-4-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-(1-fluorovinyl)-20-ethyl-5-cis-13-trans prostadiene |
| 416 | 1-trans-tri-n-butylstannyl-3-vinyl-3-trimethylsiloxy-1-decene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-15a-hydroxy-1-hydroxymethyl-1,9-dioxo-15-vinyl-20-ethyl-5-cis-13-trans prostadiene |
| 417 | 1-trans-tri-n-butylstannyl-4-(1-fluorovinyl)-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-(1-fluorovinyl)-20-nor-2-homo-5-cis-13-trans prostadiene |
| 418 | 1-trans-tri-n-butylstannyl-3-vinyl-3-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-15a-hydroxy-1-hydroxymethyl-1,9-dioxo-15-vinyl-20-nor-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 419 | 1-trans-iodo-4-vinyl-7-chloro-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-vinyl-19-chloro-2-homo-20-nor-5-cis-13-trans prostadiene |
| 420 | 1-trans-iodo-4-methyl-7-chloro-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-19-chloro-2-homo-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 421 | 1-trans-tri-n-butylstannyl-4-methyl-4-trimethylsiloxy-1-pentene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-methyl-2-homo-18,19,20-trinor-5-cis-13-trans prostadiene |
| 422 | 1-trans-tri-n-butylstannyl-4-(1-fluorovinyl)- | 2-[7-(4-methoxy-2,2-dimethyl-1,3-dioxolan- | dl-16-hydroxy-1-hydroxymethyl-1,9-dioxo-16-(1-fluorovinyl)- |

TABLE II-continued

| | CYCLOPENTENONE | VINYL TIN | PRODUCT PROSTAGLANDIN OF THE PGE2 SERIES |
|---|---|---|---|
| | 4-trimethylsiloxy-1-octene | 4-yl)hept-2-cis-enyl]-4-(2-methoxypropyl-2-oxy)cyclopent-2-en-1-one | 2-homo-5-cis-13-trans prostadiene |
| 423 | 1-trans-tri-n-butylstannyl-3-vinyl-3-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-15a-hydroxy-1-hydroxymethyl-1,9-dioxo-15-vinyl-2-homo-5-cis-13-trans prostadiene |
| 424 | 1-trans-tri-n-butylstannyl-4-(1-fluorovinyl)-4-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16-hydroxy-1-hydroxymethyl-1,9-dioxo-16-(1-fluorovinyl)-20-methyl-2-homo-5-cis-13-trans prostadiene |
| 425 | 1-trans-tri-n-butylstannyl-3-vinyl-3-trimethylsiloxy-1-nonene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-15a-hydroxy-1-hydroxymethyl-1,9-dioxo-15-vinyl-20-methyl-2-homo-5-cis-13-trans prostadiene |
| 426 | 1-trans-tri-n-butylstannyl-4-(1-fluorovinyl)-4-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-16a-hydroxy-1-hydroxymethyl-1,9-dioxo-16-(1-fluorovinyl)-20-ethyl-2-homo-5-cis-13-trans prostadiene |
| 427 | 1-trans-tri-n-butylstannyl-3-vinyl-3-trimethylsiloxy-1-decene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-15a-hydroxy-1-hydroxymethyl-1,9-dioxo-15-vinyl-20-ethyl-2-homo-5-cis-13-trans prostadiene |

| EXAMPLE | CYCLOPENTENONE | VINYL TIN | PRODUCT PROSTAGLANDIN OF THE PGE2 SERIES |
|---|---|---|---|
| 428 | 2-[5-(4-methoxy-2,2-dimethyl-1,3-dioxolan-4-yl)pent-2-cis-enyl]-4-(2-methoxypropyl-2-oxy)cyclopent-2-en-1-one | 1-trans-tri-n-butylstannyl-4-methyl-4-trimethylsiloxy-1,7-octadiene | dl-11a,16-dihydroxy-1-hydroxymethyl-1,9-dioxo-16-methyl-2-nor-5-cis-13-trans-19 prostatriene |
| 429 | 2-[6-(4-methoxy-2,2-dimethyl-1,3-dioxolan-4-yl)hex-2-cis-enyl]-4-(2-methoxypropyl-2-oxy)cyclopent-2-en-1-one | 1-trans-tri-n-butylstannyl-4-methyl-4-trimethylsiloxy-1,7-octadiene | dl-11a,16-dihydroxy-1-hydroxymethyl-1,9-dioxo-16-methyl-5-cis-13-trans-19 prostatriene |
| 430 | 2-[7-(4-methoxy-2,2-dimethyl-1,3-dioxolan-4-yl)hept-2-cis-enyl]-4-(2-methoxypropyl-2-oxy)cyclopent-2-en-1-one | 1-trans-tri-n-butylstannyl-4-methyl-4-trimethylsiloxy-1,7-octadiene | dl-16-hydroxy-1-hydroxymethyl-1,9-dioxo-16-methyl-2-homo-5-cis-13-trans-19 prostatriene |
| 431 | 2-[6-(4-methoxy-2,2-dimethyl-1,3-dioxolan-4-yl)hex-2-cis-enyl]-4R-(2-methoxypropyl-2-oxy)cyclopent-2-en-1-one | 1-trans-tri-n-butylstannyl-4-methyl-4-trimethylsiloxy-1,7-octadiene | nat-11a,16-dihydroxy-1-hydroxymethyl-1,9-dioxo-16-methyl-5-cis-13-trans-19 prostatriene |
| 432 | 2-[5-(4-methoxy-2,2-dimethyl-1,3-dioxolan-4-yl)pent-2-cis-enyl]-4-(2-methoxypropyl-2-oxy)cyclopent-2-en-1-one | 1-trans-tri-n-butylstannyl-4-methyl-4-trimethylsiloxy-1,7-octadiene | dl-16-hydroxy-1-hydroxymethyl-1,9-dioxo-16-methyl-2-nor-5-cis-13-trans-19 prostatriene |
| 433 | 2-[6-(4-methoxy-2,2-dimethyl-1,3-dioxolan-4-yl)hex-2-cis-enyl]-4-(2-methoxypropyl-2-oxy)cyclopent-2-en-1-one | 1-trans-tri-n-butylstannyl-4-methyl-4-trimethylsiloxy-1,7-octadiene | dl-16-hydroxy-1-hydroxymethyl-1,9-dioxo-16-methyl-5-cis-13-trans-19 prostatriene |

| EXAMPLE | CYCLOPENTENONE | VINYL TIN | PRODUCT PROSTAGLANDIN OF THE 11-DEOXY PGE2 SERIES |
|---|---|---|---|
| 434 | 2-[7-(4-methoxy-2,2-dimethyl-1,3-dioxolan-4-yl)hept-2-cis-enyl]-4-(2-methoxypropyl-2-oxy)cyclopent-2-en-1-one | 1-trans-tri-n-butylstannyl-4-methyl-4-trimethylsiloxy-1,7-octadiene | dl-16-hydroxy-1-hydroxymethyl-1,9-dioxo-16-methyl-2-homo-5-cis-13-trans-19 prostatriene |

| EXAMPLE | CYCLOPENTENONE | VINYL IODIDE | PRODUCT PROSTAGLANDIN OF THE PGE2 SERIES |
|---|---|---|---|
| 435 | 2-[5-(4-methoxy-2,2-dimethyl-1,3-dioxolan-4-yl)pent-2-cis-enyl]-4-(2-methoxypropyl-2-oxy)cyclopent-2-en-1-one | 1-trans-iodo-4-vinyl-7-chloro-4-trimethylsiloxy-1-heptene | dl-11a,16-dihydroxy-1-hydroxymethyl-1,9-dioxo-16-vinyl-19-chloro-2-nor-20-nor-5-cis-13-trans prostadiene |
| 436 | 2-[5-(4-methoxy-2,2-dimethyl-1,3-dioxolan-4-yl)pent-2-cis-enyl]-4-(2-methoxypropyl-2-oxy)cyclopent-2-en-1-one | 1-trans-iodo-7-chloro-4-triethylsiloxy-1-heptene | dl-11a,16-dihydroxy-1-hydroxymethyl-1,9-dioxo-19-chloro-2-nor-20-nor-5-cis-13-trans prostadiene |
| 437 | 2-[5-(4-methoxy-2,2-dimethyl-1,3-dioxolan-4-yl)pent-2-cis-enyl]-4-(2-methoxypropyl-2-oxy)cyclopent-2-en-1-one | 1-trans-iodo-4-allenyl-7-chloro-4-trimethylsiloxy-1-heptene | dl-11a,16-dihydroxy-1-hydroxymethyl-1,9-dioxo-16-allenyl-19-chloro-2-nor-20-nor-5-cis-13-trans prostadiene |

TABLE II-continued

| EXAMPLE | VINYL TIN | CYCLOPENTENONE | PRODUCT PROSTAGLANDIN OF THE PGE2 SERIES |
|---|---|---|---|
| 438 | 1-trans-tri-n-butylstannyl-4-trimethylsilylethynyl-7-oxa-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-ethynyl-19-oxa-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 439 | 1-trans-iodo-4-vinyl-7-oxa-4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-11a,16-dihydroxy-1-hydroxymethyl-1,9-dioxo-16-vinyl-19-oxa-2-nor-5-cis-13-trans prostadiene |
| 440 | 1-trans-iodo-4-vinyl-7-chloro-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-vinyl-19-chloro-20-nor-5-cis-13-trans prostadiene |
| 441 | 1-trans-iodo-7-chloro-4-triethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-19-chloro-20-nor-5-cis-13-trans prostadiene |
| 442 | 1-trans-iodo-4-allenyl-7-chloro-4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-allenyl-19-chloro-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 443 | 1-trans-tri-n-butylstannyl-4-trimethylsilylethynyl-7-oxa-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-ethynyl-19-oxa-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 444 | 1-trans-iodo-4-vinyl-7-oxa-4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-11a,16-dihydroxy-1-hydroxymethyl-1,9-dioxo-16-vinyl-19-oxa-5-cis-13-trans prostadiene |
| 445 | 1-trans-iodo-4-vinyl-7-chloro-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-vinyl-19-chloro-2-homo-20-nor-5-cis-13-trans prostadiene |
| 446 | 1-trans-iodo-7-chloro-4-triethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-19-chloro-2-homo-20-nor-5-cis-13-trans prostadiene |
| 447 | 1-trans-iodo-4-allenyl-7-chloro-4-trimethylsiloxy-1-heptene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-allenyl-19-chloro-2-homo-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 448 | 1-trans-ti-n-butylstannyl-4-trimethylsilylethynyl-7-oxa-4-trimethylsiloxy-1-octene | 2-[7-(4-methoxy-2,2-dimethyl-1,3-dioxolan-4-yl)hept-2-cis-enyl]-4-(2-methyoxypropyl-2-oxy)cyclopent-2-en-1-one | dl-11a,16-dihydroxy-1-hydroxymethyl-1,9-dioxo-16-ethynyl-19-oxa-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 449 | 1-trans-iodo-4-vinyl-7-oxa-4-trimethylsiloxy-1-octene | 2-[7-(4-methoxy-2,2-dimethyl-1,3-dioxolan-4-yl)hept-2-cis-enyl]-4-(2-methoxypropyl-2-oxy)cyclopent-2-en-1-one | dl-11a,16-dihydroxy-1-hydroxymethyl-1,9-dioxo-16-vinyl-19-oxa-2-homo-5-cis-13-trans prostadiene |
| 450 | 1-trans-iodo-4-vinyl-7-chloro-4-trimethylsiloxy-1-heptene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-vinyl-19-chloro-20-nor-5-cis-13-trans prostadiene |
| 451 | 1-trans-iodo-7-chloro-4-triethylsiloxy-1-heptene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-19-chloro-20-nor-5-cis-13-trans prostadiene |

TABLE II-continued

| | | | |
|---|---|---|---|
| 452 | 1-trans-iodo-4-allenyl-7-chloro 4-trimethylsiloxy-1-heptene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-allenyl-19-chloro-20-nor-5-cis-13-trans prostadiene |
| EXAMPLE | VINYL TIN | CYCLOPENTENONE | PRODDUCT PROSTAGLANDIN OF THE PGE2 SERIES |
| 453 | 1-trans-tri-n-butylstannyl-4-trimethylsilylethynyl-7-oxa 4-trimethylsiloxy-1-octene | 2-[6-(4-methoxy-2,2-dimethyl-1,3-dioxolan-4-yl)hex-2-cis-enyl]-4R-(2-methyoxypropyl-2-oxy)cyclopent-2-en-1-one | nat-11a,16-dihydroxy-1-hydroxymethyl-1,9-dioxo-16-ethynyl-19-oxa-5-cis-13-trans prostadiene |
| EXAMPLE | VINYL IODINE | CYCLOPENTENONE | PRODUCT PROSTAGLANDIN OF THE PGE2 SERIES |
| 454 | 1-trans-iodo-4-vinyl-7-oxa 4-trimethylsiloxy-1-octene | 2-[6-(4-methoxy-2,2-dimethyl-1,3-dioxolan-4-yl)hex-2-cis-enyl]-4R-(2-methoxypropyl-2-oxy)cyclopent-2-en-1-one | nat-11a,16-dihydroxy-1-hydroxymethyl-1,9-dioxo-16-vinyl-19-oxa-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 455 | 1-trans-iodo-4-vinyl-7-chloro 4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-vinyl-19-chloro-2-nor-20-nop-5-cis-13-trans prostadiene |
| 456 | 1-trans-iodo-7-chloro 4-trimethylsiloxy-1-heptene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-19-chloro-2-nor-20-nop-5-cis-13-trans prostadiene |
| 457 | 1-trans-iodo-4-allenyl-7-chloro 4-trimethylsiloxy-1-heptene | 2-[5-(4-methoxy-2,2-dimethyl-1,3-dioxolan-4-yl)pent-2-cis-enyl]-4-(2-methoxypropyl-2-oxy9 cyclopent-2-en-1-one | dl-16-hydroxy-1-hydroxymethyl-1,9-dioxo-16-allenyl-19-chloro-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 458 | 1-trans-tri-n-butylstannyl-4-trimethylsilylethynyl-7-oxa 4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-ethynyl-19-oxa-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 459 | 1-trans-iodo-4-vinyl-7-oxa 4-trimethylsiloxy-1-octene | 2-[5-(4-methoxy-2,2-dimethyl-1,3-dioxolan-4-yl)pent-2-cis-enyl]-4-(2-methoxypropyl-2-oxy)cyclopent-2-en-1-one | dl-16-hydroxy-1-hydroxymethyl-1,9-dioxo-16-vinyl-19-oxa-2-nor-5-cis-13-trans prostadiene |
| 460 | 1-trans-iodo-4-vinyl-7-chloro 4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-vinyl-19-oxa-5-cis-13-trans prostadiene |
| 461 | 1-trans-iodo-7-chloro 4-triethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-19-chloro-20-nor-5-cis-13-trans prostadiene |
| 462 | 1-trans-iodo-4-allenyl-7-chloro 4-trimethylsiloxy-1-heptene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-allenyl-19-chloro-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 463 | 1-trans-tri-n-butylstannyl-4-trimethylsilylethynyl-7-oxa 4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-ethynyl-19-oxa-5-cis-13-trans prostadiene |
| EXAMPLE | VINYL IODIDE | CYCLOPENTENONE | PRDUCT PROSTAGLANDIN OF THE 11-DEOXY PGE2 SERIES |
| 464 | 1-trans-iodo-4-vinyl-7-oxa 4-trimethylsiloxy-1-octene | 2-[6-(4-methoxy-2,2-dimethyl-1,3-dioxolan-4-yl)hex-2-cis-enyl]-4-(2-methoxypropyl-2-oxy)cyclopent-2-en-1-one | dl-16-hydroxy-1-hydroxymethyl-1,9-dioxo-16-vinyl-19-oxa-5-cis-13-trans prostadiene |

TABLE II-continued

| | | | |
|---|---|---|---|
| 465 | 1-trans-iodo-4-vinyl-7-chloro 4-trimethylsiloxy-1-heptene | 2-[7-(4-methoxy-2,2-dimethyl-1,3-dioxolan-4-yl)hept-2-cis-enyl]-4-(2-methoxypropyl-2-oxy) cyclopent-2-en-1-one | dl-16-hydroxy-1-hydroxymethyl-1,9-dioxo-16-vinyl-19-chloro-2-homo-20-nor-5-cis-13-trans prostadiene |
| 466 | 1-trans-iodo-7-chloro 4-triethylsiloxy-1-heptene | 2-[7-(4-methoxy-2,2-dimethyl-1,3-dioxolan-4-yl)hept-2-cis-enyl]-4-(2-methoxypropyl-2-oxy) cyclopent-2-en-1-one | dl-16-hydroxy-1-hydroxymethyl-1,9-dioxo-19-chloro-2-homo-20-nor-5-cis-13-trans prostadiene |
| 467 | 1-trans-iodo-4-allenyl-7-chloro 4-trimethylsiloxy-1-heptene | 2-[7-(4-methoxy-2,2-dimethyl-1,3-dioxolan-4-yl)hept-2-cis-enyl]-4-(2-methoxypropyl-2-oxy) cyclopent-2-en-1-one | dl-16-hydroxy-1-hydroxymethyl-1,9-dioxo-16-allenyl-19-chloro-2-homo-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 468 | 1-trans-tri-n-butylstannyl-4-trimethylsilylethynyl-7-oxa 4-trimethylsiloxy-1-octene | 2-[7-(4-methoxy-2,2-dimethyl-1,3-dioxolan-4-yl)hept-2-cis-enyl]-4-(2-methoxypropyl-2-oxy) cyclopent-2-en-1-one | dl-16-hydroxy-1-hydroxymethyl-1,9-dioxo-16-ethynyl-19-oxa-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 469 | 1-trans-iodo-4-vinyl-7-oxa 4-trimethylsiloxy-1-octene | 2-[7-(4-methoxy-2,2-dimethyl-1,3-dioxolan-4-yl)hept-2-cis-enyl]-4-(2-methoxypropyl-2-oxy) cyclopent-2-en-1-one | dl-16-hydroxy-1-hydroxymethyl-1,9-dioxo-16-vinyl-19-oxa-2-homo-5-cis-13-trans prostadiene |

EXAMPLE 470

Treatment of the PGE$_1$ compounds of Table I and the PGE$_2$ compounds of Table II with lithium-selectride$^R$ (Aldrich, 1 M. solution in THF in accordance with the procedure of Reference Example 131, is productive of the corresponding 9α-hydroxy-PGF$_{1α}$ compound corresponding to the starting PGE$_1$ compound and the 9α-hydroxy-PGF$_{2α}$ compound corresponding to the starting PGE$_2$ compound of Table II.

While specific embodiments of this invention have been described with particularly herein, it will be understood that the invention embraces all changes and modifications of the particular compounds chosen for purposes of illustration herein which do not depart from the spirit and scope of the invention.

EXAMPLE 472 dl-Dimethyl-t-butylsily 11α,15α-bis-dimethyl-t-butyl silyloxy-16,16-dimethyl-9-methylene-5-cis,13-trans prostadienoate To a solution of dl-11α,15α-dihydroxy-16,16-dimethyl-9-methylene-5-cis,13-trans-prostadienoic acid (0.05 mol) in 150 ml of dimethylformamide is added dimethyl-t-butylchlorosilane (0.16 mol). The mixture is maintained at 40° C. for 5 hours at 25° C. for 19 hours. The mixture is poured into water and extracted with an ether-petroleum ether mixture. The organic layer is wash with cold dilute hydrochloric acid followed by a solution of sodium bicarbonate. The solution is dried over sodium sulfate and the solvent is removed to give the title compound.

EXAMPLE 473 dl-11α,15α-bis-dimethyl-t-butylsilyloxy-16,16-dimethyl-9-methylene-5-cis,13-trans-prostadienoyl chloride To a solution of dl-dimethyl-t-butylsily-11α,15α-bis-dimethyl-t-butylsilyloxy-16,16-dimethyl-9-methylene-5-cis,13-trans-prostadienoate (0.05 mol) in 150 ml of methylene chloride containing 0.1 ml of dimethylformamide is added with stirring at 0° C. oxalyl chloride (0.05 mol). The solution is maintained at 0° C. for 2.5 hr and at 25° C. for 1 hr. The solvent is removed. The residue is dissolved in a mixture of ether-petroleum ether and filtered. The solvent is removed to give the title compound.

EXAMPLE 474 dl-11α,15α-dihydroxy-16,16-dimethyl-9-methylene-1-hydroxymethyl-1-oxo-5-cis,13-trans prostadiene

Method A

To an etheral solution of dl-11α,15α-bis-dimethyl-t-butylsilyoxy-16,16-dimethyl-9-methylene-5-cis,13-trans prostadienoyl chloride (0.02 mol) is added at 0° C. with stirring an etheral solution of (0.06 mol) of diazomethane. After 1 hr the ether and excess diazomethane is removed in a stream of nitrogen. The residue is mixed with tetrahydrofuran and dilute sulfuric acid. The mixture is stirred at 60° C. till TLC indicates complete reaction. The mixture is saturated with sodium chloride and extracted with ether. The ether solution is washed with a solution of sodium bicarbonate and dried over magnesium sulfate. The product is purified by silica gel chromatography to give the title compound.

EXAMPLE 475 dl-11α,15α-dihydroxy-16,16-dimethyl-9-methylene-1-hydroxymethyl-1-oxo-5-cis,13-trans prostadiene

Method B

A solution of dl-11α,15α-bis-dimethyl-t-butylsilyoxy-16,16-dimethyl-9-methylene-5-cis,13-trans prostdienoyl chloride (0.02 mol) and tris-trimethylsilyloxyethylene (0.04 mol) in chlorobenzene is refluxed for 5 hr. The solvent is removed. The residue is heated in a mixture of dilute hydrochloric acid and tetrahydrofuran for 5 hr. The mixture is saturated with sodium chloride and extracted with ether. The ether solution is washed with a solution of sodium bicarbonate and dried over magnesium sulfate. The solvent is removed and the residue is purified by silica gel chromatography to give the title compound.

EXAMPLES 476 to 481

In the manner described hereinabove in Examples 472 to 475. The following 9-methylene-1-hydroxymethyl-1-oxo analogs are prepared from the corresponding carboxylic acids.

dl-11α,15α-dihydroxy-15-methyl-9-methylene-1-hydroxymethyl-1-oxo-5-cis,13-trans prostadiene.

dl-11α,15α-dihydroxy-9-methylene-1-hydroxymethyl-1-oxo-16-(m-chlorophenoxy-17,18,19,20-tetranor-5-cis,13-trans prostadiene.

dl-11α,15α-dihydroxy-9-methylene-1-hydroxymethyl-1-oxo-5-cis,13-trans prostadiene.

dl-11α,16-dihydroxy-9-methylene-1-hydroxymethyl-1-oxo-16-methyl-5-cis,13-trans prostadiene.

dl-11α,16-dihydroxy-9-methylene-1-hydroxymethyl-1-oxo-16-methyl-13-trans prostene.

dl-11α,16-dihydroxy-9-methylene-1-hydroxymethyl-1-oxo-16-vinyl-13-trans prostene.

EXAMPLE 482

Diethyl α-Phenylthiosuberate

To a stirred, ice-cold solution of sodium ethoxide in ethanol (prepared from 5.98 g of sodium spheres and 175 ml of ethanol) is added a solution of 29.8 g of thiophenol in 30 ml of ethanol during 15 min. After 10 min. this solution is treated at 0°–15° with a solution of 79.5 g of diethyl α-bromosuberate in 70 ml of ethanol during 15 min. The stirred mixture is warmed to room temperature during 60 min. and finally is heated at reflux for 60 min. The cooled solution is treated with 3 ml of gl acetic acid and concentrated. The residue is partitioned between ether and water. The ether layer is washed with water and brine, dried over MgSO$_4$, and concentrated. The residue is subjected to fractional distillation to provide a light amber liquid, bp. 165°–180° (0.15 mm).

EXAMPLE 483

7-Carbethoxy-7-Phenylthioheptanoic Acid

To a stirred, ice-cold solution of 20.4 g of diethyl α-phenylthiosuberate in 100 ml of ethanol is added dropwise a solution of 2.41 g of sodium hydroxide in 12 ml of water. The resulting solution is kept at 0° for 3 days and at room temperature for 2 hours. The bulk of the ethanol is evaporated, and the residue is partitioned with water and ether. The aqueous layer is acidified with hydrochloric acid and extracted with ether. The extract is washed with water and brine, dried over MgSO$_4$, and evaporated. The residue is subjected to dry column chromatography on silica gel with 30: 20: 1 ethyl acetate-heptane-acetic acid to provide a light yellow oil.

EXAMPLE 484

7-(2-Furoyl)-2-Phenylthioheptanoic Acid

To a stirred, ice-cold solution of 7.75 g of 7-carbethoxy-7-phenylthioheptanoic acid in 25 ml of dichloromethane is added 3.5 ml of trifluoroacetic anhydride during 2 min. The solution is warmed to 20° during 10 min., recooled to 0°, and treated with 3.6 ml of furan during 2 min. The resulting solution is stirred at ambient temperature for 2.5 days, diluted with 1: 1 ether-petroleum ether, and washed with aqueous NaHCO$_3$, water, and brine. The solution is dried over MgSO$_4$ and concentrated.

The residue (3.16 g) is treated with a solution of 2.97 g of potassium hydroxide in 40 ml of ethanol and 5 ml of water. The resulting solution is refluxed for 30 min., cooled, and concentrated. The residue is partitioned with water and ether. The aqueous layer is acidified with hydrochloric acid and extracted with ether. The extract is washed with water and brine, dried over MgSO$_4$, and concentrated.

The residue is subjected to dry column chromatography on silica gel with 30: 20: 1 ethylacetate-heptaneacetic acid to provide an oil.

EXAMPLE 485

8-(2-Furoyl)-8-Hydroxy-2-Phenylthiooctanoic Acid

To a stirred solution of 3.61 g of 7-(2-furoyl)-2-phenylthioheptanoic acid in 15 ml of DME is added 25 ml of water and 5.45 ml of 1.0 M aqueous sodium carbonate. The resulting solution is treated furing 1 min. with 0.41 g of sodium borohydride in small portions. The mixture is stirred at ambient temperature for 3.5 hours, diluted with ethyl acetate, cooled to 0°, and treated with 4 M hydrochloric acid. The ethyl acetate layer is washed with water and brine, dried over MgSO$_4$, and concentrated to give an oil.

EXAMPLE 486

2-(6-carboxy-phenylthio)-4-hydroxy-cyclopent-2-en-1-one

To a stirred mixture of 54.4 g of 8-(2-furoyl)-8-hydroxy-2-phenylthiooctanoic acid, 0.5 g of hydroquinone, 8.5 ml of dimethoxyethane, and 6.0 ml of water is added 12.0 g of sodium bicarbonate and 122 ml of 90% formic acid. The resulting solution is stirred at reflux temperature for 24 hours. The solution is cooled, treated dropwise with 40 ml of 98% sulfuric acid during 15 min., and then refluxed for 18 hours. The solution is cooled, diluted with ethyl acetate, and saturated with solid NaCl. The organic layer is washed with brine, dried over MgSO$_4$, and concentrated. The residue is subjected to column chromatography on silica gel with chloroform progressively enriched in ether to give an oil.

EXAMPLE 487

2-(8-Hydroxy-7-oxo-6-phenylthiooctyl)-4-hydroxy-cyclopent-2-en-1-one

To a stirred solution of 3.34 g 2-(6-carboxy-6-phenylthiohexyl)-4-hydroxy-cyclopent-2-en-1-one in 10 ml of DMF is added 3.26 g of imidazole and 3.32 of t-butylchlorodimethylsilane. The resulting mixture is stirred at 55°–60° for 4 hours, cooled and diluted with petroleum ether and water. The organic layer is washed with water and brine, dried over MgSO$_4$, and filtered. The filtrate is concentrated to give an oil.

To a stirred, ice-cold solution of this oil (4.55 g) and 0.06 ml of DMF in 11 ml of THF is added 0.77 ml of oxalyl chloride during 10 min. After 30 min. at 0°, the stirred solution is maintained at ambient temperature for 2 hours, and concentrated under high vacuum. The residue is stirred with hexane and filtered through celite. The filtrate is concentrated to give a light yellow liquid (3.8 g).

A solution of the acid chloride prepared in the preceding paragraph, 5.21 g of Tris-trimethylsilooxyethene, and 16 ml of chlorobenzene is stirred at reflux temperature for 4 hours, cooled, and subjected to evaporation under vacuum. The residue is treated with 40 of THF and 8.0 ml of 1 N hydrochloric acid. The mixture is stirred at reflux temperature for 2 hours, cooled, and concentrated. The residue is partitioned with ethyl acetate and water. The organic layer is washed successively with brine, aqueous NaHCO$_3$, and brine, dried over MgSO$_4$, and concentrated. The residue is subjected to dry column chromatography on silica gel with 10:1 ethyl acetate-methanol to give an oil.

EXAMPLE 488

2-(7-oxo-6-thiophenoxy-8-trimethylsilyloxyoctyl)-4-trimethylsilyloxy cyclopent-2-en-1-one To a solution of 2-(6-carboxy-5-thiophenoxyhexyl)-4-hydroxy cyclopent-2-en-1-one in 11 ml of pyridine was added 2.8 ml of hexamethyldisilazane and 1.4 ml of trimethylsilylchloride. After stirring 4 hr., the solvent is removed and the residue is taken up in hexane and filtered. The solvent is removed to give 1.65 g of the title compound.

EXAMPLE 489 dl-11α,15α-dihydroxy-1,9-dioxo-1-hydroxymethyl-16,16-dimethyl-2-thiophenoxy-13-trans prostene and the corresponding 15β isomer To a solution of the cuprate reagent prepared from 1-trans-tri n-butylstannyl-3-trimethylsilyloxy-4,4-dimethyl octene, copper pentyne, HMPTA, and n-butyl lithium by the methods described hereinabove is maintained at −78° C. To this solution is added 0.98 g of 2-(7-oxo-6-thiophenoxy-8-trimethylsilyloxyoctyl)-4-trimethylsiloxy cyclopent-2-en-1-one. The mixture is stirred 90 min. at −40°. The solution is worked up as described hereinabove. The product is deblocked by with 20 ml of acetic acid, THF, water (4: 2: 1) by stirring for 1 hr. The solvents are removed and the residue is taken up in ethyl acetate. The ethylacetate solution is washed with brine and dried over magnesium sulfate. The solvent is removed. The residue was chromatographed on silica gel, giving the title compound and its corresponding 15β isomer.

EXAMPLE 490 dl-11α,15α-dihydroxy-1,9-dioxo-1-hydroxymethyl-16,16-dimethyl-2-trans, 13-trans prostadiene To a solution of 0.172 g of dl-11α,15α-dihydroxy-1,9-dioxo-1-hydroxymethyl-16,16-dimethyl-2-thiophenoxy-13-trans prostene in 2 ml of mthylene chloride is added at −78° C. a solution of 0.077 g of m-chloroperbenzoic acid in 1.4 ml of methylene chloride. The solution is allowed to warm to 0° C. and 0.3 ml of 10% sodium sulfite is added. The mixture is extracted with ether. The ether solution is washed with a solution of sodium bicarbonate and brine. The solution is dried over magnesium sulfate. The solvent is removed and the residue is dissolved in dimethoxyethane. The solution is refluxed till TLC indicates that no starting material remains. The solvent is removed and the residue is purified by silica gel chromatography to give the title compound.

EXAMPLE 491

Treatment of the undeblocked PGE$_1$ compounds of Table I and the undeblocked PGE$_2$ compounds of Table II with lithium-selectride$^R$ (Aldrich, 1 M. solution in THF in accordance with the procedure of Reference Example 131, is productive of the corresponding 9α-hydroxy-PGF$_{1α}$ compound corresponding to the starting PGE$_1$ compound of Table I and the 9α-hydroxy-PGF$_{2α}$ compound corresponding to the starting PGE$_2$ compound of Table II.

While specific embodiments of this invention have been described with particularity herein, it will be understood that the invention embraces all changes and modifications of the particular compounds chosen for purposes of illustration herein which do not depart from the spirit and scope of the invention.

EXAMPLE 492

Treatment of the undeblocked PGE$_1$ compounds of Table I and the undeblocked compounds of Table II with excess sodium borohydride in ethanol followed by removal of the protecting groups with mild acid hydrolysis is productive of the 9β-hydroxy PGF$_{1β}$ compounds corresponding to the starting PGE$_1$ compound of Table I and the 9β-hydroxy-PGF$_{2β}$ compound corresponding to the starting PGE$_2$ compound of Table II.

What is claimed is:

1. An optically active compound of the formula:

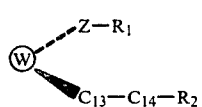

or the racemic mixture of that compound and its mirror image wherein Z is —(CH$_2$)$_g$—wherein g is an integer from 5 to 7 inclusive; C$_{13}$—C$_{14}$ is trans-vinylene; W is

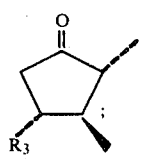

R$_3$ is hydrogen or hydroxyl; R$_1$ is selected from the group consisting of

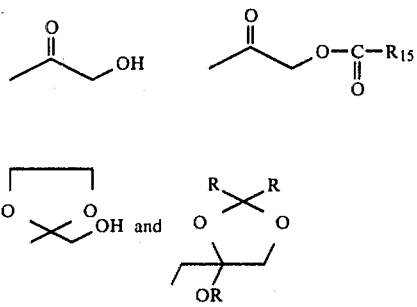

wherein R is C$_1$-C$_4$ alkyl, and R$_{15}$ is selected from the group consisting of C$_1$-C$_4$ alkyl, di-(C$_1$-C$_4$)- alkylamino, C$_1$-C$_4$ alkoxy and phenyl or phenyl substituted with one or more substituents selected from the group consisting of C$_1$-C$_4$ alkyl, —OR, —SR, F or Cl wherein R is as previously defined; R$_2$ is

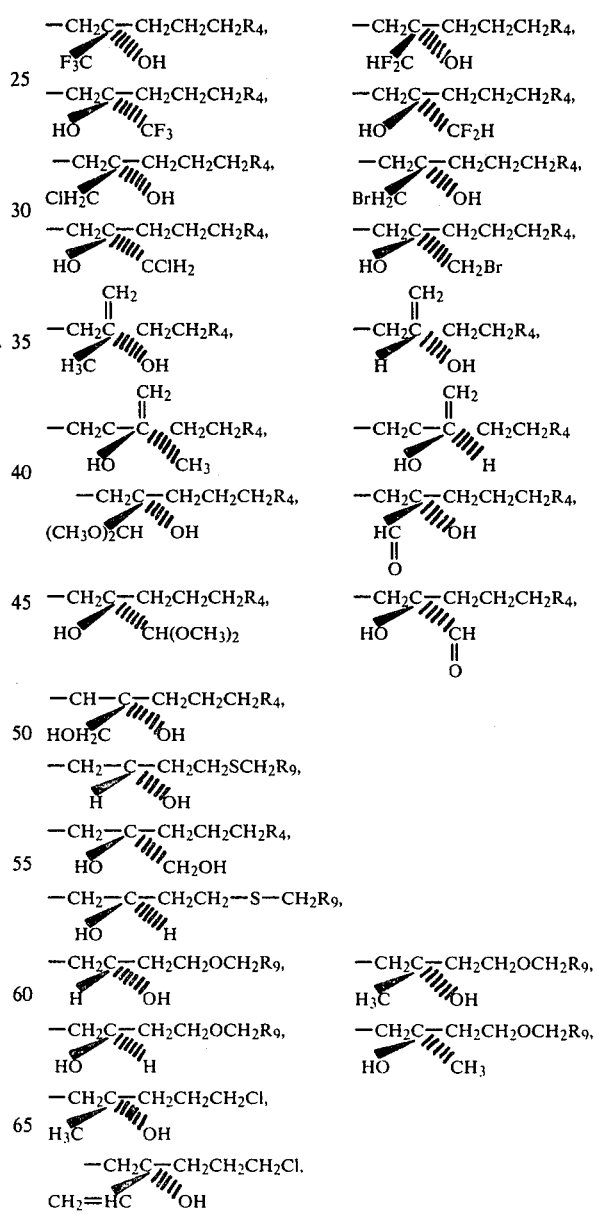

-continued

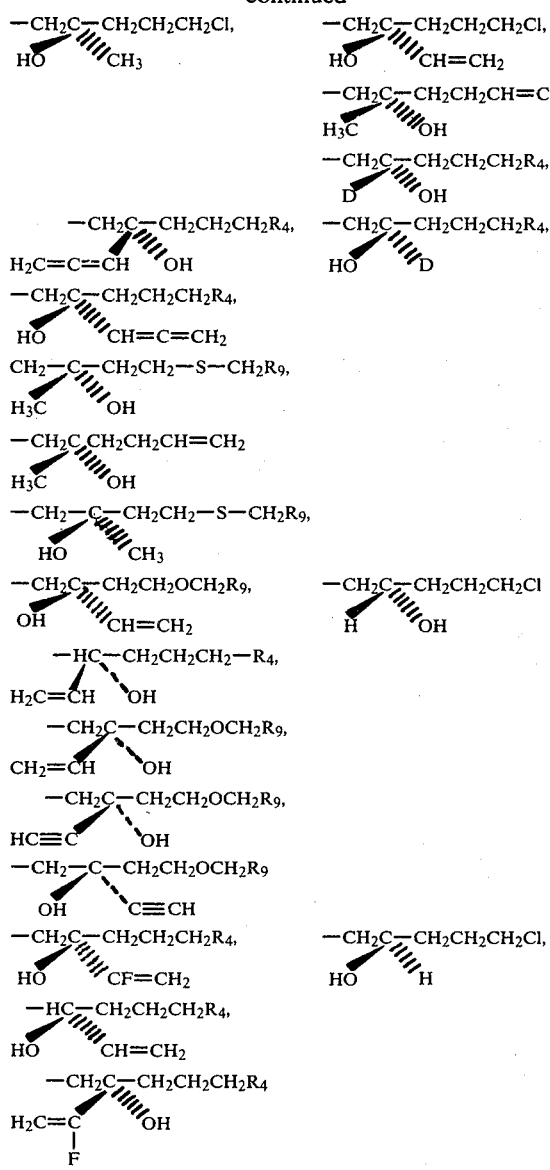

wherein R₄ is hydrogen, chloro, methyl, ethyl or propyl; R₉ is hydrogen or $C_1$ to $C_3$ alkyl.

2. The compound according to claim 1 wherein $R_1$ is:

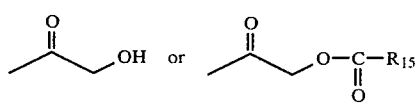

3. The compound according to claim 1 wherein $R_1$ is:

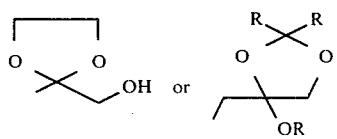

wherein R is as previously defined.

4. The compound according to claim 2 wherein Z is —$(CH_2)_6$— and $C_{13}$–$C_{14}$ is trans-vinylene.

5. The compound according to claim 3 wherein Z is —$(CH_2)_6$— and $C_{13}$–$C_{14}$ is trans-vinylene.

6. The compound according to claim 4 wherein $R_2$ is selected from the group consisting of:

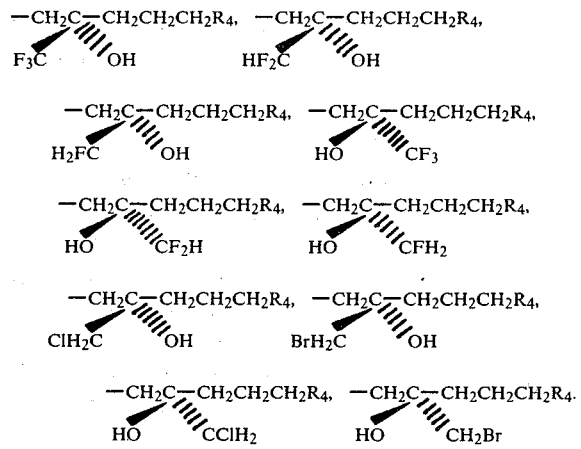

7. The optically active compound according to claim 6 wherein said $R_2$ group includes a 16α-hydroxy substituent.

8. The optically active compound according to claim 6 wherein said $R_2$ group includes a 16β-hydroxyl substituent.

9. The compound according to claim 4 wherein $R_2$ is selected from the group consisting of:

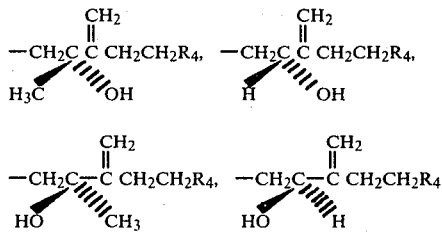

10. The optically active compound according to claim 9.

11. The compound according to claim 4 wherein $R_2$ is selected from the group consisting of:

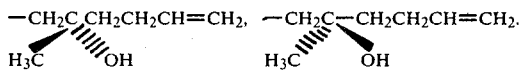

12. The optically active compound according to claim 11.

13. The compound according to claim 4 wherein $R_2$ is selected from the group consisting of:

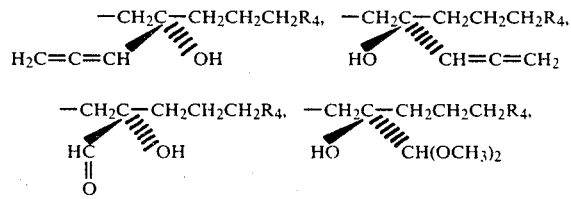

-continued

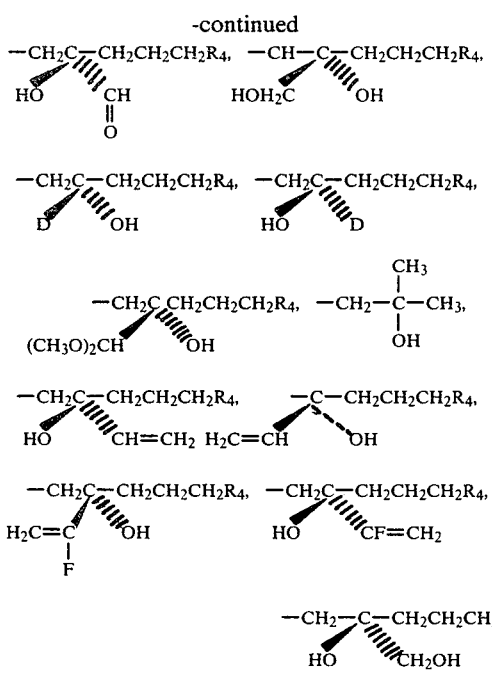

14. The optically active compound according to claim 13.

15. The compound according to claim 4 wherein $R_2$ is selected from the group consisting of:

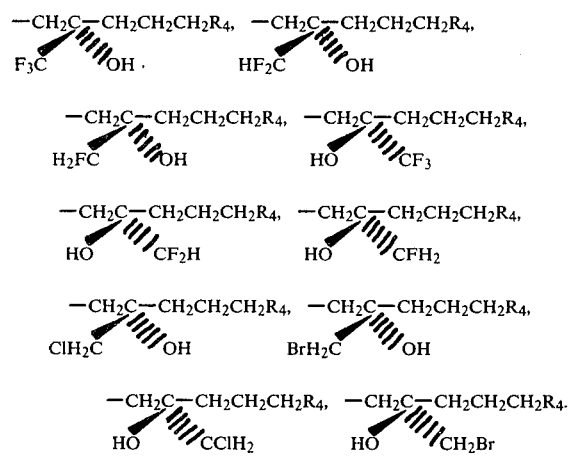

16. The optically active compound according to claim 15.

17. The compound according to claim 4 wherein $R_2$ is selected from the group consisting of:

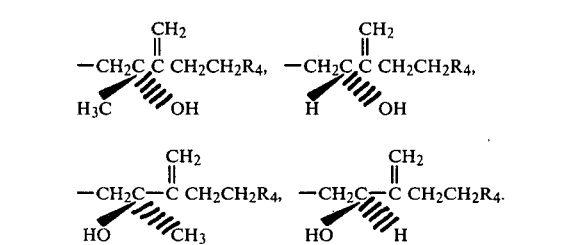

-continued

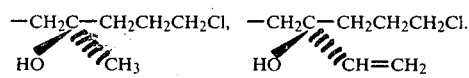

18. The optically active compound according to claim 17.

19. The compound according to claim 5 wherein $R_2$ is selected from the group consisting of:

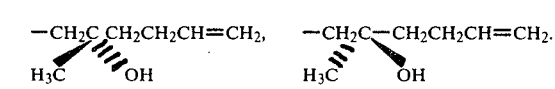

20. The optically active compound according to claim 19 wherein said $R_2$ group includes a 16α-hydroxy substituent.

21. The optically active compound according to claim 19 wherein said $R_2$ group includes a 16β-hydroxyl substituent.

22. The compound according to claim 5 wherein $R_2$ is selected from the group consisting of:

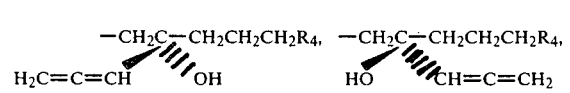

23. The optically active compound according to claim 22.

24. The compound according to claim 5 wherein $R_2$ is selected from the group consisting of:

—CH$_2$C(CH$_3$)(OH)CH$_2$CH$_2$CH=CH$_2$,  —CH$_2$C(CH$_3$)(OH)CH$_2$CH$_2$CH=CH$_2$.

25. The optically active compound according to claim 24.

26. The compound according to claim 5 wherein $R_2$ is selected from the group consisting of:

—CH$_2$C(H$_2$C=C=CH)(OH)CH$_2$CH$_2$CH$_2$R$_4$,  —CH$_2$C(HO)(CH=C=CH$_2$)CH$_2$CH$_2$CH$_2$R$_4$

-continued

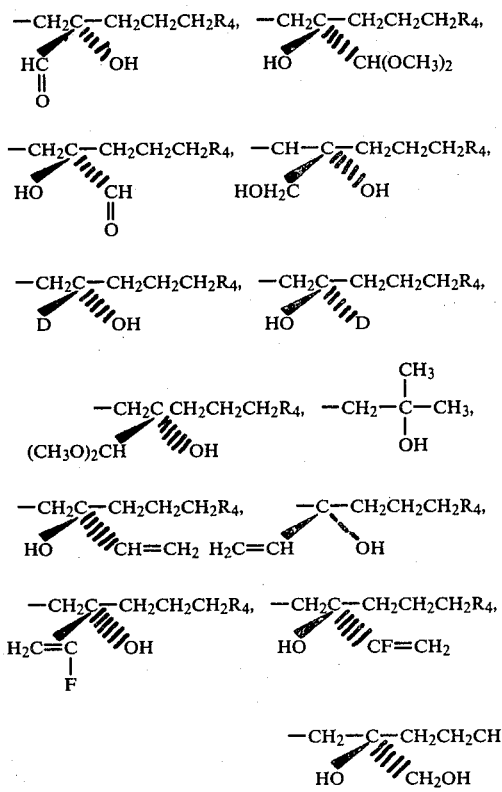

27. The optically active compound according to claim 26.

28. The compound according to claim 5 wherein $R_2$ is selected from the group consisting of:

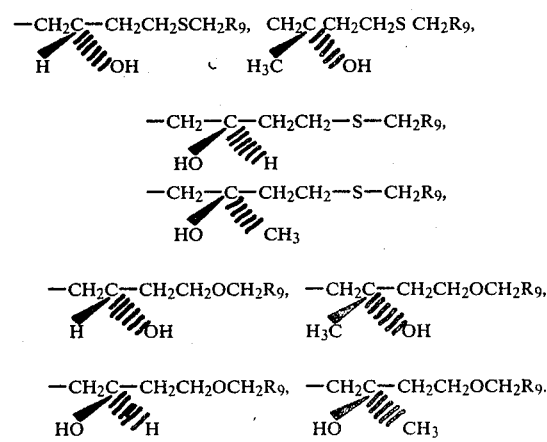

-continued

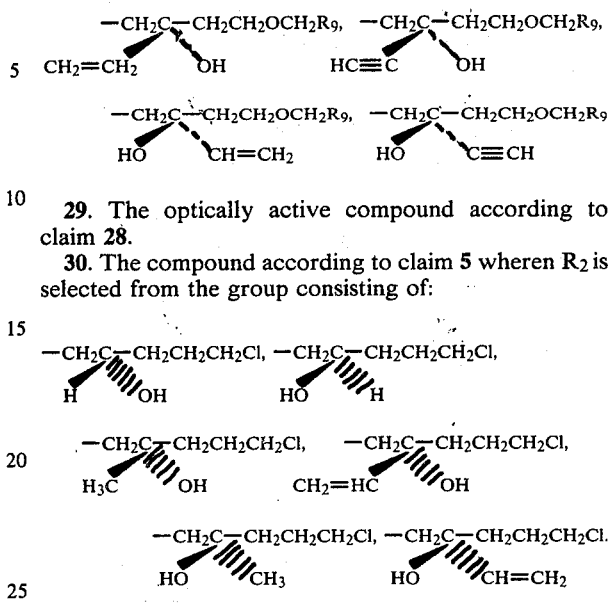

29. The optically active compound according to claim 28.

30. The compound according to claim 5 wheren $R_2$ is selected from the group consisting of:

—CH$_2$C—CH$_2$CH$_2$CH$_2$Cl, —CH$_2$C—CH$_2$CH$_2$CH$_2$Cl,
H   OH                HO   H

—CH$_2$C—CH$_2$CH$_2$CH$_2$Cl, —CH$_2$C—CH$_2$CH$_2$CH$_2$Cl,
H$_3$C  OH             CH$_2$=HC  OH

—CH$_2$C—CH$_2$CH$_2$CH$_2$Cl, —CH$_2$C—CH$_2$CH$_2$CH$_2$Cl.
HO   CH$_3$           HO   CH=CH$_2$

31. The optically active compound according to claim 30.

32. The racemic compound according to claim 9, 11α,16-dihydroxy-1-hydroxymethyl-1,9-dioxo-16-methyl-17-methylene-13-trans-prostene, and the optically active compound of this formula having a 16α- or 16β-hydroxyl substituent.

33. The racemic compound according to claim 6, 11α,16-dihydroxy-1-hydroxymethyl-1,9-dioxo-16-trifluoro-methyl-13-trans-prostene, and the optically active compound of this formula having a 16α- or 16β-hydroxy substituent.

34. The racemic compound according to claim 6, 11α,16-dihydroxy-1-hydroxymethyl-1,9-dioxo-16-fluoromethyl-13-trans-prostene, and the optically active compound of this formula having a 16α- or 16β-hydroxy substituent.

35. The racemic compound according to claim 17, 11α,16-dihydroxy-1-hydroxymethyl-1,9-dioxo-19-chloro-16-methyl-20-nor-13-trans-prostene, and the optically active compound of this formula having a 16α- or 16β-hydroxy substituent.

36. The racemic compound according to claim 13, 11α,15-dihydroxy-1-hydroxymethyl-1,9-dioxo-15-vinyl-13-trans-prostene, and the optically active compound of this formula.

37. The racemic compound according to claim 13 11α,16-dihydroxy-1-hydroxymethyl-1,9-dioxo-16-(1-fluorovinyl)-13-trans-prostene.

* * * * *

UNITED STATES PATENT OFFICE
CERTIFICATE OF CORRECTION

Patent No. 4,254,036  Dated  March 3, 1981

Inventor(s) Allan Wissner

It is certified that error appears in the above-identified patent and that said Letters Patent are hereby corrected as shown below:

Claim 1, column 226, lines 35 and 40, the correct formula should be as follows:

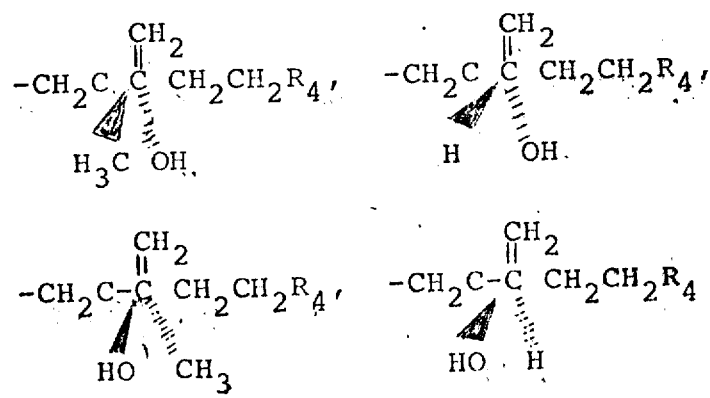

Signed and Sealed this

Seventeenth Day of November 1981

[SEAL]

Attest:

GERALD J. MOSSINGHOFF

Attesting Officer  Commissioner of Patents and Trademarks